US010006007B2

(12) United States Patent
Kariko et al.

(10) Patent No.: US 10,006,007 B2
(45) Date of Patent: *Jun. 26, 2018

(54) RNA PREPARATIONS COMPRISING PURIFIED MODIFIED RNA FOR REPROGRAMMING CELLS

(71) Applicant: The Trustees of the University of Pennsylvania, Philadelphia, PA (US)

(72) Inventors: Katalin Kariko, Rydal, PA (US); Drew Weissman, Wynnewood, PA (US); Gary Dahl, Madison, WI (US); Anthony Person, Madison, WI (US); Judith Meis, Fitchburg, WI (US); Jerome Jendrisak, Madison, WI (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/160,062

(22) Filed: May 20, 2016

(65) Prior Publication Data

US 2016/0369243 A1 Dec. 22, 2016

Related U.S. Application Data

(63) Continuation of application No. 14/801,075, filed on Jul. 16, 2015, now Pat. No. 9,371,511, which is a continuation of application No. 14/644,680, filed on Mar. 11, 2015, now Pat. No. 9,163,213, which is a continuation of application No. 12/962,468, filed on Dec. 7, 2010, now Pat. No. 9,012,219.

(Continued)

(51) Int. Cl.

| | |
|---|---|
| *C12N 5/00* | (2006.01) |
| *C12N 5/02* | (2006.01) |
| *C12Q 1/68* | (2018.01) |
| *C12N 5/074* | (2010.01) |
| *C12N 15/87* | (2006.01) |
| *C12N 15/85* | (2006.01) |
| *A61K 38/17* | (2006.01) |
| *A61K 38/18* | (2006.01) |
| *A61K 38/44* | (2006.01) |
| *A61K 38/46* | (2006.01) |
| *A61K 38/50* | (2006.01) |
| *A61K 48/00* | (2006.01) |
| *C07K 14/47* | (2006.01) |
| *C07K 14/505* | (2006.01) |
| *C12N 9/02* | (2006.01) |
| *C12N 9/22* | (2006.01) |
| *C12N 9/78* | (2006.01) |
| *C12N 15/117* | (2010.01) |

(52) U.S. Cl.
CPC ........ *C12N 5/0696* (2013.01); *A61K 38/1709* (2013.01); *A61K 38/1816* (2013.01); *A61K 38/44* (2013.01); *A61K 38/465* (2013.01); *A61K 38/50* (2013.01); *A61K 48/005* (2013.01); *A61K 48/0075* (2013.01); *C07K 14/47* (2013.01); *C07K 14/4712* (2013.01); *C07K 14/505* (2013.01); *C12N 9/0075* (2013.01); *C12N 9/22* (2013.01); *C12N 9/78* (2013.01); *C12N 15/117* (2013.01); *C12N 15/85* (2013.01); *C12N 15/87* (2013.01); *C12N 2310/17* (2013.01); *C12N 2310/335* (2013.01); *C12N 2320/30* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/02* (2013.01); *C12Y 114/13039* (2013.01); *C12Y 301/04012* (2013.01); *C12Y 305/04004* (2013.01)

(58) Field of Classification Search
CPC .................................................. A61K 48/0041
See application file for complete search history.

(56) References Cited

U.S. PATENT DOCUMENTS

| | | |
|---|---|---|
| 5,824,497 A | 10/1998 | Andrews et al. |
| 7,335,471 B2 | 2/2008 | Guillerez et al. |

(Continued)

FOREIGN PATENT DOCUMENTS

| | | |
|---|---|---|
| EP | 2072618 | 6/2009 |
| JP | 2002-507121 | 3/2002 |

(Continued)

OTHER PUBLICATIONS

Buganim (2012,Cell, 150:1209-1222).*
Thomson et al. (PNAS, 92:7844-7848 (Aug. 1995).*
NIH (Stem Cells: Scientific Progress and Future Research Directions, Department of Health and Human Services, Chapter 1, pp. 1-4, Jun. 2001).*
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44.

(Continued)

*Primary Examiner* — Valarie E Bertoglio
(74) *Attorney, Agent, or Firm* — Casimir Jones, S.C.; Jason R. Bond

(57) ABSTRACT

The present invention provides compositions and methods for reprogramming somatic cells using purified RNA preparations comprising single-strand mRNA encoding an iPS cell induction factor. The purified RNA preparations are preferably substantially free of RNA contaminant molecules that: i) would activate an immune response in the somatic cells, ii) would decrease expression of the single-stranded mRNA in the somatic cells, and/or iii) active RNA sensors in the somatic cells. In certain embodiments, the purified RNA preparations are substantially free of partial mRNAs, double-stranded RNAs, un-capped RNA molecules, and/or single-stranded run-on mRNAs.

19 Claims, 41 Drawing Sheets

Related U.S. Application Data

(60) Provisional application No. 61/267,312, filed on Dec. 7, 2009.

(56) References Cited

U.S. PATENT DOCUMENTS

| | | | |
|---|---|---|---|
| 7,807,815 | B2 | 10/2010 | MacLachlan et al. |
| 8,039,214 | B2 | 10/2011 | Dahl et al. |
| 8,278,036 | B2 | 10/2012 | Kariko et al. |
| 8,329,887 | B2 | 12/2012 | Dahl et al. |
| 8,808,982 | B2 | 8/2014 | Dahl et al. |
| 9,012,219 | B2 | 4/2015 | Kariko et al. |
| 9,163,213 | B2 | 10/2015 | Kariko et al. |
| 2005/0137155 | A1 | 6/2005 | McSwiggen et al. |
| 2007/0087437 | A1 | 4/2007 | Hu |
| 2007/0281336 | A1 | 12/2007 | Jendrisak et al. |
| 2008/0239143 | A1 | 11/2008 | Lin et al. |
| 2009/0286852 | A1 | 11/2009 | Kariko et al. |
| 2010/0167286 | A1 | 7/2010 | Reijo Pera et al. |
| 2010/0273220 | A1 | 10/2010 | Yanik et al. |
| 2011/0065103 | A1 | 3/2011 | Sahin et al. |
| 2012/0046346 | A1 | 2/2012 | Rossi et al. |
| 2012/0065252 | A1 | 3/2012 | Schrum et al. |
| 2012/0195936 | A1 | 8/2012 | Rudolph et al. |
| 2012/0237978 | A1 | 9/2012 | Schrum et al. |
| 2012/0251618 | A1 | 10/2012 | Schrum et al. |
| 2012/0322864 | A1 | 12/2012 | Rossi et al. |
| 2012/0322865 | A1 | 12/2012 | Rossi et al. |
| 2013/0189741 | A1 | 7/2013 | Dahl et al. |
| 2014/0315988 | A1 | 10/2014 | Dahl et al. |
| 2014/0328825 | A1 | 11/2014 | Meis et al. |
| 2015/0315572 | A1 | 11/2015 | Kariko et al. |

FOREIGN PATENT DOCUMENTS

| | | |
|---|---|---|
| JP | 2002-508299 | 3/2002 |
| JP | 2008-504827 | 2/2008 |
| WO | WO 2007/024708 | 3/2007 |
| WO | WO 2008/052770 | 5/2008 |
| WO | WO 2008/151058 | 12/2008 |
| WO | WO 2009/077134 | 6/2009 |
| WO | WO 2009/093022 | 7/2009 |
| WO | WO 2009/101407 | 8/2009 |
| WO | WO 2009/127230 | 10/2009 |
| WO | WO 2010/115781 | 10/2010 |
| WO | WO 2011/071931 | 6/2011 |
| WO | WO 2011/071936 | 6/2011 |
| WO | WO 2013/003475 | 1/2013 |
| WO | WO 2013/102203 | 7/2013 |

OTHER PUBLICATIONS

Li et al., Effects of Chemically Modified Messenger RNA on Protein Expression. Bioconjug Chem. Mar. 16, 2016;27(3):849-53.
Aasen et al. 2008. Efficient and rapid generation of induced pluripotent stem cells from human keratinocytes. Nature Biotech 26: 1276-84.
Abuchowski et al. 1981. Reduction of plasma urate levels in the cockerel with polyethylene glycol-uricase, J Pharmacol Exp Ther. 219:352-354.
Abuchowski et al. 1981. Immunosuppressive properties and circulating life of Achromobacter glutaminase-asparaginase covalently attached to polyethylene glycol in man, Cancer Treat Rep. 65:1077-81.
Andrews-Pfannkoch et al. 2010. Applied and Environmental Microbiology 76: 5039-5045.
Angel & Yanik. 2010. Innate Immune Suppression Enables Frequent Transfection with RNA Encoding Reprogramming Proteins. PLoS One 5(7):e11756, 7 pages.
Aoi et al. 2008. Generation of pluripotent stem cells from adult mouse liver and stomach cells. Science 321: 699-702.
Amarasinghe et al. 2001. *Escherichia coli* Ribonuclease III: Affinity Purification of Hexahistidine-Tagged Enzyme and Assays for Substrate Binding and Cleavage. Methods in Enzymology. Academic Press. 342:143-158.
Baker et al. 2005. RNA-Guided RNA modification: functional organization of the archeal H/ACA RNP. Genes & Dev. 19:1239-1248.
Banerjee. 1980. 5'-terminal cap structure in eucaryotic messenger ribonucleic acids. Microbiol Rev 44: 175-205.
Barber. 1966. The chromatographic separation of ribonucleic acids. Biochem. Biophys. Acta 114:422-424.
Barkay. 1982. Processing of Bacteriophage T4 Primary Trascripts with Ribonuclease III. J Mol Virol 162:299-315.
Bernstein et al, Role for a bidentate ribonuclease in the initiation step of RNA interference. Nature 2001; 409(6818): 363-6.
Biocca et al. "Intracellular Expression of Anti-p21ras Single Chain Fv Fragments Inhibits Meiotic Maturation of Xenopus Oocytes." Biochemical and Biophysical Research Communications., 1993, 197:422-427.
Bose, et al. 2004. Role of Nucleolin in Human Parainfluenza Virus Type 3 Infection of Human Lung Epithelial Cells. J. Virol. 78:8146-58.
Buccoliero et al, Elevation of lung surfactant phosphatidylcholine in mouse models of Sandhoff and of Niemann—Pick A disease. J Inherit Metab Dis 2004;27(5): 641-8.
Campbell et al. 2002. Pre-steady-state and Stopped-flow Fluorescence Analysis of *Escherichia coli* Ribonuclease III: Insights into Mechanism and Conformational Changes Associated with Binding and Catalysis. J Mol Biol 317:21-40.
Capoccia et. al. "G-CSF and AMD3100 mobilize monocytes into the blood that stimulate angiogenesis in vivo through a paracrine mechanism," Blood. 2006. 108(7): 2438-2445.
Caudy et al. 2002. Fragile X-related protein and ViG associate with the RNA interference machinery. Genes & Devel 16: 2491-96.
Cazenave et al. 1994. RNA template-directed RNA synthesis by T7 RNA polymerase. Proc Natl Acad Sci USA 91: 6972-6976.
Chan et al. 2009. Live cell imaging distinguishes bona fide human iPS cells from partially reprogrammed cells. Nat Biotechnol 27: 1033-1037.
Clawson and Smuckler. 1982. Increased Amounts of Double-Stranded RNA in the Cytoplasm of the Rat Liver following Treatment with Carcinogens. Cancer Research 42: 3228-3231.
Conrad & Rauhut. 2002. Ribonuclease III: new sense from nuisance. The International Joural of Biochemistry & Cell Biology 34:116-129.
Copreni et al, Lentivirus-mediated gene transfer to the respiratory epithelium: a promising approach to gene therapy of cystic fibrosis. GeneTher 2004; 11 Suppl 1: S67-75.
Desrosiers et al. 1974. Identification of Mehtylated Nucleosides in Messenger RNA from Novikoff Hepatoma Cells. PNAS. 71:3971-3975.
Dong et al. 2005. Poly(d,l-lactide-co-glycolide)/montmorillonite nanoparticles for oral delivery of anticancer drugs. Biomaterials 26:6068-76.
Drews et al. 2012. The cytotoxic and immunological hurdles associated with non-viral mRNA-mediated reprogramming of human fibroblasts. Biomaterials 33: 4059-4068.
Dunn. 1976. Rnase III Cleavage of Single-stranded RNA. J Biol Chem 251:3807-3814.
Dunn. 1982. Ribonuclease III. The Enzymes. Paul D. Boyer ed. Academic Press. pp. 485-499.
Easton et al. 2010. Rapid, nondenaturing RNA purification and using weak anion-exchange fast performance liquid chromatography. RNA 16: 647-653.
Ebert et al. 2009. Induced pluripotent stem cells from a spinal muscular atrophy patient. Nature 457: 277-280.
Edmonds. 1990. Polyadenylate polymerases. Methods Enzymol 181: 161-170.
Epicentre Forum Publication, vol. 14-1 Published in Apr. 2007, 24 pages.
Faissner et al. 1982. Analysis of Poly peptides of the Tree Shrew (*Tupaia*) Herpesvirus by Gel Electrophoresis. J. Gen. Virol. 59:139-148.
Feng et al. 2008. PU.1 and C/EBPa/b convert fibroblasts into macrophage-like cells. Proc. Natl Acad. Sci. USA 105: 6057-6062.

(56) References Cited

OTHER PUBLICATIONS

Filippov et al. 2000. A novel type of RNase III family proteins in eukaryotes. Gene. 245: 213-221.
Franklin. 1966. Purification and Properties of the Replicative Intermediate of the RNA Bacteriophage R17. Proc. Natl. Acad. Sci. USA 55:1504-1511.
Gantier et al. 2007. The response of mammalian cells to double-stranded RNA. Cytokine Growth Factor Rev 18: 363-371.
Gasche et al. 1999. Sequential Treatment of Anemia in Ulcerative Colitis with Intravenous Iron and Erythropletin. Digestion. 60:262-267.
Gershon. 2000. (A)-tail of two polymerase structures. Nat Struct Biol 7: 819-821.
Gjerde et al. 2009. RNA Purification and Analysis, Wiley-VCH Only TOC Provided.
Gonzalez et al. 2009. Generation of mouse-induced pluripotent stem cells by transient expression of a single nonviral polycistronic vector. Proc Natl Acad Sci U S A 106: 8918-8922.
Graf and Enver. 2009. Forcing cells to change lineages. Nature 462: 587-594.
Grentzmann et al, A dual-luciferase reporter system for studying recoding signals. RNA 1998;4(4): 479-86.
Grudzien et al. 2004. Novel cap analogs for in vitro synthesis of mRNAs with high translational efficiency. RNA 10: 1479-1487.
Grudzien-Nogalska et al. 2007. Phosphorothioate cap analogs stabilize mRNA and increase translational efficiency in mammalian cells. RNA 13: 1745-1755.
Gunnery & Matthews. 1995. Functional mRNA Can Be Generated by RNA Polymerase III.
Guo et al. 2000. Structure and function of a cap-independent translation element that functions in either the 3' or the 5' untranslated region. RNA. 6:1808-1820.
Hagen et al. 1978. Effect of RNase III on efficiency of translation of bacteriophage T7 lysozyme mRNA. J Virol 26: 793-804.
Hancock. 1995. Reticulocyte Lysate Assay for in Vitro Translation and Posttranslational Modification of Ras Proteins. Methods in Enzymology. 255:60-65.
Higman et al. 1992. The vaccinia virus mRNA (guanine-N7-)-methyltransferase requires both subunits of the mRNA capping enzyme for activity. J Biol Chem 267: 16430-16437.
Higman et al. 1994. The mRNA (guanine-7-)methyltransferase domain of the vaccinia virus mRNA capping enzyme. Expression in *Escherichia coli* and structural and kinetic comparison to the intact capping enzyme. J Biol Chem 269: 14974-14981.
Hornung et al. 2006. 5'-Triphosphate RNA is the ligand for RIG-I. Science 314: 994-997.
Huangfu et al. 2008. Induction of pluripotent stem cells from primary human fibroblasts with only Oct4 and Sox2. Nat Biotechnol 26: 1269-1275.
Ieda et al. 2010. Direct reprogramming of fibroblasts into functional cardiomyocytes by defined factors. Cell 142: 375-386.
Jemielity et al. 2003. Novel "anti-reverse" cap analogs with superior translational properties. RNA 9: 1108-1122.
Jiang, et al, 2005. Topical application of ketoconazole stimulates hair growth in C3H/HeN mice. J Dermatol, 32(4): 243-7.
Jiang et al. 2011. Structural basis of RNA recognition and activation by innate immune receptor RIG-I. Nature 479: 423-427.
Kalal et al. 2002. Tipping the balance between necrosis and apoptosis in human and murine cells treated with interferon and dsRNA. Cell Death and Differentiation 9: 981-994.
Kariko et al, 1998, Phosphate-enhanced transfection of cationic lipid-complexed mRNA and plasmid DNA. Biochim Biophys Acta 1369, 320-334.
Kariko et al. 2004. mRNA is an endogenous ligand for toll-like receptor 3. J Biol Chem 279: 12542-12550.
Kariko et al. 2005. Suppression of RNA recognition by Toll-like receptors: the impact of nucleoside modification and the evolutionary origin of RNA. Immunity 23: 165-175.
Kariko et al., Naturally occurring nucleoside modifications suppress the immunostimulatory activity of RNA: implication for therapeutic RNA development, Curr Opin Drug Discov Develop, 2007, 10:523-32.
Kariko et al., Impacts of Nucleoside Modification on RNA-Mediated Activation of Toll-Like Receptors, Nucleic Acids in Innate Immunity, Eds. Ishii and Akira, 2008, pp. 171-188.
Kariko et al. 2008. Incorporation of pseudouridine into mRNA yields superior nonimmunogenic vector with increased translational capacity and biological stability. Mol Ther 16: 1833-1840.
Kariko et al. 2011. Generating the optimal mRNA for therapy: HPLC purification eliminates immune activation and improves translation of nucleoside-modified, protein-encoding mRNA. Nucleic Acid Res 39:e142, 10 pages.
Kariko et al. 2012. Increased Erythropoiesis in Mice Injected with Submicrogram Quantities of Pseudouridine-containing mRNA Encoding Erythropoietin. Mol Ther 20:948-953.
Kato et al. 2008. Length-dependent recognition of double-stranded ribonucleic acids by retinoic acid-inducible gene-I and melanoma differentiation-associated gene 5. J Exp. Med. 205: 1601-1610.
Katre et al., 1987. Chemical modification of recombinant interleukin 2 by polyethylene glycol increases its potency in the murine Meth A sarcoma model. PNAS 84:1487-91.
Kim et al., 2008. Generation of human induced pluripotent stem cells by dirct delivery of reprogramming proteins. Cell Stem Cell 4:472-476.
Kiyota et al. 2011. An *Arabidopsis* RNase III-like protein, AtRTL2, cleaves double-stranded RNA in vitro. J Plant Res. 124: 405-414.
Kormann et al. 2011. Expression of therapeutic proteins after delivery of chemically modified mRNA in mice. Nature Biotechnology 29:154-157.
Koski et al. 2004. Cutting Edge: Innate Immune System Discriminates between RNA Containing Bacterial versus Eukaryotic Structural Features that Prime for High-Level IL-12 Secretion by Dendritic Cells. J Immunol. 127:3989-3993.
Kowalska et al. 2008. Synthesis and characterization of mRNA cap analogs containing phosphorothioate substitutions that bind tightly to eIF4E and are resistant to the decapping pyrophosphatase DcpS. RNA 14: 1119-1131.
Kozak 1987. An analysis of 5'-noncoding sequences from 699 vertebrate messenger RNAs. Nucleic Acids Res. 15: 8125-8148.
Kreig and Melton. 1984. Functional messenger RNAs are produced by SP6 in vitro transcription of cloned cDNAs. Nucleic Acid Res 12:7057-7070.
Ladewig et al. 2012. Small molecules enable highly efficient neuronal conversion of human fibroblasts. Nat Methods 9:575-578.
Langer. 1990. New methods of drug delivery Science 249: 1527-1533.
Lee et al. 2003. The nuclear RNase III Drosha initiates microRNA processing. Nature 425: 415-419.
Lee et al. 2009. Modelling pathogenesis and treatment of familial dysautonomia using patient-specific iPSCs. Nature 461: 402-406.
Leonard et al. 2008. The TLR3 signaling complex forms by cooperative receptor dimerization. Proc Natl Acad Sci USA 105: 258-263.
Lewandowski et al. 1971. Separation of the infectious ribonucleic acid of potato spindle tuber virus from double-stranded ribonucleic acid of plant tissue extracts. J. Virol. 8: 809-812.
Li et al. 1993. Ribonuclease III cleavage of bacteriophage T7 processing signal. Divalent cation specificity, and specific anion effects. Nucleic Acids Res 21: 1919-1925.
Lobenberg. et al. 1998. Improved body distribution of 14C-labelled AZT bound to nanoparticles in rats determined by radioluminography. J Drug Target 5:171.
Lopez-Berestien. 1989. Treatment of Systemic Fungal Infections with Liposomal-Amphotericin B, in Liposomes in the Therapy of Infectious Diseases and Cancer. Lopez-Erestein & Fidler eds. pp. 317-327.
Lukacs. 1994. Detection of virus infection in plants and differentiation between coexisting viruses by monoclonal antibodies to double-stranded RNA. J. Virol. Methods 47: 255-272.

(56) References Cited

OTHER PUBLICATIONS

Lukacs. 1997. Detection of sense: antisense duplexes by structure-specific anti-RNA antibodies. In: Antisense Technology. A Practical Approach, C. Lichtenstein and W. Nellen (eds), pp. 281-295. IRL Press, Oxford.
McAllister et al. 1993. The phage RNA polymerases are related to DNA polymerases and reverse transcriptases. Molecular Microbiology 10: 1-6.
McElwee et al, Transfer of CD8(+) cells induces localized hair loss whereas CD4(+)/CD25(−) cells promote systemic alopecia areata and CD4(+)/CD25(+) cells blockade disease onset in the C3H/HeJ mouse model. J Invest Dermatol 2005;124(5): 947-57.
McGlynn, et al, Differential subcellular localization of cholesterol, gangliosides, and glycosaminoglycans in murine models of mucopolysaccharide storage disorders. J Comp Neurol 2004 20;480(4): 415-26.
Mackie. 1988. Vectors for the synthesis of specific RNAs in vitro. Biotechnology 10: 253-267.
Maehr et al. 2009. Generation of pluripotent stem cells from patients with type 1 diabetes. Proc Natl Acad Sci U S A 106: 15768-15773.
Martin et al. 1975. Purification of mRNA guanylyltransferase and mRNA (guanine-7-) methyltransferase from vaccinia virions. J Biol Chem 250: 9322-9329.
Matsuda et al. 2000. Molecular cloning and characterization of a novel human gene Herna which encodes a putative RNA-helicase. Biochim. Biophys. Acta. 1490: 163-169.
Mellits et al. 1990. Removal of double-stranded contaminants from RNA transcripts: synthesis of adenovirus VA RNA1 from a T7 vector. Nucleic Acids Research 18: 5401-5406.
Minskaia et al. 2006. Discovery of an RNA virus 3'->5' exoribonuclease that is critically involved in coronavirus RNA synthesis. Proc Natl Acad Sci USA. 103: 5108-5113.
Myette and Niles. 1996. Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem 271: 11936-11944.
Nakagawa et al. 2008. Generation of induced pluripotent stem cells without Myc from mouse and human fibroblasts. Nat Biotechnol 26: 101-106.
Naz et al. 2002. Novel human prostate-specific cDNA: molecular cloning, expression, and immunobiology of the recombinant protein. Biochem Biophys Res Commun. 297:1075-84.
Nicholson. 1996. Structure, reactivity, and biology of double-stranded RNA. Progr Nucleic Acid Res Mol Biol 52: 1-65.
Nielsen PE. 1999. Peptide nucleic acids as therapeutic agents. Curr Opin Struct Biol 9:353-57.
Newmark et al. 1982. Preparation and Properties of Adducts of Streptokinase and Streptokinase-Plasmin Complex with Poly ethylene Glycol and Pluronic Polyol F38. J. Appl. Biochem. 4:185-189.
Okita et al. 2008. Generation of mouse induced pluripotent stem cells without viral vectors. Science 322: 949-953.
Ozawa et al. 2006. Amplification and analysis of cDNA generated from a single cell by 5'-RACE: application to isolation of antibody heavy and light chain variable gene sequences from single B cells. Biotechniques 40: 469-470, 472, 474 passim.
Pang et al. 2011. Induction of human neuronal cells by defined transcription factors. Nature 476: 220-223.
Passini et al, AAV vector-mediated correction of brain pathology in a mouse model of Niemann—Pick A disease. Mol Ther 2005;11(5): 754-62.
Pays. 1977. Characterization of Double-Stranded Ribonucleic Acid Sequences Present in the Intial Transcription Products of Rat Liver Chromatin. Biochem. J. 165:237-245.
Pe'ery et al. 1997. Synthesis and Purification of Single-=Stranded RNA for Use in Experiments with PKR and in Cell-Free Translation Systems. Methods: A companion to Methods in Enzymology, Academic Press Inc., New York, 11(4):371-381.
Peng et al. 2002. Synthesis and application of a chain-terminating dinucleotide mRNA cap analog. Org Lett 4: 161-164.

Petit et al. "G-CSF Induces Stem Cell Mobilization by Decreasing Bone Marrow SDF-1 and Up-Regulating CXCR4," Nature Immunol., 2002, 3: 687-694.
Pichlmair et al. 2006. RIG-I-mediated antiviral responses to single-stranded RNA bearing 5'-triphosphates. Science 314: 997-1001.
Plews et al. 2010. Activation of pluripotency genes in human fibroblast cells by a novel mRNA based approach, PLoS One 5(12):e14397, 12 pages.
Pradilla et al. 2004. Prevention of vasospasm following subarachnoid hemorrage in rabbits by anti-CD11/CD18 monoclonal antibody therapy. J Neurosurg. 101:88-92.
Probst et al. 2006. Characterization of the ribonuclease activity on the skin surface. Genet Vaccines Ther. 4: 4, 9 pages.
Purchio et al. Methods in Enzymology: Methods for molecular cloning in eukaryotic cells (2003).
Qi et al. 2010. Cap binding and immune evasion revealed by Lassa nucleoprotein structure. Nature 468: 779-783.
Racila et al. 2010. Transient expression of OCT 4 is sufficient to allow human keratinocytes to change their differentiation pathway. Gene Therapy 18:294-303.
Robertson et al. 1968. Purification and Properties of Ribonuclease III from *Escherichia coli*. J Biol Chem 243:82-91.
Robertson et al. 1975. Sensitive methods for detection and characterization of double helical ribonucleic acid. J Biol Chem 250: 418-425.
Robertson. 1982. *Escherichia coli* Ribonuclease III Cleavage Sites. Cell 30:669-672.
Robertson et al. 1996. Paradoxical interactions between human delta hepatitis agent RNA and the cellular protein kinase PKR. Journal of Virology 70(8):5611-5617.
Rosa & Brivanlou. 2010. Synthetic mRNAs: Powerful Tools for Reprogramming and Differentiation of Human Cells. Cell Stem Cell 7:549-550.
Saito et al. 2008. Innate immunity induced by composition-dependent RIG-I recognition of hepatitis C virus RNA. Nature 454: 523-527.
Sakuma et al. 1999. Mucoadhesion of polystyrene nanoparticles having surface hydrophilic polymeric chains in the gastrointestinal tract. Int J Pharm 177:161-72.
Sambrook and Russell, eds., Molecular Cloning, (2001) Only TOC Provided.
Santini et al., 2000. Type I interferon as a powerful adjuvant for monocyte-derived dendritic cell development and activity in vitro and in Hu-PBL-SCID mice. J Exp Med 191: 1777-178.
Satoh et al, X-linked immunodeficient mice spontaneously produce lupus-related anti¬20 RNA helicase A autoantibodies, but are resistant to pristane-induced lupus. Int Immunol 2003, 15(9):1117-24.
Schlee et al. 2009. Approaching the RNA ligand for RIG-I. Immunol Rev 227: 66-74.
Scholte, et al (Animal models of cystic fibrosis. J Cyst Fibros 2004; 3 Suppl2: 183-90.
Schonborn et al. 1991. Monoclonal antibodies to double-stranded RNA as probes of RNA structure in crude nucleic acid extracts. Nucleic Acids Res. 19: 2993-3000.
Shuman et al. 1980. Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme). J Biol Chem 255: 11588-11598.
Shuman. 1995. Capping enzyme in eukaryotic mRNA synthesis. Prog Nucleic Acid Res Mol Biol 50: 101-129.
Shuman. 2001. Structure, mechanism, and evolution of the mRNA capping apparatus. Prog Nucleic Acid Res Mol Biol 66: 1-40.
Simonaro et al, Joint and bone disease in mucopolysaccharidoses VI and VII: identification of new therapeutic targets and biomarkers using animal models. Pediatr Res 2005;57(5 Pt 1): 701-7.
Sousa et al. 2000. Use of T7 RNA Polymerase and its Mutants for Incorporation of Nucleoside Analogs into RNA. Methods in Enzymology. 317:65-74.
Stadtfeld et al. 2008. Induced pluripotent stem cells generated without viral integration. Science 322: 945-949.

(56) References Cited

OTHER PUBLICATIONS

Stepinski et al. 2001. Synthesis and properties of mRNAs containing the novel "anti-reverse" cap analogs 7-methyl(3'-O-methyl)GpppG and 7-methyl (3'-deoxy)GpppG. RNA 7: 1486-1495.
Stewart et al. 1972. Increased susceptibility of cells treated with interferon to the toxicity of polyriboinosinic: polyribocytidylic acid. Proc Nat Acad Sci USA 69: 1851-1854.
Studier et al. 1986. Use of bacteriophage T7 RNA polymerase to direct selective high-level expression of cloned genes. J Mol Biol 189: 113-130.
Sul et al. 2012. Perspectives on cell reprogramming with RNA. Cell 30: 243-249.
Szabo et al. 2010. Direct conversion of human fibroblasts to multilineage blood progenitors. Nature. 468: 521-526.
Takahashi and Yamanaka. 2006. Induction of pluripotent stem cells from mouse embryonic and adult fibroblast cultures by defined factors. Cell 126: 663-676.
Takahashi et al. 2007. Induction of pluripotent stem cells from adult human fibroblasts by defined factors. Cell 131: 861-872.
Tanaka et al. 2005. Inhibition of heart transplant injury and graft coronary artery disease after prolonged organ ischemia by selective protein kinase C regulators. J Thorac Cardiovasc Surg 129(5): 1160-7.
Tavernier et al. 2012. Activation of pluripotency-associated genes in mouse embryonic fibroblasts by non-viral transfection with in vitro-derived mRNAs encoding Oct4, Sox2, Klf4 and cMyc. Biomaterials 33:412-417.
Treat et al., In Liposomes in the Therapy of Infectious Disease and Cancer, Lopez-Berestein and Fidler (eds.), Liss, New York, pp. 353-365 (1989).
Triana-Alonso et al. 1995. Self-coded 3'-extension of run-off transcripts produces aberrant products during in vitro transcription with T7 RNA polymerase. J Biol Chem 270: 6298-6307.
Uzri et al. 2009. Nucleotide sequences and modifications that determine RIG-I/RNA binding and signaling activities. J. Virol. 83: 4174-4184.
Vierbuchen T et al. 2010. Direct conversion of fibroblasts to functional neurons by defined factors. Nature 463: 1035-1041.
Virovic et al. 2005. Novel delivery methods for treatment of viral hepatitis: an update. Expert Opin Drug Deliv 2:707-17.
Wan et al. 2010. HOTAIR: Flight of noncoding RNA in genome regulation: Prospects and mechanisms. Cell Cycle 9: 3391-3392.
Wang et al. 1997. Phylogeny of mRNA capping enzymes. Proc Natl Acad Sci U S A 94: 9573-9578.
Wang et al. 2011. Phosphorylation regulates c-Myc's oncogenic activity in the mammary gland. Cancer Res. 71: 925-936.
Warren et al. 2010. Highly Efficient Reprogramming to Pluripotency and Directed Differentiation of Human Cells with Synthetic Modified mRNA. Cell Stem Cell 7:618-630.
Wasylishen et al. 2011. New model systems provide insights into Myc-induced transformation. Oncogene. 30: 3727-3734.
Weissman et al, 2000. HIV Gag mRNA Transfection of Dendritic Cells (DC) Delivers Encoded Antigen to MHC Class I and II Molecules, Causes DC Maturation, and Induces a Potent Human in Vitro Primary Immune Response. J Immunol 165:4710-4717.
Wernig et al. 2002. Tau EGFP embryonic stem cells: an efficient tool for neuronal lineage selection and transplantation. J. Neurosci. Res. 69: 918-924.
Wianny et al. 2000. Specific interference with gene function by double-stranded RNA in early mouse development. Nat. Cell Biol. 2: 70-75.
Wilusz. 1988. A 64 kd nuclear protein binds to RNA segments that include the AAUAAA polyadenylation motif. Cell 52: 221-228.
Woltjen et al. 2009. piggyBac transposition reprograms fibroblasts to induced pluripotent stem cells. Nature 458: 766-770.
Woo et al. 2007. HOTAIR lifts noncoding RNAs to new levels. Cell 129: 1257-1259.
Wu et al. 2000. Human RNase III is a 160-kDa protein involved in preribosomal RNA processing [In Process Citation]. J. Biol. Chem. 275: 36957-65.
Xu et al. 2001. Feeder-free growth of undifferentiated human embryonic stem cells. Nat Biotechnol 19: 971-974.
Yakubov et al. 2010. Reprogramming of human fibroblasts to pluripotent stem cells using mRNA of four transcription factors. Biochemical and Biophysical Research Communications 394:189-193.
Yang et al. 2001. Specific double-stranded RNA interference in undifferentiated mouse embryonic stem cells. Mol Cell Biol 21: 7807-7816.
Yang et al. 2002. Short RNA duplexes produced by hydrolysis with *Escherichia coli* Rnase III mediate effective RNA interference in mammalian cells. PNAS. 99:9942-9947.
Yang et al. 2011. Induced neuronal cells: how to make and define a neuron. Cell Stem Cell 9: 517-525.
Yu et al, Sustained correction of B-cell development and function in a murine model of X-linked agammaglobulinemia (XLA) using retroviral-mediated gene transfer. Blood. 2004 104(5): 1281-90.
Yu et al. 2007. Induced pluripotent stem cell lines derived from human somatic cells. Science 318: 1917-1920.
Yu et al. 2009. Human induced pluripotent stem cells free of vector and transgene sequences. Science 324: 797-801.
Zelcer et al. 1981. The detection and characterization of viral-related double-stranded RNAs in tobacco mosaic virus-infected plants, Virology, 113(2):417-27.
Zelcer et al. 1982. Potato Spindle Tuber Viroid-infected Tissues Contain RNA Complementary to the Entire Viroid. J. Gen. Virol. 59: 139-148.
Zhou et al. 2009. Generation of induced pluripotent stem cells using recombinant proteins. Cell Stem Cell 4: 381-384.
Zimmerman et al. 2001. Electrolyte-and pH-stabilities of aqueous solid lipid nanoparticle (SLN) dispersions in artificial gastrointestinal media. Eur J Pharm Biopharm 52:203.
Zonta et al, Uretero-neocystostomy in a swine model of kidney transplantation: a new technique. J Surg Res. Apr. 2005;124(2):250-5.
Zust et al. 2011. Ribose 2'-O-methylation provides a molecular signature for the distinction of self and non-self mRNA dependent on the RNA sensor Mda5. Nature Immunol. 12: 137-143.
Extended European Search Report for EP 10836557.8, dated May 13, 2014, 12 pages.
International Search Report and Written Opinion for PCT/US2010/059317, dated Aug. 22, 2011, 13 pages.
International Search Report and Written Opinion for PCT/US2010/059305, dated Aug. 23, 2011, 12 pages.
International Search Report and Written Opinion for PCT/US2012/072301, dated May 14, 2013, 33 pages.

\* cited by examiner

FIG. 2
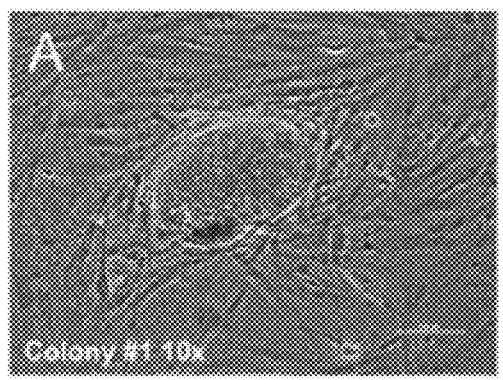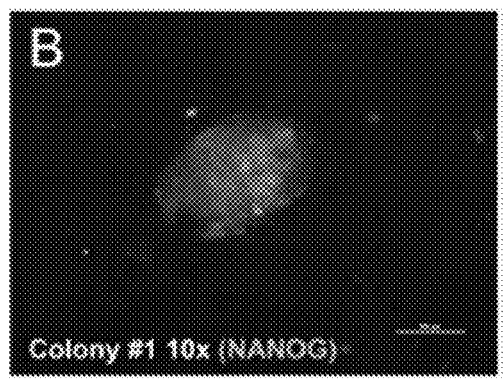
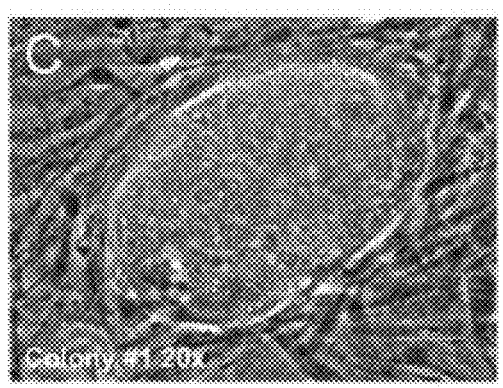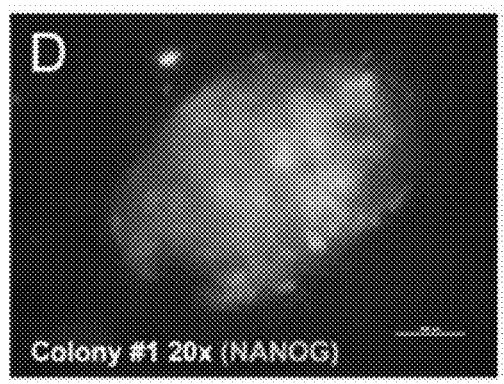

FIG. 9B

|  | TNF-α* pg/ml | CD80 | CD86 |
|---|---|---|---|
|  |  | mean fluorescence | |
| lipofectin | 0 | 7.6 | 55.3 |
| poly(I):(C) | 45.6 | 59.4 | 257.4 |
| R848 | 48.3 | 55.2 | 235.4 |
| RNA-1866 |  |  |  |
| *unmodified* | 26.7 | 52.7 | 246.4 |
| *m5C* | 0 | 16.4 | 108.6 |
| *m6A* | 0 | 12.4 | 78.4 |
| *Ψ* | 0 | 12.0 | 87.5 |
| *s2U* | 0 | 8.0 | 62.7 |
| *m6A/Ψ* | 0 | 8.6 | 68.4 |

FIG. 10B

| Modified nucleoside in reaction[a] (%) | 0 | 1 | 10 | 50 | 90 | 99 | 100 | 1 | 10 | 50 | 90 | 99 | 100 | 1 | 10 | 50 | 90 | 99 | 100 |
|---|---|---|---|---|---|---|---|---|---|---|---|---|---|---|---|---|---|---|---|
| | | | m6A | | | | | | | Ψ | | | | | | m5C | | | |
| in RNA[b] | | | | | | | | | | | | | | | | | | | |
| expected (%) | 0 | 1 | 3.2 | 16 | 28 | 32 | 32 | 0.3 | 2.9 | 14 | 26 | 28 | 29 | 0.2 | 1.7 | 9 | 16 | 17 | 17 |
| measured (%) | 0 | <0.2 | 0.9 | 11 | 28 | 31 | 32 | 0.2 | 1.9 | 12 | 24 | 28 | 28 | 0.4 | 1.4 | 9 | 15 | 17 | 17 |
| measured (number) | 0 | <3 | 14 | 176 | 443 | 490 | 505 | 3 | 29 | 193 | 381 | 441 | 451 | 6 | 23 | 135 | 230 | 270 | 273 |

FIG. 11A

| | | |
|---|---|---|
| ORN1-control | 5'pUGGAUCCGGCUUUGAGAUCUU | SEQ ID NO: 6 |
| ORN2-Um | 5'pUGGAUCCGGCUmUGAGAUCUU | SEQ ID NO: 7 |
| ORN3-m5C | 5'pUGGAUm5CCGGCUUUGAGAUCUU | SEQ ID NO: 8 |
| ORN4-Ψ | 5'pUGGAUCCGGCUΨUGAGAUCUU | SEQ ID NO: 9 |
| ORN5 | 5'pppGGGAGACAGGGGUGUCCGCCAUUUCCAGGUU | SEQ ID NO: 10 |
| ORN6 | 5'pppGGGAGACAGGCUAUAACUCACAUAAUGUAUU | SEQ ID NO: 11 |

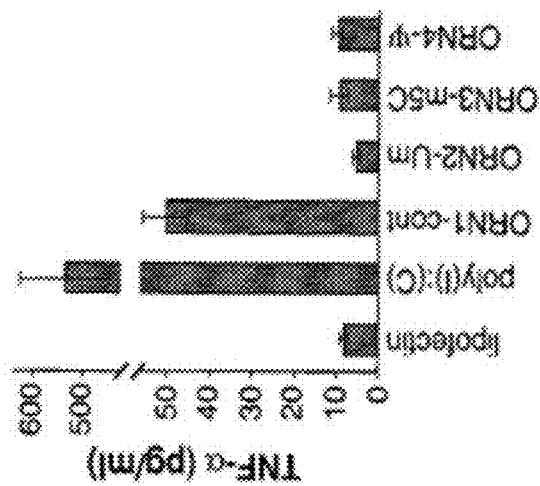
FIG. 11B
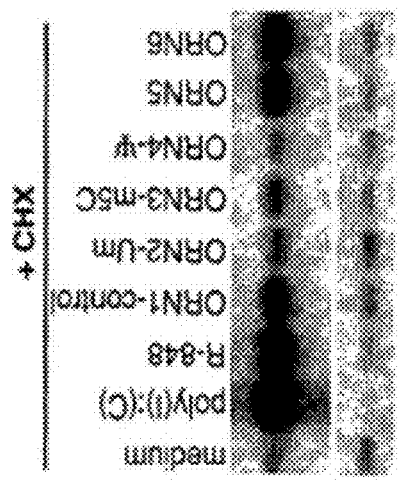
FIG. 11C

FIG. 15A
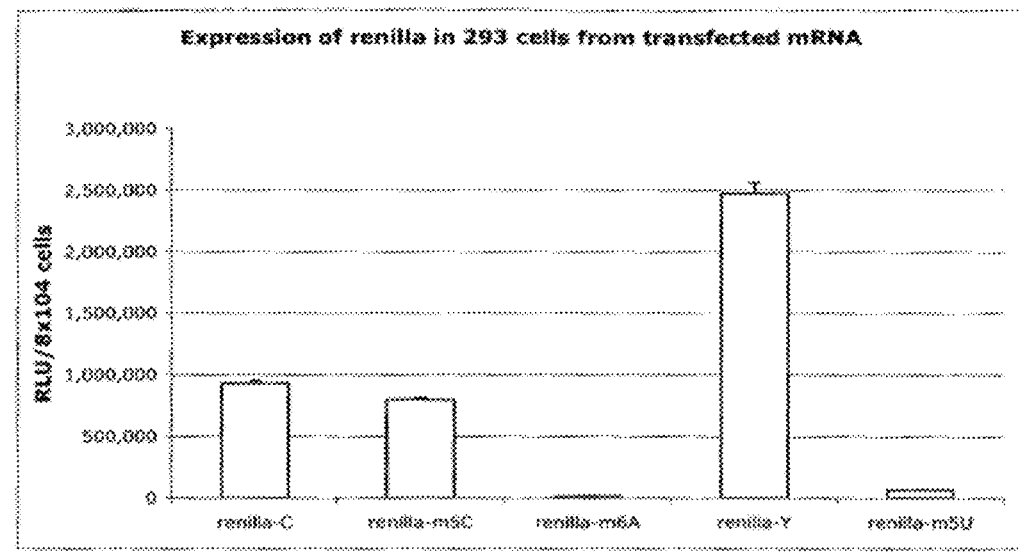
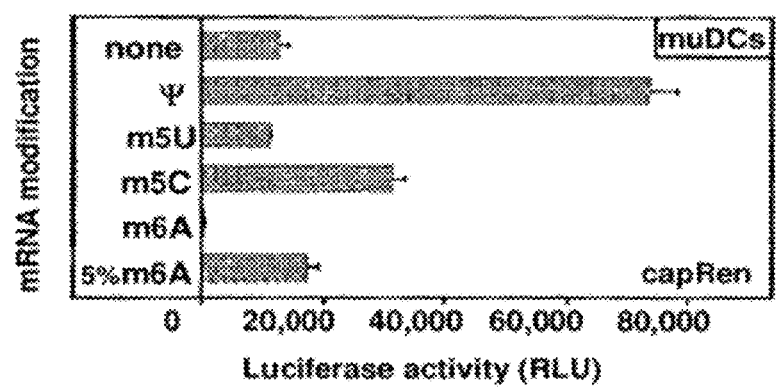
FIG. 15B

FIG. 23A
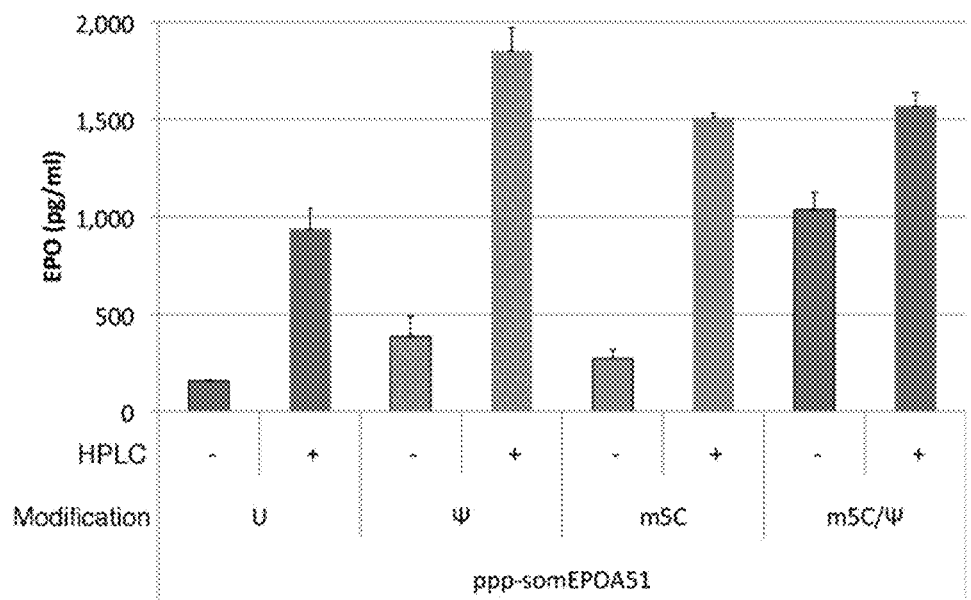
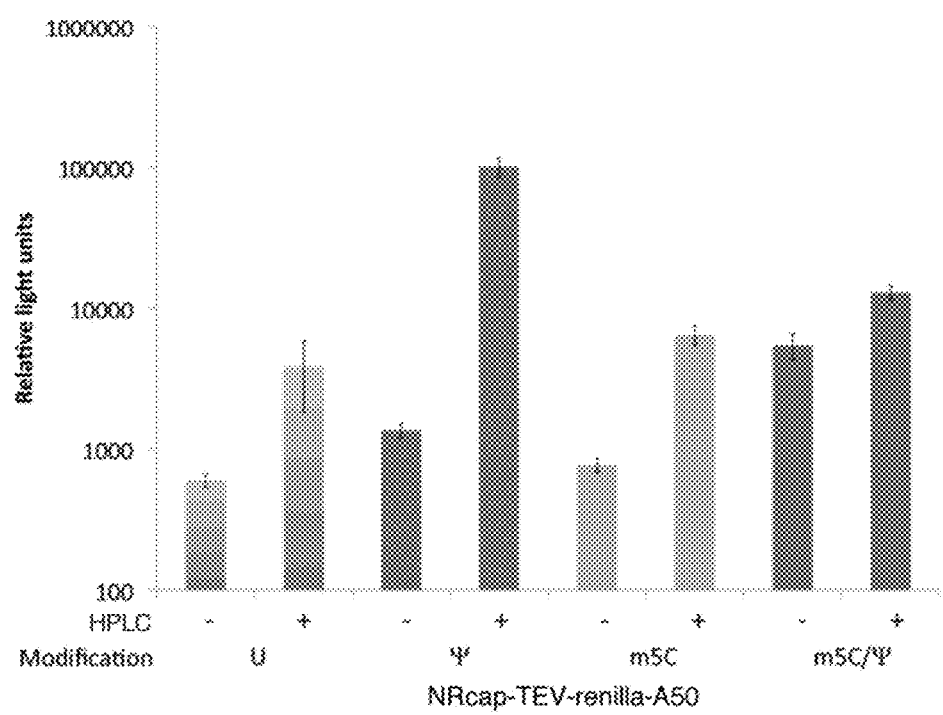
FIG. 23B

FIG. 24A
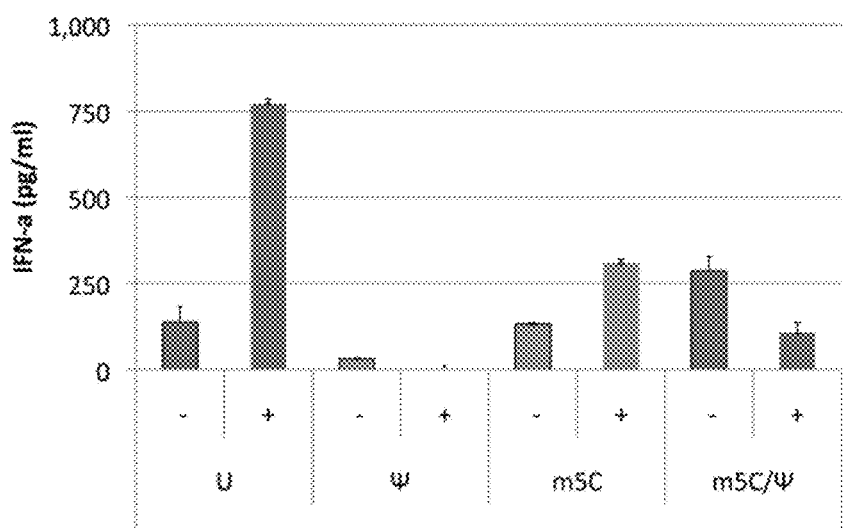
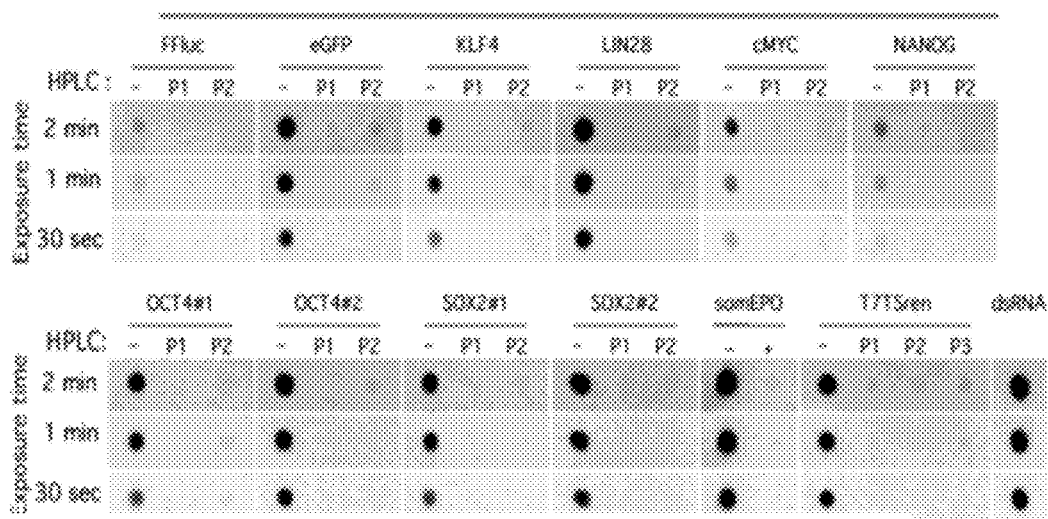
FIG. 24B

FIG. 25

KLF4 mRNA cds (SEQ ID NO:12)

5' AUGAGGCAGCCACCUGGCGAGUCUGACAUGGCUGUCAGCGACGCGCUGCUCCCAUCUUUCUC
CACGUUCGCGUCUGGCCCGGCGGGAAGGGAGAAGACACUGCGUCAAGCAGGUGCCCCGAAUAAC
CGCUGGCGGGAGGAGCUCUCCCACAUGAAGCGACUUCCCCCAGUGCUUCCCGGCCGCCCCUAUG
ACCUGGCGGCGGCGACCGUGGCCACAGACCUGGAGAGCGGCGGAGCCGGUGCGGCUUGCGGCGG
UAGCAACCUGGCGCCCUACCUCGGAGAGAGACCGAGGAGUUCAACGAUCUCCUGGACCUGGAC
UUUAUUCUCUCCAAUUCGCUGACCCAUCCUCCGGAGUCAGUGGCCGCCACCGUGUCCUCGUCAG
CGUCAGCCUCCUCUUCGUCGUCGCCGUCAGCAGCGGCCCUGCCAGCGCGCCCUCCACCUGCAG
CUUCACCUAUCCGAUCCGGGCCGGGAACGACCCGGGCGUGGCGCCGGGCGGCACGGGCGGAGGC
CUCCUCUAUGGCAGGGAGUCCGCUCCCCCUCCGACGGCUCCCUUCAACCUGGCGGACAUCAACG
ACGUGAGCCCCUCGGGCGGCUUCGUGGCCGAGCUCCUGCGGCCAGAAUUGGACCCGGUGUACAU
UCCGCCGCAGCAGCCGCAGCCGCCAGGUGGCGGGCUGAUGGGCAAGUUCGUGCUGAAGGCGUCG
CUGAGCGCCCCUGGCAGCGAGUACGGCAGCCCGUCGGUCAUCAGCGUCAGCAAAGGCAGCCCUG
ACGGCAGCCACCCGGUGGUGGUGGCGCCCUACAACGGCGGGCCGCCGCGCACGUGCCCCAAGAU
CAAGCAGGAGGCGGUCUCUUCGUGCACCCACUUGGGCGCUGGACCCCCUCUCAGCAAUGGCCAC
CGGCCGGCUGCACACGACUUCCCCCUGGGGCGGCAGCUCCCCAGCAGGACUACCCCGACCCUGG
GUCUUGAGGAAGUGCUGAGCAGCAGGGACUGUCACCCUGCCCUGCCGCUUCCUCCCGGCUUCCA
UCCCCACCCGGGGCCCAAUUACCCAUCCUUCCUGCCCGAUCAGAUGCAGCCGCAAGUCCCGCCG
CUCCAUUACCAAGAGCUCAUGCCACCCGGUUCCUGCAUGCCAGAGGAGCCCAAGCCAAAGAGGG
GAAGACGAUCGUGGCCCCGGAAAAGGACCGCCACCCACACUUGUGAUUACGCGGGCUGCGGCAA
AACCUACACAAAGAGUUCCCAUCUCAAGGCACACCUGCGAACCCACACAGGUGAGAAACCUUAC
CACUGUGACUGGGACGGCUGUGGAUGGAAAUUCGCCCGCUCAGAUGAACUGACCAGGCACUACC
GUAAACACACGGGGCACCGCCCGUUCCAGUGCCAAAAAUGCGACCGAGCAUUUUCCAGGUCGGA
CCACCUCGCCUUACACAUGAAGAGGCAUUUUUAA-3'

LIN28 mRNA cds (SEQ ID NO:13)

5' AUGGGCUCCGUGUCCAACCAGCAGUUUGCAGGUGGCUGCGCCAAGGCGGCAGAAGAGGCGCC
CGAGGAGGCGCCGGAGGACGCGGCCCGGCGGCGGACGAGCCUCAGCUGCUGCACGGUGCGGGC
AUCUGUAAGUGGUUCAACGUGCGCAUGGGGUUCGGCUUCCUGUCCAUGACCGCCCGCGCCGGGG
UCGCGCUCGACCCCCAGUGGAUGUCUUUGUGCACCAGAGUAAGCUGCACAUGGAAGGGUUCCG
GAGCUUGAAGGAGGGUGAGGCAGUGGAGUUCACCUUUAAGAAGUCAGCCAAGGGUCUGGAAUCC
AUCCGUGUCACCGGACCUGGUGGAGUAUUCUGUAUUGGGAGUGAGAGGCGGCCAAAAGGAAAGA
GCAUGCAGAAGCGCAGAUCAAAAGGAGACAGGUGCUACAACUGUGGAGGUCUAGAUCAUCAUGC
CAAGGAAUGCAAGCUGCCACCCCAGCCCAAGAAGUGCCACUUCUGCCAGAGCAUCAGCCAUAUG
GUAGCCUCAUGUCCGCUGA-3'

FIG. 26 cMYC mRNA cds (SEQ ID NO:14)

5AUGGAUUUUUUUCGGGUAGUGGAAAACCAGCAGCCUCCCGCGACGAUGCCCCUCAACGUUAGC
UUCACCAACAGGAACUAUGACCUCGACUACGACUCGGUGCAGCCGUAUUUCUACUGCGACGAGG
AGGAGAACUUCUACCAGCAGCAGCAGCAGAGCGAGCUGCAGCCCCGGCGCCCAGCGAGGAUAU
CUGGAAGAAAUUCGAGCUGCUGCCCACCCCGCCCCUGUCCCCUAGCCGCCGCUCCGGGCUCUGC
UCGCCCUCCUACGUUGCGGUCACACCCUUCUCCCUUCGGGGAGACAACGACGGCGGUGGCGGGA
GCUUCUCCACGGCCGACCAGCUGGAGAUGGUGACCGAGCUGCUGGGAGGAGACAUGGUGAACCA
GAGUUUCAUCUGCGACCCGGACGACGAGACCUUCAUCAAAAACAUCAUCAUCCAGGACUGUAUG
UGGAGCGGCUUCUCGGCCGCCGCCAAGCUCGUCUCAGAGAAGCUGGCCUCCUACCAGGCUGCGC
GCAAAGACAGCGGCAGCCCGAACCCCGCCCGCGGCCACAGCGUCUGCUCCACCUCCAGCUUGUA
CCUGCAGGAUCUGAGCGCCGCCGCCUCAGAGUGCAUCGACCCCUCGGUGGUCUUCCCCUACCCU
CUCAACGACAGCAGCUCGCCCAAGUCCUGCGCCUCGCAAGACUCCAGCGCCUUCUCUCCGUCCU
CGGAUUCUCUGCUCUCCUCGACGGAGUCCUCCCCGCAGGGCAGCCCCGAGCCCCUGGUGCUCCA
UGAGGAGACACCGCCCACCACCAGCAGCGACUCUGAGGAGGAACAAGAAGAUGAGGAAGAAAUC
GAUGUUGUUUCUGUGGAAAAGAGGCAGGCUCCUGGCAAAAGGUCAGAGUCUGGAUCACCUUCUG
CUGGAGGCCACAGCAAACCUCCUCACAGCCCACUGGUCCUCAAGAGGUGCCACGUCUCCACACA
UCAGCACAACUACGCAGCGCCUCCCUCCACUCGGAAGGACUAUCCUGCUGCCAAGAGGGUCAAG
UUGGACAGUGUCAGAGUCCUGAGACAGAUCAGCAACAACCGAAAAUGCACCAGCCCCAGGUCCU
CGGACACCGAGGAGAAUGUCAAGAGGCGAACACACAACGUCUUGGAGCGCCAGAGGAGGAACGA
GCUAAAACGGAGCUUUUUUGCCCUGCGUGACCAGAUCCCGGAGUUGGAAAACAAUGAAAAGGCC
CCCAAGGUAGUUAUCCUUAAAAAAGCCACAGCAUACAUCCUGUCCGUCCAAGCAGAGGAGCAAA
AGCUCAUUUCUGAAGAGGACUUGUUGCGGAAACGACGAGAACAGUUGAAACACAAACUUGAACA
GCUACGGAACUCUUGUGCGUAA-3'

NANOG mRNA cds (SEQ ID NO:15)
5'-
AUGAGUGUGGAUCCAGCUUGUCCCCAAAGCUUGCCUUGCUUUGAAGCAUCCGACUGUAAAGAAU
CUUCACCUAUGCCUGUGAUUUGUGGGCCUGAAGAAAACUAUCCAUCCUUGCAAAUGUCUUCUGC
UGAGAUGCCUCACACAGAGACUGUCUCUCCUCUUCCUUCCUCCAUGGAUCUGCUUAUUCAGGAC
AGCCCUGAUUCUUCCACCAGUCCCAAAGGCAAACAACCCACUUCUGCAGAGAAUAGUGUCGCAA
AAAAGGAAGACAAGGUCCCGGUCAAGAAACAGAAGACCAGAACUGUGUUCUCUUCCACCCAGCU
GUGUGUACUCAAUGAUAGAUUUCAGAGACAGAAAUACCUCAGCCUCCAGCAGAUGCAAGAACUC
UCCAACAUCCUGAACCUCAGCUACAAACAGGUGAAGACCUGGUUCCAGAACCAGAGAAUGAAAU
CUAAGAGGUGGCAGAAAAACAACUGGCCGAAGAAUAGCAAUGGUGUGACGCAGAAGGCCUCAGC
ACCUACCUACCCCAGCCUCUACUCUUCCUACCACCAGGGAUGCCUGGUGAACCCGACUGGGAAC
CUUCCAAUGUGGAGCAACCAGACCUGGAACAAUUCAACCUGGAGCAACCAGACCCAGAACAUCC
AGUCCUGGAGCAACCACUCCUGGAACACUCAGACCUGGUGCACCCAAUCCUGGAACAAUCAGGC
CUGGAACAGUCCCUUCUAUAACUGUGGAGAGGAAUCUCUGCAGUCCUGCAUGCACUUCCAGCCA
AAUUCUCCUGCCAGUGACUUGGAGGCUGCCUUGGAAGCUGCUGGGGAAGGCCUUAAUGUAAUAC
AGCAGACCACUAGGUAUUUUAGUACUCCACAAACCAUGGAUUUAUUCCUAAACUACUCCAUGAA
CAUGCAACCUGAAGACGUGUGA-3'

FIG. 27

OCT4 mRNA cds (SEQ ID NO:16)
5'-
AUGGCGGGACACCUGGCUUCAGAUUUUGCCUUCUCGCCCCCUCCAGGUGGUGGAGGUGAUGGGC
CAGGGGGGCCGGAGCCGGGCUGGGUUGAUCCUCGGACCUGGCUAAGCUUCCAAGGCCCUCCUGG
AGGGCCAGGAAUCGGGCCGGGGGUUGGGCCAGGCUCUGAGGUGUGGGGGAUUCCCCCAUGCCCC
CCGCCGUAUGAGUUCUGUGGGGGGAUGGCGUACUGUGGGCCCCAGGUUGGAGUGGGGCUAGUGC
CCCAAGGCGGCUUGGAGACCUCUCAGCCUGAGGGCGAAGCAGGAGUCGGGGUGGAGAGCAACUC
CGAUGGGGCCUCCCCGGAGCCCUGCACCGUCACCCCUGGUGCCGUGAAGCUGGAGAAGGAGAAG
CUGGAGCAAAACCCGGAGGAGUCCCAGGACAUCAAAGCUCUGCAGAAAGAACUCGAGCAAUUUG
CCAAGCUCCUGAAGCAGAAGAGGAUCACCCUGGGAUAUACACAGGCCGAUGUGGGGCUCACCCU
GGGGGUUCUAUUUGGGAAGGUAUUCAGCCAAACGACCAUCUGCCGCUUUGAGGCUCUGCAGCUU
AGCUUCAAGAACAUGUGUAAGCUGCGGCCCUUGCUGCAGAAGUGGGUGGAGGAAGCUGACAACA
AUGAAAAUCUUCAGGAGAUAUGCAAAGCAGAAACCCUCGUGCAGGCCCGAAAGAGAAAGCGAAC
CAGUAUCGAGAACCGAGUGAGAGGCAACCUGGAGAAUUUGUUCCUGCAGUGCCCGAAACCCACA
CUGCAGCAGAUCAGCCACAUCGCCCAGCAGCUUGGGCUCGAGAAGGAUGUGGUCCGAGUGUGGU
UCUGUAACCGGCGCCAGAAGGGCAAGCGAUCAAGCAGCGACUAUGCACAACGAGAGGAUUUUGA
GGCUGCUGGGUCUCCUUUCUCAGGGGGACCAGUGUCCUUUCCUCUGGCCCCAGGGCCCCAUUUU
GGUACCCCAGGCUAUGGGAGCCCUCACUUCACUGCACUGUACUCCUCGGUCCCUUUCCCUGAGG
GGGAAGCCUUUCCCCCUGUCUCUGUCACCACUCUGGGCUCUCCCAUGCAUUCAAACUGA-3'

SOX2 mRNA cds (SEQ ID NO:17)
5'-
AUGUACAACAUGAUGGAGACGGAGCUGAAGCCGCCGGGCCCGCAGCAAACUUCGGGGGGCGGCG
GCGGCAACUCCACCGCGGCGGCGGCCGGCGGCAACCAGAAAAACAGCCCGGACCGCGUCAAGCG
GCCCAUGAAUGCCUUCAUGGUGUGGUCCCGCGGGCAGCGGCGCAAGAUGGCCCAGGAGAACCCC
AAGAUGCACAACUCGGAGAUCAGCAAGCGCCUGGGCGCCGAGUGGAAACUUUUGUCGGAGACGG
AGAAGCGGCCGUUCAUCGACGAGGCUAAGCGGCUGCGAGCGCUGCACAUGAAGGAGCACCCGGA
UUAUAAAUACCGGCCCCGGCGGAAAACCAAGACGCUCAUGAAGAAGGAUAAGUACACGCUGCCC
GGCGGGCUGCUGGCCCCCGGCGGCAAUAGCAUGGCGAGCGGGGUCGGGGUGGGCGCCGGCCUGG
GCGCGGGCGUGAACCAGCGCAUGGACAGUUACGCGCACAUGAACGGCUGGAGCAACGGCAGCUA
CAGCAUGAUGCAGGACCAGCUGGGCUACCCGCAGCACCCGGGCCUCAAUGCGCACGGCGCAGCG
CAGAUGCAGCCCAUGCACCGCUACGACGUGAGCGCCCUGCAGUACAACUCCAUGACCAGCUCGC
AGACCUACAUGAACGGCUCGCCCACCUACAGCAUGUCCUACUCGCAGCAGGGCACCCCUGGCAU
GGCUCUUGGCUCCAUGGGUUCGGUGGUCAAGUCCGAGGCCAGCUCCAGCCCCCCUGUGGUUACC
UCUUCCUCCCACUCCAGGGCGCCCUGCCAGGCCGGGGACCUCCGGGACAUGAUCAGCAUGUAUC
UCCCCGGCGCCGAGGUGCCGGAACCCGCCGCCCCAGCAGACUUCACAUGUCCCAGCACUACCA
GAGCGGCCCGGUGCCCGGCACGGCCAUUAACGGCACACUGCCCCUCUCACACAUGUGA-3'

RNA PREPARATIONS COMPRISING PURIFIED MODIFIED RNA FOR REPROGRAMMING CELLS

The present application is a continuation of U.S. patent application Ser. No. 14/801,075, filed Jul. 16, 2015, now U.S. Pat. No. 9,371,511, which is a continuation of U.S. patent application Ser. No. 14/644,380, filed Mar. 11, 2015, now U.S. Pat. No. 9,163,213, which is a continuation of U.S. patent application Ser. No. 12/962,468, filed Dec. 7, 2010, now U.S. Pat. No. 9,012,219, which claims priority to U.S. Provisional Application Ser. No. 61/267,312 filed Dec. 7, 2009, each of which is herein incorporated by reference in its entirety.

FIELD OF THE INVENTION

The present invention relates to compositions and methods for changing or reprogramming the state of differentiation of eukaryotic cells, including human or other animal cells, by contacting the cells with purified RNA preparations comprising or consisting of one or more different single-strand mRNA molecules that each encode a reprogramming factor (e.g., an iPS cell induction factor). The purified single-stranded mRNA molecules preferably comprise at least one modified nucleoside (e.g., selected from the group consisting of a pseudouridine (abbreviated by the Greek letter "psi" or "ψ"), 5-methylcytosine ($m^5C$), 5-methyluridine ($m^5U$), 2'-O-methyluridine (Um or $m^{2'-O}U$), 2-thiouridine ($s^2U$), and $N^6$-methyladenosine ($m^6A$)) in place of at least a portion of the corresponding unmodified canonical nucleoside (e.g., in place of substantially all of the corresponding unmodified A, C, G, or T canonical nucleoside). In addition, the single-stranded mRNA molecules are preferably purified to be substantially free of RNA contaminant molecules that would activate an unintended response, decrease expression of the single-stranded mRNA, and/or activate RNA sensors in the cells. In certain embodiments, the purified RNA preparations are substantially free of RNA contaminant molecules that are: shorter or longer than the full-length single-stranded mRNA molecules, double-stranded, and/or uncapped RNA.

BACKGROUND

In 2006, it was reported (Takahashi and Yamanaka 2006) that the introduction of genes encoding four protein factors (OCT4 (Octamer-4; POU class 5 homeobox 1), SOX2 (SRY (sex determining region Y)-box 2), KLF4 (Krueppel-like factor 4), and c-MYC) into differentiated mouse somatic cells induced those cells to become pluripotent stem cells, (referred to herein as "induced pluripotent stem cells," "iPS cells," or "iPSCs"). Following this original report, pluripotent stem cells were also induced by transforming human somatic cells with genes encoding the similar human protein factors (OCT4, SOX2, KLF4, and c-MYC) (Takahashi et al. 2007), or by transforming human somatic cells with genes encoding human OCT4 and SOX2 factors plus genes encoding two other human factors, NANOG and LIN28 (Lin-28 homolog A) (Yu et al. 2007). All of these methods used retroviruses or lentiviruses to integrate genes encoding the reprogramming factors into the genomes of the transformed cells and the somatic cells were reprogrammed into iPS cells only over a long period of time (e.g., in excess of a week).

The generation iPS cells from differentiated somatic cells offers great promise as a possible means for treating diseases through cell transplantation. The possibility to generate iPS cells from somatic cells from individual patients also may enable development of patient-specific therapies with less risk due to immune rejection. Still further, generation of iPS cells from disease-specific somatic cells offers promise as a means to study and develop drugs to treat specific disease states (Ebert et al. 2009, Lee et al. 2009, Maehr et al. 2009).

Viral delivery of genes encoding protein reprogramming factors (or "iPSC factors") provides a highly efficient way to make iPS cells from somatic cells, but the integration of exogenous DNA into the genome, whether random or non-random, creates unpredictable outcomes and can ultimately lead to cancer (Nakagawa et al. 2008). New reports show that iPS cells can be created (at lower efficiency) by using other methods that do not require genome integration. For example, repeated transfections of expression plasmids containing genes for OCT4, SOX2, KLF4 and c-MYC into mouse embryonic fibroblasts to generate iPS cells was demonstrated (Okita et al. 2008). Induced pluripotent stem cells were also generated from human somatic cells by introduction of a plasmid that expressed genes encoding human OCT4, SOX2, c-MYC, KLF4, NANOG and LIN28 (Yu et al. 2009). Other successful approaches for generating iPS cells include treating somatic cells with: recombinant protein reprogramming factors (Zhou et al. 2009); non-integrating adenoviruses (Stadtfeld et al. 2008); or piggyBac transposons (Woltjen et al. 2009) to deliver reprogramming factors. Presently, the generation of iPS cells using these non-viral delivery techniques to deliver reprogramming factors is extremely inefficient. Future methods for generating iPS cells for potential clinical applications will need to increase the speed and efficiency of iPS cell formation while maintaining genome integrity.

SUMMARY OF THE INVENTION

The present invention provides compositions and methods for reprogramming the state of differentiation of eukaryotic cells, including human or other animal cells, by contacting the cells with purified RNA preparations comprising or consisting of one or more different single-strand mRNA molecules that each encode a reprogramming factor (e.g., an iPS cell induction factor). The purified single-stranded mRNA molecules preferably comprise at least one modified nucleoside (e.g., selected from the group consisting of a pseudouridine (ψ), 5-methylcytosine ($m^5C$), 5-methyluridine ($m^5U$), 2'-O-methyluridine (Um or $m^{2'-O}U$), 2-thiouridine ($s^2U$), and $N^6$-methyladenosine ($m^6A$)) in place of at least a portion (e.g., including substantially all) of the corresponding unmodified canonical nucleoside of the corresponding unmodified A, C, G, or T canonical nucleoside. In addition, the single-stranded mRNA molecules are preferably purified to be substantially free of RNA contaminant molecules that would activate an unintended response, decrease expression of the single-stranded mRNA, and/or activate RNA sensors (e.g., double-stranded RNA-dependent enzymes) in the cells. In certain embodiments, the purified RNA preparations are substantially free of RNA contaminant molecules that are: shorter or longer than the full-length single-stranded mRNA molecules, double-stranded, and/or uncapped RNA. In some preferred embodiments, the invention provides compositions and methods for reprogramming differentiated eukaryotic cells, including human or other animal somatic cells, by contacting the cells with purified RNA preparations comprising or consisting of one or more different single-strand mRNA molecules that each encode an iPS cell induction factor.

In some embodiments, the present invention provides methods for changing the state of differentiation of a somatic cell comprising: introducing an mRNA encoding an iPS cell induction factor into a somatic cell to generate a reprogrammed dedifferentiated cell, wherein the mRNA comprises at least one 5-methylcytidine (or other modified based described herein).

In certain embodiments, the present invention provides methods for reprogramming a cell that exhibits a first differentiated state or phenotype to a cell that exhibits a second differentiated state or phenotype comprising: introducing into the cell that exhibits a first differentiated state a purified RNA preparation comprising modified mRNA molecules that encode at least one reprogramming factor and culturing the cell under conditions wherein the cell exhibits a second differentiated state. In certain embodiments, the modified mRNA molecules contain at least one modified nucleoside selected from the group consisting of psuedouridine or 5-methylcytidine. In certain embodiments, the cell is from a human or animal. In further embodiments, the purified RNA preparation: i) comprises first single-stranded mRNAs encoding a first iPS cell induction factor, wherein substantially all of the first single-stranded complete mRNAs comprise at least one pseudouridine residue and/or at least one 5-methylcytidine residue, and ii) is substantially free of RNA contaminant molecules which are able to activate RNA sensors in said somatic cell. In certain embodiments, the RNA contaminant molecules are selected from the group consisting of: partial mRNAs encoding only a portion of said iPS cell induction factor, RNA molecules that are smaller than the full-length mRNA, RNA molecules that are larger than the full-length mRNA, double-stranded mRNA molecules, and un-capped mRNA molecules.

In some embodiments, the present invention provides methods for reprogramming a somatic cell (e.g., dedifferentiating or transdifferentiating) comprising: contacting a somatic cell with a purified RNA preparation to generate a reprogrammed cell, wherein the purified RNA preparation: i) comprises first single-stranded mRNAs encoding a first iPS cell induction factor, wherein substantially all of the first single-stranded complete mRNAs comprise at least one pseudouridine residue and/or at least one 5-methylcytidine residue, and ii) is substantially free of contaminant molecules (e.g., RNA contaminant molecules) which are able to activate RNA sensors in the somatic cell. In particular embodiments, the RNA contaminant molecules comprise: partial mRNAs encoding only a portion of the iPS cell induction factor, single-stranded run-on mRNAs encoding the iPS cell induction factor and encoding at least an additional portion of the iPS cell induction factor, double-stranded mRNA molecules, and un-capped mRNA molecules. In certain embodiments, the first single-stranded mRNAs do not also encoding an additional portion of the first iPS cell induction factor.

In some embodiments, the reprogrammed cell is a dedifferentiated cell (e.g., stem cell or stem cell-like cell). In other embodiments, the reprogrammed cell is a transdifferentiated cells (e.g., a skin cells is reprogrammed into a neuronal cell, or other type of change). In further embodiments, the first single-stranded mRNAs encode the complete first iPS induction factor (e.g, the mRNA encodes the entire coding sequence for a particular iPS induction factor). In other embodiments, the contacting further comprises contacting the somatic cell with a growth factor and/or cytokine (e.g., after a period of time). In further embodiments, the contact further comprises contacting the somatic cell with an immune response inhibitor.

In certain embodiments, all or nearly all of the uridine nucleosides in the first single-stranded mRNA are replaced by pseudouridine nucleosides. In other embodiments, all or nearly all of the cytidine nucleosides in the first single-stranded mRNA are replaced by 5-methylcytidine nucleosides or another base recited herein.

In particular embodiments, the present invention provides methods for generating a reprogrammed cell comprising: contacting a somatic cell with a purified RNA preparation to generate a reprogrammed cell that is able to survive in culture for at least 10 days (e.g., at least 10 days . . . at least 13 days . . . at least 16 days . . . at least 20 days . . . at least 40 days . . . or is able to form a cell-line), wherein the purified RNA preparation comprises first single-stranded mRNAs encoding an iPS cell induction factor, and wherein a majority of the first single-stranded mRNAs comprise at least one pseudouridine residue and/or at least one 5-methylcytidine residue.

In certain embodiments, the purified RNA preparation is free of an amount of RNA contaminant molecules that would activate an immune response in the somatic cell sufficient to prevent the reprogrammed cell from surviving at least 10 days in culture (e.g., at least 10 days . . . at least 15 days . . . at least 20 days . . . at least 40 days, or longer). In other embodiments, the RNA contaminant molecules include: partial mRNAs encoding only a portion of the iPS cell induction factor, single-stranded run-on mRNAs fully encoding the iPS cell induction factor and encoding at least an additional portion of the iPS cell induction factor, double-stranded mRNA molecules, un-capped mRNA molecules, and mixtures thereof. In certain embodiments, the reprogrammed cell that is generated is able to form a reprogrammed cell-line. In other embodiments, the purified RNA preparation is free of an amount of RNA contaminant molecules that would activate an immune response in the somatic cell sufficient to prevent generation of the reprogrammed cell-line.

In particular embodiments, the RNA contaminant molecules are selected from the group consisting of: partial mRNAs encoding only a portion of the iPS cell induction factor, single-stranded run-on mRNAs encoding the iPS cell induction factor and encoding at least an additional portion of the iPS cell induction factor, double-stranded mRNA molecules, un-capped mRNA molecules, and mixtures thereof.

In some embodiments, the present invention provides methods for generating a reprogrammed cell-line comprising: a) contacting a somatic cell with a purified RNA preparation to generate a reprogrammed cell, wherein the purified RNA preparation comprises mRNAs encoding an iPS cell induction factor, and wherein a majority of the mRNAs comprise at least one pseudouridine residue and/or at least one 5-methylcytidine residue, and b) culturing the dedifferentiated cell to generate a reprogrammed cell-line. In other embodiments, the purified RNA preparation is free of an amount of contaminant molecules that would activate an immune response in the somatic cell sufficient to prevent generation of the reprogrammed cell-line. In certain embodiments, the immune response involves activation of RNA sensors in the somatic cell.

In some embodiments, the present invention provides methods for reprogramming a somatic cell comprising: contacting a somatic cell with a purified RNA preparation to generate a reprogrammed cell, wherein the purified RNA preparation: i) comprises first single-stranded mRNAs encoding a first iPS cell induction factor, wherein substantially all of the first single-stranded mRNAs comprise at least one pseudouridine residue and/or at least one 5-methylcytidine residue, and ii) is substantially free of: a) partial mRNAs encoding only a portion of the first iPS cell induction factor, and b) double-stranded mRNA molecules. In further embodiments, the first single-stranded mRNA do not also encode an additional portion of the first iPS cell induction factor. In particular embodiments, the first single-stranded mRNA fully encode the first iPS cell induction factor. In other embodiments, the purified RNA preparation is also substantially free (or essentially free or virtually free or free) of single-stranded run-on mRNAs encoding the first iPS cell induction factor and encoding at least an additional portion of the first iPS cell induction factor. In other embodiments, the substantially all of the first single-stranded complete mRNAs are 5' capped. In other embodiments, the purified RNA preparation is also substantially free of un-capped mRNA molecules. In some embodiments, substantially all of the first single-stranded mRNAs comprise at least one psuedouridine residue. In additional embodiments, substantially all of the first single-stranded mRNAs comprise at least one 5-methylcytidine residue. In other embodiments, substantially all of the first single-stranded mRNAs comprise at least one psuedouridine residue and at least one 5-methycytidine residue.

In certain embodiments, the purified RNA preparation comprises a transfection reagent. In other embodiments, the purified RNA preparation is obtained by HPLC purification of an RNA sample that contains a substantial amount of the partial mRNAs and the double-stranded mRNAs. In further embodiments, the purified RNA preparation is essentially free of the partial mRNAs and the single-stranded run-on mRNAs. In some embodiments, the purified RNA preparation is essentially free or virtually free or free of double-stranded mRNA molecules. In other embodiments, the purified RNA preparation is essentially free or virtually free or free of un-capped mRNA molecules. In some embodiments, substantially all of the first single-stranded mRNAs are polyadenylated. In other embodiments, the first single-stranded complete mRNAs are capped with 7-methylguanosine.

In some embodiments, the first iPS cell induction factor is selected from the group consisting of KLF4, LIN28, c-MYC, NANOG, OCT4, and SOX2. In other embodiments, the purified RNA preparation: i) further comprises second single-stranded mRNAs encoding a second iPS cell induction factor, wherein the second single-stranded mRNAs comprise at least one pseudouridine residue and/or at least one 5-methylcytidine residue, and ii) is further substantially free of: a) partial mRNAs encoding only a portion of the second iPS cell induction factor, and b) double-stranded mRNAs. In other embodiments, the purified RNA preparation is further substantially free of single-stranded run-on mRNAs encoding a second iPS cell induction factor and encoding at least an additional portion of the second iPS cell induction factor. In some embodiments, the second iPS cell induction factor is selected from the group consisting of KLF4, LIN28, c-MYC, NANOG, OCT4, and SOX2. In certain embodiments, the somatic cell is a fibroblast. In other embodiments, the reprogrammed cell is a pluripotent stem cell. In other embodiments, the dedifferentiated cell expresses NANOG and TRA-1-60. In some embodiments, the cell is in vitro. In further embodiments, the cell resides in culture. In particular embodiments, the cell resides in MEF-conditioned medium.

In some embodiments, the present invention provides compositions comprising a purified RNA preparation, wherein the purified RNA preparation: i) comprises first single-stranded mRNAs encoding a first iPS cell induction factor, wherein the first single-stranded mRNAs comprise at least one pseudouridine residue and/or at least one 5-methylcytidine residue, and ii) is substantially free of RNA contaminant molecules, which are able to activate RNA sensors in a somatic cell. In certain embodiments, the present invention provides compositions comprising a purified RNA preparation, wherein the purified RNA preparation: i) comprises first single-stranded mRNAs encoding a first iPS cell induction factor, wherein the first single-stranded complete mRNAs comprise at least one pseudouridine residue and/or at least one 5-methylcytidine residue, and ii) is substantially free of: a) partial mRNAs encoding only a portion of the first iPS cell induction factor, and b) double-stranded RNA.

In certain embodiments, the purified RNA preparation is also substantially free of single-stranded run-on mRNAs encoding the first iPS cell induction factor and encoding at least an additional portion of the first iPS cell induction factor. In some embodiments, the purified RNA preparation: i) further comprises second single-stranded mRNAs encoding a second iPS cell induction factor, wherein the second single-stranded complete mRNAs comprise at least one pseudouridine residue and/or at least one 5-methylcytidine residue, and ii) is substantially free of: a) partial mRNAs encoding only a portion of the second iPS cell induction factor, and b) single-stranded run-on mRNAs encoding second first iPS cell induction factor and encoding at least an additional portion of the second iPS cell induction factor.

In some embodiments, the present invention provides compositions comprising an in vitro-synthesized mRNA encoding the MYC gene, wherein the in vitro-synthesized mRNA comprises at least one pseudouridine residue and/or at least one 5-methylcytidine residue. In certain embodiments, the compositions are substantially free of RNA contaminant molecules which are able to activate RNA sensors in a somatic cell.

In particular embodiments, the present invention provides methods for inducing a mammalian cell to produce the MYC protein comprising: contacting a mammalian cell with an in vitro-synthesized mRNA encoding the MYC gene, wherein the in vitro-synthesized mRNA comprises at least one pseudouridine residue and/or at least one 5-methylcytidine residue, thereby inducing the mammalian cell to produce the MYC protein. In other embodiments, the mammalian cell is a dendritic cell. In other embodiments, the mammalian cell is an alveolar cell, an astrocyte, a microglial cell, or a neuron.

In some embodiments, the present invention provides methods of treating a subject comprising contacting a subject with the MYC protein producing mammalian cell described above and herein.

In additional embodiments, the present invention provides methods of synthesizing an in vitro-transcribed RNA molecule encoding the MYC gene comprising: combining an isolated RNA polymerase, a template nucleic acid sequence encoding the MYG gene, unmodified nucleotides, and pseudouridine or 5-methylcytidine modified nucleotides under conditions such that an in vitro-transcribed RNA molecule encoding the MYC gene is generated that comprises at least one pseudouridine or 5-methylcytidine residue.

Experiments conducted during the development of embodiments of the present invention demonstrated that mRNA molecules can be administered to cells and induce a dedifferentiation process to generate dedifferentiated cells—including pluripotent stem cells. Thus, the present invention provides compositions and methods for generating iPS cells. Surprisingly, the administration of mRNA can provide highly efficient generation of iPS cells.

The present invention also provides RNA, oligoribonucleotide, and polyribonucleotide molecules comprising pseudouridine or a modified nucleoside, gene therapy vectors comprising same, methods of synthesizing same, and methods for gene replacement, gene therapy, gene transcription silencing, and the delivery of therapeutic proteins to tissue in vivo, comprising the molecules. The present invention also provides methods of reducing the immunogenicity of RNA, oligoribonucleotide, and polyribonucleotide molecules.

In some embodiments, the present invention provides methods for dedifferentiating a somatic cell comprising: introducing mRNA encoding one or more iPSC induction factors into a somatic cell to generate a dedifferentiated cell.

In some embodiments, the present invention provides methods for dedifferentiating a somatic cell comprising: introducing mRNA encoding one or more iPSC induction factors into a somatic cell and maintaining the cell under conditions wherein the cell is viable and the mRNA that is introduced into the cell is translated in sufficient amount and for sufficient time to generate a dedifferentiated cell. In some preferred embodiments, the dedifferentiated cell is an induced pluripotent stem cell (iPSC).

In some embodiments, the present invention provides methods for changing the state of differentiation (or differentiated state) of a eukaryotic cell comprising: introducing mRNA encoding one or more reprogramming factors into a cell and maintaining the cell under conditions wherein the cell is viable and the mRNA that is introduced into the cell is translated in sufficient amount and for sufficient time to generate a cell that exhibits a changed state of differentiation compared to the cell into which the mRNA was introduced.

In some embodiments, the present invention provides methods for changing the state of differentiation of a eukaryotic cell comprising: introducing mRNA encoding one or more reprogramming factors into a cell and maintaining the cell under conditions wherein the cell is viable and the mRNA that is introduced into the cell is translated in sufficient amount and for sufficient time to generate a cell that exhibits a changed state of differentiation compared to the cell into which the mRNA was introduced. In some embodiments, the changed state of differentiation is a dedifferentiated state of differentiation compared to the cell into which the mRNA was introduced. For example, in some embodiments, the cell that exhibits the changed state of differentiation is a pluripotent stem cell that is dedifferentiated compared to a somatic cell into which the mRNA was introduced (e.g., a somatic cell that is differentiated into a fibroblast, a cardiomyocyte, or another differentiated cell type). In some embodiments, the cell into which the mRNA is introduced is a somatic cell of one lineage, phenotype, or function, and the cell that exhibits the changed state of differentiation is a somatic cell that exhibits a lineage, phenotype, or function that is different than that of the cell into which the mRNA was introduced; thus, in these embodiments, the method results in transdifferentiation (Graf and Enver 2009).

The methods of the invention are not limited with respect to a particular cell into which the mRNA is introduced. In some embodiments of any of the above methods, the cell into which the mRNA is introduced is derived from any multi-cellular eukaryote. In some embodiments of any of the above methods, the cell into which the mRNA is introduced is selected from among a human cell and another animal cell. Although the work presented herein was performed using cells of humans or other animals, the applicants further claim that the methods of the present invention comprising reprogramming human and animal cells by contacting the cells with a purified RNA preparation that consists of one or more purified single-stranded mRNA molecules, each of which encodes a protein reprogramming factor (e.g., a transcription factor) also pertains to reprogramming of other eukaryotic cells (e.g., plant cells and a fungal cells). In some embodiments of any of the above methods, the cell into which the mRNA is introduced is a normal cell that is from an organism that is free of a known disease. In some embodiments of any of the above methods, the cell into which the mRNA is introduced is a cell from an organism that has a known disease. In some embodiments of any of the above methods, the cell into which the mRNA is introduced is a cell that is free of a known pathology. In some embodiments of any of the above methods, the cell into which the mRNA is introduced is a cell that exhibits a disease state or a known pathology (e.g., a cancer cell, or a pancreatic beta cell that exhibits metabolic properties characteristic of a diabetic cell).

The invention is not limited to the use of a specific cell type (e.g., to a specific somatic cell type) in embodiments of the methods comprising introducing mRNA encoding one or more iPSC cell induction factors in order to generate a dedifferentiated cell (e.g., an iPS cell). Any cell that is subject to dedifferentiation using iPS cell induction factors is contemplated. Such cells include, but are not limited to, fibroblasts, keratinocytes, adipocytes, lymphocytes, T-cells, B-Cells, cells in mononuclear cord blood, buccal mucosa cells, hepatic cells, HeLa, MCF-7 or other cancer cells. In some embodiments, the cells reside in vitro (e.g., in culture) or in vivo. In some embodiments, when generated in culture, a cell-free conditioned medium (e.g., MEF-conditioned medium) is used. As demonstrated below, such a medium provided enhanced iPS cell generation. The invention is not limited, however, to the culturing conditions used. Any culturing condition or medium now known or later identified as useful for the methods of the invention (e.g., to generate iPS cells from somatic cells and maintain said cells) is contemplated for use with the invention. For example, although not preferred, in some embodiments of the method, a feeder cell layer is used instead of conditioned medium for culturing the cells that are treated using the method.

In some embodiments of any of these methods, the step of introducing mRNA comprises delivering the mRNA into the cell (e.g., a human or other animal somatic cell) with a transfection reagent (e.g., TRANSIT™ mRNA transfection reagent, MirusBio, Madison, Wis.).

However, the invention is not limited by the nature of the transfection method utilized. Indeed, any transfection process known, or identified in the future that is able to deliver mRNA molecules into cells in vitro or in vivo, is contemplated, including methods that deliver the mRNA into cells in culture or in a life-supporting medium, whether said cells comprise isolated cells or cells comprising a eukaryotic tissue or organ, or methods that deliver the mRNA in vivo into cells in an organism, such as a human, animal, plant or fungus. In some embodiments, the transfection reagent comprises a lipid (e.g., liposomes, micelles, etc.). In some embodiments, the transfection reagent comprises a nanoparticle or nanotube. In some embodiments, the transfection reagent comprises a cationic compound (e.g., polyethylene imine or PEI). In some embodiments, the transfection method uses an electric current to deliver the mRNA into the cell (e.g., by electroporation). In some embodiments, the transfection method uses a bolistics method to deliver the mRNA into the cell (e.g., a "gene gun" or biolistic particle delivery system.)

The data presented herein shows that, with respect to the mRNA introduced into the cell, certain amounts of the mRNAs used in the EXAMPLES described herein resulted in higher efficiency and more rapid induction of pluripotent stem cells from the particular somatic cells used than other amounts of mRNA. However, the methods of the present invention are not limited to the use of a specific amount of mRNA to introduce into the cell. For example, in some embodiments, a total of three doses, with each dose comprising 18 micrograms of each of six different mRNAs, each encoding a different human reprogramming factor, was used to introduce the mRNA into approximately $3\times10^5$ human fibroblast cells in a 10-cm plate (e.g., delivered using a lipid-containing transfection reagent), although in other embodiments, higher or lower amounts of the mRNAs were used to introduce into the cells.

The invention is not limited to a particular chemical form of the mRNA used, although certain forms of mRNA may produce more efficient results. However, in some preferred embodiments, the mRNA comprises at least one modified nucleoside (e.g., selected from the group consisting of a pseudouridine ($\psi$), 5-methylcytosine ($m^5C$), 5-methyluridine ($m^5U$), 2'-O-methyluridine (Um or $m^{2'-O}U$), 2-thiouridine ($s^2U$), and $N^6$-methyladenosine ($m^6A$)) in place of at least a portion of the corresponding unmodified canonical nucleoside (e.g., in some preferred embodiments, at least one modified nucleoside in place of substantially all of the corresponding unmodified A, C, G, or T canonical nucleoside). In some embodiments, the mRNA is polyadenylated. In some preferred embodiments, the mRNA is prepared by polyadenylation of an in vitro-transcribed (IVT) RNA, the method comprising contacting the IVT RNA using a poly(A) polymerase (e.g., yeast RNA polymerase or E. coli poly(A) polymerase). In some embodiments, the mRNA is polyadenylated during IVT by using a DNA template that encodes the poly(A) tail. Regardless of whether the RNA is polyadenylated using a poly(A) polymerase or during IVT of a DNA template, in some preferred embodiments, the mRNA comprises a poly-A tail (e.g., a poly-A tail having 50-200 nucleotides, e.g., preferably 100-200, 150-200 nucleotides, or greater than 150 nucleotides), although in some embodiments, a longer or a shorter poly-A tail is used. In some embodiments, the mRNA used in the methods is capped. To maximize efficiency of expression in the cells, it is preferred that the majority of mRNA molecules contain a cap. In some preferred embodiments, the mRNA molecules used in the methods are synthesized in vitro by incubating uncapped primary RNA in the presence a capping enzyme system. In some preferred embodiments, the primary RNA used in the capping enzyme reaction is synthesized by in vitro transcription (IVT) of a DNA molecule that encodes the RNA to be synthesized. The DNA that encodes the RNA to be synthesized contains an RNA polymerase promoter, to which, an RNA polymerase binds and initiates transcription therefrom. It is also known in the art that mRNA molecules often have regions of differing sequence located before the translation start codon and after the translation stop codon that are not translated. These regions, termed the five prime untranslated region (5' UTR) and three prime untranslated region (3' UTR), respectively, can affect mRNA stability, mRNA localization, and translational efficiency of the mRNA to which they are joined. Certain 5' and 3' UTRs, such as those for alpha and beta globins are known to improve mRNA stability and expression of mRNAs. Thus, in some preferred embodiments, the mRNAs that encode reprogramming factors (e.g., iPSC induction factors) exhibit a 5' UTR and/or a 3' UTR that results in greater mRNA stability and higher expression of the mRNA in the cells (e.g., an alpha globin or a beta globin 5' UTR and/or 3' UTR; e.g., a Xenopus or human alpha globin or a beta globin 5' UTR and/or 3' UTR, or, e.g., a tobacco etch virus (TEV) 5' UTR).

The IVT can be performed using any RNA polymerase as long as synthesis of the mRNA from the DNA template that encodes the RNA is specifically and sufficiently initiated from a respective cognate RNA polymerase promoter and full-length mRNA is obtained. In some preferred embodiments, the RNA polymerase is selected from among T7 RNA polymerase, SP6 RNA polymerase and T3 RNA polymerase. In some other embodiments, capped RNA is synthesized co-transcriptionally by using a dinucleotide cap analog in the IVT reaction (e.g., using an AMPLICAP™ T7 Kit or a MESSAGEMAX™ T7 ARCA-CAPPED MESSAGE Transcription Kit; EPICENTRE or CellScript, Madison, Wis., USA). If capping is performed co-transcriptionally, preferably the dinucleotide cap analog is an anti-reverse cap analog (ARCA). However, use of a separate IVT reaction, followed by capping with a capping enzyme system, which results in approximately 100% of the RNA being capped, is preferred over co-transcriptional capping, which typically results in only about 80% of the RNA being capped. Thus, in some preferred embodiments, a high percentage of the mRNA molecules used in a method of the present invention are capped (e.g., greater than 80%, greater than 90%, greater than 95%, greater than 98%, greater than 99%, greater than 99.5%, or greater than 99.9% of the population of mRNA molecules are capped). In some preferred embodiments, the mRNA used in the methods of the present invention has a cap with a cap1 structure, meaning that the 2' hydroxyl of the ribose in the penultimate nucleotide with respect to the cap nucleotide is methylated. However, in some embodiments, mRNA used in the methods has a cap with a cap0 structure, meaning that the 2' hydroxyl of the ribose in the penultimate nucleotide with respect to the cap nucleotide is not methylated. With some but not all transcripts, transfection of eukaryotic cells with mRNA having a cap with a cap1 structure results in a higher level or longer duration of protein expression in the transfected cells compared to transfection of the same cells with the same mRNA but with a cap having a cap0 structure. In some embodiments, the mRNA used in the methods of the present invention has a modified cap nucleotide. In some experiments performed prior to the experiments presented in the EXAMPLES herein, the present applicants found that, when 1079 or IMR90 human fibroblast cells were transfected with OCT4 mRNA that contained either uridine, or pseudouridine in place of uridine, the pseudouridine-containing mRNA was translated at a higher level or for a longer duration than the mRNA that contained uridine. Therefore, in some preferred embodiments, one or more or all of the uridines contained in the mRNA(s) used in the methods of the present invention is/are replaced by pseudouridine (e.g., by substituting pseudouridine-5'-triphosphate in the IVT reaction to synthesize the RNA in place of uridine-5'-triphosphate). However, in some embodiments, the mRNA used in the methods of the invention contains uridine and does not contain pseudouridine. In some preferred embodiments, the mRNA comprises at least one modified nucleoside (e.g., selected from the group consisting of a pseudouridine ($\psi$), 5-methylcytosine ($m^5C$), 5-methyluridine ($m^5U$), 2'-O-methyluridine (Um or $m^{2'-O}U$), 2-thiouridine ($s^2U$), and $N^6$-methyladenosine ($m^6A$)) in place of at least a portion of the corresponding unmodified canonical nucleoside (e.g., in place of substantially all of the corresponding unmodified A, C, G, or T canonical nucleoside). In some preferred embodiments, the mRNA comprises at least one modified nucleoside selected from the group consisting of a pseudouridine (ψ) and 5-methylcytosine ($m^5C$). In some preferred embodiments, the mRNA comprises both pseudouridine (ψ) and 5-methylcytosine ($m^5C$). In addition, in order to accomplish specific goals, a nucleic acid base, sugar moiety, or internucleotide linkage in one or more of the nucleotides of the mRNA that is introduced into a eukaryotic cell in any of the methods of the invention may comprise a modified nucleic acid base, sugar moiety, or internucleotide linkage.

The invention is also not limited with respect to the source of the mRNA that is delivered into the eukaryotic cell in any of the methods of the invention. In some embodiments, such as those described in the EXAMPLES, the mRNA is synthesized by in vitro transcription of a DNA template comprising a gene cloned in a linearized plasmid vector or by in vitro transcription of a DNA template that is synthesized by PCR or RT-PCR (i.e., by IVT of a PCR amplification product), capping using a capping enzyme system or by co-transcriptional capping by incorporation of a dinucleotide cap analog (e.g., an ARCA) during the IVT, and polyadenylation using a poly(A) polymerase. In some preferred embodiments, the mRNA is synthesized by IVT of a DNA template comprising a gene cloned in a linearized plasmid vector or a PCR or RT-PCR amplification product, wherein the DNA template encodes a 3'poly(A) tail. In some other embodiments, the mRNA that is delivered into the eukaryotic cell in any of the methods of the invention is derived directly from a cell or a biological sample. For example, in some embodiments, the mRNA derived from a cell or biological sample is obtained by amplifying the mRNA from the cell or biological sample using an RNA amplification reaction, and capping the amplified mRNA using a capping enzyme system or by co-transcriptional capping by incorporation of a dinucleotide cap analog (e.g., an ARCA) during the IVT, and, if the amplified mRNA does not already contain a template-encoded poly(A) tail from the RNA amplification reaction, polyadenylating the amplified mRNA using a poly(A) polymerase.

With respect to the methods comprising introducing mRNA encoding one or more iPS cell induction factors in order to generate a dedifferentiated cell (e.g., an iPS cell), the invention is not limited by the nature of the iPS cell induction factors used. Any mRNA encoding one or more protein induction factors now known, or later discovered, that find use in dedifferentiation, are contemplated for use in the present invention. In some embodiments, one or more mRNAs encoding for KLF4, LIN28, c-MYC, NANOG, OCT4, or SOX2 are employed. Oct-3/4 and certain members of the Sox gene family (Sox1, Sox2, Sox3, and Sox15) have been identified as transcriptional regulators involved in the induction process. Additional genes, however, including certain members of the Klf family (Klf1, Klf2, Klf4, and Klf5), the Myc family (C-myc, L-myc, and N-myc), Nanog, and LIN28, have been identified to increase the induction efficiency. Any one or more such factors may be used as desired.

While the compositions and methods of the invention may be used to generate iPS cells, the invention is not limited to the generation of such cells. For example, in some embodiments, mRNA encoding one or more reprogramming factors is introduced into a cell in order to generate a cell with a changed state of differentiation compared to the cell into which the mRNA was introduced. For example, in some embodiments, mRNA encoding one or more iPS cell induction factors is used to generate a dedifferentiated cell that is not an iPS cells. Such cells find use in research, drug screening, and other applications.

In some embodiments, the present invention further provides methods employing the dedifferentiated cells generated by the above methods. For example, such cells find use in research, drug screening, and therapeutic applications in humans or other animals. For example, in some embodiments, the cells generated find use in the identification and characterization of iPS cell induction factors as well as other factors associated with differentiation or dedifferentiation. In some embodiments, the generated dedifferentiated cells are transplanted into an organism or into a tissue residing in vitro or in vivo. In some embodiments, an organism, tissue, or culture system housing the generated cells is exposed to a test compound and the effect of the test compound on the cells or on the organism, tissue, or culture system is observed or measured.

In some other embodiments, a dedifferentiated cell generated using the above methods (e.g., an iPS cell) is further treated to generate a differentiated cell that has the same state of differentiation or cell type compared to the somatic cell from which the dedifferentiated cell was generated. In some other embodiments, the dedifferentiated cell generated using the above methods (e.g., an iPS cell) is further treated to generate a differentiated cell that has a different state of differentiation or cell type compared to the somatic cell from which the dedifferentiated cell was generated. In some embodiments, the differentiated cell is generated from the generated dedifferentiated cell (e.g., the generated iPS cell) by introducing mRNA encoding one or more reprogramming factors into the generated iPS cell during one or multiple treatments and maintaining the cell into which the mRNA is introduced under conditions wherein the cell is viable and is differentiated into a cell that has a changed state of differentiation or cell type compared to the generated dedifferentiated cell (e.g., the generated iPS cell) into which the mRNA encoding the one or more reprogramming factors is introduced. In some of these embodiments, the generated differentiated cell that has the changed state of differentiation is used for research, drug screening, or therapeutic applications (e.g., in humans or other animals). For example, the generated differentiated cells find use in the identification and characterization of reprogramming factors associated with differentiation. In some embodiments, the generated differentiated cells are transplanted into an organism or into a tissue residing in vitro or in vivo. In some embodiments, an organism, tissue, or culture system housing the generated differentiated cells is exposed to a test compound and the effect of the test compound on the cells or on the organism, tissue, or culture system is observed or measured.

In some preferred embodiments of the method comprising introducing mRNA encoding one or more iPSC induction factors into a somatic cell and maintaining the cell under conditions wherein the cell is viable and the mRNA that is introduced into the cell is expressed in sufficient amount and for sufficient time to generate a dedifferentiated cell (e.g., wherein the dedifferentiated cell is an induced pluripotent stem cell), the sufficient time to generate a dedifferentiated cell is less than one week. In some preferred embodiments of this method, the reprogramming efficiency for generating dedifferentiated cells is greater than or equal to 50 dedifferentiated cells (e.g., iPSCs) per $3\times10^5$ input cells into which the mRNA is introduced. In some preferred embodiments of this method, the reprogramming efficiency for generating dedifferentiated cells is greater than or equal to 100 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 150 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 200 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 300 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 400 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 500 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 600 dedifferentiated cells per $3 \times 10^5$ input cells (e.g., iPSCs) into which the mRNA is introduced. In some preferred embodiments of this method, the reprogramming efficiency for generating dedifferentiated cells is greater than or equal to 700 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 800 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 900 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 1000 dedifferentiated cells (e.g., iPSCs) per $3 \times 10^5$ input cells into which the mRNA is introduced. Thus, in some preferred embodiments, this method was greater than 2-fold more efficient than the published protocol comprising delivery of reprogramming factors with a viral vector (e.g., a lentivirus vector). In some preferred embodiments, this method was greater than 5-fold more efficient than the published protocol comprising delivery of reprogramming factors with a viral vector (e.g., a lentivirus vector). In some preferred embodiments, this method was greater than 10-fold more efficient than the published protocol comprising delivery of reprogramming factors with a viral vector (e.g., a lentivirus vector). In some preferred embodiments, this method was greater than 20-fold more efficient than the published protocol comprising delivery of reprogramming factors with a viral vector (e.g., a lentivirus vector). In some preferred embodiments, this method was greater than 25-fold more efficient than the published protocol comprising delivery of reprogramming factors with a viral vector (e.g., a lentivirus vector). In some preferred embodiments, this method was greater than 30-fold more efficient than the published protocol comprising delivery of reprogramming factors with a viral vector (e.g., a lentivirus vector). In some preferred embodiments, this method was greater than 35-fold more efficient than the published protocol comprising delivery of reprogramming factors with a viral vector (e.g., a lentivirus vector). In some preferred embodiments, this method was greater than 40-fold more efficient than the published protocol comprising delivery of reprogramming factors with a viral vector (e.g., a lentivirus vector).

The present invention further provides compositions (systems, kits, reaction mixtures, cells, mRNA) used or useful in the methods and/or generated by the methods described herein. For example, in some embodiments, the present invention provides an mRNA encoding an iPS cell induction factor, the mRNA having pseudouridine in place of uridine.

The present invention further provides compositions comprising a transfection reagent and an mRNA encoding an iPS cell induction factor (e.g., a mixture of transfection reagent and mRNA). In some embodiments, the compositions comprise mRNA encoding a plurality (e.g., 2 or more, 3 or more, 4 or more, 5 or more, or 6) of iPS cell induction factors, including, but not limited to, KLF4, LIN28, c-MYC, NANOG, OCT4, and SOX2.

The compositions may further comprise any other reagent or component sufficient, necessary, or useful for practicing any of the methods described herein. Such reagents or components include, but are not limited to, transfection reagents, culture medium (e.g., MEF-condition medium), cells (e.g., somatic cells, iPS cells), containers, boxes, buffers, inhibitors (e.g., RNase inhibitors), labels (e.g., fluorescent, luminescent, radioactive, etc.), positive and/or negative control molecules, reagents for generating capped mRNA, dry ice or other refrigerants, instructions for use, cell culture equipment, detection/analysis equipment, and the like.

This invention provides RNA, oligoribonucleotide, and polyribonucleotide molecules comprising pseudouridine or a modified nucleoside, gene therapy vectors comprising same, gene therapy methods and gene transcription silencing methods comprising same, methods of reducing an immunogenicity of same, and methods of synthesizing same.

In one embodiment, the present invention provides a messenger RNA comprising a pseudouridine residue. In another embodiment, the present invention provides an RNA molecule encoding a protein of interest, said RNA molecule comprising a pseudouridine residue. In another embodiment, the present invention provides an in vitro-transcribed RNA molecule, comprising a pseudouridine or a modified nucleoside. In another embodiment, the present invention provides an in vitro-synthesized oligoribonucleotide, comprising a pseudouridine or a modified nucleoside, wherein the modified nucleoside is $m^5C$, $m^5U$, $m^6A$, $s^2U$, $\psi$, or 2'-O-methyl-U. In another embodiment, the present invention provides a gene-therapy vector, comprising an in vitro-synthesized polyribonucleotide molecule, wherein the polyribonucleotide molecule comprises a pseudouridine or a modified nucleoside.

In another embodiment, the present invention provides a double-stranded RNA (dsRNA) molecule containing, as part of its sequence, a pseudouridine or a modified nucleoside and further comprising an siRNA or shRNA. In another embodiment, the dsRNA molecule is greater than 50 nucleotides in length. Each possibility represents a separate embodiment of the present invention.

In another embodiment, the present invention provides a method for inducing a mammalian cell to produce a recombinant protein, comprising contacting the mammalian cell with an in vitro-synthesized RNA molecule encoding the recombinant protein, the in vitro-synthesized RNA molecule comprising a pseudouridine or a modified nucleoside, thereby inducing a mammalian cell to produce a recombinant protein.

In another embodiment, the present invention provides a method for treating anemia in a subject, comprising contacting a cell of the subject with an in vitro-synthesized RNA molecule, the in vitro-synthesized RNA molecule encoding erythropoietin, thereby treating anemia in a subject.

In another embodiment, the present invention provides a method for treating a vasospasm in a subject, comprising contacting a cell of the subject with an in vitro-synthesized RNA molecule, the in vitro-synthesized RNA molecule encoding inducible nitric oxide synthase (iNOS), thereby treating a vasospasm in a subject.

In another embodiment, the present invention provides a method for improving a survival rate of a cell in a subject, comprising contacting the cell with an in vitro-synthesized RNA molecule, the in vitro-synthesized RNA molecule encoding a heat shock protein, thereby improving a survival rate of a cell in a subject.

In another embodiment, the present invention provides a method for decreasing an incidence of a restenosis of a blood vessel following a procedure that enlarges the blood vessel, comprising contacting a cell of the blood vessel with an in vitro-synthesized RNA molecule, the in vitro-synthesized RNA molecule encoding a heat shock protein, thereby decreasing an incidence of a restenosis in a subject.

In another embodiment, the present invention provides a method for increasing a hair growth from a hair follicle is a scalp of a subject, comprising contacting a cell of the scalp with an in vitro synthesized RNA molecule, the in vitro-synthesized RNA molecule encoding a telomerase or an immunosuppressive protein, thereby increasing a hair growth from a hair follicle.

In another embodiment, the present invention provides a method of inducing expression of an enzyme with antioxidant activity in a cell, comprising contacting the cell with an in vitro-synthesized RNA molecule, the in vitro-synthesized RNA molecule encoding the enzyme, thereby inducing expression of an enzyme with antioxidant activity in a cell.

In another embodiment, the present invention provides a method for treating cystic fibrosis in a subject, comprising contacting a cell of the subject with an in vitro-synthesized RNA molecule, the in vitro-synthesized RNA molecule encoding Cystic Fibrosis Transmembrane Conductance Regulator (CFTR), thereby treating cystic fibrosis in a subject.

In another embodiment, the present invention provides a method for treating an X-linked agammaglobulinemia in a subject, comprising contacting a cell of the subject with an in vitro synthesized RNA molecule, the in vitro-synthesized RNA molecule encoding a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with an in vitro-synthesized RNA molecule, the in vitro-synthesized RNA molecule encoding an ADA, thereby treating an ADA SCID.

In another embodiment, the present invention provides a method for producing a recombinant protein, comprising contacting an in vitro translation apparatus with an in vitro-synthesized polyribonucleotide, the in vitro-synthesized polyribonucleotide comprising a pseudouridine or a modified nucleoside, thereby producing a recombinant protein.

In another embodiment, the present invention provides a method of synthesizing an in vitro-transcribed RNA molecule comprising a modified nucleotide with a pseudouridine modified nucleoside, comprising contacting an isolated polymerase with a mixture of unmodified nucleotides and the modified nucleotide.

In another embodiment, the present invention provides an in vitro transcription apparatus, comprising: an unmodified nucleotide, a nucleotide containing a pseudouridine or a modified nucleoside, and a polymerase. In another embodiment, the present invention provides an in vitro transcription kit, comprising: an unmodified nucleotide, a nucleotide containing a pseudouridine or a modified nucleoside, and a polymerase. Each possibility represents a separate embodiment of the present invention.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIG. 2 shows that mRNA encoding human reprogramming factors (KLF4, LIN28, c-MYC, NANOG, OCT4, and SOX2) produce iPS cells in human somatic cells. FIG. 2 shows bright-field (A,C) and immunofluorescent (B,D) images of an iPS cell colony at 12 days after the final transfection with mRNA encoding reprogramming factors. NANOG staining is observed in colony #1 (B, D). Images A and B are at 10× magnification. C and D are at 20× magnification.

FIG. 3 shows phase contrast (A,D,G) and immunofluorescent (B,C,E,F,H,I) images of iPS colonies derived from 1079 cells (A, D) and IMR90 cells (G). The same iPS colony shown in (A) is positive for both NANOG (B) and TRA-1-60 (C). The iPS colony shown in (D) is NANOG-positive (E) and TRA-1-60-positive (F). The iPS colony generated from IMR90 fibroblasts (G) is also positive for both NANOG (H) and TRA-1-60 (I). All images are at 20× magnification.

FIGS. 9A-B. Activation of DC by RNA demonstrates that all nucleoside modification inhibits the RNA-mediated DC activation. MDDC were treated for 20 h with Lipofectin® alone, Lipofectin®-R-848 (1 µg/ml) or RNA-1571, modified as indicated (5 µg/ml). (A) CD83 and HLA-DR staining. (B) TNF-α levels in the supernatants and mean fluorescence of CD80 and CD86 in response to incubation with RNA. The volume of medium was increased 30-fold for flow cytometry, as indicated by the asterisk. Data are representative of four independent experiments.

FIGS. 10A-C. Capped RNA-1571 containing different amounts (0, 1, 10, 50, 90, 99 and 100% of modified nucleoside, relative to the corresponding unmodified NTP) were transcribed, and it was found that modification of only a few nucleosides resulted in an inhibition of activation of DC. A. All transcripts were digested to monophosphates and analyzed by reversed-phase HPLC to determine the relative amount of modified nucleoside incorporation. Representative absorbance profiles obtained at the indicated (ψ:U) ratios are shown. Elution times are noted for 3'-monophosphates of pseudouridine (ψ), cytidine (C), guanosine (G), uridine (U), 7-methylguanosine ("m7G") and adenosine ("A"). (B) Modified nucleoside content of RNA-1571. The expected percentage of $m^6A$, ψ (pseudouridine), or $m^5C$ in RNA-1571 was calculated based on the relative amount of modified NTP in the transcription reaction and the nucleoside composition of RNA-1571 (A: 505, U: 451, C: 273, G: 342). Values for measured modified nucleoside content were determined based on quantitation of the HPLC chromatograms. Notes: A: values (%) for $m^6ATP$, ψTP and $m^5CTP$ relative to ATP, UTP and CTP, respectively. B: values for $m^6A$, ψ and $m^5C$ monophosphates relative to all NMPs. (C) MDDC were transfected with Lipofectin® complexed capped RNA-1571 (5 µg/ml) containing the indicated amount of $m^6A$, ψ or $m^5C$. After 8 h, TNF-α was measured in the supernatants. Data expressed as relative inhibition of TNF-α. Mean values±SEM obtained in 3 independent experiments are shown.

FIGS. 11A-C. TNF-α expression by oligoribonucleotide-transfected DCs demonstrates that as few as one modified nucleoside reduces DC activation. (A) Sequences of oligoribonucleotides (ORN) synthesized chemically (ORN1-4) (SEQ ID NOs: 6-9) or transcribed in vitro (ORN5-6) (SEQ ID NOs: 10-11) are shown. Positions of modified nucleosides Um (2'-O-methyluridine), $m^5C$ and ψ are highlighted. Human MDDC were transfected with Lipofectin® alone (medium), R-848 (1 µg/ml) or Lipofectin® complexed with RNA (5 µg/ml). Where noted, cells were treated with 2.5 µg/ml cycloheximide (CHX). (B). After 8 h incubation, TNF-α was measured in the supernatant. (C) RNA from the cells was analyzed by Northern blot. Representative mean values±SEM of 3 independent experiments are shown.

FIGS. 15A-B. Increased expression of *renilla* from pseudouridine-containing mRNA in cultured cells. A. 293 cells. B. Murine primary, bone marrow-derived mouse dendritic cells. *renilla*-Y: mRNA with pseudouridine modification; *renilla*-C:unmodified RNA.RNA was modified with $m^5C$, $m^6A$, and $m^5U$ as noted.

FIGS. 23A-B show the results from Example 37: (A) EPO encoding mRNA with the indicated modifications and with or without HPLC purification were delivered to murine DCs and EPO levels in the supernatant were measured 24 hr later. While m5C/ψ-modified mRNA had the highest level of translation prior to HPLC purification, ψ-modified mRNA had the highest translation after HPLC purification. (B) Human DCs were transfected with *renilla* encoding mRNA with the indicated modifications with or without HPLC purification.

FIGS. 24A-C shows the results from Example 38: (A) Human DCs were transfected with RNA complexed to TransIT with the indicated modifications with or without HPLC purification. IFN-α levels were measured after 24 hr. HPLC purification increased the immunogenicity of unmodified RNA, which is dependent on the sequence, as other unmodified RNAs had similar levels of IFN-α or reduced levels after HPLC purification. ψ-modified RNA had unmeasurable levels of IFN-α, similar to control treated DCs. (B) ψ-modified RNA before (−) and after HPLC purification (P1 and P2) was analyzed for dsRNA using dot blotting with a monoclonal antibody specific for dsRNA (J2). Purification of RNA removed dsRNA contamination. (C) ψ-modified RNA encoding iPS factors are immunogenic, which is removed by HPLC purification of the RNA.

FIG. 25 provides the mRNA coding sequence for KLF4 (SEQ ID NO:12) and LIN28 (SEQ ID NO:13).

FIG. 26 provides the mRNA coding sequence for cMYC (SEQ ID NO:14) and NANOG (SEQ ID NO:15).

FIG. 27 provides the mRNA coding sequence for OCT4 (SEQ ID NO:16) and SOX2 (SEQ ID NO:17).

FIG. 28 shows phase contrast images of HEKn cells at 2 days (A) and iPS colony formation at 11 days (B) and 20 days (C) after the final transfection with mRNA encoding 4 reprogramming factors. Images are at 10× magnification.

FIG. 29 shows phase contrast images of colonies derived from HEKn cells (A, D, and G). The same iPS colony shown in (A) is positive for both KLF4 (B) and LIN28 (C). The iPS colony shown in (D) is SSEA4-positive (E) and TRA-1-60-positive (F). The iPS colony shown in (G) is NANOG-positive (H). All images are at 20× magnification.

DEFINITIONS

Figure 1:
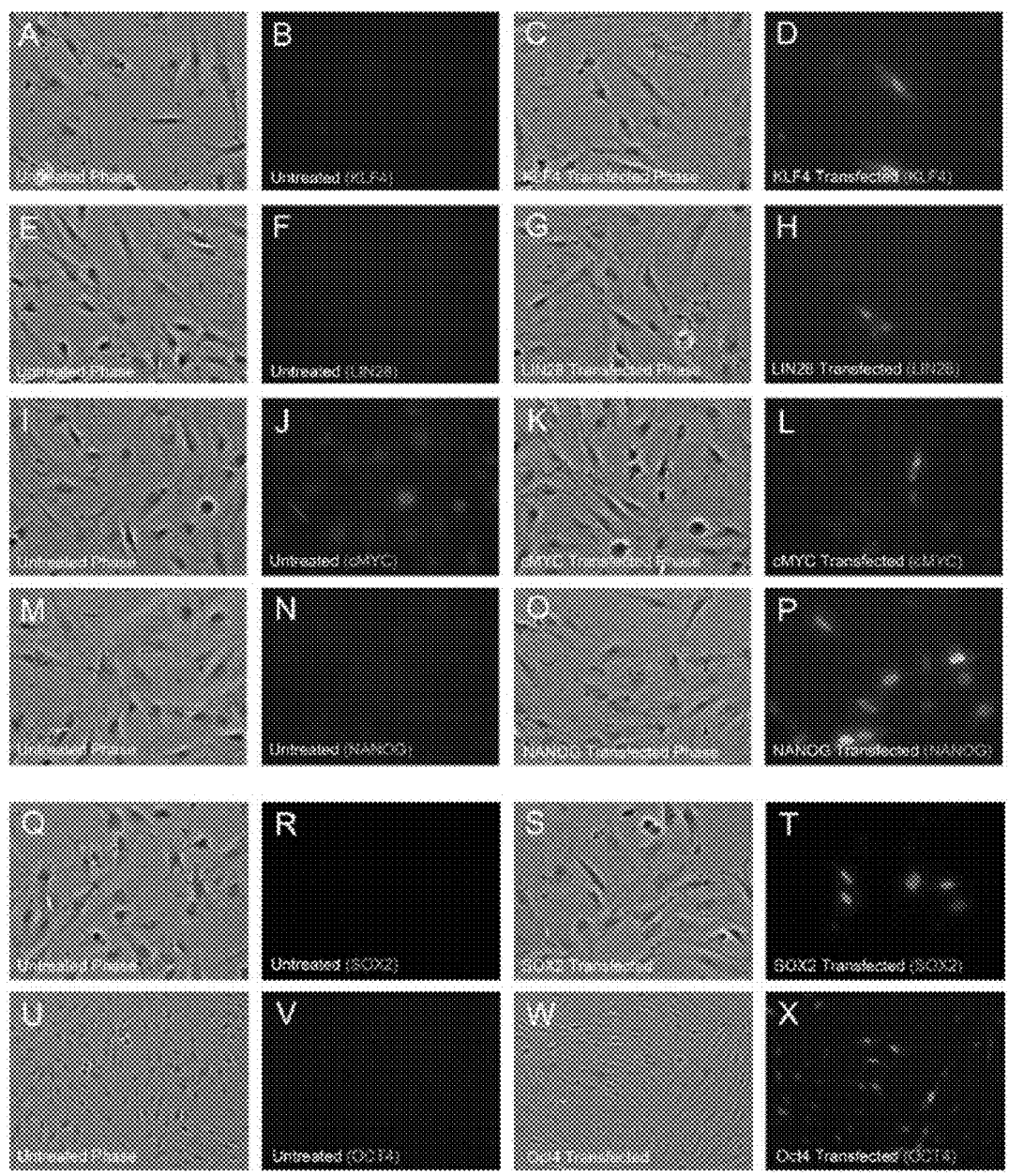
FIG. 1 shows that mRNAs encoding each of the six human reprogramming factors, prepared as described in the EXAMPLES, are translated and localized to the predicted subcellular locations after transfection into human newborn 1079 fibroblasts. Untreated human 1079 fibroblasts: Photos A, E, I, M, Q, and U show phase contrast images of the untreated human 1079 fibroblasts which were not transfected with an mRNA encoding a reprogramming factor and photos B, F, J, N, R, and V show fluorescent images of the same fields after the cells were stained with an antibody specific for each reprogramming factor; these results show that there was little or none of these endogenous reprogramming factor proteins in untreated human 1079 fibroblasts. Treated human 1079 fibroblasts: Photos C, G, K, O, S, and W show phase contrast images of the human 1079 fibroblasts which were transfected with an mRNA encoding the indicated reprogramming factor, and photos D, H, L, P, T, and X show fluorescent images of the same fields after the cells were stained with an antibody specific for each reprogramming factor 24 hours after transfection. These results show that each of the reprogramming factor proteins was expressed in the human 1079 fibroblast cells 24 hours after transfection with the respective reprogramming factor-encoding mRNAs and that the reprogramming factor proteins were localized in the predicted subcellular locations. A-T are at 20× magnification. U-X are at 10× magnification.

The present invention will be understood and interpreted based on terms as defined below.

As used herein "substantially all," in reference to single-stranded complete mRNAs comprising a pseudouridine or 5-methylcytidine residue, means that of all the single-stranded complete mRNAs present in a sample, at least 95% have either a pseudouridine or 5-methylcytidine residue.

As used herein "essentially all," in reference to single-stranded complete mRNAs comprising a pseudouridine or 5-methylcytidine residue, means that of all the single-stranded complete mRNAs present in a sample, at least 99% have either a pseudouridine or 5-methylcytidine residue.

As used herein "RNA contaminant molecules" are molecules that comprise RNA residues and that can at least partially activate an immune response when transfected into a cell (e.g., by activating RNA sensors such as RNA-dependent protein kinase (PKR), retinoic acid-inducible gene-I (RIG-I), Toll-like receptor (TLR)3, TLR7, TLR8, and oligoadenylate synthetase (OAS), or RNA molecules that can at least partially activate an RNA interference (RNAi) response (e.g., including a response to large double-stranded RNA molecules or to small double-stranded RNA molecules (siRNAs)) in the cell. Exemplary RNA contaminant molecules include, but are not limited to: partial or non-full-length mRNAs encoding only a portion of a reprogramming factor (e.g., a non-full-length iPS cell induction factor); single-stranded mRNAs that are greater than the full-length mRNA that encodes a reprogramming factor (e.g., an iPS cell induction factor), e.g., without being bound by theory, by "run-on IVT" or other mechanisms; double-stranded large or small mRNA molecules; and uncapped mRNA molecules.

As used herein, a purified RNA preparation is "substantially free" of RNA contaminant molecules (or a particular recited RNA contaminant), when less than 0.5% of the total RNA in the purified RNA preparation consists of RNA contaminant molecules (or a particularly recited RNA contaminant). The amounts and relative amounts of non-contaminant mRNA molecules and RNA contaminant molecules (or a particular RNA contaminant) may be determined by HPLC or other methods used in the art to separate and quantify RNA molecules.

As used herein, a purified RNA preparation is "essentially free" of RNA contaminant molecules (or a particular recited RNA contaminant), when less than 1.0% of the total RNA in the purified RNA preparation consists of RNA contaminant molecules (or a particularly recited RNA contaminant). The amounts and relative amounts of non-contaminant mRNA molecules and RNA contaminant molecules (or a particular RNA contaminant) may be determined by HPLC or other methods used in the art to separate and quantify RNA molecules.

As used herein, a purified RNA preparation is "virtually free" of RNA contaminant molecules (or a particular recited RNA contaminant), when less than 0.1% of the total RNA in the purified RNA preparation consists of RNA contaminant molecules (or a particularly recited RNA contaminant). The amounts and relative amounts of non-contaminant mRNA molecules and RNA contaminant molecules (or a particular RNA contaminant) may be determined by HPLC or other methods used in the art to separate and quantify RNA molecules.

As used herein, a purified RNA preparation is "free" of RNA contaminant molecules (or a particular recited RNA contaminant), when less than 0.01% of the total RNA in the purified RNA preparation consists of RNA contaminant molecules (or a particularly recited RNA contaminant). The amounts and relative amounts of non-contaminant mRNA molecules and RNA contaminant molecules (or a particular RNA contaminant) may be determined by HPLC or other methods used in the art to separate and quantify RNA molecules.

The terms "comprising", "containing", "having", "include", and "including" are to be construed as "including, but not limited to" unless otherwise noted. The terms "a," "an," and "the" and similar referents in the context of describing the invention and, specifically, in the context of the appended claims, are to be construed to cover both the singular and the plural unless otherwise noted. The use of any and all examples or exemplary language ("for example", "e.g.", "such as") is intended merely to illustrate aspects or embodiments of the invention, and is not to be construed as limiting the scope thereof, unless otherwise claimed.

With respect to the use of the word "derived", such as for an RNA (including mRNA) or a polypeptide that is "derived" from a sample, biological sample, cell, tumor, or the like, it is meant that the RNA or polypeptide either was present in the sample, biological sample, cell, tumor, or the like, or was made using the RNA in the sample, biological sample, cell, tumor, or the like by a process such as an in vitro transcription reaction, or an RNA amplification reaction, wherein the RNA or polypeptide is either encoded by or a copy of all or a portion of the RNA or polypeptide molecules in the original sample, biological sample, cell, tumor, or the like. By way of example, such RNA can be from an in vitro transcription or an RNA amplification reaction, with or without cloning of cDNA, rather than being obtained directly from the sample, biological sample, cell, tumor, or the like, so long as the original RNA used for the in vitro transcription or an RNA amplification reaction was from the sample, biological sample, cell, tumor, or the like. The terms "sample" and "biological sample" are used in their broadest sense and encompass samples or specimens obtained from any source that contains or may contain eukaryotic cells, including biological and environmental sources. As used herein, the term "sample" when used to refer to biological samples obtained from organisms, includes bodily fluids (e.g., blood or saliva), feces, biopsies, swabs (e.g., buccal swabs), isolated cells, exudates, and the like. The organisms include fungi, plants, animals, and humans. However, these examples are not to be construed as limiting the types of samples or organisms that find use with the present invention. In addition, in order to perform research or study the results related to use of a method or composition of the invention, in some embodiments, a "sample" or "biological sample" comprises fixed cells, treated cells, cell lysates, and the like. In some embodiments, such as embodiments of the method wherein the mRNA is delivered into a cell from an organism that has a known disease or into a cell that exhibits a disease state or a known pathology, the "sample" or "biological sample" also comprises bacteria or viruses.

As used herein, the term "incubating" and variants thereof mean contacting one or more components of a reaction with another component or components, under conditions and for sufficient time such that a desired reaction product is formed.

As used herein, a "nucleoside" consists of a nucleic acid base (e.g., the canonical nucleic acid bases: guanine (G), adenine (A), thymine (T), uracil (U), and cytosine (C)); or a modified nucleic acid base (e.g., 5-methylcytosine ($m^5C$)), that is covalently linked to a pentose sugar (e.g., ribose or 2'-deoxyribose), whereas and a "nucleotide" or "mononucleotide" consists of a nucleoside that is phosphorylated at one of the hydroxyl groups of the pentose sugar. Linear nucleic acid molecules are said to have a "5' terminus" (5' end) and a "3' terminus" (3' end) because, except with respect to capping or adenylation (e.g., adenylation by a ligase), mononucleotides are joined in one direction via a phosphodiester linkage to make oligonucleotides or polynucleotides, in a manner such that a phosphate on the 5' carbon of one mononucleotide sugar moiety is joined to an oxygen on the 3' carbon of the sugar moiety of its neighboring mononucleotide. Therefore, an end of a linear single-stranded oligonucleotide or polynucleotide or an end of one strand of a linear double-stranded nucleic acid (RNA or DNA) is referred to as the "5' end" if its 5' phosphate is not joined or linked to the oxygen of the 3' carbon of a mononucleotide sugar moiety, and as the "3' end" if its 3' oxygen is not joined to a 5' phosphate that is joined to a sugar of another mononucleotide. A terminal nucleotide, as used herein, is the nucleotide at the end position of the 3' or 5' terminus.

In order to accomplish specific goals, a nucleic acid base, sugar moiety, or internucleoside (or internucleotide) linkage in one or more of the nucleotides of the mRNA that is introduced into a eukaryotic cell in any of the methods of the invention may comprise a modified base, sugar moiety, or internucleoside linkage. For example, in addition to the other modified nucleotides discussed elsewhere herein for performing the methods of the present invention, one or more of the nucleotides of the mRNA can also have a modified nucleic acid base comprising or consisting of: xanthine; allyamino-uracil; allyamino-thymidine; hypoxanthine; 2-aminoadenine; 5-propynyl uracil; 5-propynyl cytosine; 4-thiouracil; 6-thioguanine; an aza or deaza uracil; an aza or deaza thymidine; an aza or deaza cytosines; an aza or deaza adenine; or an aza or deaza guanines; or a nucleic acid base that is derivatized with a biotin moiety, a digoxigenin moiety, a fluorescent or chemiluminescent moiety, a quenching moiety or some other moiety in order to accomplish one or more specific other purposes; and/or one or more of the nucleotides of the mRNA can have a sugar moiety, such as, but not limited to: 2'-fluoro-2'-deoxyribose or 2'-O-methylribose, which provide resistance to some nucleases; or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

In some embodiments of the invention, one or more of the nucleotides of the mRNA comprises a modified internucleoside linkage, such as a phosphorothioate, phosphorodithioate, phosphoroselenate, or phosphorodiselenate linkage, which are resistant to some nucleases, including in a dinucleotide cap analog (Grudzien-Nogalska et al. 2007) that is used in an IVT reaction for co-transcriptional capping of the RNA, or in the poly(A) tail (e.g., by incorporation of a nucleotide that has the modified phosphorothioate, phosphorodithioate, phosphoroselenate, or phosphorodiselenate linkage during IVT of the RNA or, e.g., by incorporation of ATP that contains the modified phosphorothioate, phosphorodithioate, phosphoroselenate, or phosphorodiselenate linkage into a poly(A) tail on the RNA by polyadenylation using a poly(A) polymerase). The invention is not limited to the modified nucleic acid bases, sugar moieties, or internucleoside linkages listed, which are presented to show examples which may be used for a particular purpose in a method.

As used herein, a "nucleic acid" or a "polynucleotide" or an "oligonucleotide" is a covalently linked sequence of nucleotides in which the 3' position of the sugar moiety of one nucleotide is joined by a phosphodiester bond to the 5' position of the sugar moiety of the next nucleotide (i.e., a 3' to 5' phosphodiester bond), and in which the nucleotides are linked in specific sequence; i.e., a linear order of nucleotides. In some embodiments, the nucleic acid or polynucleotide or oligonucleotide consists of or comprises 2'-deoxyribonucleotides (DNA). In some embodiments, the oligonucleotide consists of or comprises ribonucleotides (RNA).

The terms "isolated" or "purified" when used in relation to a polynucleotide or nucleic acid, as in "isolated RNA" or "purified RNA" refers to a nucleic acid that is identified and separated from at least one contaminant with which it is ordinarily associated in its source. Thus, an isolated or purified nucleic acid (e.g., DNA and RNA) is present in a form or setting different from that in which it is found in nature, or a form or setting different from that which existed prior to subjecting it to a treatment or purification method. For example, a given DNA sequence (e.g., a gene) is found on the host cell chromosome together with other genes as well as structural and functional proteins, and a specific RNA (e.g., a specific mRNA encoding a specific protein), is found in the cell as a mixture with numerous other RNAs and other cellular components. The isolated or purified polynucleotide or nucleic acid may be present in single-stranded or double-stranded form.

A "cap" or a "cap nucleotide" means a nucleoside-5'-triphosphate that, under suitable reaction conditions, is used as a substrate by a capping enzyme system and that is thereby joined to the 5'-end of an uncapped RNA comprising primary RNA transcripts or RNA having a 5'-diphosphate. The nucleotide that is so joined to the RNA is also referred to as a "cap nucleotide" herein. A "cap nucleotide" is a guanine nucleotide that is joined through its 5' end to the 5' end of a primary RNA transcript. The RNA that has the cap nucleotide joined to its 5' end is referred to as "capped RNA" or "capped RNA transcript" or "capped transcript." A common cap nucleoside is 7-methylguanosine or $N^7$-methylguanosine (sometimes referred to as "standard cap"), which has a structure designated as "$m^7G$," in which case the capped RNA or "$m^7G$-capped RNA" has a structure designated as $m^7G(5)ppp(5')N_1(pN)_x$—OH(3'), or more simply, as $m^7GpppN_1(pN)_x$ or $m^7G[5']ppp[5']N$, wherein $m^7G$ represents the 7-methylguanosine cap nucleoside, ppp represents the triphosphate bridge between the 5' carbons of the cap nucleotide and the first nucleotide of the primary RNA transcript, $N_1(pN)_x$—OH(3') represents the primary RNA transcript, of which $N_1$ is the most 5'-nucleotide, "p" represents a phosphate group, "G" represents a guanosine nucleoside, "$m^7$" represents the methyl group on the 7-position of guanine, and "[5']" indicates the position at which the "p" is joined to the ribose of the cap nucleotide and the first nucleoside of the mRNA transcript ("N"). In addition to this "standard cap," a variety of other naturally-occurring and synthetic cap analogs are known in the art. RNA that has any cap nucleotide is referred to as "capped RNA." The capped RNA can be naturally occurring from a biological sample or it can be obtained by in vitro capping of RNA that has a 5' triphosphate group or RNA that has a 5' diphosphate group with a capping enzyme system (e.g., vaccinia capping enzyme system or *Saccharomyces cerevisiae* capping enzyme system). Alternatively, the capped RNA can be obtained by in vitro transcription (IVT) of a DNA template that contains an RNA polymerase promoter, wherein, in addition to the GTP, the IVT reaction also contains a dinucleotide cap analog (e.g., a $m^7GpppG$ cap analog or an $N^7$-methyl, 2'-O-methyl-GpppG ARCA cap analog or an $N^7$-methyl, 3'-O-methyl-GpppG ARCA cap analog) using methods known in the art (e.g., using an AMPLICAP™ T7 capping kit or a MESSAGEMAX™ T7 ARCA-CAPPED MESSAGE Transcription Kit, EPICENTRE or CellScript).

Capping of a 5'-triphosphorylated primary mRNA transcript in vivo (or using a capping enzyme system in vitro) occurs via several enzymatic steps (Higman et al. 1992, Martin et al. 1975, Myette and Niles 1996).

The following enzymatic reactions are involved in capping of eukaryotic mRNA:

(1) RNA triphosphatase cleaves the 5'-triphosphate of mRNA to a diphosphate, $pppN_1(p)N_x$—OH(3')→$ppN_1(pN)_x$—OH(3')+Pi; and then (2) RNA guanyltransferase catalyzes joining of GTP to the 5'-diphosphate of the most 5' nucleotide ($N_1$) of the mRNA, $ppN_1(pN)_x$—OH(3')+GTP→$G(5')ppp(5')N_1(pN)_x$—OH(3')+PPi; and finally, (3) guanine-7-methyltransferase, using S-adenosyl-methionine (AdoMet) as a co-factor, catalyzes methylation of the 7-nitrogen of guanine in the cap nucleotide, $G(5')ppp(5')N_1(pN)_x$—OH(3')+AdoMet→$m^7G(5')ppp(5')N_1(pN)_x$—OH(3')+AdoHyc. RNA that results from the action of the RNA triphosphatase and the RNA guanyltransferase enzymatic activities, as well as RNA that is additionally methylated by the guanine-7-methyltransferase enzymatic activity, is referred to herein as "5' capped RNA" or "capped RNA", and a "capping enzyme system" or, more simply, a "capping enzyme" herein means any combination of one or more polypeptides having the enzymatic activities that result in "capped RNA." Capping enzyme systems, including cloned forms of such enzymes, have been identified and purified from many sources and are well known in the art (Banerjee 1980, Higman et al. 1992, Higman et al. 1994, Myette and Niles 1996, Shuman 1995, Shuman 2001, Shuman et al. 1980, Wang et al. 1997). Any capping enzyme system that can convert uncapped RNA that has a 5' polyphosphate to capped RNA can be used to provide a capped RNA for any of the embodiments of the present invention. In some embodiments, the capping enzyme system is a poxvirus capping enzyme system. In some preferred embodiments, the capping enzyme system is vaccinia virus capping enzyme. In some embodiments, the capping enzyme system is *Saccharomyces cerevisiae* capping enzyme. Also, in view of the fact that genes encoding RNA triphosphatase, RNA guanyltransferase and guanine-7-methyltransferase from one source can complement deletions in one or all of these genes from another source, the capping enzyme system can originate from one source, or one or more of the RNA triphosphatase, RNA guanyltransferase, and/or guanine-7-methyltransferase activities can comprise a polypeptide from a different source.

A "modified cap nucleotide" of the present invention means a cap nucleotide wherein the sugar, the nucleic acid base, or the internucleoside linkage is chemically modified compared to the corresponding canonical 7-methylguanosine cap nucleotide. Examples of a modified cap nucleotide include a cap nucleotide comprising: (i) a modified 2'- or 3'-deoxyguanosine-5'-triphosphate (or guanine 2'- or 3'-deoxyribonucleic acid-5'-triphosphate) wherein the 2'- or 3'-deoxy position of the deoxyribose sugar moiety is substituted with a group comprising an amino group, an azido group, a fluorine group, a methoxy group, a thiol (or mercapto) group or a methylthio (or methylmercapto) group; or (ii) a modified guanosine-5'-triphosphate, wherein the $O^6$ oxygen of the guanine base is methylated; or (iii) 3'-deoxyguanosine. For the sake of clarity, it will be understood herein that an "alkoxy-substituted deoxyguanosine-5'-triphosphate" can also be referred to as an "O-alkyl-substituted guanosine-5'-triphosphate"; by way of example, but without limitation, 2'-methoxy-2'-deoxyguanosine-5'-triphosphate (2'-methoxy-2'-dGTP) and 3'-methoxy-3'-deoxyguanosine-5'-triphosphate (3'-methoxy-3'-dGTP) can also be referred to herein as 2'-O-methylguanosine-5'-triphosphate (2'-OMe-GTP) and 3'-O-methylguanosine-5'-triphosphate (3'-OMe-GTP), respectively. Following joining of the modified cap nucleotide to the 5'-end of the uncapped RNA comprising primary RNA transcripts (or RNA having a 5'-diphosphate), the portion of said modified cap nucleotide that is joined to the uncapped RNA comprising primary RNA transcripts (or RNA having a 5'-diphosphate) may be referred to herein as a "modified cap nucleoside" (i.e., without referring to the phosphate groups to which it is joined), but sometimes it is referred to as a "modified cap nucleotide".

A "modified-nucleotide-capped RNA" is a capped RNA molecule that is synthesized using a capping enzyme system and a modified cap nucleotide, wherein the cap nucleotide on its 5' terminus comprises the modified cap nucleotide, or a capped RNA that is synthesize co-transcriptionally in an in vitro transcription reaction that contains a modified dinucleotide cap analog wherein the dinucleotide cap analog contains the chemical modification in the cap nucleotide. In some embodiments, the modified dinucleotide cap analog is an anti-reverse cap analog or ARCA (Grudzien et al. 2004, Jemielity et al. 2003, Grudzien-Nogalska et al. 2007, Peng et al. 2002, Stepinski et al. 2001).

A "primary RNA" or "primary RNA transcript" means an RNA molecule that is synthesized by an RNA polymerase in vivo or in vitro and which RNA molecule has a triphosphate on the 5'-carbon of its most 5' nucleotide.

An "RNA amplification reaction" or an "RNA amplification method" means a method for increasing the amount of RNA corresponding to one or multiple desired RNA sequences in a sample. For example, in some embodiments, the RNA amplification method comprises: (a) synthesizing first-strand cDNA complementary to the one or more desired RNA molecules by RNA-dependent DNA polymerase extension of one or more primers that anneal to the desired RNA molecules; (b) synthesizing double-stranded cDNA from the first-strand cDNA using a process wherein a functional RNA polymerase promoter is joined thereto; and (c) contacting the double-stranded cDNA with an RNA polymerase that binds to said promoter under transcription conditions whereby RNA corresponding to the one or more desired RNA molecules is obtained. Unless otherwise stated related to a specific embodiment of the invention, an RNA amplification reaction according to the present invention means a sense RNA amplification reaction, meaning an RNA amplification reaction that synthesizes sense RNA (e.g., RNA having the same sequence as an mRNA or other primary RNA transcript, rather than the complement of that sequence). Sense RNA amplification reactions known in the art, which are encompassed within this definition include, but are not limited to, the methods which synthesize sense RNA described in Ozawa et al. (Ozawa et al. 2006) and in U.S. Patent Application Nos. 20090053775; 20050153333; 20030186237; 20040197802; and 20040171041. The RNA amplification method described in U.S. Patent Application No. 20090053775 is a preferred method for obtaining amplified RNA derived from one or more cells, which amplified RNA is then used to make mRNA for use in the methods of the present invention.

A "poly-A polymerase" ("PAP") means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (Edmonds 1990) are highly conserved structurally (Gershon 2000) and lack intrinsic specificity for particular sequences or sizes of RNA molecules if the PAP is separated from proteins that recognize AAUAAA polyadenylation signals (Wilusz and Shenk 1988), purified wild-type and recombinant PAP enzymes from any of a variety of sources can be used for the present invention. In some embodiments, a PAP enzyme from *Saccharomyces* (e.g., from *S. cerevisiae*) is used for polyadenylation to make purified RNA preparations comprising or consisting of one or more modified mRNAs, each of which encodes a reprogramming factor (e.g., an iPS cell induction factor). In some embodiments, a PAP enzyme from *E. coli* is used for polyadenylation to make purified RNA preparations comprising or consisting of one or more modified mRNAs, each of which encodes a reprogramming factor (e.g., an iPS cell induction factor).

A "reprogramming factor" means a protein, polypeptide, or other biomolecule that, when used alone or in combination with other factors or conditions, causes a change in the state of differentiation of a cell in which the reprogramming factor is introduced or expressed. In some preferred embodiments of the methods of the present invention, the reprogramming factor is a protein or polypeptide that is encoded by an mRNA that is introduced into a cell, thereby generating a cell that exhibits a changed state of differentiation compared to the cell in which the mRNA was introduced. In some preferred embodiments of the methods of the present invention, the reprogramming factor is a transcription factor. One embodiment of a reprogramming factor used in a method of the present invention is an "iPS cell induction factor."

An "iPS cell induction factor" or "iPSC induction factor" is a protein, polypeptide, or other biomolecule that, when used alone or in combination with other reprogramming factors, causes the generation of iPS cells from somatic cells. Examples of iPS cell induction factors include OCT4, SOX2, c-MYC, KLF4, NANOG and LIN28. iPS cell induction factors include full length polypeptide sequences or biologically active fragments thereof. Likewise an mRNA encoding an iPS cell induction factor may encode a full length polypeptide or biologically active fragments thereof. The mRNA coding sequence for exemplary iPS induction factors are shown in FIGS. 25 (KLF4 and LIN28), 26 (cMYC and NANOG), and 27 (OCT4 and SOX2). In certain embodiments, the present invention employs the sequences or similar sequences shown in these figures, including mRNA molecules that additionally comprise, joined to these mRNA sequences, oligoribonucleotides which exhibit any of the 5' and 3' UTR sequences, Kozak sequences, IRES sequences, cap nucleotides, and/or poly(A) sequences used in the experiments described herein, or which are generally known in the art and which can be used in place of those used herein by joining them to these protein-coding mRNA sequences for the purpose of optimizing translation of the respective mRNA molecules in the cells and improving their stability in the cell in order to accomplish the methods described herein.

"Differentiation" or "cellular differentiation" means the naturally occurring biological process by which a cell that exhibits a less specialized state of differentiation or cell type (e.g., a fertilized egg cell, a cell in an embryo, or a cell in a eukaryotic organism) becomes a cell that exhibits a more specialized state of differentiation or cell type. Scientists, including biologists, cell biologists, immunologists, and embryologists, use a variety of methods and criteria to define, describe, or categorize different cells according to their "cell type," "differentiated state," or "state of differentiation." In general, a cell is defined, described, or categorized with respect to its "cell type," "differentiated state," or "state of differentiation" based on one or more phenotypes exhibited by that cell, which phenotypes can include shape, a biochemical or metabolic activity or function, the presence of certain biomolecules in the cell (e.g., based on stains that react with specific biomolecules), or on the cell (e.g., based on binding of one or more antibodies that react with specific biomolecules on the cell surface). For example, in some embodiments, different cell types are identified and sorted using a cell sorter or fluorescent-activated cell sorter (FACS) instrument. "Differentiation" or "cellular differentiation" can also occur to cells in culture.

The term "reprogramming" as used herein means differentiation or cellular differentiation that occurs in response to delivery of one or more reprogramming factors into the cell, directly (e.g., by delivery of protein or polypeptide reprogramming factors into the cell) or indirectly (e.g., by delivery of the purified RNA preparation of the present invention which comprises one or more mRNA molecules, each of which encodes a reprogramming factor) and maintaining the cells under conditions (e.g., medium, temperature, oxygen and $CO_2$ levels, matrix, and other environmental conditions) that are conducive for differentiation. The term "reprogramming" when used herein is not intended to mean or refer to a specific direction or path of differentiation (e.g., from a less specialized cell type to a more specialized cell type) and does not exclude processes that proceed in a direction or path of differentiation than what is normally observed in nature. Thus, in different embodiments of the present invention, "reprogramming" means and includes any and all of the following:

(1) "Dedifferentiation", meaning a process of a cell that exhibits a more specialized state of differentiation or cell type (e.g., a mammalian fibroblast, a keratinocyte, a muscle cell, or a neural cell) going to a cell that exhibits a less specialized state of differentiation or cell type (e.g., an iPS cell);

(2) "Transdifferentiation", meaning a process of a cell that exhibits a more specialized state of differentiation or cell type (e.g., a mammalian fibroblast, a keratinocyte, or a neural cell) going to another more specialized state of differentiation or cell type (e.g., from a fibroblast or keratinocyte to a muscle cell); and (3) "Redifferentiation" or "Expected Differentiation" or Natural Differentiation", meaning a process of a cell that exhibits any particular state of differentiation or cell type going to another state of differentiation or cell type as would be expected in nature if the cell was present in its natural place and environment (e.g., in an embryo or an organism), whether said process occurs in vivo in an organism or in culture (e.g., in response to one or more reprogramming factors).

DESCRIPTION OF THE INVENTION

The present invention provides compositions and methods for reprogramming the state of differentiation of eukaryotic cells, including human or other animal cells, by contacting the cells with purified RNA preparations comprising or consisting of one or more different single-strand mRNA molecules that each encode a reprogramming factor (e.g., an iPS cell induction factor). The purified single-stranded mRNA molecules preferably comprise at least one modified nucleoside selected from the group consisting of a pseudouridine (Ψ), 5-methylcytosine ($m^5C$), 5-methyluridine ($m^5U$), 2'-O-methyluridine (Um or $m^{2'-O}U$), 2-thiouridine ($s^2U$), and $N^6$-methyladenosine ($m^6A$) in place of at least a portion (e.g., including substantially all) of the corresponding unmodified canonical nucleoside of the corresponding unmodified A, C, G, or T canonical nucleoside. In addition, the single-stranded mRNA molecules are preferably purified to be substantially free of RNA contaminant molecules that would activate an unintended response, decrease expression of the single-stranded mRNA, and/or activate RNA sensors in the cells. In certain embodiments, the purified RNA preparations are substantially free of RNA contaminant molecules that are: shorter or longer than the full-length single-stranded mRNA molecules, double-stranded, and/or uncapped RNA. In some preferred embodiments, the invention provides compositions and methods for reprogramming differentiated eukaryotic cells, including human or other animal somatic cells, by contacting the cells with purified RNA preparations comprising or consisting of one or more different single-strand mRNA molecules that each encode an iPS cell induction factor.

In certain embodiments, the mRNA used in the purified RNA preparations is purified to remove substantially, essentially, or virtually all of the contaminants, including substantially, essentially, or virtually all of the RNA contaminants. The present invention is not limited with respect to the purification methods used to purify the mRNA, and the invention includes use of any method that is known in the art or developed in the future in order to purify the mRNA and remove contaminants, including RNA contaminants, that interfere with the intended use of the mRNA. For example, in preferred embodiments, the purification of the mRNA removes contaminants that are toxic to the cells (e.g., by inducing an innate immune response in the cells, or, in the case of RNA contaminants comprising double-stranded RNA, by inducing RNA interference (RNAi), e.g., via siRNA or long RNAi molecules) and contaminants that directly or indirectly decrease translation of the mRNA in the cells). In some embodiments, the mRNA is purified by HPLC using a method described herein, including in the Examples. In certain embodiments, the mRNA is purified using on a polymeric resin substrate comprising a C18 derivatized styrene-divinylbenzene copolymer and a triethylamine acetate (TEAA) ion pairing agent is used in the column buffer along with the use of an acetonitrile gradient to elute the mRNA and separate it from the RNA contaminants in a size-dependent manner; in some embodiments, the mRNA purification is performed using HPLC, but in some other embodiments a gravity flow column is used for the purification. In some embodiments, the mRNA is purified using a method described in the book entitled "RNA Purification and Analysis" by Douglas T. Gjerde, Lee Hoang, and David Hornby, published by Wiley-VCH, 2009, herein incorporated by reference. In some embodiments, the mRNA purification is carried out in a non-denaturing mode (e.g., at a temperature less than about 50 degrees C., e.g., at ambient temperature). In some embodiments, the mRNA purification is carried out in a partially denaturing mode (e.g., at a temperature less than about 50 degrees C. and 72 degrees C.). In some embodiments, the mRNA purification is carried out in a denaturing mode (e.g., at a temperature greater than about 72 degrees C.). Of course, those with knowledge in the art will know that the denaturing temperature depends on the melting temperature (Tm) of the mRNA that is being purified as well as on the melting temperatures of RNA, DNA, or RNA/DNA hybrids which contaminate the mRNA. In some other embodiments, the mRNA is purified as described by Mellits K H et al. (Removal of double-stranded contaminants from RNA transcripts: synthesis of adenovirus VA RNA1 from a T7 vector. Nucleic Acids Research 18: 5401-5406, 1990, herein incorporated by reference in its entirety). These authors used a three step purification to remove the contaminants which may be used in embodiments of the present invention. Step 1 was 8% polyacrylamide gel electrophoresis in 7M urea (denaturing conditions). The major RNA band was excised from the gel slice and subjected to 8% polyacrylamide gel electrophoresis under nondenaturing condition (no urea) and the major band recovered from the gel slice. Further purification was done on a cellulose CF-11 column using an ethanol-salt buffer mobile phase which separates double stranded RNA from single stranded RNA (Franklin R M. 1966. Proc. Natl. Acad. Sci. USA 55: 1504-1511; Barber R. 1966. Biochem. Biophys. Acta 114:422; and Zelcer A et al. 1982. J. Gen. Virol. 59: 139-148, all of which are herein incorporated by reference) and the final purification step was cellulose chromatography. In some other embodiments, the mRNA is purified using an hydroxylapatite (HAP) column under either non-denaturing conditions or at higher temperatures (e.g., as described by Pays E. 1977. Biochem. J. 165: 237-245; Lewandowski L J et al. 1971. J. Virol. 8: 809-812;

Clawson G A and Smuckler E A. 1982. Cancer Research 42: 3228-3231; and/or Andrews-Pfannkoch C et al. 2010. Applied and Environmental Microbiology 76: 5039-5045, all of which are herein incorporated by reference). In some other embodiments, the mRNA is purified by weak anion exchange liquid chromatography under non-denaturing conditions (e.g., as described by Easton L E et al. 2010. RNA 16: 647-653 to clean up in vitro transcription reactions, herein incorporated by reference). In some embodiments, the mRNA is purified using a combination of any of the above methods or another method known in the art or developed in the future. In still another embodiment, the mRNA used in the compositions and methods of the present invention is purified using a process which comprises treating the mRNA with an enzyme that specifically acts (e.g., digests) one or more contaminant RNA or contaminant nucleic acids (e.g., including DNA), but which does not act on (e.g., does not digest) the desired mRNA. For example, in some embodiments, the mRNA used in the compositions and methods of the present invention is purified using a process which comprises treating the mRNA with a ribonuclease III (RNase III) enzyme (e.g., E. coli RNase III) and the mRNA is then purified away from the RNase III digestion products. A ribonuclease III (RNase III) enzyme herein means an enzyme that digests double-stranded RNA greater than about twelve basepairs to shore double-stranded RNA fragments. In some embodiments, the mRNA used in the compositions and methods of the present invention is purified using a process which comprises treating the mRNA with one or more other enzymes that specifically digest one or more contaminant RNAs or contaminant nucleic acids (e.g., including DNA).

This invention provides RNA, oligoribonucleotide, and polyribonucleotide molecules comprising pseudouridine or a modified nucleoside, gene therapy vectors comprising same, gene therapy methods and gene transcription silencing methods comprising same, methods of reducing an immunogenicity of same, and methods of synthesizing same. These modified sequences are preferably present in the purified RNA preparations described herein.

In one embodiment, the present invention provides a messenger RNA comprising a pseudouridine residue. In another embodiment, the messenger RNA encodes a protein of interest. Each possibility represents a separate embodiment of the present invention. In another embodiment, the present invention provides an RNA molecule encoding a protein of interest, said RNA molecule comprising a pseudouridine residue. In another embodiment, the present invention provides in vitro-transcribed RNA molecule, comprising a pseudouridine. In another embodiment, the present invention provides an in vitro-transcribed RNA molecule, comprising a modified nucleoside.

As provided herein, the present invention provides methods for synthesizing in vitro-transcribed RNA molecules, comprising pseudouridine and/or modified nucleosides. In another embodiment, the present invention provides a messenger RNA molecule comprising a pseudouridine residue.

In another embodiment, an in vitro-transcribed RNA molecule of methods and compositions of the present invention is synthesized by T7 phage RNA polymerase. In another embodiment, the molecule is synthesized by SP6 phage RNA polymerase. In another embodiment, the molecule is synthesized by T3 phage RNA polymerase. In another embodiment, the molecule is synthesized by a polymerase selected from the above polymerases. In another embodiment, the in vitro-transcribed RNA molecule is an oligoribonucleotide. In another embodiment, the in vitro-transcribed RNA molecule is a polyribonucleotide. Each possibility represents a separate embodiment of the present invention. In another embodiment, the present invention provides an in vitro-synthesized oligoribonucleotide, comprising a pseudouridine or a modified nucleoside, wherein the modified nucleoside is $m^5C$, $m^5U$, $m^6A$, $s^2U$, $\psi$ or 2'-O-methyl-U. In another embodiment, the present invention provides an in vitro-synthesized polyribonucleotide, comprising a pseudouridine or a modified nucleoside, wherein the modified nucleoside is $m^5C$, $m^5U$, $m^6A$, $s^2U$, $\psi$ or 2'-O-methyl-U.

In another embodiment, the in vitro-synthesized oligoribonucleotide or polyribonucleotide is a short hairpin (sh) RNA. In another embodiment, the in vitro-synthesized oligoribonucleotide is a small interfering RNA (siRNA). In another embodiment, the in vitro-synthesized oligoribonucleotide is any other type of oligoribonucleotide known in the art. Each possibility represents a separate embodiment of the present invention.

In another embodiment, an RNA, oligoribonucleotide, or polyribonucleotide molecule of methods and compositions of the present invention further comprises an open reading frame that encodes a functional protein. In another embodiment, the RNA molecule or oligoribonucleotide molecule functions without encoding a functional protein (e.g. in transcriptional silencing), as an RNzyme, etc. Each possibility represents a separate embodiment of the present invention.

In another embodiment, the RNA, oligoribonucleotide, or polyribonucleotide molecule further comprises a poly-A tail. In another embodiment, the RNA, oligoribonucleotide, or polyribonucleotide molecule does not comprise a poly-A tail. Each possibility represents a separate embodiment of the present invention.

In another embodiment, the RNA, oligoribonucleotide, or polyribonucleotide molecule further comprises an m7GpppG cap. In another embodiment, the RNA, oligoribonucleotide, or polyribonucleotide molecule does not comprise an m7GpppG cap. Each possibility represents a separate embodiment of the present invention.

In another embodiment, the RNA, oligoribonucleotide, or polyribonucleotide molecule further comprises a cap-independent translational enhancer. In another embodiment, the RNA, oligoribonucleotide, or polyribonucleotide molecule does not comprise a cap-independent translational enhancer. In another embodiment, the cap-independent translational enhancer is a tobacco etch virus (TEV) cap-independent translational enhancer. In another embodiment, the cap-independent translational enhancer is any other cap-independent translational enhancer known in the art. Each possibility represents a separate embodiment of the present invention.

In another embodiment, the present invention provides a gene-therapy vector, comprising an in vitro-synthesized polyribonucleotide molecule, wherein the polyribonucleotide molecule comprises a pseudouridine or a modified nucleoside.

In another embodiment, an RNA, oligoribonucleotide, or polyribonucleotide molecule of methods and compositions of the present invention comprises a pseudouridine. In another embodiment, the RNA molecule or oligoribonucleotide molecule comprises a modified nucleoside. In another embodiment, the RNA molecule or oligoribonucleotide molecule is an in vitro-synthesized RNA molecule or oligoribonucleotide. Each possibility represents a separate embodiment of the present invention.

"Pseudouridine" refers, in another embodiment, to $m^1acp^3\psi$ (1-methyl-3-(3-amino-3-carboxypropyl) pseudouridine. In another embodiment, the term refers to $m^1\psi$ (1-methylpseudouridine). In another embodiment, the term refers to $\psi m$ (2'-O-methylpseudouridine. In another embodiment, the term refers to $m^5D$ (5-methyldihydrouridine). In another embodiment, the term refers to $m^3\psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In another embodiment, an RNA, oligoribonucleotide, or polyribonucleotide molecule of methods and compositions of the present invention is a therapeutic oligoribonucleotide.

In another embodiment, the present invention provides a method for delivering a recombinant protein to a subject, the method comprising the step of contacting the subject with an RNA, oligoribonucleotide, polyribonucleotide molecule, or a gene-therapy vector of the present invention, thereby delivering a recombinant protein to a subject.

In another embodiment, the present invention provides a double-stranded RNA (dsRNA) molecule comprising a pseudouridine or a modified nucleoside and further comprising an siRNA or short hairpin RNA (shRNA). In another embodiment, the dsRNA molecule is greater than 50 nucleotides in length. Each possibility represents a separate embodiment of the present invention.

In another embodiment, the pseudouridine or a modified nucleoside is within the siRNA sequence. In another embodiment, the pseudouridine or a modified nucleoside is outside the siRNA sequence. In another embodiment, 1 or more pseudouridine and/or a modified nucleoside residues are present both within and outside the siRNA sequence. Each possibility represents a separate embodiment of the present invention.

In another embodiment, the siRNA or shRNA is contained internally in the dsRNA molecule. In another embodiment, the siRNA or shRNA is contained on one end of the dsRNA molecule. In another embodiment, one or more siRNA or shRNA is contained on one end of the dsRNA molecule, while another one or more is contained internally. Each possibility represents a separate embodiment of the present invention.

In another embodiment, the length of an RNA, oligoribonucleotide, or polyribonucleotide molecule (e.g. a single-stranded RNA (ssRNA) or dsRNA molecule) of methods and compositions of the present invention is greater than 30 nucleotides in length. In another embodiment, the RNA molecule or oligoribonucleotide is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides. Each possibility represents a separate embodiment of the present invention.

In another embodiment, a dsRNA molecule of methods and compositions of the present invention is manufactured by in vitro-transcription. In another embodiment, the step of in vitro-transcription utilizes T7 phage RNA polymerase. In another embodiment, the in vitro-transcription utilizes SP6 phage RNA polymerase. In another embodiment, the in vitro-transcription utilizes T3 phage RNA polymerase. In another embodiment, the in vitro-transcription utilizes an RNA polymerase selected from the above polymerases. In another embodiment, the in vitro-transcription utilizes any other RNA polymerase known in the art. Each possibility represents a separate embodiment of the present invention.

In another embodiment, the dsRNA molecule is capable of being processed by a cellular enzyme to yield the siRNA or shRNA. In another embodiment, the cellular enzyme is an endonuclease. In another embodiment, the cellular enzyme is Dicer. Dicer is an RNase III-family nuclease that initiates RNA interference (RNAi) and related phenomena by generation of the small RNAs that determine the specificity of these gene silencing pathways (Bernstein E, Caudy A A et al, Role for a bidentate ribonuclease in the initiation step of RNA interference. Nature 2001; 409(6818): 363-6). In another embodiment, the cellular enzyme is any other cellular enzyme known in the art that is capable of cleaving a dsRNA molecule. Each possibility represents a separate embodiment of the present invention.

In another embodiment, the dsRNA molecule contains two siRNA or shRNA. In another embodiment, the dsRNA molecule contains three siRNA or shRNA. In another embodiment, the dsRNA molecule contains more than three siRNA or shRNA. In another embodiment, the siRNA and/or shRNA are liberated from the dsRNA molecule by a cellular enzyme. Each possibility represents a separate embodiment of the present invention.

In another embodiment, the present invention provides a method for administering an siRNA or shRNA to a cell, comprising administering a dsRNA molecule of the present invention, wherein the cell processes the dsRNA molecule to yield the siRNA or shRNA, thereby administering a siRNA or shRNA to a cell.

In another embodiment, the nucleoside that is modified in an RNA, oligoribonucleotide, or polyribonucleotide molecule of methods and compositions of the present invention is uridine (U). In another embodiment, the modified nucleoside is cytidine (C). In another embodiment, the modified nucleoside is adenosine (A). In another embodiment the modified nucleoside is guanosine (G). Each possibility represents a separate embodiment of the present invention.

In another embodiment, the modified nucleoside of methods and compositions of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is ψ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am(2'-O-methyladenosine); $ms^2m^GA$ (2-methylthio-$N^6$-methyladenosine); $i^GA$(~isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonylcarbamoyladenosine); $m^6t^6A$ ($N^6$-methyl-$N^6$-threonylcarbamoyladenosine); $hn^6A$ ($N^6$hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $S^2C$ (2thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2,2'$-O-dimethylguanosine); $m^2_2Gm$ ($N^2,N^2,2'$-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosylqueuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $S^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnmse^2U$ (5-methylaminomethyl-2-selenouridine); $ncm^5U$ (5-carbamoylmethyluridine); $ncm^5Um$ (5-carbamoylmethyl-2'-O-methyluridine); $cnnm^5U$ (5-carboxymethylaminomethyluridine); $cmnm^5Um$ (5-carboxymethylaminomethyl-2'-methyluridine); $cmnm^5s^2U$ (5-carboxymethylaminomethyl-2-thiouridine); $m^6_2A$ ($N^6,N^6$-dimethyladenosine); Im (2'-O-methylinosine); $m^4C$ ($N^4$-methylcytidine); $m^4Cm$ ($N^4,2'$-O-dimethylcytidine); $hm^5C$ (5-hydroxymethylcytidine); $m^3U$ (3-methyluridine); $cm^5U$ (5-carboxymethyluridine); $m^6Am$ ($N^6,2'$-Odimethyladenosine); $m^6_2Am$ ($N^6,N^6,2'$-O-trimethyladenosine); $m^{2,7}G$($N^2,7$-dimethylguanosine); $m^{2,2,7}G$ ($N^2,N^2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $τm^5U$ (5-taurinomethyluridine); $τm5s2U$ (5-taurinomethyl-2-thiouridine)); imG-14 (4-demethylwyosine); imG2 (isowyosine); or $ac^6A$ ($N^6$-acetyladenosine). Each possibility represents a separate embodiment of the present invention.

In another embodiment, an RNA, oligoribonucleotide, or polyribonucleotide molecule of methods and compositions of the present invention comprises a combination of 2 or more of the above modifications. In another embodiment, the RNA molecule or oligoribonucleotide molecule comprises a combination of 3 or more of the above modifications. In another embodiment, the RNA molecule or oligoribonucleotide molecule comprises a combination of more than 3 of the above modifications. Each possibility represents a separate embodiment of the present invention.

In another embodiment, between 0.1% and 100% of the residues in the RNA, oligoribonucleotide, or polyribonucleotide molecule of methods and compositions of the present invention are modified (e.g. either by the presence of pseudouridine or a modified nucleoside base). In another embodiment, 0.1% of the residues are modified. In another embodiment, 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleotide (uridine, cytidine, guanosine, or adenine) are modified. In another embodiment, the fraction of the nucleotide is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction of the given nucleotide is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, the terms "ribonucleotide," "oligoribonucleotide," and "polyribonucleotide" refers to a string of at least 2 base-sugar-phosphate combinations. The term includes, in another embodiment, compounds comprising nucleotides in which the sugar moiety is ribose. In another embodiment, the term includes both RNA and RNA derivatives in which the backbone is modified. "Nucleotides" refers, in another embodiment, to the monomeric units of nucleic acid polymers. RNA may be, in another embodiment, in the form of a tRNA (transfer RNA), snRNA (small nuclear RNA), rRNA (ribosomal RNA), mRNA (messenger RNA), antisense RNA, small interfering RNA (siRNA), micro RNA (miRNA) and ribozymes. The use of siRNA and miRNA has been described (Caudy A A et al, Genes & Devel 16: 2491-96 and references cited therein). In addition, these forms of RNA may be single, double, triple, or quadruple stranded. The term also includes, in another embodiment, artificial nucleic acids that may contain other types of backbones but the same bases. In another embodiment, the artificial nucleic acid is a PNA (peptide nucleic acid). PNA contain peptide backbones and nucleotide bases and are able to bind, in another embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57~and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention In another embodiment, the term "oligoribonucleotide" refers to a string comprising fewer than 25 nucleotides (nt). In another embodiment, "oligoribonucleotide" refers to a string of fewer than 24 nucleotides. In another embodiment, "oligoribonucleotide" refers to a string of fewer than 23 nucleotides. In another embodiment, "oligoribonucleotide" refers to a string of fewer than 22 nucleotides. In another embodiment, "oligoribonucleotide" refers to a string of fewer than 21 nucleotides. In another embodiment, "oligoribonucleotide" refers to a string of fewer than 20 nucleotides. In another embodiment, "oligoribonucleotide" refers to a string of fewer than 19 nucleotides. In another embodiment, "oligoribonucleotide" refers to a string of fewer than 18 nucleotides. In another embodiment, "oligoribonucleotide" refers to a string of fewer than 17 nucleotides. In another embodiment, "oligoribonucleotide" refers to a string of fewer than 16 nucleotides. Each possibility represents a separate embodiment of the present invention.

In another embodiment, the term "polyribonucleotide" refers to a string comprising more than 25 nucleotides (nt). In another embodiment, "polyribonucleotide" refers to a string of more than 26 nucleotides. In another embodiment, "polyribonucleotide" refers to a string of more than 28 nucleotides. In another embodiment, "the term" refers to a string of more than 30 nucleotides. In another embodiment, "the term" refers to a string of more than 32 nucleotides. In another embodiment, "the term" refers to a string of more than 35 nucleotides. In another embodiment, "the term" refers to a string of more than 40 nucleotides. In another embodiment, "the term" refers to a string of more than 50 nucleotides. In another embodiment, "the term" refers to a string of more than 60 nucleotides. In another embodiment, "the term" refers to a string of more than 80 nucleotides. In another embodiment, "the term" refers to a string of more than 100 nucleotides. In another embodiment, "the term" refers to a string of more than 120 nucleotides. In another embodiment, "the term" refers to a string of more than 150 nucleotides. In another embodiment, "the term" refers to a string of more than 200 nucleotides. In another embodiment, "the term" refers to a string of more than 300 nucleotides. In another embodiment, "the term" refers to a string of more than 400 nucleotides. In another embodiment, "the term" refers to a string of more than 500 nucleotides. In another embodiment, "the term" refers to a string of more than 600 nucleotides. In another embodiment, "the term" refers to a string of more than 800 nucleotides. In another embodiment, "the term" refers to a string of more than 1000 nucleotides. In another embodiment, "the term" refers to a string of more than 1200 nucleotides. In another embodiment, "the term" refers to a string of more than 1400 nucleotides. In another embodiment, "the term" refers to a string of more than 1600 nucleotides. In another embodiment, "the term" refers to a string of more than 1800 nucleotides. In another embodiment, "the term" refers to a string of more than 2000 nucleotides. Each possibility represents a separate embodiment of the present invention.

In another embodiment, the present invention provides a method for inducing a mammalian cell to produce a protein of interest, comprising contacting the mammalian cell with an in vitro-synthesized RNA molecule encoding the recombinant protein, the in vitro-synthesized RNA molecule comprising a pseudouridine or a modified nucleoside, thereby inducing a mammalian cell to produce a protein of interest. In another embodiment, the protein of interest is a recombinant protein. Each possibility represents a separate embodiment of the present invention.

"Encoding" refers, in another embodiment, to an RNA molecule that encodes the protein of interest. In another embodiment, the RNA molecule comprises an open reading frame that encodes the protein of interest. In another embodiment, one or more other proteins is also encoded. In another embodiment, the protein of interest is the only protein encoded. Each possibility represents a separate embodiment of the present invention.

In another embodiment, the present invention provides a method of inducing a mammalian cell to produce a recombinant protein, comprising contacting the mammalian cell with an in vitro-transcribed RNA molecule encoding the recombinant protein, the in vitro-transcribed RNA molecule further comprising a pseudouridine or a modified nucleoside, thereby inducing a mammalian cell to produce a recombinant protein.

In another embodiment, an RNA, oligoribonucleotide, or polyribonucleotide molecule of methods and compositions of the present invention is translated in the cell more efficiently than an unmodified RNA molecule with the same sequence. In another embodiment, the RNA, oligoribonucleotide, or polyribonucleotide molecule exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 5-fold factor. In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts. Each possibility represents a separate embodiment of the present invention.

Methods of determining translation efficiency are well known in the art, and include, e.g. measuring the activity of an encoded reporter protein (e.g. luciferase or *renilla* [Examples herein] or green fluorescent protein [Wall A A, Phillips A M et al, Effective translation of the second cistron in two *Drosophila* dicistronic transcripts is determined by the absence of in-frame AUG codons in the first cistron. J Biol Chem 2005; 280(30): 27670-8]), or measuring radioactive label incorporated into the translated protein (Ngosuwan J, Wang N M et al, Roles of cytosolic Hsp70 and Hsp40 molecular chaperones in post-translational translocation of presecretory proteins into the endoplasmic reticulum. J Biol Chem 2003; 278(9): 7034-42). Each method represents a separate embodiment of the present invention.

Figure 17A:
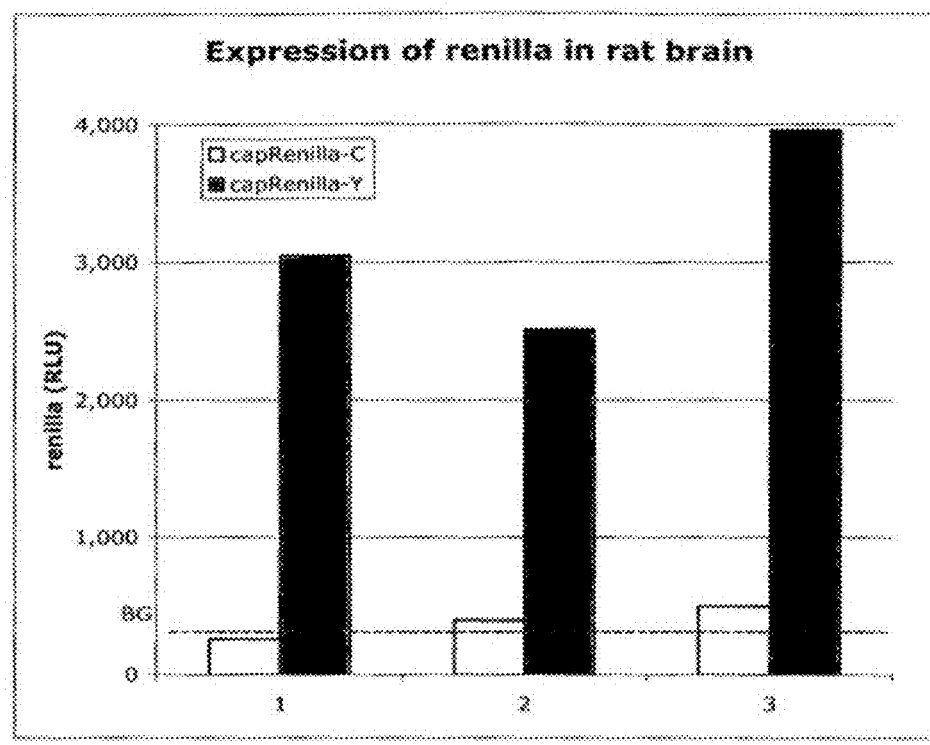
FIGS. 17A-D. A. Expression of *renilla* following intracerebral injection of modified or unmodified encoding mRNA. Rat brain cortex was injected at 8 sites/animals. One hemisphere was injected with capped, *renilla*-encoding RNA with pseudouridine modification (cap*Renilla*-Y), while the corresponding hemisphere with capped RNA with no nucleoside modification (cap*Renilla*-C). Data from 2 animals (6 injection sites) are shown. BG; lower level of detection of the assay. B. Intravenously-delivered ψ-modified mRNA is expressed in spleen. Lipofectin-complexed ψmRNA (0.3 μg capTEVlucAn/mouse) was administered by tail vein injection. Animals were sacrificed at 2 and 4 h post-injection and luciferase activities measured in aliquots (1/10th) of organs homogenized in lysis buffer. Values represent luciferase activities in the whole organs. C. ψ-modified mRNA exhibits greater stability and translation in vivo. Lipofectin-complexed capTEVlucAn (0.3 μg/60 μl/animal) with or without ψ modifications was delivered i.v. to mice. Animals were sacrificed at 1, 4 and 24 h post-injection, and ½ of their spleens were processed for luciferase enzyme measurements (left panel) and the other half for RNA analyses (right panel). Luciferase activities were measured in aliquots (⅕th) of the homogenate made from half of the spleens. Plotted values represent luciferase activities in the whole spleen and are expressed as the mean±s.e.m. (n=3 or 4/point). D. Expression of firefly luciferase following intratracheal injection of mRNA. capTEVluc-Y: capped, firefly luciferase encoding pseudouridine-modified RNA. CapTEVluc-C: capped RNA with no nucleoside modification.
Figure 17B:
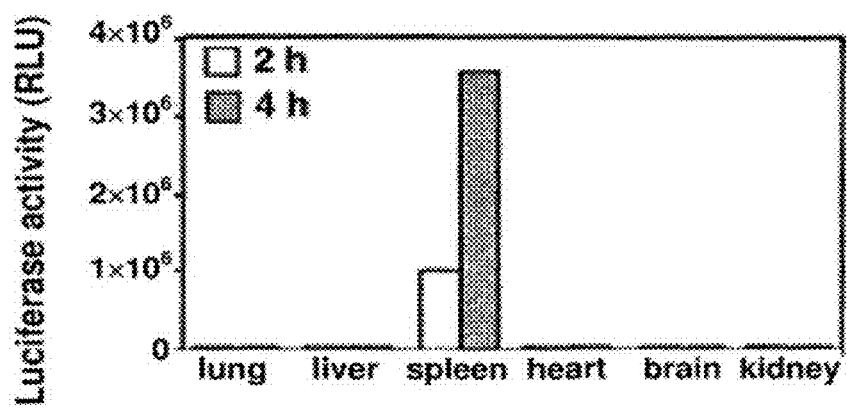

In some expression studies provided herein, translation was measured from RNA complexed to Lipofectin® (Gibco BRL, Gaithersburg, Md., USA) and injected into the tail vein of mice. In the spleen lysates, pseudouridine-modified RNA was translated significantly more efficiently than unmodified RNA (FIG. 17B). Under the conditions utilized herein, efficiency of transfection-based methods of the present invention correlates with the ability of the transfection reagent to penetrate into tissues, providing an explanation for why the effect was most pronounced in spleen cells. Splenic blood flow is an open system, with blood contents directly contacting red and white pulp elements including lymphoid cells.

In another experiment, in vitro phosphorylation assays were performed using recombinant human PKR and its substrate, eIF2α in the presence of capped, *renilla*-encoding mRNA (0.5 and 0.05 ng/μl). mRNA containing pseudouridine (ψ) did not activate PKR, as detected by lack of both self-phosphorylation of PKR and phosphorylation of eIF2α, while RNA without nucleoside modification and mRNA with m5C modification activated PKR. Phosphorylated eIF2α is known to block initiation of mRNA translation, therefore lack of phosphorylation enables, in another embodiment, enhanced translation of the mRNA containing pseudouridine (ψ).

In another embodiment, the enhanced translation is in a cell (relative to translation in the same cell of an unmodified RNA molecule with the same sequence; Examples 13-14). In another embodiment, the enhanced translation is in vitro (e.g. in an in vitro translation mix or a reticulocyte lysate; Examples 13-14. In another embodiment, the enhanced translation is in vivo (Example 13). In each case, the enhanced translation is relative to an unmodified RNA molecule with the same sequence, under the same conditions. Each possibility represents a separate embodiment of the present invention.

In another embodiment, the RNA, oligoribonucleotide, or polyribonucleotide molecule of methods and compositions of the present invention is significantly less immunogenic than an unmodified in vitro-synthesized RNA molecule with the same sequence. In another embodiment, the modified RNA molecule is 2-fold less immunogenic than its unmodified counterpart. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a 20-fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

In another embodiment, "significantly less immunogenic" refers to a detectable decrease in immunogenicity. In another embodiment, the term refers to a fold decrease in immunogenicity (e.g. one of the fold decreases enumerated above). In another embodiment, the term refers to a decrease such that an effective amount of the RNA, oligoribonucleotide, or polyribonucleotide molecule can be administered without triggering a detectable immune response. In another embodiment, the term refers to a decrease such that the RNA, oligoribonucleotide, or polyribonucleotide molecule can be repeatedly administered without eliciting an immune response sufficient to detectably reduce expression of the recombinant protein. In another embodiment, the decrease is such that the RNA, oligoribonucleotide, or polyribonucleotide molecule can be repeatedly administered without eliciting an immune response sufficient to eliminate detectable expression of the recombinant protein.

"Effective amount" of the RNA, oligoribonucleotide, or polyribonucleotide molecule refers, in another embodiment, to an amount sufficient to exert a therapeutic effect. In another embodiment, the term refers to an amount sufficient to elicit expression of a detectable amount of the recombinant protein. Each possibility represents a separate embodiment of the present invention.

Reduced immunogenicity of RNA, oligoribonucleotide, and polyribonucleotide molecules of the present invention is demonstrated herein (Examples 4-11).

Methods of determining immunogenicity are well known in the art, and include, e.g. measuring secretion of cytokines (e.g. IL-12, IFN-α, TNF-α, RANTES, MIP-1α or β, IL-6, IFN-β, or IL-8; Examples herein), measuring expression of DC activation markers (e.g. CD83, HLA-DR, CD80 and CD86; Examples herein), or measuring ability to act as an adjuvant for an adaptive immune response. Each method represents a separate embodiment of the present invention.

In another embodiment, the relative immunogenicity of the modified nucleotide and its unmodified counterpart are determined by determining the quantity of the modified nucleotide required to elicit one of the above responses to the same degree as a given quantity of the unmodified nucleotide. For example, if twice as much modified nucleotide is required to elicit the same response, than the modified nucleotide is two-fold less immunogenic than the unmodified nucleotide.

In another embodiment, the relative immunogenicity of the modified nucleotide and its unmodified counterpart are determined by determining the quantity of cytokine (e.g. IL-12, IFN-α, TNF-α, RANTES, MIP-1α or β, IL-6, IFN-β, or IL-8) secreted in response to administration of the modified nucleotide, relative to the same quantity of the unmodified nucleotide. For example, if one-half as much cytokine is secreted, than the modified nucleotide is two-fold less immunogenic than the unmodified nucleotide. In another embodiment, background levels of stimulation are subtracted before calculating the immunogenicity in the above methods. Each possibility represents a separate embodiment of the present invention.

In another embodiment, a method of present invention further comprises mixing the RNA, oligoribonucleotide, or polyribonucleotide molecule with a transfection reagent prior to the step of contacting. In another embodiment, a method of present invention further comprises administering the RNA, oligoribonucleotide, or polyribonucleotide molecule together with the transfection reagent. In another embodiment, the transfection reagent is a cationic lipid reagent (Example 6).

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin® or Lipofectamine®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water soluble compounds and range in size from 0.05 to several microns in diameter. In another embodiment, liposomes can deliver RNA to cells in a biologically active form.

Each type of transfection reagent represents a separate embodiment of the present invention.

In another embodiment, the target cell of methods of the present invention is an antigen—presenting cell. In another embodiment, the cell is an animal cell. In another embodiment, the cell is a dendritic cell (Example 14). In another embodiment, the cell is a neural cell. In another embodiment, the cell is a brain cell (Example 16). In another embodiment, the cell is a spleen cell. In another embodiment, the cell is a lymphoid cell. In another embodiment, the cell is a lung cell (Example 16). In another embodiment, the cell is a skin cell. In another embodiment, the cell is a keratinocyte. In another embodiment, the cell is an endothelial cell. In another embodiment, the cell is an astrocyte, a microglial cell, or a neuron (Example 16). In another embodiment, the cell is an alveolar cell (Example 16). In another embodiment, the cell is a surface alveolar cell (Example 16). In another embodiment, the cell is an alveolar macrophage. In another embodiment, the cell is an alveolar pneumocyte. In another embodiment, the cell is a vascular endothelial cell. In another embodiment, the cell is a mesenchymal cell. In another embodiment, the cell is an epithelial cell. In another embodiment, the cell is a hematopoietic cell. In another embodiment, the cell is colonic epithelium cell. In another embodiment, the cell is a lung epithelium cell. In another embodiment, the cell is a bone marrow cell.

In other embodiments, the target cell is a Claudius' cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell,' juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolarmacrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, or zymogenic cell. Each possibility represents a separate embodiment of the present invention.

A variety of disorders may be treated by employing methods of the present invention including, inter alia, monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like. In another embodiment, the disorder treated involves one of the proteins listed below. Each possibility represents a separate embodiment of the present invention.

In another embodiment, the recombinant protein encoded by an RNA, oligoribonucleotide, or polyribonucleotide molecule of methods and compositions of the present invention is ecto-nucleoside triphosphate diphosphohydrolase.

In another embodiment, the recombinant protein is erythropoietin (EPO). In other embodiments, the encoded recombinant protein is ABCA4; ABCD3; ACADM; AGL; AGT; ALDH4AI; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2; CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPDX; PPT1; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPSI; CRYGA; CRYGEP1; CYP1B1; CYP27A1; DBI; DES; DYSF; EDAR; EFEMPI; EIF2AK3; ERCC3; FSHR; GINGF; GLC1B; GPD2; GYPC; HADHA; HADHB; HOXD13; HPE2; IGKC; IHH; IRSI; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB1; DEM; ETM1; FANCD2; FIH; FOXL2; GBE1; GLB1; GLC1C; GNAI2; GNATI; GP9; GPX1; HGD; HRG; ITIH1; KNG; LPP; LRS1; MCCCI; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3BI; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMD1A; LOX; LTC4S; MAN2A1; MCC; MCCC2; MSH3; MSX2; NR3C1; PCSK1; PDE6A; PFBI; RASAI; SCZDI; SDHA; SGCD; SLC22A5; SLC26A2; SLC6A3; SM1; SMA@; SMN1; SMN2; SPINK5; TCOF1; TELAB1; TGFBI; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPBI; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFC1; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GHRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYP11B1; CYP11B2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFIPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF;

BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; LLT3; MROS; MSSE; NOTCH1; ORM1; PAPPA; PIP5K1B; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOA1; APOA4; APOC3; ATM; BSCL2; BWS; CALCA; CAT; CCND1; CD3E; CD3G; CD59; CDKN1C; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MILL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRNI; WT1; WT2; ZNF145; A2M; AAAS; ACADS; ACLS; ACVRL1; ALDH2; AMHR2; AOM; AQP2; ATD; ATP2A2; BDC; C1R; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1; ERCC5; F10; F7; GJB2; GJB6; IPF1; MBS1; MCOR; NYS4; PCCA; RB1; RHOK; SCZD7; SGCG; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MCOP; MID; MNG1; MPD1; MPS3C; MYH6; MYH7; NP; NPC2; PABPN1; PSEN1; PYGL; RPGRIP1; SERPINA1; SERPINA3; SERPINA6; SLC7A7; SPG3A; SPTB; TCL1A; TGM1; TITF1; TMIP; TRA@; TSHR; USH1A; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MY05A; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VDI; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK1; GCGR; GFAP; GH1; GH2; GP1BA; GPSC; GUCY2D; ITGA2B; ITGB3; ITGB4; KRT10; KRT12; KRT13; KRT14; KRT14L1; KRT14L2; KRT14L3; KRT16; KRT16L1; KRT16L2; KRT17; KRT9; MAPT; MDB; MDCR; MGI; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RN/TSA1; RP17; RSS; SCN4A; SERPINF2; SGCA; SGSH; SHBG; SLC2A4; SLC4A1; SLC6A4; SMCR; SOST; SOX9; SSTR2; SYM1; SYNSI; TCF2; THRA; TIMP2; TOC; TOP2A; TP53; TRIM37; VBCH; ATP8B1; BCL2; CNSN; CORD1I; CYB5; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; E11S; ELA2; EPOR; ERCC2; ETFB; EXT3; EYCLI; FTL; FUT1; FUT2; FUT6; GAMT; GCDH; GPI; GUSM; HB1; HCL1; HHC2; HHC3; ICAM3; INSR; JAK3; KLK3; LDLR; LHB; LIG1; LOH19CR1; LYL1; MAN2B 1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NE2; OGS2; PDGFB; PPARA; PRODH; SCO2; SCZD4; SERPIND1; SLC5AI; SOXI0; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN; BTK; BZX; C1HR; CACNA1F; CALB3; CBBM; CCT; CDR1; CFNS; CGF1; CHM; CHR39C; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2C; HYR; IDS; IHG1; IL2RG; INDX; IP1; IP2; JMS; KAL1; KFSD; LICAM; LAMP2; MAA; MAFD2; MAOA; MAOB; MCF2; MCS; MEAX; MECP2; MF4; MGCI; MICS; MID1; MLLT7; MLS; MRSD; MRX14; MRX1; MRX20; MRX2; MRX3; MRX40; MRXA; MSD; MTMI; MYCL2; MYPI; NDP; NHS; NPHLI; NROBI; NSX; NYSI; NYX; OAI; OASD; OCRL; ODTI; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA; PLP1; POF1; POLA; POU3F4; PPMX; PRD; PRPSI; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIMP1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZFI; AZF2; DAZ; GCY; RPS4Y; SMCY; SRY; ZFY; ABAT; AEZ; AFA; AFD1; ASAH1; ASD1; ASMT; CCAT; CECR9; CEPA; CLA3; CLN4; CSF2RA; CTSI; DF; DIH1; DWS;

DYT2; DYT4; EBR3; ECT; EEF1A1L14; EYCL2; FANCB; GCSH; GCSL; GIP; GTS; HHG; HMI; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2; MPFD; MS; MSS; MTATP6; MTCOI; MTCO3; MTCYB; MTND1; MTND2; MTND4; MTND5; MTND6; MTRNR1; MTRNR2; MTTE; MTTG; MTTI; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO; SUOX; THM; or TTD. Each recombinant protein represents a separate embodiment of the present invention.

In another embodiment, the present invention provides a method for treating anemia in a subject, comprising contacting a cell of the subject with an in vitro-synthesized RNA molecule, the in vitro synthesized RNA molecule encoding erythropoietin, thereby treating anemia in a subject. In another embodiment, the in vitro-synthesized RNA molecule further comprises a pseudouridine or a modified nucleoside. Each possibility represents a separate embodiment of the present invention. In another embodiment, the cell is a subcutaneous tissue cell. In another embodiment, the cell is a lung cell. In another embodiment, the cell is a fibroblast. In another embodiment, the cell is a lymphocyte. In another embodiment, the cell is a smooth muscle cell. In another embodiment, the cell is any other type of cell known in the art. Each possibility represents a separate embodiment of the present invention.

In another embodiment, the present invention provides a method for treating a vasospasm in a subject, comprising contacting a cell of the subject with an in vitro-synthesized RNA molecule, the in vitro-synthesized RNA molecule encoding inducible nitric oxide synthase (iNOS), thereby treating a vasospasm in a subject.

In another embodiment, the present invention provides a method for improving a survival rate of a cell in a subject, comprising contacting the cell with an in vitro-synthesized RNA molecule, the in vitro-synthesized RNA molecule encoding a heat shock protein, thereby improving a survival rate of a cell in a subject.

In another embodiment, the cell whose survival rate is improved is an ischemic cell. In another embodiment, the cell is not ischemic. In another embodiment, the cell has been exposed to an ischemic environment. In another embodiment, the cell has been exposed to an environmental stress. Each possibility represents a separate embodiment of the present invention.

In another embodiment, the present invention provides a method for decreasing an incidence of a restenosis of a blood vessel following a procedure that enlarges the blood vessel, comprising contacting a cell of the blood vessel with an in vitro-synthesized RNA molecule, the in vitro-synthesized RNA molecule encoding a heat shock protein, thereby decreasing an incidence of a restenosis in a subject.

In another embodiment, the procedure is an angioplasty. In another embodiment, the procedure is any other procedure known in the art that enlarges the blood vessel. Each possibility represents a separate embodiment of the present invention.

In another embodiment, the present invention provides a method for increasing a hair growth from a hair follicle is a scalp of a subject, comprising contacting a cell of the scalp with an in vitro-synthesized RNA molecule, the in vitro-synthesized RNA molecule encoding a telomerase or an immunosuppressive protein, thereby increasing a hair growth from a hair follicle.

In another embodiment, the immunosuppressive protein is α-melanocyte-stimulating hormone (α-MSH). In another embodiment, the immunosuppressive protein is transforming growth factor-β 1 (TGF-β 1). In another embodiment, the immunosuppressive protein is insulin-like growth factor-I (IGF-I). In another embodiment, the immunosuppressive protein is any other immunosuppressive protein known in the art. Each possibility represents a separate embodiment of the present invention.

In another embodiment, the present invention provides a method of inducing expression of an enzyme with antioxidant activity in a cell, comprising contacting the cell with an in vitro-synthesized RNA molecule, the in vitro-synthesized RNA molecule encoding the enzyme, thereby inducing expression of an enzyme with antioxidant activity in a cell.

In one embodiment, the enzyme is catalase. In another embodiment, the enzyme is glutathione peroxidase. In another embodiment, the enzyme is phospholipid hydroperoxide glutathione peroxidase. In another embodiment, the enzyme is superoxide dismutase-1. In another embodiment, the enzyme is superoxide dismutase-2. In another embodiment, the enzyme is any other enzyme with antioxidant activity that is known in the art. Each possibility represents a separate embodiment of the present invention.

In another embodiment, the present invention provides a method for treating cystic fibrosis in a subject, comprising contacting a cell of the subject with an in vitro-synthesized RNA molecule, the in vitro-synthesized RNA molecule encoding Cystic Fibrosis Transmembrane Conductance Regulator (CFTR), thereby treating cystic fibrosis in a subject.

In another embodiment, the present invention provides a method for treating an X-linked agammaglobulinemia in a subject, comprising contacting a cell of the subject with an in vitro synthesized RNA molecule, the in vitro-synthesized RNA molecule encoding a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with an in vitro-synthesized RNA molecule, the in vitro-synthesized RNA molecule encoding an ADA, thereby treating an ADA SCID.

In another embodiment, the present invention provides a method for reducing immune responsiveness of the skin and improving skin pathology, comprising contacting a cell of the subject with an in vitro-synthesized RNA molecule, the in vitro-synthesized RNA molecule encoding an ecto-nucleoside triphosphate diphosphohydrolase, thereby reducing immune responsiveness of the skin and improving skin pathology.

In another embodiment, an RNA molecule or ribonucleotide molecule of the present invention is encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171. 1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707.2005); and Zimmermann E et al., Electrolyte- and pH-stabilities of aqueous solid lipid nanoparticle (SLN) dispersions in artificial gastrointestinal media. Eur J Pharm Biopharm 52:203.2001). Each method represents a separate embodiment of the present invention.

Various embodiments of dosage ranges of compounds of the present invention can be used in methods of the present invention. In one embodiment, the dosage is in the range of 1-10 µg/day. In another embodiment, the dosage is 2-10 µg/day. In another embodiment, the dosage is 3-10 µg/day. In another embodiment, the dosage is 5-10 µg/day. In another embodiment, the dosage is 2-20 µg/day. In another embodiment, the dosage is 3-20 µg/day. In another embodiment, the dosage is 5-20 µg/day. In another embodiment, the dosage is 10-20 µg/day. In another embodiment, the dosage is 3-40 µg/day. In another embodiment, the dosage is 5-40 µg/day. In another embodiment, the dosage is 10-40 µg/day. In another embodiment, the dosage is 20-40 µg/day. In another embodiment, the dosage is 5-50 µg/day. In another embodiment, the dosage is 10-50 µg/day. In another embodiment, the dosage is 20-50 µg/day. In one embodiment, the dosage is 1-100 µg/day. In another embodiment, the dosage is 2-100 µg/day. In another embodiment, the dosage is 3-100 µg/day. In another embodiment, the dosage is 5-100 µg/day. In another embodiment the dosage is 10-100 µg/day. In another embodiment the dosage is 20-100 µg/day. In another embodiment the dosage is 40-100 µg/day. In another embodiment the dosage is 60-100 µg/day.

In another embodiment, the dosage is 0.1 µg/day. In another embodiment, the dosage is 0.2 µg/day. In another embodiment, the dosage is 0.3 µg/day. In another embodiment, the dosage is 0.5 µg/day. In another embodiment, the dosage is 1 µg/day. In another embodiment, the dosage is 2 mg/day. In another embodiment, the dosage is 3 µg/day. In another embodiment, the dosage is 5 µg/day. In another embodiment, the dosage is 10 µg/day. In another embodiment, the dosage is 15 µg/day. In another embodiment, the dosage is 20 µg/day. In another embodiment, the dosage is 30 µg/day. In another embodiment, the dosage is 40 µg/day. In another embodiment, the dosage is 60 µg/day. In another embodiment, the dosage is 80 µg/day. In another embodiment, the dosage is 100 µg/day.

In another embodiment, the dosage is 10 µg/dose. In another embodiment, the dosage is 20 µg/dose. In another embodiment, the dosage is 30 µg/dose. In another embodiment, the dosage is 40 µg/dose. In another embodiment, the dosage is 60 µg/dose. In another embodiment, the dosage is 80 µg/dose. In another embodiment, the dosage is 100 µg/dose. In another embodiment, the dosage is 150 µg/dose. In another embodiment, the dosage is 200 µg/dose. In another embodiment, the dosage is 300 µg/dose. In another embodiment, the dosage is 400 µg/dose. In another embodiment, the dosage is 600 µg/dose. In another embodiment, the dosage is 800 µg/dose. In another embodiment, the dosage is 1000 µg/dose. In another embodiment, the dosage is 1.5 mg/dose. In another embodiment, the dosage is 2 mg/dose. In another embodiment, the dosage is 3 mg/dose. In another embodiment, the dosage is 5 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 50 mg/dose. In another embodiment, the dosage is 80 mg/dose. In another embodiment, the dosage is 100 mg/dose.

In another embodiment, the dosage is 10-20 µg/dose. In another embodiment, the dosage is 20-30 µg/dose. In another embodiment, the dosage is 20-40 µg/dose. In another embodiment, the dosage is 30-60 µg/dose. In another embodiment, the dosage is 40-80 µg/dose. In another embodiment, the dosage is 50-100 µg/dose. In another embodiment, the dosage is 50-150 µg/dose. In another embodiment, the dosage is 100-200 µg/dose. In another embodiment, the dosage is 200-300 µg/dose. In another embodiment, the dosage is 300-400 µg/dose. In another embodiment, the dosage is 400-600 µg/dose. In another embodiment, the dosage is 500-800 µg/dose. In another embodiment, the dosage is 800-1000 µg/dose. In another embodiment, the dosage is 1000-1500 µg/dose. In another embodiment, the dosage is 1500-2000 µg/dose. In another embodiment, the dosage is 2-3 mg/dose. In another embodiment, the dosage is 2-5 mg/dose. In another embodiment, the dosage is 2-10 mg/dose. In another embodiment, the dosage is 2-20 mg/dose. In another embodiment, the dosage is 2-30 mg/dose. In another embodiment, the dosage is 2-50 mg/dose. In another embodiment, the dosage is 2-80 mg/dose. In another embodiment, the dosage is 2-100 mg/dose. In another embodiment, the dosage is 3-10 mg/dose. In another embodiment, the dosage is 3-20 mg/dose. In another embodiment, the dosage is 3-30 mg/dose. In another embodiment, the dosage is 3-50 mg/dose. In another embodiment, the dosage is 3-80 mg/dose. In another embodiment, the dosage is 3-100 mg/dose. In another embodiment, the dosage is 5-10 mg/dose. In another embodiment, the dosage is 5-20 mg/dose. In another embodiment, the dosage is 5-30 mg/dose. In another embodiment, the dosage is 5-50 mg/dose. In another embodiment, the dosage is 5-80 mg/dose. In another embodiment, the dosage is 5-100 mg/dose. In another embodiment, the dosage is 10-20 mg/dose. In another embodiment, the dosage is 10-30 mg/dose. In another embodiment, the dosage is 10-50 mg/dose. In another embodiment, the dosage is 10-80 mg/dose. In another embodiment, the dosage is 10-100 mg/dose.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose. As described below, in another embodiment, an advantage of RNA, oligoribonucleotide, or polyribonucleotide molecules of the present invention is their greater potency, enabling the use of smaller doses.

In another embodiment, the present invention provides a method for producing a recombinant protein, comprising contacting an in vitro translation apparatus with an in vitro-synthesized oligoribonucleotide, the in vitro-synthesized oligoribonucleotide comprising a pseudouridine or a modified nucleoside, thereby producing a recombinant protein.

In another embodiment, the present invention provides a method for producing a recombinant protein, comprising contacting an in vitro translation apparatus with an in vitro-transcribed RNA molecule of the present invention, the in vitro-transcribed RNA molecule comprising a pseudouridine or a modified nucleoside, thereby producing a recombinant protein.

In another embodiment, the present invention provides an in vitro transcription apparatus, comprising: an unmodified nucleotide, a nucleotide containing a pseudouridine or a modified nucleoside, and a polymerase. In another embodiment, the present invention provides an in vitro transcription kit, comprising: an unmodified nucleotide, a nucleotide containing a pseudouridine or a modified nucleoside, and a polymerase. Each possibility represents a separate embodiment of the present invention.

In another embodiment, the in vitro translation apparatus comprises a reticulocyte lysate. In another embodiment, the reticulocyte lysate is a rabbit reticulocyte lysate.

In another embodiment, the present invention provides a method of reducing an immunogenicity of an oligoribonucleotide molecule or RNA molecule, the method comprising the step of replacing a nucleotide of the oligoribonucleotide molecule or RNA molecule with a modified nucleotide that contains a modified nucleoside or a pseudouridine, thereby reducing an immunogenicity of an oligoribonucleotide molecule or RNA molecule.

In another embodiment, the present invention provides a method of reducing an immunogenicity of a gene-therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby reducing an immunogenicity of a gene-therapy vector.

In another embodiment, the present invention provides a method of enhancing in vitro translation from an oligoribonucleotide molecule or RNA molecule, the method comprising the step of replacing a nucleotide of the oligoribonucleotide molecule or RNA molecule with a modified nucleotide that contains a modified nucleoside or a pseudouridine, thereby enhancing in vitro translation from an oligoribonucleotide molecule or RNA molecule.

In another embodiment, the present invention provides a method of enhancing in vivo translation from a gene-therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby enhancing in vivo translation from a gene-therapy vector.

In another embodiment, the present invention provides a method of increasing efficiency of delivery of a recombinant protein by a gene therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby increasing efficiency of delivery of a recombinant protein by a gene therapy vector.

In another embodiment, the present invention provides a method of increasing in vivo stability of gene therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby increasing in vivo stability of gene therapy vector.

In another embodiment, the present invention provides a method of synthesizing an in vitro-transcribed RNA molecule comprising a pseudouridine nucleoside, comprising contacting an isolated polymerase with a mixture of unmodified nucleotides and the modified nucleotide (Examples 5 and 10).

In another embodiment, in vitro transcription methods of the present invention utilize an extract from an animal cell. In another embodiment, the extract is from a reticulocyte or cell with similar efficiency of in vitro transcription. In another embodiment, the extract is from any other type of cell known in the art. Each possibility represents a separate embodiment of the present invention.

Any of the RNA molecules or oligoribonucleotide molecules of the present invention may be used, in another embodiment, in any of the methods of the present invention.

In another embodiment, the present invention provides a method of enhancing an immune response to an antigen, comprising administering the antigen in combination with mitochondrial (mt) RNA (Examples 4 and 8).

In another embodiment, the present invention provides a method of reducing the ability of an RNA molecule to stimulate a dendritic cell (DC), comprising modifying a nucleoside of the RNA molecule by a method of the present invention (e.g., see EXAMPLES).

In another embodiment, the DC is a DC1 cell. In another embodiment, the DC is a DC2 cell. In another embodiment, the DC is a subtype of a DC1 cell or DC2 cell. Each possibility represents a separate embodiment of the present invention.

In another embodiment, the present invention provides a method of reducing the ability of an RNA molecule to stimulate signaling by TLR3, comprising modifying a nucleoside of the RNA molecule by a method of the present invention. In another embodiment, the present invention provides a method of reducing the ability of an RNA molecule to stimulate signaling by TLR7, comprising modifying a nucleoside of the RNA molecule by a method of the present invention. In another embodiment, the present invention provides a method of reducing the ability of an RNA molecule to stimulate signaling by TLR8, comprising modifying a nucleoside of the RNA molecule by a method of the present invention. Each possibility represents a separate embodiment of the present invention.

In another embodiment, all of the internucleoside or internucleotide linkages in the RNA, oligoribonucleotide, or polyribonucleotide molecule are phosphodiester. In another embodiment, the inter-nucleotide linkages are predominantly phosphodiester. In another embodiment, most of the internucleotide linkages are phosphorothioate. In another embodiment, most the inter-nucleotide linkages are phosphodiester. Each possibility represents a separate embodiment of the present invention.

In another embodiment, the percentage of the inter-nucleotide linkages in the RNA, oligoribonucleotide, or polyribonucleotide molecule that are phosphodiester is above 50%. In another embodiment, the percentage is above 10%. In another embodiment, the percentage is above 15%. In another embodiment, the percentage is above 20%. In another embodiment, the percentage is above 25%. In another embodiment, the percentage is above 30%. In another embodiment, the percentage is above 35%. In another embodiment, the percentage is above 40%. In another embodiment, the percentage is above 45%. In another embodiment, the percentage is above 55%. In another embodiment, the percentage is above 60%. In another embodiment, the percentage is above 65%. In another embodiment, the percentage is above 70%. In another embodiment, the percentage is above 75%. In another embodiment, the percentage is above 80%. In another embodiment, the percentage is above 85%. In another embodiment, the percentage is above 90%. In another embodiment, the percentage is above 95%.

In another embodiment, a method of the present invention comprises increasing the number, percentage, or frequency of modified nucleosides in the RNA molecule to decrease immunogenicity or increase efficiency of translation. As provided herein (e.g., see EXAMPLES), the number of modified residues in an RNA, oligoribonucleotide, or polyribonucleotide molecule determines, in another embodiment, the magnitude of the effects observed in the present invention.

In another embodiment, the present invention provides a method for introducing a recombinant protein into a cell of a subject, comprising contacting the subject with an in vitro-transcribed RNA molecule encoding the recombinant protein, the in vitro-transcribed RNA molecule further comprising a pseudouridine or another modified nucleoside, thereby introducing a recombinant protein into a cell of a subject.

In another embodiment, the present invention provides a method for decreasing TNF-α production in response to a gene therapy vector in a subject, comprising the step of engineering the vector to contain a pseudouridine or a modified nucleoside base, thereby decreasing TNF-α production in response to a gene therapy vector in a subject.

In another embodiment, the present invention provides a method for decreasing IL-12 production in response to a gene therapy vector in a subject, comprising the step of engineering the vector to contain a pseudouridine or a modified nucleoside base, thereby decreasing IL-12 production in response to a gene therapy vector in a subject.

In another embodiment, the present invention provides a method of reducing an immunogenicity of a gene therapy vector, comprising introducing a modified nucleoside into said gene therapy vector, thereby reducing an immunogenicity of a gene therapy vector.

As provided herein, findings of the present invention show that primary DC have an additional RNA signaling entity that recognizes m5C- and m6A-modified RNA and whose signaling is inhibited by modification of U residues.

In another embodiment, an advantage of an RNA, oligoribonucleotide, and polyribonucleotide molecules of the present invention is that RNA does not incorporate to the genome (as opposed to DNA-based vectors). In another embodiment, an advantage is that translation of RNA, and therefore appearance of the encoded product, is instant. In another embodiment, an advantage is that the amount of protein generated from the mRNA can be regulated by delivering more or less RNA. In another embodiment, an advantage is that repeated delivery of purified pseudouridine or other modified RNA, oligoribnucleotide, or polyribonucleotide molecules does not induce an immune response, whereas repeated delivery of unmodified RNA could induce signaling pathways though RNA sensors.

In another embodiment, an advantage is lack of immunogenicity, enabling repeated delivery without generation of inflammatory cytokines. In another embodiment, stability of RNA is increased by circularization, decreasing degradation by exonucleases.

In another embodiment, the present invention provides a method of treating a subject with a disease that comprises an immune response against a self-RNA molecule, comprising administering to the subject an antagonist of a TLR-3 molecule, thereby treating a subject with a disease that comprises an immune response against a self-RNA molecule.

In another embodiment, the present invention provides a method of treating a subject with a disease that comprises an immune response against a self-RNA molecule, comprising administering to the subject an antagonist of a TLR-7 molecule, thereby treating a subject with a disease that comprises an immune response against a self-RNA molecule.

In another embodiment, the present invention provides a method of treating a subject with a disease that comprises an immune response against a self-RNA molecule, comprising administering to the subject an antagonist of a TLR-8 molecule, thereby treating a subject with a disease that comprises an immune response against a self-RNA molecule.

In another embodiment, the disease that comprises an immune response against a self-RNA molecule is an autoimmune disease. In another embodiment, the disease is systemic lupus erythematosus (SLE). In another embodiment, the disease is another disease known in the art that comprises an immune response against a self-RNA molecule. Each possibility represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In another embodiment, the present invention provides a kit for measuring or studying signaling by a TLR-3, TLR-7 and TLR-8 receptor, as exemplified in Example 7.

In another embodiment, a treatment protocol of the present invention is therapeutic. In another embodiment, the protocol is prophylactic. Each possibility represents a separate embodiment of the present invention.

In one embodiment, the phrase "contacting a cell" or "contacting a population" refers to a method of exposure, which can be direct or indirect. In one method such contact comprises direct injection of the cell through any means well known in the art, such as microinjection. In another embodiment, supply to the cell is indirect, such as via provision in a culture medium that surrounds the cell, or administration to a subject, or via any route known in the art. In another embodiment, the term "contacting" means that the molecule of the present invention is introduced into a subject receiving treatment, and the molecule is allowed to come in contact with the cell in vivo. Each possibility represents a separate embodiment of the present invention.

Methods for quantification of reticulocyte frequency and for measuring EPO biological activity are well known in the art, and are described, for Example, in Ramos, A S et al (Biological evaluation of recombinant human erythropoietin in pharmaceutical products. Braz J Med Biol Res 36:1561). Each method represents a separate embodiment of the present invention.

Compositions of the present invention can be, in another embodiment, administered to a subject by any method known to a person skilled in the art, such as parenterally, paracancerally, transmucosally, transdermally, intramuscularly, intravenously, intra-dermally, subcutaneously, intraperitoneally, intraventricularly, intra-cranially, intra-vaginally or intra-tumorally.

In another embodiment of methods and compositions of the present invention, the compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In other embodiments, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the composition is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In another embodiment, the active compound is delivered in a vesicle, e.g. a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be may be, in various embodiments, a solid carrier or diluent for solid formulations, a liquid carrier or diluent for liquid formulations, or mixtures thereof.

In another embodiment, solid carriers/diluents include, but are not limited to, a gum, a starch (e.g. com starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the compound is released over a period of time after 15 administration. Controlled- or sustained-release compositions include formulation in lipophilic depots (e.g. fatty acids, waxes, oils). In another embodiment, the composition is an immediate-release composition, i.e. a composition in which the entire compound is released immediately after administration.

In another embodiment, molecules of the present invention are modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

An active component is, in another embodiment, formulated into the composition as neutralized pharmaceutically acceptable salt forms. Pharmaceutically acceptable salts include the acid addition salts (e.g., formed with the free amino groups of a polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

EXAMPLES

The following experimental protocols were employed in the Examples provided below, unless indicated otherwise.

Materials and Methods for Examples 1-3

Cell Culture. Newborn human foreskin fibroblast 1079 cells (Cat#CRL-2097, ATCC, Manassas, Va.) and human IMR90 cells (Cat#CCL-186, ATCC) were cultured in Advanced MEM Medium (Invitrogen, Carlsbad, Calif.) supplemented with 10% heat-inactivated fetal bovine serum (FBS, Hyclone Laboratories, Logan, Utah), 2 mM Glutamax (Invitrogen), 0.1 mM β-mercaptoethanol (Sigma, St. Louis, Mo.), and Penicillin/Streptomycin (Invitrogen). All cells were grown at 37° C. and 5% $CO_2$. In some experiments, human iPS cells that were induced using methods described herein were maintained on irradiated mouse embryonic fibroblasts (MEFs) (R&D Systems, Minneapolis, Minn.) on 10-cm plates pre-coated with 0.1% gelatin (Millipore, Phillipsburg, N.J.) in DMEM/F12 medium supplemented with 20% KnockOut serum replacer, 0.1 mM L-glutamine (all from Invitrogen), 0.1 mM β-mercaptoethanol (Sigma) and 100 ng/ml basic fibroblast growth factor (Invitrogen). In some experiments, human iPS cells that were induced using methods described herein were maintained in MEF-conditioned medium that had been collected as previously described (Xu et al. 2001).

Constructions of Vectors. The cDNAs for the open reading frames (ORFs) of KLF4, LIN28, NANOG, and OCT4 were PCR amplified from cDNA clones (Open Biosystems, Huntsville, Ala.), cloned into a plasmid vector downstream of a T7 RNA polymerase promoter (Mackie 1988, Studier and Moffatt 1986) (e.g., various pBluescript™, Agilent, La Jolla, Calif. or pGEM™, Promega, Madison, Wis., vectors) and sequenced. The ORF of SOX2 was PCR amplified from a cDNA clone (Invitrogen) and the ORF of c-MYC was isolated by RT-PCR from HeLa cell total RNA. Both SOX2 and c-MYC ORF were also cloned into a plasmid vector downstream of a T7 RNA polymerase promoter and sequenced.

Alternative plasmid vectors containing human open reading frames of (KLF4, LIN28, c-MYC, NANOG, OCT4 and SOX2) were cloned into pBluescriptII. These pBluescriptII vectors where constructed by ligating the above open reading frames into the EcoRV (cMyc) or EcoRV/SpeI (KLF4, LIN28, NANOG, OCT4, and SOX2) sites between the 5' and 3' *Xenopus laevis* beta-globin untranslated regions described (Krieg and Melton 1984).

mRNA Production. The T7 RNA polymerase promoter-containing plasmid constructs (pT7-KLF4, pT7-LIN28, pT7-c-MYC, pT7-OCT4, pT7-SOX2, or pT7-XBg-KLF4, pT7-XBg-LIN28, pT7-XBg-c-MYC, pT7-XBg-OCT4, and pT7-XBg-SOX2) were linearized with BamHI and pT7-NANOG and pT7-XBg-NANOG were linearized with Xba I. The mSCRIPT™ mRNA production system (EPICENTRE or CellScript, Madison, Wis., USA) was used to produce mRNA with a 5' Cap1 structure and a 3' Poly (A) tail (e.g., with approximately 150 A residues), except that pseudouridine-5'-triphosphate (TRILINK, San Diego, Calif.) was used in place of uridine-5'-triphosphate in the T7 RNA polymerase in vitro transcription reactions.

mRNA Purification and Analysis. In some experimental embodiments, the mRNA was purified by HPLC, column fractions were collected, and the mRNA fractions were analyzed for purity an immunogenicity as described in "Materials and Methods for Examples 35-38" and/or as described and shown for FIGS. 22-24. In some experimental embodiments, purified RNA preparations comprising or consisting of mRNAs encoding one or more reprogramming factors which exhibited little or no immunogenicity were used for the experiments for reprogramming human somatic cells to iPS cells.

Reprogramming of Human Somatic Cells on MEFs. 1079 fibroblasts were plated at $1 \times 10^5$ cells/well of a 6-well dish pre-coated with 0.1% gelatin (Millipore) and grown overnight. The 1079 fibroblasts were transfected with equal amounts of each reprogramming factor mRNA (KLF4, LIN28, c-MYC, NANOG, OCT4, and SOX2) using TransIT mRNA transfection reagent (MirusBio, Madison, Wis.). A total of three transfections were performed, with one transfection being performed every other day, with media changes the day after the first and second transfection. The day after the third transfection, the cells were trypsinized and $3.3 \times 10^5$ cells were plated in 1079 medium onto 0.1% gelatin pre-coated 10-cm plate seeded with $7.5 \times 10^5$ MEFs the day before. The day after plating the transfected 1079 fibroblasts onto MEFs, the medium was changed to iPS cell medium. The iPS cell medium was changed every day. Eight days after plating the transfected cells onto MEFs, MEF-conditioned medium was used. MEF conditioned medium was collected as previously described (Xu et al. 2001). Plates were screened every day for the presence of colonies with an iPS morphology using an inverted microscope.

Alternative protocols for reprogramming 1079 and IMR90 fibroblasts on MEFs were also used. MEFs were plated at $1.25 \times 10^5$ cells/well of a 0.1% gelatin pre-coated 6 well dish and incubated overnight in complete fibroblast media. 1079 or IMR90 fibroblasts were plated at $3 \times 10^4$ cells/well of a 6 well dish seeded with MEFs the previous day and grown overnight at 37° C./5% $CO_2$. The mScript Kit was then used to generate Cap1/poly-adenylated mRNA from the following vectors (pT7-Xβg-KLF4, pT7-Xβg-LIN28, pT7-Xβg-c-MYC, pT7-Xβg-NANOG, pT7-Xβg-OCT4, and pT7-Xβg-SOX2) for use in these daily transfections. All six reprogramming mRNAs were diluted to 100 ng/µl of each mRNA. Equal molarity of each mRNA was added together using the following conversion factors (OCT4 is set at 1 and all of the other mRNAs are multiplied by these conversion factors to obtain equal molarity in each mRNA mix). KLF=1.32, LIN28=0.58, c-MYC=1.26, NANOG=0.85, OCT4=1, and SOX2=0.88. To obtain equal molarity of each factor 132 µl of KLF4, 58 µl of LIN28, 126 µl of c-MYC, 85 µl of NANOG, 100 µl of OCT4 and 88 µl of SOX2 mRNA (each at 100 ng/µl) would be added together. A 600 µg total dose for transfections would mean that 100 ng (using molarity conversions above) of each of six reprogramming mRNAs was used. Trans-IT mRNA transfection reagent was used to transfect these mRNA doses. For all transfections, mRNA pools were added to 250 µl of either DMEM/F12 media without additives or Advanced MEM media without additives. 5 µl of mRNA boost reagent and 6 µl of TransIT transfection reagent was added to each tube and incubated at room temp for two minutes before adding the transfection mix to 2.5 mls of either Advanced MEM media with 10% FBS+100 ng/ml of hFGFb or iPS media containing 100 ng/ml of hFGFb. Transfections were repeated everyday for 10-16 days. The media was changed 4 hours after each transfection. In some experiments, the cells were trypsinized and replated onto new MEF plates between 5-8 days after the initial transfection. 1079 cells were split ⅙ or ¹/₁₂ onto new MEF plates while IMR90 cells were split ⅓ or ⅙ onto new MEF plates.

Reprogramming of Human Somatic Cells in MEF-Conditioned Medium. 1079 or IMR90 fibroblasts were plated at $3 \times 10^5$ cells per 10 cm dishes pre-coated with 0.1% gelatin (Millipore) and grown overnight. The 1079 or IMR90 fibroblasts were transfected with equal amounts of reprogramming factor mRNA (KLF4, LIN28, c-MYC, NANOG, OCT4, and SOX2) using TransIT mRNA transfection reagent (MirusBio, Madison, Wis.). For each transfection, either 6 µg, 18 µg, or 36 µg of each reprogramming mRNA (KLF4, LIN28, c-MYC, NANOG, OCT4, and SOX2) was used per 10-cm dish. A total of three transfections were performed, with one transfection being performed every other day with the medium being changed the day after each of the first and second transfections. All transfections were performed in MEF-conditioned medium. The day after the third transfection, the cells were trypsinized and $3 \times 10^5$ cells were plated on new 10-cm dishes pre-coated with 0.1% gelatin (Millipore). The cells were grown in MEF-conditioned medium for the duration of the experiment.

Similar daily mRNA transfections were also performed as described in the previous section with the only difference being that MEFs were not used as feeder layers, only MEF conditioned media was used.

Immunoflourescence. The 1079 cells or 1079-derived iPS cell plates were washed with PBS and fixed in 4% paraformaldehyde in PBS for 30 minutes at room temperature. The iPS cells were then washed 3 times for 5 minutes each wash with PBS followed by three washes in PBS+0.1% Triton X-100. The iPS cells were then blocked in blocking buffer (PBS+0.1% Triton, 2% FBS, and 1% BSA) for 1 hour at room temperature. The cells were then incubated for 2 hours at room temperature with the primary antibody (mouse anti-human OCT4 Cat#sc-5279, Santa Cruz Biotechnology, Santa Cruz, Calif.), (rabbit anti-human NANOG Cat #3580, rabbit anti-human KLF4 Cat #4038, mouse anti-human LIN28 Cat#5930, rabbit anti-human c-MYC Cat#5605, rabbit anti-human SOX2 Cat#3579, and mouse anti-TRA-1-60 all from Cell Signaling Technology, Beverly, Mass.) at a 1:500 dilution in blocking buffer. After washing 5 times in PBS+0.1% Triton X-100, the iPS cells were incubated for 2 hours with the anti-rabbit Alexa Fluor 488 antibody (Cat #4412, Cell Signaling Technology), anti-mouse FITC secondary (Cat#F5262, Sigma), or an anti-mouse Alexa Fluor 555 (Cat#4409, Cell Signaling Technology) at 1:1000 dilutions in blocking buffer. Images were taken on a Nikon TS 100F inverted microscope (Nikon, Tokyo, Japan) with a 2-megapixel monochrome digital camera (Nikon) using NIS-elements software (Nikon).

Example 1

This Example describes tests to determine if transfections with mRNA encoding KLF4, LIN28, c-MYC, NANOG, OCT4 and SOX2 resulted in expression and proper subcellular localization of each respective protein product in newborn fetal foreskin 1079 fibroblasts. The mRNAs used in the experiments were made with pseudouridine-5'-triphosphate substituting for uridine-5'-triphosphate (Kariko et al. 2008). The 1079 fibroblasts were transfected with 4 µg of each mRNA per well of a 6-well dish and immunofluorescence analysis was performed 24 hours post-transfection. Endogenous KLF4, LIN28, NANOG, OCT4 and SOX2 protein levels were undetectable by immunoflourescence in untransfected 1079 cells (FIG. 1: B, F, N, R, V). Endogenous levels of c-MYC were relatively high in untransfected 1079 cells (FIG. 1J). Transfections with mRNAs encoding the transcription factors, KLF4, c-MYC, NANOG, OCT4, and SOX2 all resulted in primarily nuclear localization of each protein 24 hours after mRNA transfections (FIG. 1: D, L, P, T, X). The cytoplasmic mRNA binding protein, LIN28, was localized to the cytoplasm (FIG. 1: H).

Example 2

Having demonstrated efficient mRNA transfection and proper subcellular localization of the reprogramming proteins, this Example describes development of a protocol for iPS cell generation from somatic fibroblasts. Equal amounts (by weight) of KLF4, LIN28, c-MYC, NANOG, OCT4, and SOX2 mRNAs were transfected into 1079 fibroblasts three times (once every other day). The day after the third transfection, the cells were plated onto irradiated MEF feeder cells and grown in iPS cell medium. Six days after plating the 1079 fibroblasts onto irradiated MEFs, two putative iPS cell colonies became apparent on the 10-cm plate transfected with 3 µg of each reprogramming factor mRNA (KLF4, LIN28, c-MYC, NANOG, OCT4, and SOX2). The colonies were allowed to grow until 12 days after the last transfection before they were fixed for immunofluorescence analysis. The inner cell mass-specific marker NANOG is often used to assay whether iPS cell colonies are truly iPS colonies (Gonzalez et al. 2009, Huangfu et al. 2008). NANOG expression arising from the mRNAs that were transfected 12 days earlier would be negligible based on previous reports on the duration of mRNA stability and expression (Kariko et al. 2008). Staining for NANOG showed that both of the two iPS cell colonies were NANOG positive (FIG. 2B, D, and not shown). The surrounding fibroblasts that were not part of the iPS cell colony were NANOG negative, suggesting that they were not reprogrammed into iPS cells.

Figure 3:
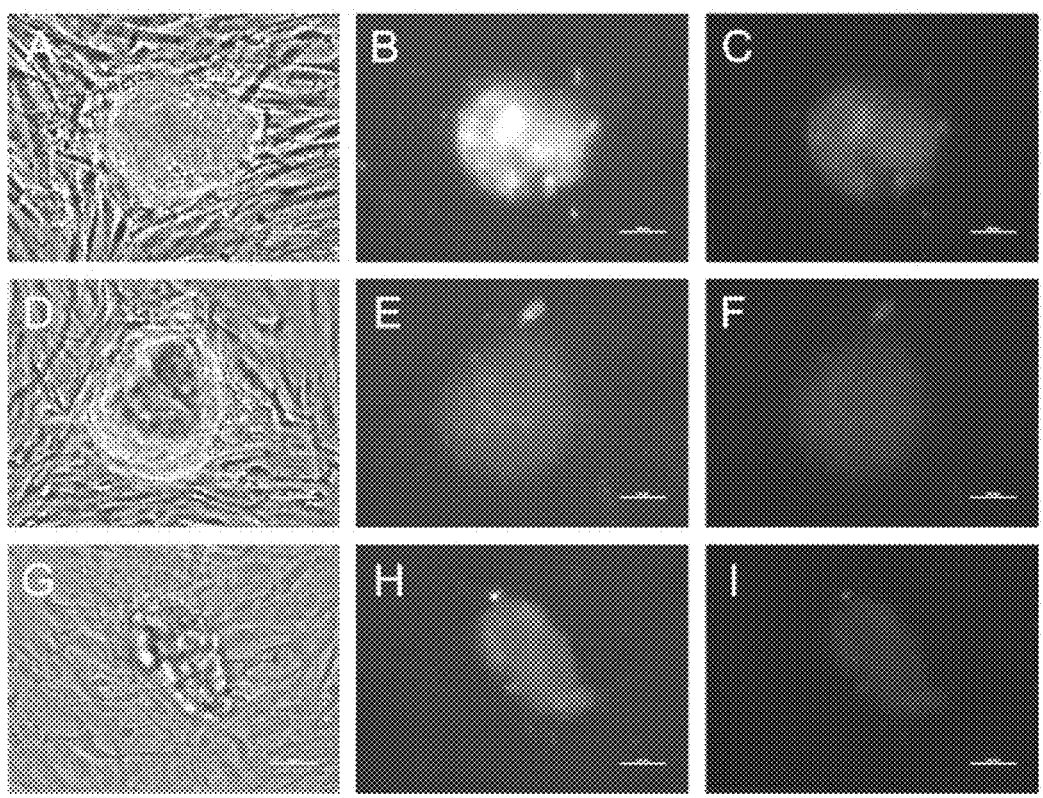
FIG. 3 shows that iPS colonies derived from human 1079 and IMR90 somatic cells are positive for NANOG and TRA-1-60.

In a subsequent experiment using the same protocol, both 1079 fibroblasts and human IMR90 fibroblasts were transfected with the same reprogramming mRNAs. Multiple colonies were detected as early as 4 days after plating the transfected cells on irradiated MEFs. When 6 µg of each mRNA (KLF4, LIN28, c-MYC, NANOG, OCT4, and SOX2) were used in transfections in 6-well dishes, 3 putative iPS cell colonies were later detected in both cell lines after plating on MEFs in 10-cm plates (FIG. 3). In addition to analyzing these colonies for expression of NANOG, TRA-1-60, a more stringent marker of fully reprogrammed iPS cells (Chan et al. 2009), was also used for immunofluorescence analysis. iPS colonies generated from 1079 fibroblasts (FIG. 3A-F) and from IMR90 fibroblasts (FIG. 3G-I) were positive for both NANOG and TRA-1-60, indicating that these colonies are fully reprogrammed type III iPS cell colonies. This protocol comprising three transfections of mRNAs encoding all six reprogramming factors and then plating onto MEF feeder cells resulted in a similar reprogramming efficiency (3-6 iPS colonies per $1 \times 10^6$ input cells) as was previously reported by protocols comprising delivery of the same reprogramming factors by transfection of an expression plasmid (Aoi et al. 2008).

Example 3

This Example describes attempts to improve the efficiency of reprogramming differentiated cells using mRNA.

Figure 4:
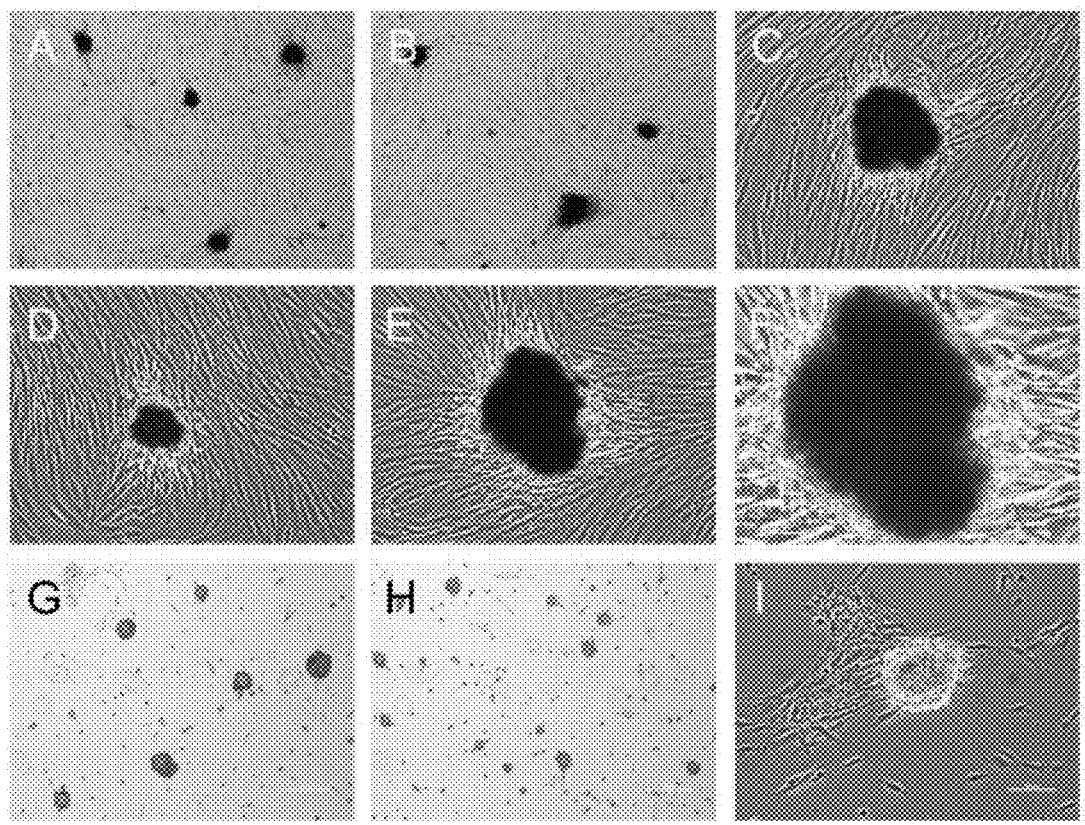
FIG. 4 shows that rapid, enhanced-efficiency iPSC colony formation is achieved by transfecting cells with mRNA encoding reprogramming factors in MEF-conditioned medium. Over 200 colonies were detected 3 days after the final transfection; in the 10-cm dish, IMR90 cells were transfected three times with 36 µg of each reprogramming mRNA (i.e., encoding KLF4, LIN28, c-MYC, NANOG, OCT4, and SOX2). Representative iPSC colonies are shown at 4× (A, B), 10× (C-E) and 20× magnification (F). Eight days after the final mRNA transfection with mRNAs encoding the six reprogramming factors, more than 1000 iPSC colonies were counted in IMR90 cells transfected with 18 µg (G, I) or 36 µg (H) of each of the six mRNAs. Representative colonies are shown at 4× magnification (G-H) and at 10× magnification (I).
Figure 5:
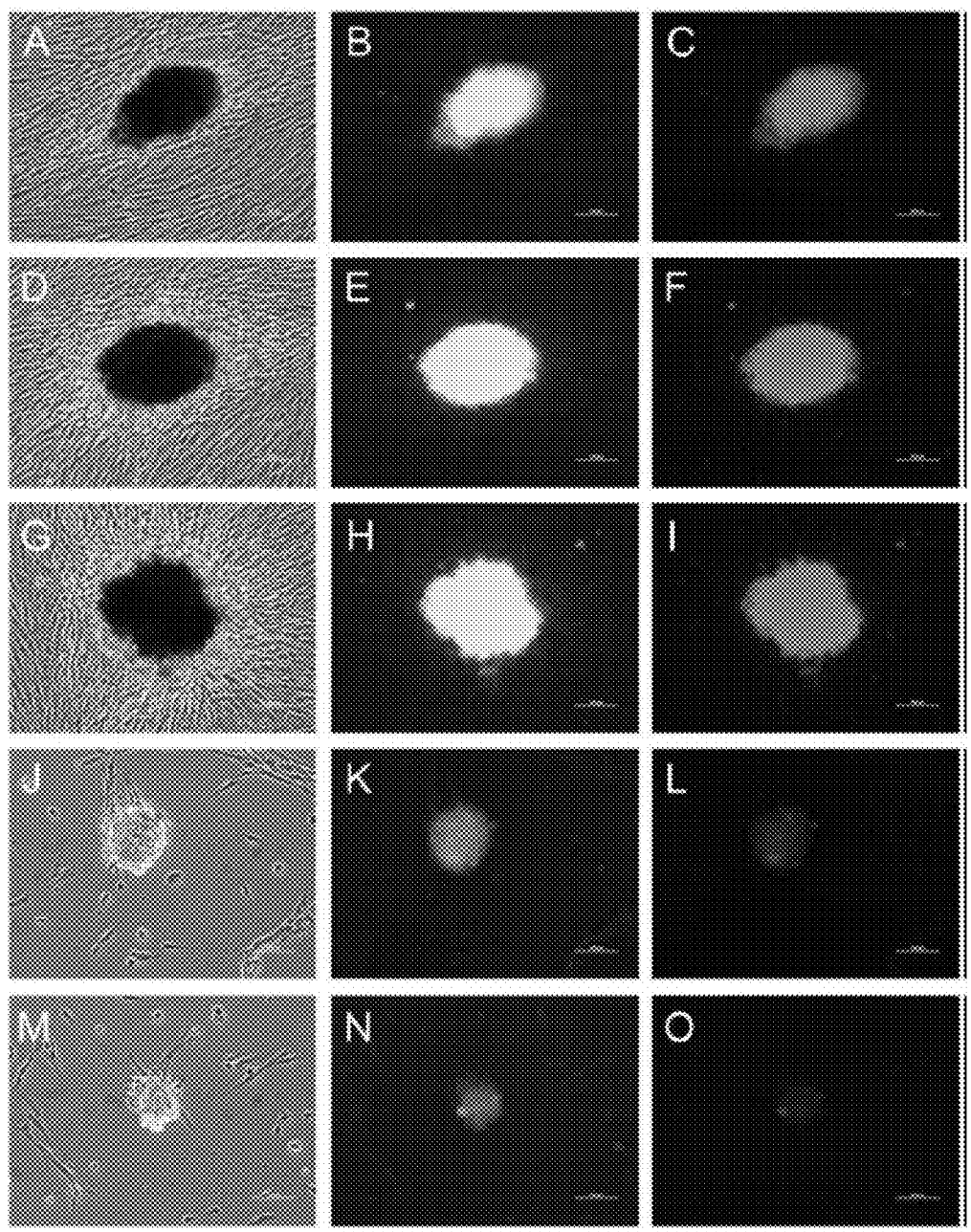
FIG. 5 shows that 1079- and IMR90-derived iPSC colonies are positive for both NANOG and TRA-1-60. Eight days after the final mRNA transfection with 36 µg of mRNA for each of the six reprogramming factors, the 1079-derived iPSC colonies (shown in A, D, and G) are positive for NANOG (B, E, and H) and TRA-1-60 (C, F, and I). Eight days after the final mRNA transfection with 18 µg (J-L) or 36 µg (M-O) of mRNA for each of the six reprogramming factors, IMR90-derived iPS colonies are also positive for NANOG (K, N) and TRA-1-60 (L, O).

In one approach, a protocol was used that comprised transfecting 1079 or IMR90 fibroblasts three times (once every other day) with the mRNAs encoding the six reprogramming factors in MEF-conditioned medium rather than in fibroblast medium and then growing the treated 1079 fibroblasts in MEF-conditioned medium rather than plating them on a MEF feeder layer after the treatments. At the highest transfection dose utilized (36 µg of each reprogramming factor per 10-cm dish), 208 iPS cell colonies were detected three days after the final transfection (FIG. A-F). Interestingly no iPS cell colonies were detected in the dishes transfected with either 6 or 18 µg of each of the reprogramming factors at the 3-day timepoint, suggesting that a dose above 18 µg was important, under these conditions, for iPS cell colony formation to occur within 3 days in MEF-conditioned medium. IMR90 cells showed an even higher number of iPS cell colonies, with around 200 colonies 8 days after the last transfection in the plate transfected with three 6-µg doses of each of the six reprogramming factor mRNAs and >1000 colonies in IMR90 cells transfected three times with 18-µg or 36-µg doses of each of the six reprogramming mRNAs (FIG. 4G-I). Colonies were visible 3 days after the final transfection in 1079 cells, whereas colonies only became visible 6-7 days after the final transfection in IMR90 cells. Therefore, the more mature colonies derived from the 1079 cells were larger and denser and were darker in bright-field images compared to the IMR90 colonies (FIG. 4). All of the colonies on the 1079 plate transfected three times with 36 µg of each reprogramming mRNA were positive for both NANOG and TRA-1-60 8 days after the final mRNA transfection (FIGS. A-I). All of the more immature IMR90 iPS colonies were also positive for both NANOG and TRA-1-60 (FIG. 5J-O), but showed less robust staining for both markers due to their less dense cellular nature compared to the more mature 1079 colonies (FIG. 5A-I). The present protocol comprising delivery of the mRNAs into 1079 or IMR90 cells in MEF-conditioned medium had a reprogramming efficiency of 200 to >1000 colonies per $3\times10^5$ input cells. This protocol for inducing iPS cells was faster and almost 2-3 orders of magnitude more efficient than published protocols comprising transfecting fibroblasts with DNA plasmids encoding these same six reprogramming factors in fibroblast medium (Aoi et al. 2008). Still further, this protocol was over 7-40 times more efficient than the published protocol comprising delivery of reprogramming factors with lentiviruses, based on the published data that lentiviral delivery of reprogramming factors into 1079 newborn fibroblasts, which resulted in approximately 57 iPS cell colonies per $6\times10^5$ input cells (Aoi et al. 2008). This protocol is also much faster than the published methods.

Example 4

Naturally Occurring RNA Molecules Exhibit Differential Abilities to Activate Dendritic Cells
Materials and Experimental Methods Plasmids and Reagents Plasmids pT7T3D-MART-1 and pUNO-hTLR3 were obtained from the ATCC (Manassas, Va.) and InvivoGen (San Diego, Calif.), respectively. pTEVluc was obtained from Dr Daniel Gallie (UC Riverside), contains pT7-TEV (the leader sequence of the tobacco etch viral genomic RNA)-luciferase-A50, and is described in Gallie, D R et al, 1995. The tobacco etch viral 5' leader and poly(A) tail are functionally synergistic regulators of translation. Gene 165: 233) pSVren was generated from p2luc (Grentzmann G, Ingram J A, et al, A dual-luciferase reporter system for studying recoding signals. RNA 1998; 4(4): 479-86) by removal of the firefly luciferase coding sequence with BamHI and NotI digestions, end-filling, and religation.

Human TLR3-specific siRNA, pTLR3-sh was constructed by inserting synthetic ODN encoding shRNA with 20-nt-long homology to human TLR3 (nt 703-722, accession: NM_003265) into plasmid pSilencer 4.1-CMV-neo (Ambion, Austin, Tex.). pCMV-hTLR3 was obtained by first cloning hTLR3-specific PCR product (nt 80-2887; Accession NM_003265) into pCRII-TOPO (Invitrogen, Carlsbad, Calif.), then released with Nhe I-Hind III cutting and subcloning to the corresponding sites of pcDNA3.1 (Invitrogen). LPS (E. coli 055:B5) was obtained from Sigma Chemical Co, St. Louis, Mo. CpG ODN2006 and R-848 were obtained from InvivoGen.

Cells and Cell Culture

Human embryonic kidney 293 cells (ATCC) were propagated in DMEM supplemented with glutamine (Invitrogen) and 10% FCS (Hyclone, Ogden, Utah) (complete medium). In all cases herein, "293 cells" refers to human embryonic kidney (HEK) 293 cells. 293-hTLR3 cell line was generated by transforming 293 cells with pUNO-hTLR3. Cell lines 293-hTLR7, 293-hTLR8 and 293-hTLR9 (InvivoGen) were grown in complete medium supplemented with blasticidin (10 µg/ml) (Invivogen). Cell lines 293-ELAM-luc and TLR7-293 (M. Lamphier, Eisai Research Institute, Andover Mass.), and TLR3-293 cells were cultured as described (Kariko et al, 2004, mRNA is an endogenous ligand for Toll-like receptor 3. J Biol Chem 279: 12542-12550). Cell lines 293, 293-hTLR7 and 293-hTLR8 were stably transfected with pTLR3-sh and selected with G-418 (400 µg/ml) (Invitrogen). Neo-resistant colonies were screened and only those that did not express TLR3, determined as lack of IL-8 secretion loin response to poly(I):(C), were used in further studies. Leukopheresis samples were obtained from HIV-uninfected volunteers through an IRB-approved protocol.

Murine DC Generation

Murine DCs were generated by collecting bone marrow cells from the tibia and femurs of 6-8-week-old C57BL/6 mice and lysing the red blood cells. Cells were seeded in 6-well plates at $10^6$ cells/well in 2 ml DMEM+10% FCS and 20 ng/ml muGM-CSF (R & D Systems). On day 3, 2 ml of fresh medium with muGM-CSF was added. On day 6, 2 ml medium/well was collected, and cells were pelleted and resuspended in fresh medium with muGM-CSF. On day 7 of the culture, the muDC were harvested, washed.

Natural RNA

Mitochondria were isolated from platelets obtained from the University of Pennsylvania Blood Bank using a fractionation lyses procedure (Mitochondria isolation kit; Pierce, Rockford, Ill.). RNA was isolated from the purified mitochondria, cytoplasmic and nuclear fractions of 293 cells, un-fractioned 293 cells, rat liver, mouse cell line TUBO, and DH5alpha strain of E. coli by Master Blaster® (BioRad, Hercules, Calif.). Bovine tRNA, wheat tRNA, yeast tRNA, E. coli tRNA, poly(A)+mRNA from mouse heart and poly(I):(C) were purchased from Sigma, total RNA from human spleen and E. coli RNA were purchased from Ambion. Oligoribonucleotide-5'-monophosphates were synthesized chemically (Dharmacon, Lafayette, Colo.).

Aliquots of RNA samples were incubated in the presence of Benzonase nuclease (1 U per 5 µl of RNA at 1 microgram per microliter (µg/µl) for 1 h) (Novagen, Madison, Wis.). Aliquots of RNA-730 were digested with alkaline phosphatase (New England Biolabs). RNA samples were analyzed by denaturing agarose or polyacrylamide gel electrophoresis for quality assurance. Assays for LPS in RNA preparations using the Limulus Amebocyte Lysate gel clot assay were negative with a sensitivity of 3 picograms per milliliter (pg/ml) (University of Pennsylvania, Core Facility).

HPLC Analysis

Nucleoside monophosphates were separated and visualized via HPLC. To release free nucleoside 3'-monophosphates, 5 µg aliquots of RNA were digested with 0.1 U RNase T2 (Invitrogen) in 10 µl of 50 mM NaOAc and 2 mM EDTA buffer (pH 4.5) overnight, then the samples were injected into an Agilent 1100 HPLC using a Waters Symmetry C 18 column (Waters, Milford, Mass.). At a flow rate of 1 mL/min, a gradient from 100% buffer A (30 mM $KH_2PO_4$ and 10 mM tetraethylammonium phosphate [PicA reagent, Waters], pH 6.0) to 30% buffer B (acetonitrile) was run over 60 minutes. Nucleotides were detected using a photodiode array at 254 nm. Identities were verified by retention times and spectra.

Dendritic Cell Assays

Dendritic cells in 96-well plates (approximately $1.1 \times 10^5$ cells/well) were treated with R-848, Lipofectin®, or Lipofectin®-RNA for 1 h, then the medium was changed. At the end of 8 h (unless otherwise indicated), cells were harvested for either RNA isolation or flow cytometry, while the collected culture medium was subjected to cytokine ELISA. The levels of IL-12 (p70) (BD Biosciences Pharmingen, San Diego, Calif.), IFN-α, TNF-α, and IL-8 (Biosource International, Camarillo, Calif.) were measured in supernatants by sandwich ELISA. Cultures were performed in triplicate or quadruplicate and measured in duplicate.

Northern Blot Analysis

RNA was isolated from MDDCs after an 8 h incubation following treatment as described above. Where noted, cells were treated with 2.5 µg/ml cycloheximide (Sigma) 30 min prior to the stimulation and throughout the entire length of incubation. RNA samples were processed and analyzed on Northern blots as described (Kariko et al, 2004, ibid) using human TNF-α and GAPDH probes derived from plasmids (pE4 and pHcGAP, respectively) obtained from ATCC.

Results

Figure 6:
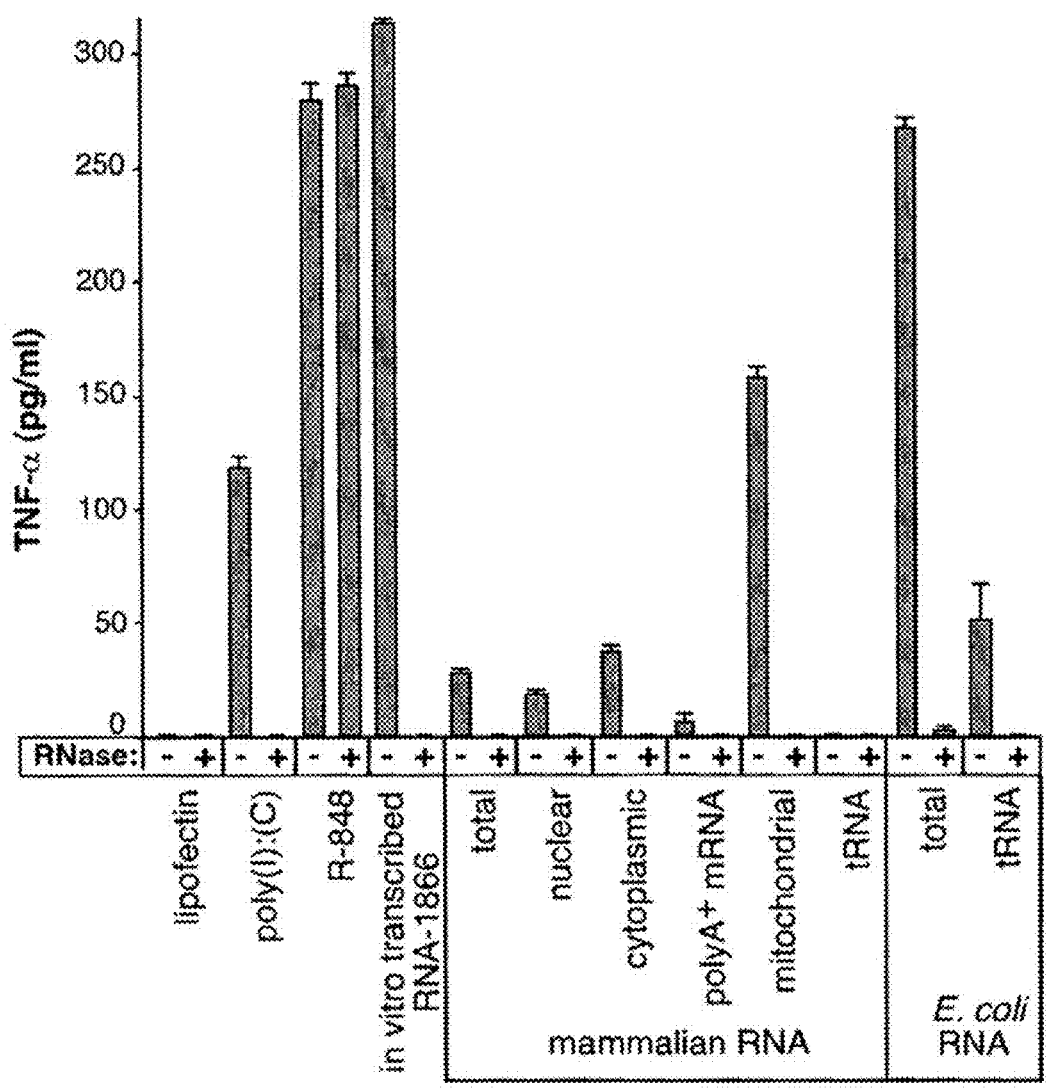
FIG. 6. Production of TNF-α by MDDCs transfected with natural RNA, demonstrating that unmodified in vitro-synthesized RNA and bacterial RNA and mammalian mitochondrial RNA is highly immunogenic, while other mammalian RNA is weakly immunogenic. Human MDDCs were incubated with Lipofectin® alone, or complexed with R-848 (1 µg/ml), or RNA (5 µg/ml) from 293 cells (total, nuclear and cytoplasmic RNAs), mouse heart (polyA+mRNA), human platelet mitochondrial RNA, bovine tRNA, bacterial tRNA and total RNA (*E. coli*) with or without RNase digestion. After 8 h, TNF-α was measured in the supernatants by ELISA. Mean values±SEM are shown. Results are representative of 3 independent experiments.

To determine the immuno-stimulatory potential of different cellular RNA subtypes, RNA was isolated from different subcellular compartments—i.e. cytoplasm, nucleus and mitochondria. These RNA fractions, as well as total RNA, tRNA and polyA-tail-selected mRNA, all from mammalian sources, were complexed to Lipofectin® and added to MDDC. While mammalian total, nuclear and cytoplasmic RNA all stimulated MDDC, as evidenced by detectable TNF-α secretion, the TNF-α levels were much lower than those induced by in vitro-synthesized mRNA (FIG. 6). Moreover, mammalian tRNA did not induce any detectable level of TNF-α, while mitochondrial (mt) RNA induced much more TNF-α than the other mammalian RNA subtypes. Bacterial total RNA was also a potent activator of MDDC; by contrast, bacterial tRNA induced only a low level of TNF-α. tRNA from other sources (yeast, wheat germ, bovine) were non-stimulatory. Similar results were observed when RNA from other mammalian sources was tested. When RNA samples were digested with Benzonase, which cleaves ssRNA and dsRNA, RNA signaling was abolished in MDDC, verifying that TNF-α secretion was due to the RNA in the preparations. The activation potentials of the RNA types tested exhibited an inverse correlation with the extent of nucleoside modification. Similar results were obtained in the experiments described in this Example for both types of cytokine-generated DC.

These findings demonstrate that the immunogenicity of RNA is affected by the extent of nucleoside modification, with a greater degree of modification tending to decrease immunogenicity.

Example 5

In Vitro Synthesis of RNA Molecules with Modified Nucleosides Materials and Experimental Methods In Vitro-Transcribed RNA Using in vitro transcription assays (MessageMachine and MegaScript kits; Ambion,) the following long RNAs were generated by T7 RNA polymerase (RNAP) as described (Kariko et al, 1998, Phosphate-enhanced transfection of cationic lipid-complexed mRNA and plasmid DNA. Biochim Biophys Acta 1369, 320-334) (Note: the names of templates are indicated in parenthesis; the number in the name of the RNA specifies the length): RNA-1866 (Nde I-linearized pTEVluc) encodes firefly luciferase and a 50 nt-long polyA-tail. RNA-1571 (Ssp I-linearized pSVren) encodes *Renilla* luciferase. RNA-730 (Hind III-linearized pT7T3D-MART-1) encodes the human melanoma antigen MART-I. RNA-713 (EcoR I-linearized pTIT3D-MART-1) corresponds to antisense sequence of MART-1, RNA497 (Bgl II-linearized pCMV-hTLR3) encodes a partial 5' fragment of hTLR3. Sequences of the RNA molecules are as follows:

```
RNA-1866:
                                   (SEQ ID No: 1)
ggaauucucaacacaacauauacaaaacaaacgaaucucaag caaucaagcauucuacuucuauugcagcaauuuaaaucauuu cuuuuaaagcaaaagcaauuuucugaaaauuuucaccauuua cgaacgauagccauggaagacgccaaaaacauaaagaaaggc ccggcgccauucuauccucuagaggauggaaccgcuggagag caacugcauaaggcuaugaagagauacgcccugguuccugga acaauugcuuuuacagaugcacauaucgaggugaacaucacg uacgcggaauacuucgaaauguccguucgguuggcagaagcu augaaacgauaugggcugaauacaaaucacagaaucgucgua ugcagugaaaacucucuucaauucuuuaugccggguguugggc gcguuauuuaucggaguugcaguugcgcccgcgaacgacauu uauaaugaacgugaauugcucaacaguaugaacauuucgcag ccuaccguaguguuuguuuccaaaaaggggguugcaaaaaauu uugaacgugcaaaaaaauuaccaauaauccagaaaauuauu aucauggauucuaaaacggauuaccagggauuucagucgaug uacacguucgucacaucucaucuaccucccgguuuuaaugaa uacgauuuguaccagaguccuuugaucgugacaaaacaauu gcacugauaaugaauuccucuggaucuacugggguuaccuaag ggugugggcccuuccgcauagaacugccugcgucagauucucg caugccagagauccuauuuuuggcaaucaaaucauuccggau
```

-continued
```
acugcgauuuuaaguguugguuccauccaucacgguuuugga
auguuuacuacacucggauauuugauauguggauuucgaguc
gucuuaauguauagauuugaagaagagcuguuuuuacgaucc
cuucaggauuacaaaauucaaagugcguugcuaguaccaacc
cuauuuucauucuucgccaaaagcacucugauugacaaauac
gauuuaucuaauuuacacgaaauugcuucgggggcgcaccu
cuuucgaaagaagucggggaagcgguugcaaaacgcuuccau
cuuccagggauacgacaaggauaugggcucacugagacuaca
ucagcuauucugauuacacccgaggggaugauaaaccgggc
gcggucgguaaaguuguuccauuuuuugaagcgaaggugug
gaucuggauaccgggaaaacgcuggggcguuaaucagagaggc
gaauuauguguvcagaggaccuaugauuaugucccgguuaugua
acaaucggaagcgaccaacgccuugauugacaaggaugga
uggcuacauucuggagacauagcuuacugggacgaagacgaa
cacuucuucauaguugaccgcuugaagucuuuaauuaaauac
aaaggauucaggugccccccgcugaauuggaaucgauauug
uuacaacacccaacaucuucgacgcgggcguggcaggucuu
cccgacgaugacgccggugaacuuccgccgccguuguuguu
uuggagcacggaaagacgaugacggaaaagagaucguggau
uacguggccagucaaguaacaaccgcgaaaaaguugcgcgga
ggaguugguuuguggacgaaguaccgaaaggucuuaccgga
aacucgacgcaagaaaaaucagagagauccucauaaaggcc
aagaagggcggaaagccaaauuguaaaauguaacucuagag
gauccccaaaaaaaaaaaaaaaaaaaaaaaaaaaaaaaaa
aaaaaaaaaaaaaaaca.
```
RNA-1571:
(SEQ ID No: 2)
```
ggcuagccaccaugacuucgaaaguuuaugauccagaacaaa
ggaaacggaugauaacugguccgcagugguggggccagaugua
acaaaugaauguucuugauucauuuauuaauuauuaugauu
cagaaaaacaugcagaaaaugcuguuauuuuuuuacaugguua
acgcggccucuucuuauuuauggcgacauguuugugccacaua
uugagccaguagcgcggguauuauaccagaccuuauuggua
ugggcaaaucaggcaaaucgguaauggu ucuuauagguuac
uugaucauuacaaauaucuuacugcaugguuugaacuucuua
auuuaccaaagaagaucauuuuugucggccaugauuggggug
cuuguugggcauucauuauagcuaugagcaucaagauaaga
ucaaagcaauaguucacgcugaaagguguaguagaugugauug
aaucaugggaugaauggccugauauugaagaagauauugcgu
ugaucaaaucugaagaaggagaaaaaaugguuuuggagaaua
acuucuucgugga aaccauguugccaucaaaaucaugaaa
```
(SEQ ID No: 3)
```
aguuagaaccagaagaauuugcagcauaucuugaaccauuca
aagagaaggugaaguucgucguccaacauuaucauggccuc
gugaaaucccguuaguaaaagguguaaaccugacguuguac
aaauuguuaggaauuauaaugcuuaucuacgugcaagugaug
auuuaccaaaaaugluuuauugaaucggacccaggauucuuuu
ccaaugcuauuguugaaggugccaagaaguuuccuaauacug
aauuugucaaaguaaaaggucuucauuuuucgcaagaagaug
caccugaugaaauggaaaauauaucaaaucguucguugagc
gaguucucaaaaaugaacaaaugucgacggggcccuagga
auuuuuaggaagaucuggccuuccuacaagggaaggccag
ggaauuuucuucagagcagaccagagccaacagccccaccag
aagagagcuucaggucuggggguagagacaacaacucccccuc
agaagcaggagccgauagacaaggaacuguauccuuuaacuu
cccucagaucacucuuuggcaacgaccccucgucacaauaaa
gauagggggcaacuaaagggaucggccgcuucgagcagaca
ugauaagauacauugaugaguuuggacaaaccacaacuagaa
ugcagugaaaaaaugcuuuauuugugaaauuugugaugcua
uugcuuuauuuguaaccauuauaagcugcaauaaacaaguua
acaacaacaauugcauucauuuuauguucagguucagggggg
aggugugggagguuuuuaaagcaaguaaaaccucuacaaau
guggu aaaaucgauaaguuuaaacagauccagguggcacuuu
ucggggaaaugugcgcggaaccccuauuuguuuauuuucua
aauacauucaaauauguauccgcucaugagacaauaacccug
auaaaugcuucaauaau.
```
RNA-730:
(SEQ ID No: 3)
```
gggaauuuggcccucgaggccaagaauucggcacgaggcacg
cggccagccagcagacagaggacucucauuaaggaaggugu
cugugcccugacccuacaagaugccaagagaagaugcucacu
ucaucuauggu uaccccaagaaggggcacggccacucuuaca
ccacggcugaagaggccgcugggaucggcauccugacaguga
uccugggagucuuacugcucaucggcuguugguauuguagaa
gacgaaauggauacagagccuugauggauaaaagucuucaug
uuggcacucaaugugccuuaacaagaagaugcccacaagaag
gguuugaucaucgggacagcaaagugucucuucaagagaaaa
acugugaaccugugguucccaaugucuccaccugcuuaugaga
aacucucugcagaacagucaccaccaccuuauuc accuuaag
agccagcgagacaccugagacaugcugaaauuauuucucuca
cacuuuugcuugaauuuaauacagacaucuaauguucuccuu
uggaauggugauaggaaaaaugcaagccaucucuaauaaauaag
ucaguguuaaaauuuuaguaggguccgcuagcaguacuaauca
ugugaggaaaugaugagaaauauuuaaauugggaaaacuccau
```

-continued caauaaauguugcaaugcaugauaaaaaaaaaaaaaaaaaa
acugcggccgca.

RNA-713
(SEQ ID No: 4)
gggaauaagcuugcggccgcaguuuuuuuuuuuuuuuuuu
aucaugcauugcaacauuuauugauggaguuuucccaauuua
auauuucucaucauuuccucacaugauuaguacugcuagcgg
accuacuaaaauuuaacacugacuuauuauuagagauggcu
ugcauuuuccuacaccauuccaaaggagaacauuagauguc
uguauaaauucaagcaaaagugugagagaaauaauuucagca
ugucucaggugucucgcuggcucuuaaggugaauaagguggu
ggugacuguucugcagagaguuucauaagcagguggagca
uugggaaccacagguucacaguuuuucucuugaagagacacu
uugcugucccgaugaucaaacccuucuguggcaucuucuu
guuaaggcacauugagugccaacaugaagacuuuuauccauc
aaggcucuguauccauuucgucuucuacaauaccaacagccg
augagcaguaagacucccaggaucacugucaggaugccgauc
ccagcggccucuucagccgugguguaagaguggccgugcccc
uucuugggguaaccauagaugaagugagcaucuucucuuggc
aucuuguagggucagggcacaggacaccuuccuuaaugagag
uccucugucugcuggcuggccgcgugccucgugccgaauu.

RNA-497:
(SEQ ID No: 5)
gggagacccaagcuggcuagcagucauccaacagaaucauga
gacagacuuugccuuguaucuacuuuuggggggggccuuuugc
ccuuugggaugcuguguugcauccuccaccaccaagugcacug
uuagccaugaaguugcugacugcagccaccugaaguugacuc
agguacccgaugaucuacccacaaacauaacaguguugaacc
uuacccauaaucaacucagaagauuaccagccgccaacuuca
caagguauagccagcuaacuagcuuggauguaggauuuaaca
ccaucucaaaacuggagccagaauugugccagaaacuuccca
uguuaaaaguuuugaaccuccagcacaaugagcuaucucaac
uuucugauaaaaccuuugccuucugcacgaauuugacugaac
uccaucucaugccaacucaauccagaaaauuaaaaauaauc
ccuuugucaagcagaagaauuuaaucacauua.

To obtain modified RNA, the transcription reaction was assembled with the replacement of one (or two) of the basic NTPs with the corresponding triphosphate-derivative(s) of the modified nucleotide 5-methylcytidine, 5-methyluridine, 2-thiouridine, $N^6$-methyladenosine or pseudouridine (Tri-Link, San Diego, Calif.). In each transcription reaction, all 4 nucleotides or their derivatives were present at 7.5 millimolar (mM) concentration. In selected experiments, as indicated, 6 mM m7GpppG cap analog (New England BioLabs, Beverly, Mass.) was also included to obtain capped RNA. ORN5 and ORN6 were generated using DNA oligodeoxynucleotide templates and T7 RNAP (Silencer® siRNA construction kit, Ambion).

Results

Figure 7A:
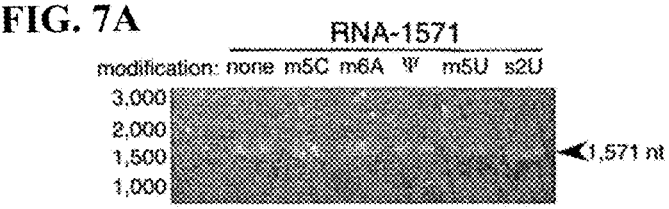
FIGS. 7A-C. TLR-dependent activation by RNA demonstrates that m6A and s2U modification blocks TLR3 signaling, while all modifications block TLR7 and TLR8 signaling, and that less modified bacterial RNA and unmodified in vitro-transcribed RNA activates all three TLR. (A) Aliquots (1 µg) of in vitro-transcribed RNA-1571 without (none) or with $m^5C$, $m^6A$, ψ, $m^5U$ or $S^2U$ nucleoside modifications were analyzed on denaturing agarose gel followed by ethidium bromide-staining and UV illumination. (B) 293 cells expressing human TLR3, TLR7, TLR8 and control vectors were treated with Lipofectin® alone, Lipofectin®-R-848 (1 µg/ml) or RNA (5 µg/ml). Modified nucleosides present in RNA-730 and RNA-1571 are noted. (C) CpG ODN-2006 (5 µg/ml), LPS (1.0 µg/ml) and RNA isolates were obtained from rat liver, mouse cell line (TUBO) and human spleen (total), human platelet mitochondrial RNA, or from two different *E. coli* sources. 293-hTLR9 cells served as control. After 8 h, IL-8 was measured in the supernatants by ELISA. Mean values±SEM are shown. Cell lines containing hTLR3-targeted siRNA are indicated with asterisk. The results are representative of four independent experiments.

To further test the effect of nucleoside modifications on immunogenicity, an in vitro system was developed for producing RNA molecules with pseudouridine or modified nucleosides. In vitro transcription reactions were performed in which 1 or 2 of the 4 nucleotide triphosphates (NTP) were substituted with a corresponding nucleoside-modified NTP. Several sets of RNA with different primary sequences ranging in length between 0.7-1.9 kb, and containing either none, 1 or 2 types of modified nucleosides were transcribed. Modified RNAs were indistinguishable from their non-modified counterparts in their mobility in denaturing gel electrophoresis, showing that they were intact and otherwise unmodified (FIG. 7A). This procedure worked efficiently with any of T7, SP6, and T3 phage polymerases, and therefore is generalizable to a wide variety of RNA polymerases.

These findings provide a novel in vitro system for production of RNA molecules with modified nucleosides.

Example 6

In Vitro-Transcribed RNA Stimulates Human TLR3, and Nucleoside Modifications Reduce the Immunogenicity of RNA Materials and Experimental Methods Parental-293; 293-hTLR7 and 293-hTLR8 cells, all expressing TLR3-specific siRNA, and 293hTLR9, TLR3-293 were seeded into 96-well plates ($5\times10^4$ cells/well) and cultured without antibiotics. On the subsequent day, the cells were exposed to R-848 or RNA complexed to Lipofectin® (Invitrogen) as described (Kariko et al, 1998, ibid). RNA was removed after one hour (h), and cells were further incubated in complete medium for 7 h. Supernatants were collected for IL-8 measurement.

Results

Figure 7B:
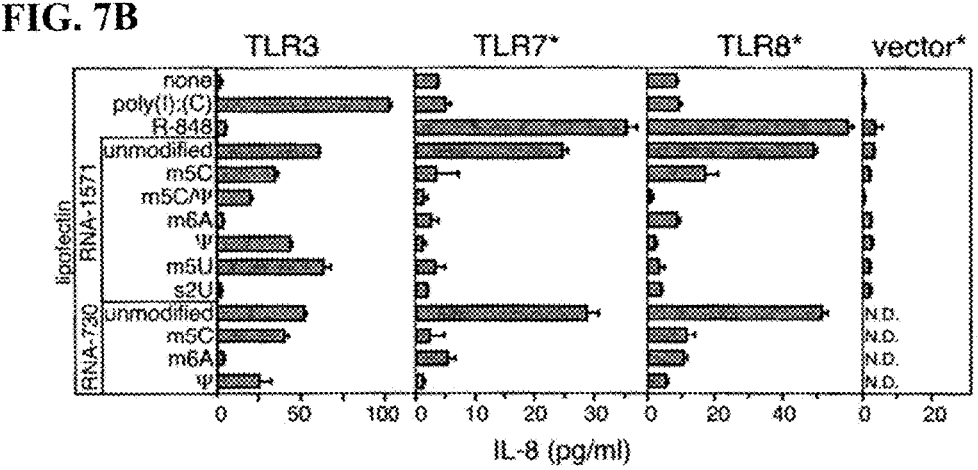

To determine whether modification of nucleosides influences the RNA-mediated activation of TLRs, human embryonic kidney 293 cells were stably transformed to express human TLR3. The cell lines were treated with Lipofectin®-complexed RNA, and TLR activation was monitored as indicated 10 by interleukin (IL)-8 release. Several different RNA molecules were tested. Unmodified, in vitro transcribed RNA elicited a high level of IL-8 secretion. RNA containing m6A or s2U nucleoside modifications, but contrast, did not induce detectable IL-8 secretion (FIG. 7B). The other nucleoside modifications tested (i.e. m5C, m5U, ψ, and m5C/ψ) had a smaller suppressive effect on TLR3 stimulation (FIG. 7B). "ψ" refers to pseudouridine.

Thus, nucleoside modifications such as $m^6A$ $S^2U$, $m^5C$, $m^5U$, ψ, reduce the immunogenicity of RNA as mediated by TLR3 signaling.

Example 7

In Vitro-Transcribed RNA Stimulates Human TLR7 and TLR8, and Nucleoside Modifications Reduce the Immunogenicity of RNA To test the possibility that 293 express endogenous TLR3 that interfere with assessing effects of RNA on specific TLR receptors, expression of endogenous TLR3 was eliminated from the 293-TLR8 cell line by stably transfecting the cells with a plasmid expressing TLR3-specific short hairpin (sh) RNA (also known as siRNA). This cell line was used for further study, since it did not respond to poly(I):(C), LPS, and CpG-containing oligodeoxynucleotides (ODNs), indicating the absence of TLR3, TLR4 and TLR9, but did respond to R-848, the cognate ligand of human TLR8 (FIG. 7B). When the 293-hTLR8 cells expressing TLR3-targeted shRNA (293-hTLR8 shRNA-TLR3 cells) were transfected with in vitro transcribed RNA, they secreted large amounts of IL-8. By contrast, RNA containing most of the nucleoside modifications (m$^5$C, m$^5$U, ψ, and m$^5$C/ψ, S$^2$U) eliminated stimulation (no more IL-8 production than the negative control, i.e. empty vector). m6A modification had a variable effect, in some cases eliminating and in other cases reducing IL-8 release (FIG. 7B).

The results of this Example and the previous Example show that (a) RNA with natural phosphodiester inter-nucleotide linkages (e.g. in vitro-transcribed RNA) stimulates human TLR3, TLR7 and TLR8; and (b) nucleoside modifications such as m6A, m5C, m5U, s2U and ψ, alone and in combination, reduce the immunogenicity of RNA as mediated by TLR3, TLR7 and TLR8 signaling. In addition, these results provide a novel system for studying signaling by specific TLR receptors.

Example 8

Figure 7C:
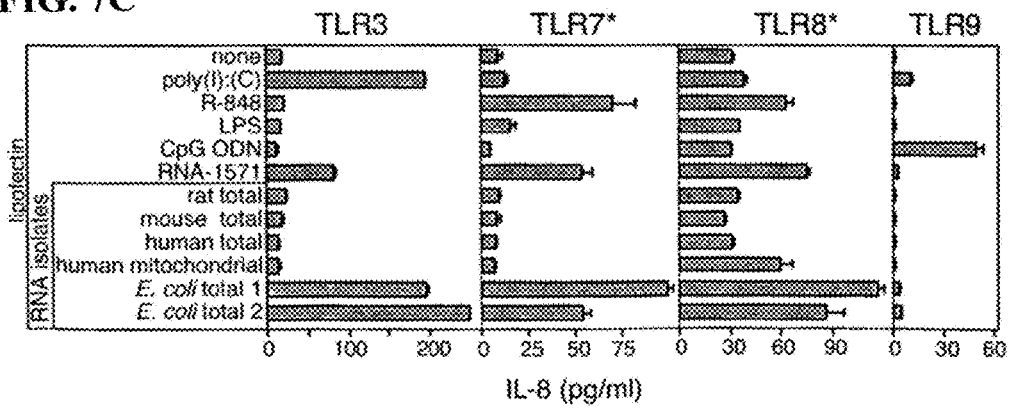

Nucleoside Modifications Reduce the Immunogenicity of RNA as Mediated by TLR7 and TLR8 Signaling The next set of experiments tested the ability of RNA isolated from natural sources to stimulate TLR3, TLR7 and TLR8. RNA from different mammalian species were transfected into the TLR3, TLR7 and TLR8-expressing 293 cell lines described in the previous Example. None of the mammalian RNA samples induced IL-8 secretion above the level of the negative control. By contrast, bacterial total RNA obtained from two different *E. coli* sources induced robust IL-8 secretion in cells transfected with TLR3, TLR7 and TLR8, but not TLR9 (FIG. 7C). Neither LPS nor unmethylated DNA (CpG ODN) (the potential contaminants in bacterial RNA isolates) activated the tested TLR3, TLR7 or TLR8. Mitochondrial RNA isolated from human platelets stimulated human TLR8, but not TLR3 or TLR7.

These results demonstrate that unmodified in vitro-transcribed and bacterial RNA are activators of TLR3, TLR7 and TLR8, and mitochondrial RNA stimulates TLR8. In addition, these results confirm the finding that nucleoside modification of RNA decreases its ability to stimulate TLR3, TLR7 and TLR8.

Example 9

Nucleoside Modifications Reduce the Capacity of RNA to Induce Cytokine Secretion and Activation Marker Expression By DC Materials and Experimental Methods
DC Stimulation Assays After 20 h of incubation with RNA, DCs were stained with CD83-phycoerythrin mAb (Research Diagnostics Inc, Flanders, N.J.), HLA-DR-Cy5PE, and CD80 or CD86-fluorescein isothiocyanate mAb and analyzed on a FACScalibur® flow cytometer using CellQuest® software (BD Biosciences). Cell culture supernatants were harvested at the end of a 20 h incubation and subjected to cytokine ELISA. The levels of IL-12 (p'70) (BD Biosciences Pharmingen, San Diego, Calif.), IFN-α, and TNF-α (Biosource International, Camarillo, Calif.) were measured in supernatants by ELISA. Cultures were performed in triplicate or quadruplicate, and each sample was measured in duplicate.

Results

Figure 8C:
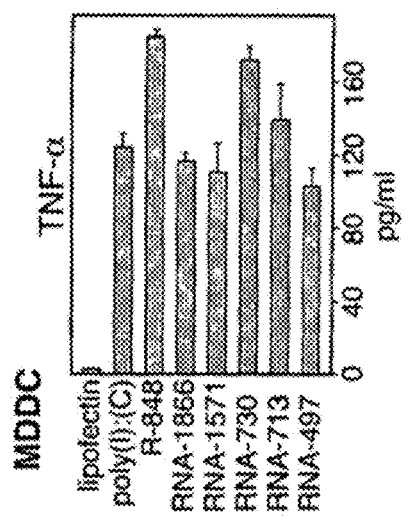
FIGS. 8A-E. Cytokine production by RNA-transfected DC demonstrates that all modifications block activation of cytokine generated DC, while only uridine modifications block blood-derived DC activation. MDDC generated with GM-CSF/IL-4 (A, C) or GM-CSF/IFN-α MDDCs (B), and primary DC1 and DC2 (D) were treated for 8 to 16 h with Lipofectin® alone, Lipofectin®-R-848 (1 µg/ml) or RNA (5 µg/ml). Modified nucleosides present in RNA-1571 are noted. TNF-α, IL-12(p70) and IFN-α were measured in the supernatant by ELISA. Mean values±SEM are shown. The results are representative of 10 (A and C), 4 (B), and 6 (D) independent experiments. E. Activation of DC by RNA. MDDC were treated for 20 h with Lipofectin® alone or complexed with 1 µg/ml poly(I):(C) or R-848 as positive controls (top panel) or Lipofectin® complexed with the indicated RNA (5 µg/ml; bottom panel). Modified nucleosides present in RNA-1886 are noted. Expression of CD83, CD80, and HLA-DR was determined by flow cytometry.
Figure 8A:
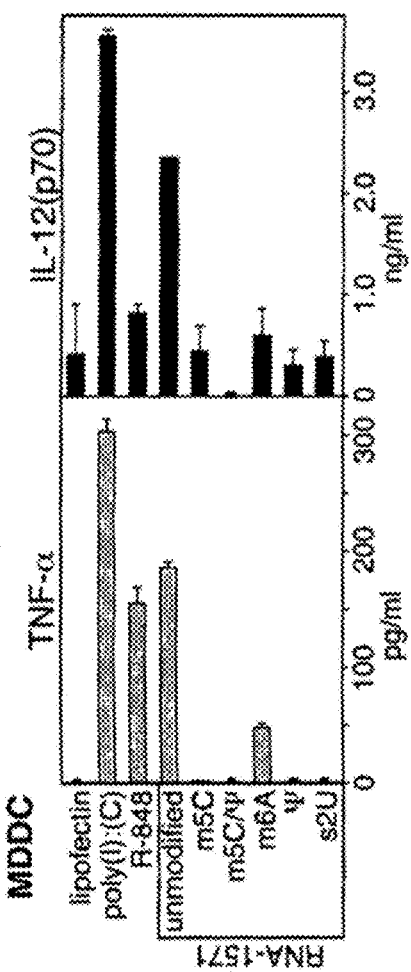
Figure 8B:
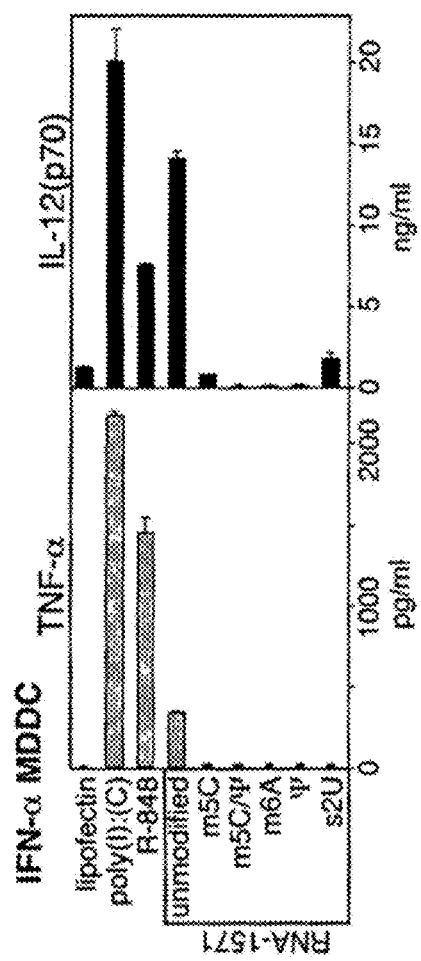

The next experiments tested the ability of RNA containing modified or unmodified nucleosides to stimulate cytokine-generated MDDC. Nucleoside modifications reproducibly diminished the ability of 5 RNA to induce TNF-α and IL-12 secretion by both GM-CSF/lL-4-generated MDDC and (GMCSF)/IFN-α-generated MDDC, in most cases to levels no greater than the negative control (FIGS. 8A and B). Results were similar when other sets of RNA with the same base modifications but different primary sequences and lengths were tested, or when the RNA was further modified by adding a 5' cap structure and/or 3'-end polyA-tail or by removing the 5' triphosphate moiety. RNAs of different length and sequence induced varying amounts of TNF-α from DC, typically less than a two-fold difference (FIG. 8C).

Figure 8D:
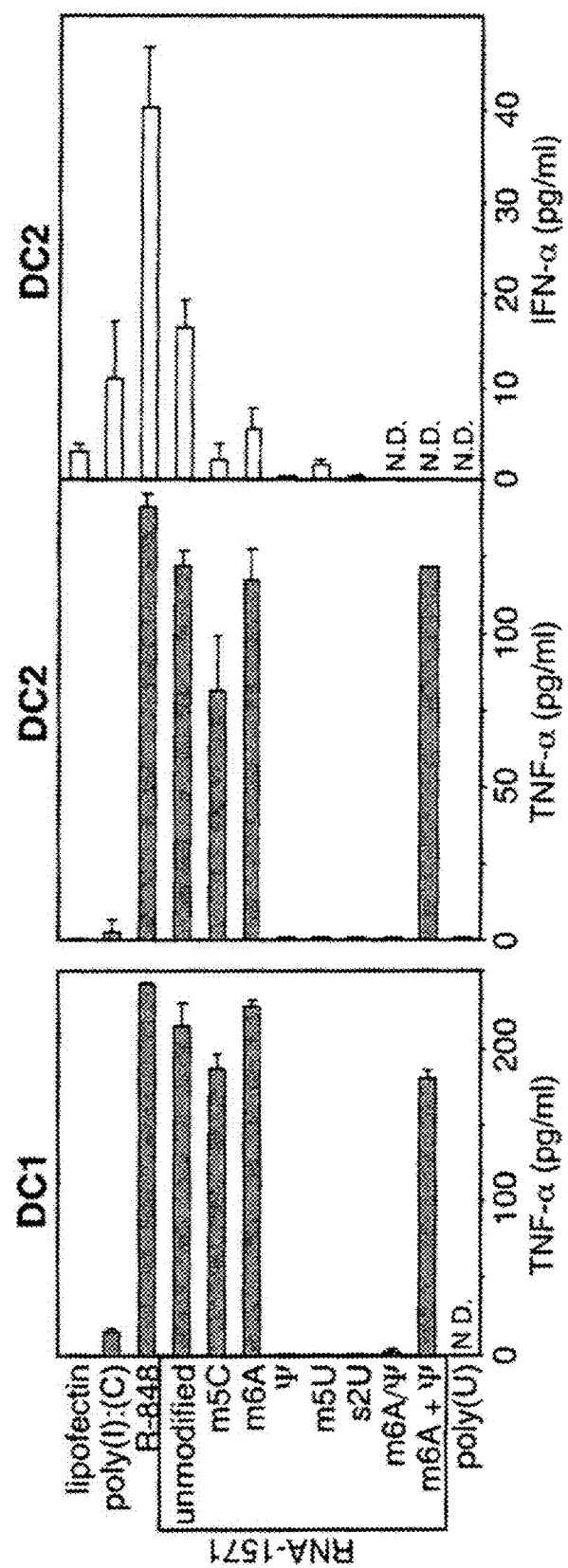
Figure 8E:
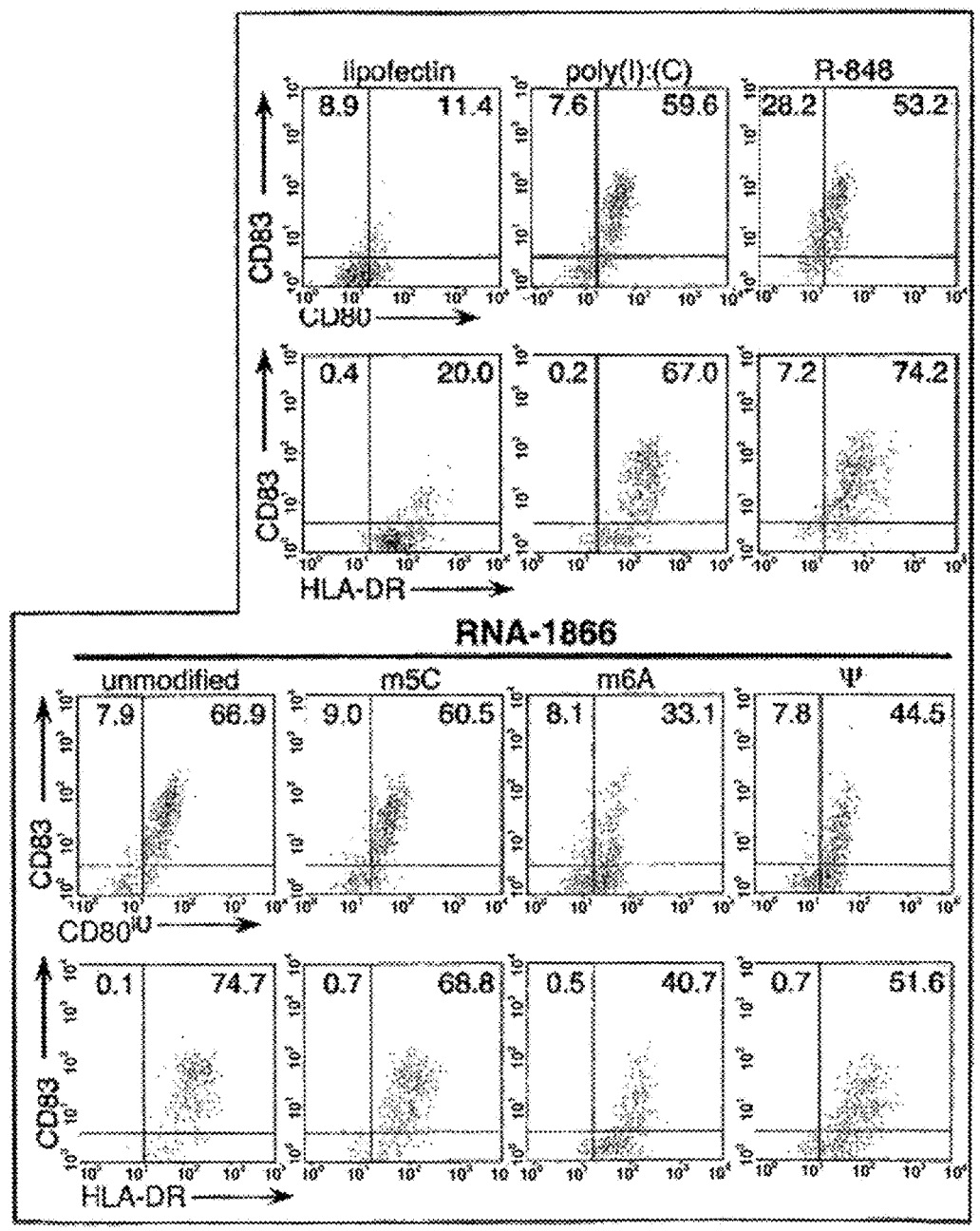

Next, the assay was performed on primary DC1 and DC2. Primary monocytoid (DCI, BDCA1$^+$) and plasmacytoid (DC2, BDCA4$^+$) DC were purified from peripheral blood. Both cell types produced TNF-α when exposed to R-848, but only DC1 responded to poly(I):(C), at a very low level, indicating an absence of TLR3 activity in DC2. Transfection of in vitro transcripts induced TNF-α secretion in both DC1 and DC2, while m5U, ψ or s2U-modified transcripts were not stimulatory (FIG. 8D). In contrast to the cytokine-generated DC, m5C and m6A modification of RNA did not decrease its stimulatory capacity in the primary DC1 and DC2. Transcripts with m6A/ψ double modification were non-stimulatory, while a mixture of RNA molecules with single type of modification (m6A+ψ) was a potent cytokine inducer. Thus, uridine modification exerted a dominant suppressive effect on an RNA molecule in cis in primary DC. These results were consistent among all donors tested.

These findings show that in vitro-transcribed RNA stimulates cytokine production by DC. In addition, since DC2 do not express TLR3 or TLR8, and m5C and m6A modification of RNA decreased its stimulatory capacity of TLR7, these findings show that primary DC have an additional RNA signaling entity that recognizes m5C- and m6A-modified RNA and whose signaling is inhibited by modification of U residues.

Figure 9A:
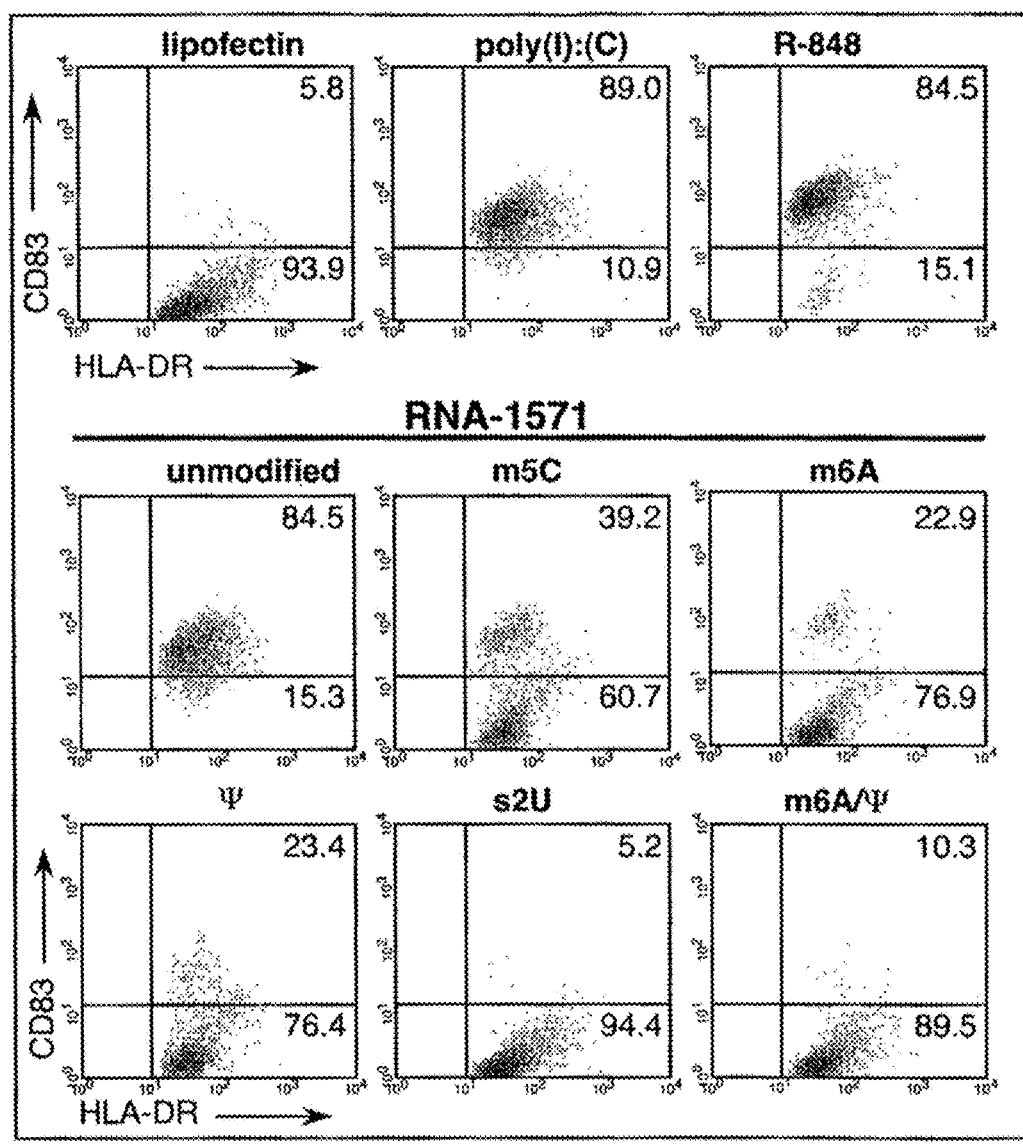

As additional immunogenicity indicators, cell surface expression of CD80, CD83, CD86 and MEW class II molecules, and secretion of TNF-α were measured by FACS analysis of MDDC treated with RNA-1571 and its modified versions. Modification of RNA with pseudouridine and modified nucleosides (m5C, m6A, s2U and m6A/ψ) decreased these markers (FIG. 9), confirming the previous findings.

In summary, RNA's capacity to induce DCs to mature and secrete cytokines depends on the subtype of DC as well as on the characteristics of nucleoside modification present in the RNA. An increasing amount of modification decreases the immunogenicity of RNA.

Example 10

Suppression of RNA-Mediated Immune Stimulation is Proportional to the Number of Modified Nucleosides Present in RNA Materials and Experimental Methods
Human DC For cytokine-generated DC, monocytes were purified from PBMC by discontinuous Percoll gradient centrifugation. The low density fraction (monocyte enriched) was depleted of B, T, and NK cells using magnetic beads (Dynal, Lake Success, N.Y.) specific for CD2, CD16, CD19, and CD56, yielding highly purified monocytes as determined by flow cytometry using anti-CD14 (>95%) or antiCD11c (>98%) mAb.

To generate immature DC, purified monocytes were cultured in AIM V serum-free medium (Life Technologies), supplemented with GM-CSF (50 ng/ml)+IL-4 (100 ng/ml) (R & D Systems, Minneapolis, Minn.) in AIM V medium (Invitrogen) for the generation of monocyte-derived DC (MDDC) as described (Weissman, D et al, 2000. J Immunol 165: 4710-4717). DC were also generated by treatment with GM-CSF (50 ng/ml)+IFN-α (1,000 V/ml) (R & D Systems) to obtain IFN-α MDDC (Santini et al., 2000. Type I interferon as a powerful adjuvant for monocyte-derived dendritic cell development and activity in vitro and in Hu-PBL-SCID mice. J Exp Med 191: 1777-178).

Primary myeloid and plasmacytoid DCs (DC1 and DC2) were obtained from peripheral blood using BDCA-1 and BDCA-4 cell isolation kits (Miltenyi Biotec Auburn, Calif.), respectively.

Results

Figure 10A:
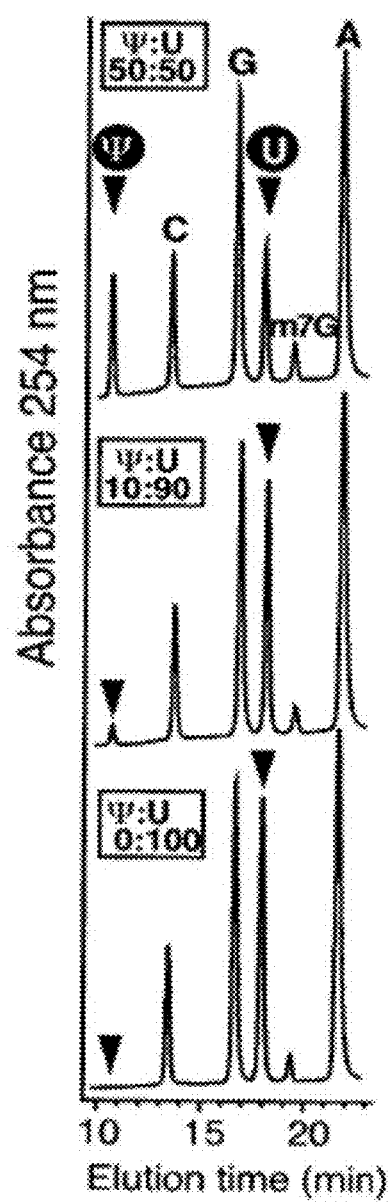
Figure 10C:
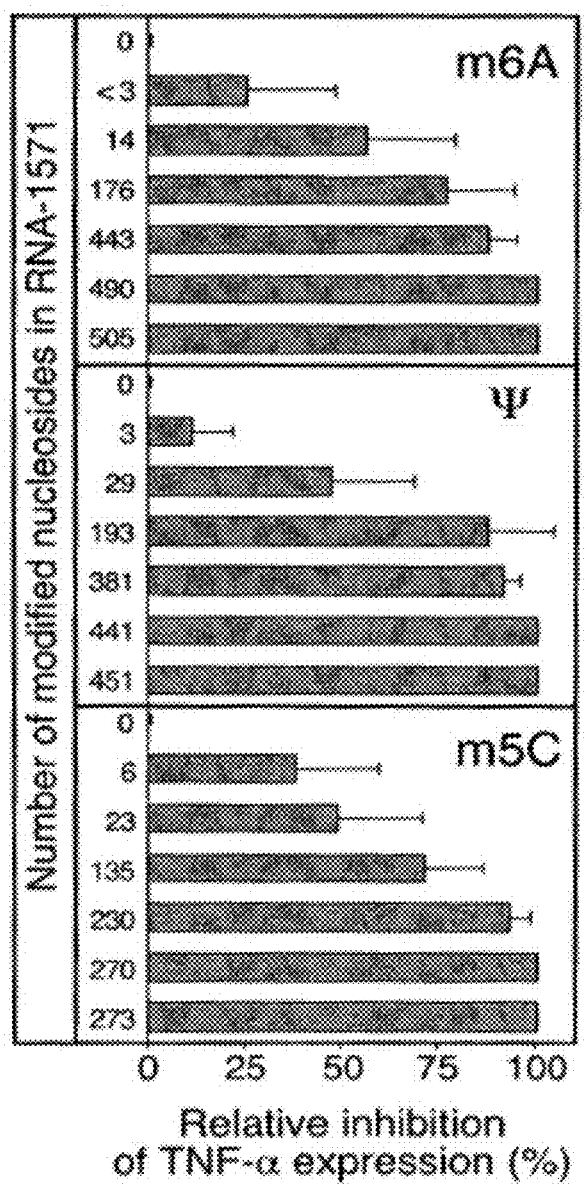

Most of the nucleoside-modified RNA utilized thus far contained one type of modification occurring in approximately 25% of the total nucleotides in the RNA (e.g. all the uridine bases). To define the minimal frequency of particular modified nucleosides that is sufficient to reduce immunogenicity under the conditions utilized herein, RNA molecules with limited numbers of modified nucleosides were generated. In the first set of experiments, RNA was transcribed in vitro in the presence of varying ratios of m6A, ψ (pseudouridine) or m5C to their corresponding unmodified NTPs. The amount of incorporation of modified nucleoside phosphates into RNA was expected to be proportional to the ratio contained in the transcription reaction, since RNA yields obtained with T7 RNAP showed the enzyme utilizes NTPs of m6A, ψ or m5C almost as efficiently as the basic NTPs. To confirm this expectation, RNA transcribed in the presence of UTP:ψ in a 50:50 ratio was digested and found to contain UMP and ψ in a nearly 50:50 ratio (FIG. 10A).

RNA molecules with increasing modified nucleoside content were transfected into MDDC, and TNF-α secretion was assessed. Each modification (m6A, ψ and m5C) inhibited TNF-α secretion proportionally to the fraction of modified bases. Even the smallest amounts of modified bases tested (0.2-0.4%, corresponding to 3-6 modified nucleosides per 1571 nt molecule), was sufficient to measurably inhibit cytokine secretion (FIG. 10B). RNA with of 1.7-3.2% modified nucleoside levels (14-29 modifications per molecule) exhibited a 50% reduction in induction of TNF-α expression. In TLR-expressing 293 cells, a higher percentage (2.5%) of modified nucleoside content was required to inhibit RNA-mediated signaling events.

Thus, pseudouridine and modified nucleosides reduce the immunogenicity of RNA molecules, even when present as a small fraction of the residues.

In additional experiments, 21-mer oligoribonucleotides (ORN) with phosphodiester inter-nucleotide linkages were synthesized wherein modified nucleosides (m5C, ψ or 2'-O-methyl-U [Um]) were substituted in a particular position (FIG. 11A). While the unmodified ORN induced TNF-α secretion, this effect was abolished by the presence of a single nucleoside modification (FIG. 11B). Similar results were obtained with TLR-7 and TLR-8-transformed 293 cells expressing TLR3-targeted siRNA.

The above results were confirmed by measuring TNF-α mRNA levels in MDDC by Northern blot assay, using both the above 21-mer ORN (ORN1) and 31-mer in vitro-synthesized transcripts (ORN5 and ORN6). To amplify the signal, cycloheximide, which blocks degradation of selected mRNAs, was added to some samples, as indicated in the Figure. The unmodified ODN increased TNF-α mRNA levels, while ORNs containing a single modified nucleoside were significantly less stimulatory; ORN2-Um exhibited the greatest decrease TNF-α production (FIG. 11C). Similar results were observed in mouse macrophage-like RAW cells and in human DC.

In summary, each of the modifications tested (m6A, m5C, m5U, s2U, ψ and 2'-O-methyl) suppressed RNA mediated immune stimulation, even when present as a small fraction of the residues. Further suppression was observed when the proportion of modified nucleosides was increased.

Example 11

Pseudouridine-Modification of RNA Reduces its Immunogenicity In Vivo

Figure 12A:
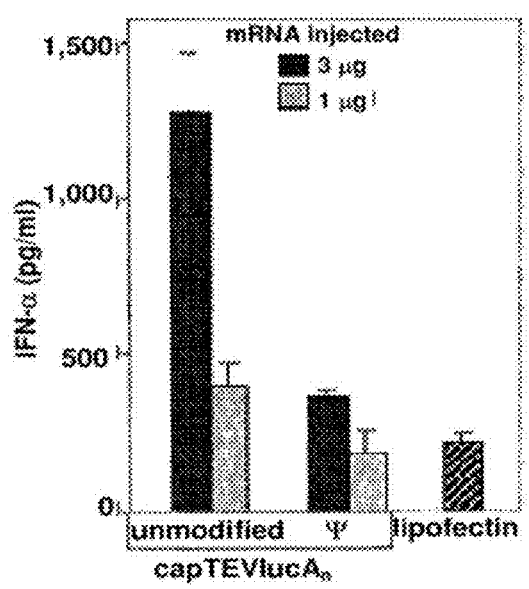
FIGS. 12A-B. A. ψ-modified mRNA does not stimulate pro-inflammatory cytokine production in vivo. Serum samples (6 h after injection) were analyzed by ELISA and revealed that 3 µg of unmodified mRNA induced a higher level of IFN-α than did 3 μg of ψ-modified mRNA (P<0.001). Levels of IFN-α induced by 3 μg of ψ-modified mRNA were similar to those obtained when animals were injected with uncomplexed lipofectin. Values are expressed as the mean±s.e.m. (n=3 or 5 animals/group). B. Similar results were observed with TNF-α.
Figure 12B:
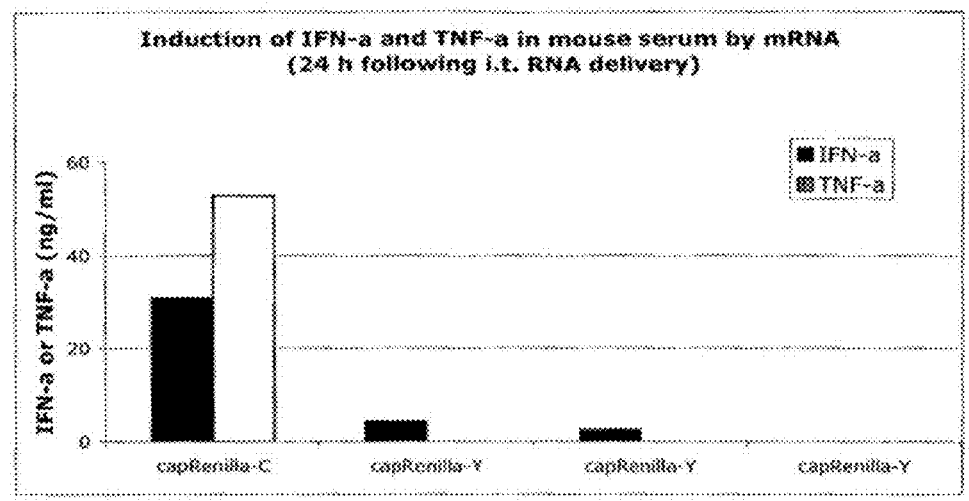

To determine the effect of pseudouridine modification on immunogenicity of RNA in vivo, 0.25 μg RNA) was complexed to Lipofectin® and injected intra-tracheally into mice, mice were bled 24 h later, and circulating levels of TNF-α and IFN-α were assayed from serum samples. Capped, pseudouridine-modified mRNA induced significantly less TNF-α. and IFN-α mRNA than was elicited by unmodified mRNA (FIG. 12A-B).

These results provide further evidence that pseudouridine-modified mRNA is significantly less immunogenic in vivo than unmodified RNA.

Example 12

Pseudouridine-Containing RNA Exhibits Decreased Ability to Activate PRK

Materials and Experimental Methods
PKR Phosphorylation Assays

Aliquots of active PKR agarose (Upstate) were incubated in the presence of magnesium/ATP coctail (Upstate), kinase buffer and [gamma$^{32}$p] ATP mix and RNA molecules for 30 min at 30° C. Unmodified RNA and RNA with nucleoside modification (m5C, pseudouridine, m6A, m5U) and dsRNA were tested. Human recombinant eIF2a (BioSource) was added, and samples were further incubated for 5 min, 30° C. Reactions were stopped by adding NuPage LDS sample buffer with reducing reagent (Invitrogen), denatured for 10 min, 70° C., and analyzed on 10% PAGE. Gels were dried and exposed to film. Heparin (1 U/μl), a PKR activator, was used as positive control.

Results

Figure 13:
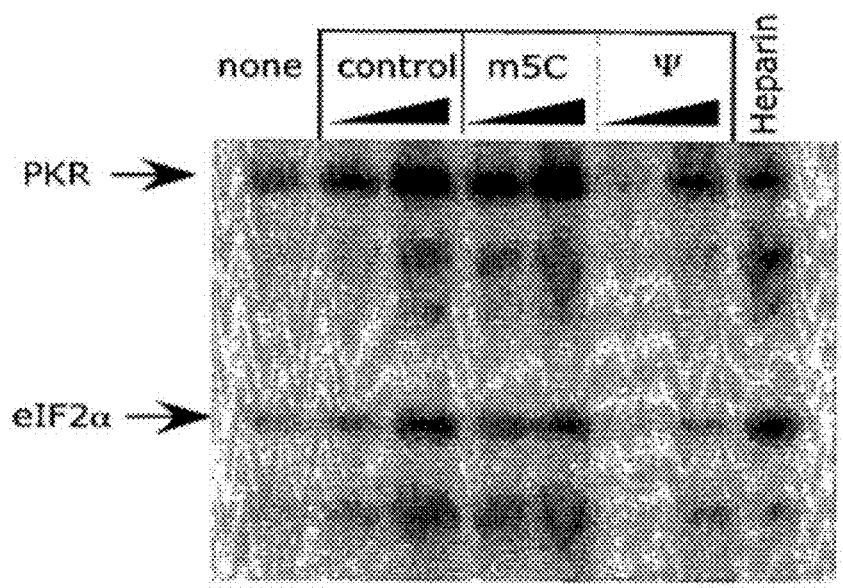
FIG. 13. mRNA containing pseudouridine (ψ) does not activate PKR. ψ: pseudouridine. Control: unmodified RNA. m5C: mRNA with $m^5C$ modification.

To determine whether pseudouridine-containing mRNA activates dsRNA-dependent protein kinase (PKR), in vitro phosphorylation assays were performed using recombinant human PKR and its substrate, eIF2α (eukaryotic initiation factor 2 alpha) in the presence of capped, *renilla*-encoding mRNA (0.5 and 0.05 ng/μl). mRNA containing pseudouridine (ψ) did not activate PKR, as detected by lack of both self-phosphorylation of PKR and phosphorylation of eIF2α, while RNA without nucleoside modification and mRNA with m$^5$C modification activated PKR (FIG. 13). Thus, pseudouridine modification decreases RNA immunogenicity.

Example 13

Figure 14:
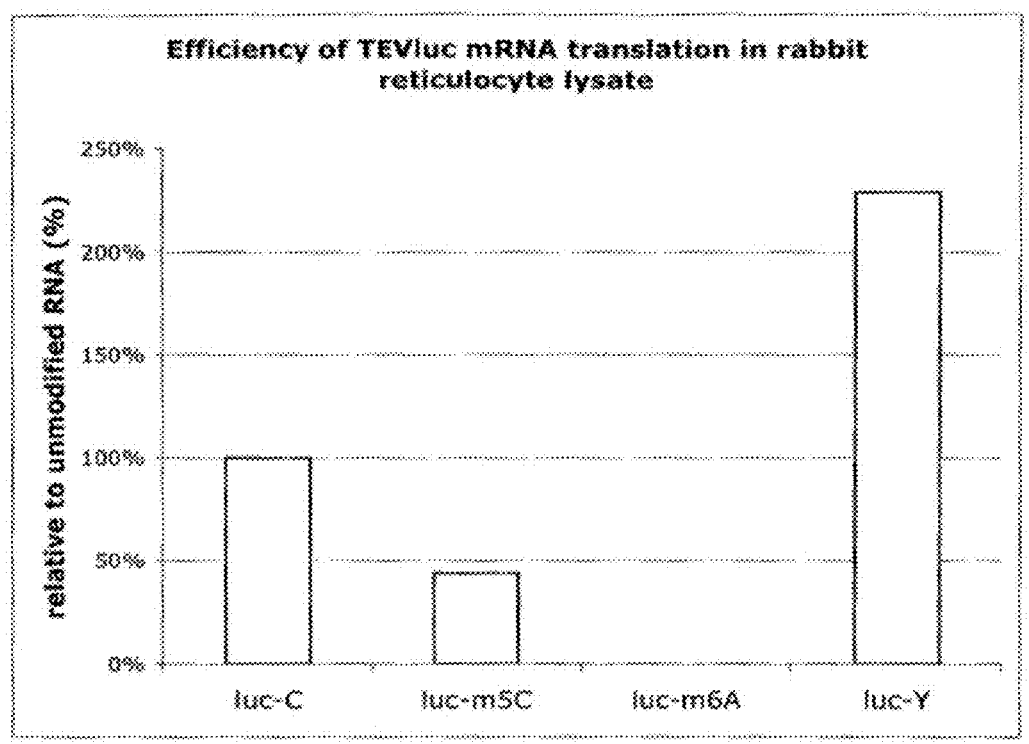
FIG. 14. Increased expression of luciferase from pseudouridine-containing mRNA in rabbit reticulocyte lysate. Luc-Y: mRNA with pseudouridine modification; luc-C: unmodified RNA. Data is expressed by normalizing luciferase activity to unmodified luciferase RNA.

Enhanced Translation of Proteins from Pseudouridine and m$^5$C-Containing RNA In Vitro Materials and Experimental Methods
In Vitro Translation of mRNA in Rabbit Reticulocyte Lysate In vitro-translation was performed in rabbit reticulocyte lysate (Promega, Madison Wis.). A 9-µl aliquot of the lysate was supplemented with 1 µl (1 µg) mRNA and incubated for 60 min at 30° C. One µl aliquot was removed for analysis using firefly and *renilla* assay systems (Promega, Madison Wis.), and a LUMAT LB 950 luminometer (Berthold/EG&G Wallac, Gaithersburg, Md.) with a 10 sec measuring time.
Results To determine the effect of pseudouridine modification on RNA translation efficiency in vitro, (0.1 µg/µl) uncapped mRNA modified with pseudouridine encoding firefly luciferase was incubated in rabbit reticulocyte lysate for 1 h at 30° C., and luciferase activity was determined. mRNA containing pseudouridine was translated more than 2-fold more efficiently than RNA without pseudouridine in rabbit reticulocyte lysates, but not in wheat extract or *E. coli* lysate (FIG. 14), showing that pseudouridine modification increases RNA translation efficiency. Similar results were obtained with m$^5$C-modified RNA. When a polyA tail was added to pseudouridine-containing mRNA, a further 10-fold increase in translation efficiency was observed. (Example 10).

Thus, pseudouridine and m$^5$C modification increases RNA translation efficiency, and addition of a polyA tail to pseudouridine-containing mRNA further increases translation efficiency.

Example 14

Enhanced Translation of Proteins from Pseudouridine Containing RNA in Cultured Cells Materials and Experimental Methods
Translation Assays in Cells Plates with 96 wells were seeded with 5×10$^4$ cells per well 1 day before transfection. Lipofectin®-mRNA complexes were assembled and added directly to the cell monolayers after removing the culture medium (0.2 µg mRNA-0.8 µg lipofectin in 50 µl per well). Cells were incubated with the transfection mixture for 1 h at 37° C., 5% CO$_2$ incubator, then the mixture was replaced with fresh, pre-warmed medium containing 10% FCS, then cells were analyzed as described in the previous Example.
Results To determine the effect of pseudouridine modification on RNA translation in cultured cells, 293 cells were transfected with in vitro-transcribed, nucleoside-modified, capped mRNA encoding the reporter protein *renilla*. Cells were lysed 3 h after initiation of transfection, and levels of *renilla* were measured by enzymatic assays. In 293 cells, pseudouridine- and m5C-modified DNA were translated almost 10 times and 4 times more efficiently, respectively, than unmodified mRNA (FIG. 15A).

Next, the experiment was performed with primary, bone marrow-derived mouse DC, in this case lysing the cells 3 h and 8 h after transfection. RNA containing the pseudouridine modification was translated 15-30 times more efficiently than unmodified RNA (FIG. 15B).

Similar expression results were obtained using human DC and other primary cells and established cell lines, including CHO and mouse macrophage-like RAW cells. In all cell types, pseudouridine modification produced the greatest enhancement of the modifications tested.

Thus, pseudouridine modification increased RNA translation efficiency in all cell types tested, including different types of both professional antigen-presenting cells and non-professional antigen-presenting cells, providing further evidence that pseudouridine modification increases the efficiency of RNA translation.

Example 15

Figure 16A:
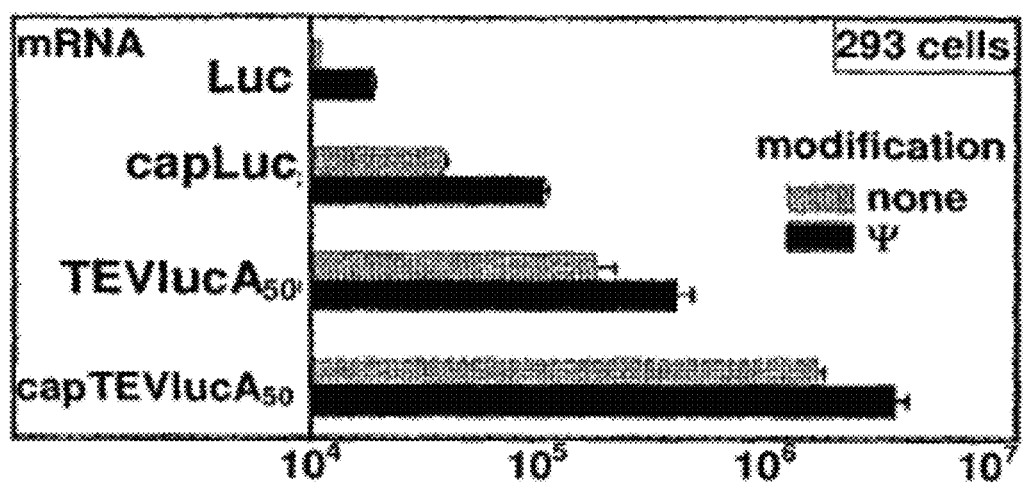
FIGS. 16A-C. A. Additive effect of 3' and 5' elements on translation efficiency of ψ-modified mRNA. 293 cells were transfected with firefly luciferase conventional and ψ-modified mRNAs that had 5' cap (capLuc), 50 nt-long 3' polyA-tail (TEVlucA50), both or neither of these elements (capTEVlucA50 and Luc, respectively). Cells were lysed 4 h later and luciferase activities measured in aliquots (1/20th) of the total lysates. B. ψ-modified mRNA is more stable than unmodified mRNA. 293 cells transfected with capTEVluc$A_n$ containing unmodified or ψ-modified nucleosides were lysed at the indicated times following transfection. Aliquots (1/20th) of the lysates were assayed for luciferase. Standard errors are too small to be visualized with error bars. C. Expression of β-galactosidase is enhanced using ψ-modified mRNA compared with conventional mRNA. 293 cells seeded in 96-well plates were transfected with lipofectin-complexed mRNAs (0.25 μg/well) encoding bacterial β-galactosidase (lacZ). The transcripts had cap and 3' polyA-tail that were either 30 nt-long (caplacZ) or ~200 nt-long (caplacZ-An). Constructs made using conventional U or ψ nucleosides were tested. Cells were fixed and stained with X-gal, 24 h post-transfection. Images were taken by inverted microscopy (40 and 100× magnification) from representative wells.

5' and 3' Elements Further Enhance the Translation of ψmRNA in Mammalian Cells To test the effect of additional RNA structural elements on enhancement of translation by pseudouridine modification, a set of firefly luciferase-encoding ψmRNAs were synthesized that contained combinations of the following modifications: 1) a unique 5' untranslated sequence (TEV, a cap independent translational enhancer), 2) cap and 3) polyA-tail. The ability of these modifications to enhance translation of ψmRNA or conventional mRNA was assessed (FIG. 16A). These structural elements additively enhanced translational efficiency of both conventional and ψmRNA, with ψmRNA exhibiting greater protein production from all constructs.

Figure 16B:
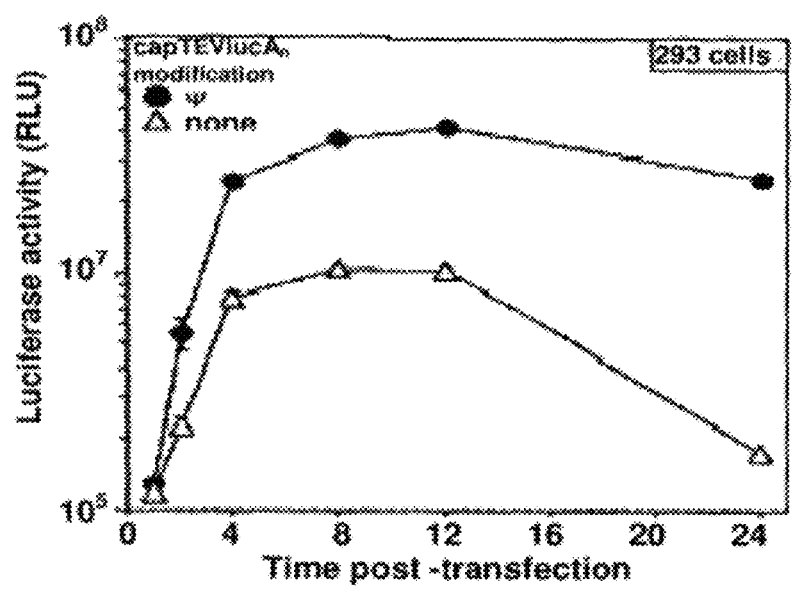

Ability of protein expression from the most efficient firefly luciferase ψmRNA construct, capTEVlucA50 (containing TEV, cap, and an extended poly(A) tail) was next examined over 24 hours in 293 cells (FIG. 16B). ψmRNA produced more protein at every time point tested and conferred more persistent luciferase expression than equivalent conventional mRNA constructs, showing that ψ-modifications stabilize mRNA.

Figure 16C:
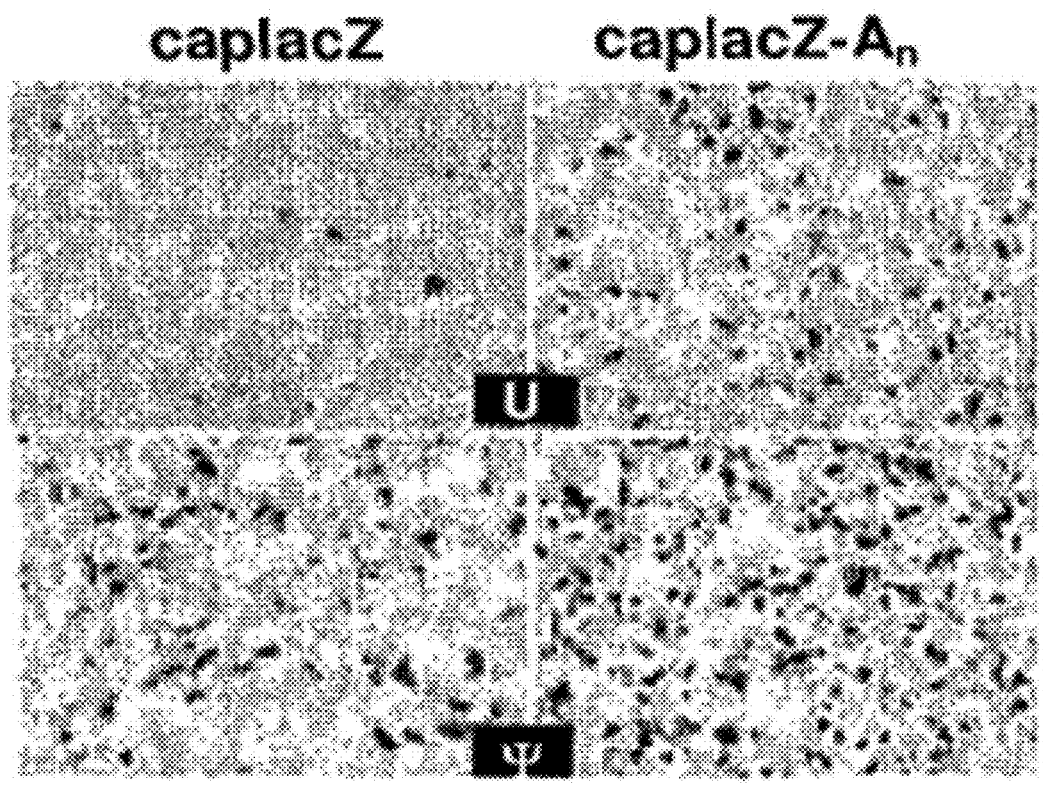

To test whether ψ-modification of mRNA improved translation efficiency in mammalian cells in situ, caplacZ-ψmRNA constructs with or without extended polyA-tails ($A_n$) and encoding β-galactosidase (lacZ) were generated and used to transfect 293 cells. 24 h after mRNA delivery, significant increases in β-galactosidase levels were detected by X-gal visualization, in both caplacZ and caplacZ-$A_n$, compared to the corresponding control (conventional) transcripts (FIG. 16C). This trend was observed when either the number of cells expressing detectable levels of β-galactosidase or the signal magnitude in individual cells was analyzed.

Example 16

Enhanced Translation of Proteins from Pseudouridine Containing RNA In Vivo Materials and Experimental Methods Intracerebral RNA Injections All animal procedures were in accordance with the *NIH Guide for Care and Use of Laboratory Animals* and approved by the Institutional Animal Care and Use Committee. Male Wistar rats (Charles River Laboratories, Wilmington, Mass.) were anesthetized by intraperitoneal injection of sodium pentobarbital (60 mg/kg body weight). Heads were placed in a stereotaxic frame, and eight evenly spaced 1.5 mm diameter burr holes were made bilaterally (coordinates relative to bregma: anterior/posterior +3,0, −3, −6 mm; lateral ±2.5 mm) leaving the dura intact. Intra-cerebral injections were made using a 25 µl syringe (Hamilton, Reno, Nev.) with a 30 gauge, 1 inch sterile needle (Beckton Dickinson Labware, Franklin Lakes, N.J.) which was fixed to a large probe holder and stereotactic arm. To avoid air space in the syringe, the needle hub was filled with 55 μl complex before the needle was attached, and the remainder of the sample was drawn through the needle. Injection depth (2 mm) was determined relative to the surface of the dura, and 4 μl complex (32 ng mRNA) was administered in a single, rapid bolus infusion. 3 hours (h) later, rats were euthanized with halothane, and brains were removed into chilled phosphate buffered saline.

Injection of RNA into Mouse Tail Vein

Tail veins of female BALB/c mice (Charles River Laboratories) were injected (bolus) with 60 μl Lipofectin®-complexed RNA (0.26 μg). Organs were removed and homogenized in luciferase or Renilla lysis buffer in microcentrifuge tubes using a pestle. Homogenates were centrifuged, and supernatants were analyzed for activity.

Delivery of RNA to the Lung

Female BALB/c mice were anaesthetized using ketamine (100 mg/kg) and xylasine (20 mg/kg). Small incisions were made in the skin adjacent to the trachea. When the trachea was exposed, 501-11 of Lipofectin®-complexed RNA (0.2 μg) was instilled into the trachea towards the lung. Incisions were closed, and animals allowed to recover. 3 hours after RNA delivery, mice were sacrificed by cervical dislocation and lungs were removed, homogenized in luciferase or Renilla lysis buffer (250 μl), and assayed for activity. In a different set of animals, blood samples (100 μl/animal) were collected from tail veins, clotted, and centrifuged. Serum fractions were used to determine levels of TNF and IFNα by ELISA as described in the Examples above, using mouse-specific antibodies.

Results

To determine the effect of pseudouridine modification on RNA translation in vivo, each hemisphere of rat brain cortexes was injected with either capped, renilla-encoding pseudouridine modified RNA or unmodified RNA, and RNA translation was measured. Pseudouridine-modified RNA was translated significantly more efficiently than unmodified RNA (FIG. 17A).

Next, expression studies were performed in mice. Firefly luciferase-encoding mRNAs because no endogenous mammalian enzyme interferes with its detection. Transcripts (unmodified and ψmRNA) were constructed with cap, TEV (capTEVA$_{50}$) and extended (−200 nt) poly(A) tails. 0.25 μg RNA Lipofectin®-complexed was injected into mice (intravenous (i.v.) tail vein). A range of organs were surveyed for luciferase activity to determine the optimum measurement site. Administration of 0.3 μg capTEVlucAn ψmRNA induced high luciferase expression in spleen and moderate expression in bone marrow, but little expression in lung, liver, heart, kidney or brain (FIG. 17B). In subsequent studies, spleens were studied.

Figure 17C:
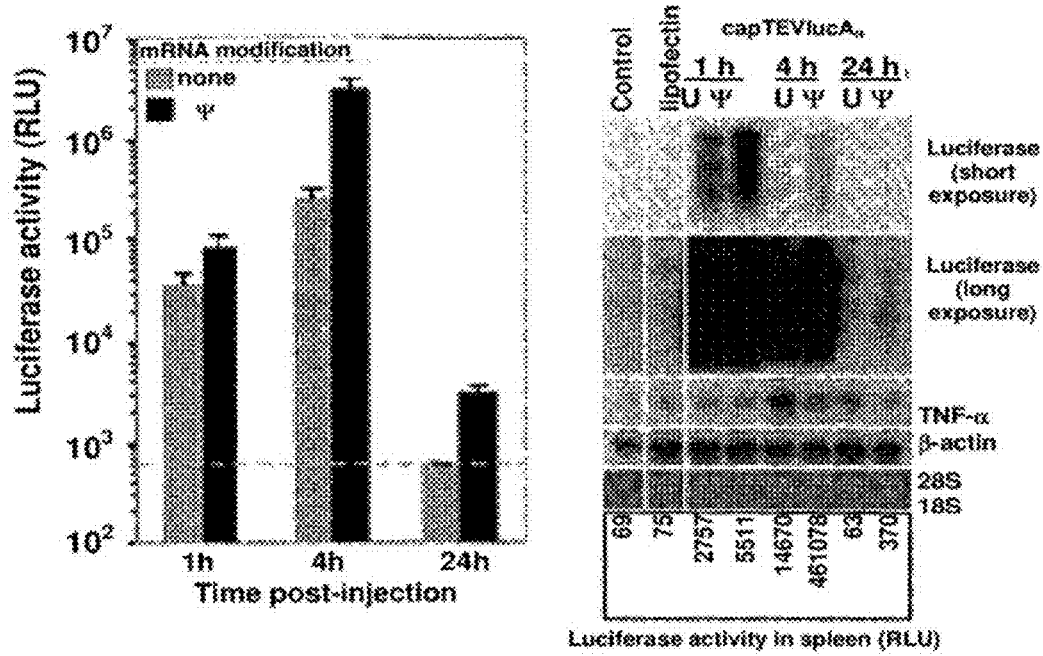

Translation efficiencies of conventional and ψmRNA (0.015 mg/kg; 0.3 μg/animal given intravenously) were next compared in time course experiments. Luciferase activity was readily detectable at 1 h, peaked at 4 h and declined by 24 h following administration of either conventional or ψmRNA, but at all times was substantially greater in animals given ψmRNA (FIG. 17C, left panel). By 24 h, only animals injected with ψmRNA demonstrated detectable splenic luciferase activity (4-fold above background). A similar relative pattern of expression (between modified and unmodified mRNA) was obtained when mRNAs encoding Renilla luciferase (capRen with or without ψ modifications) were injected into the animals instead of firefly luciferase, or when isolated mouse splenocytes were exposed to mRNA in culture.

Figure 17D:
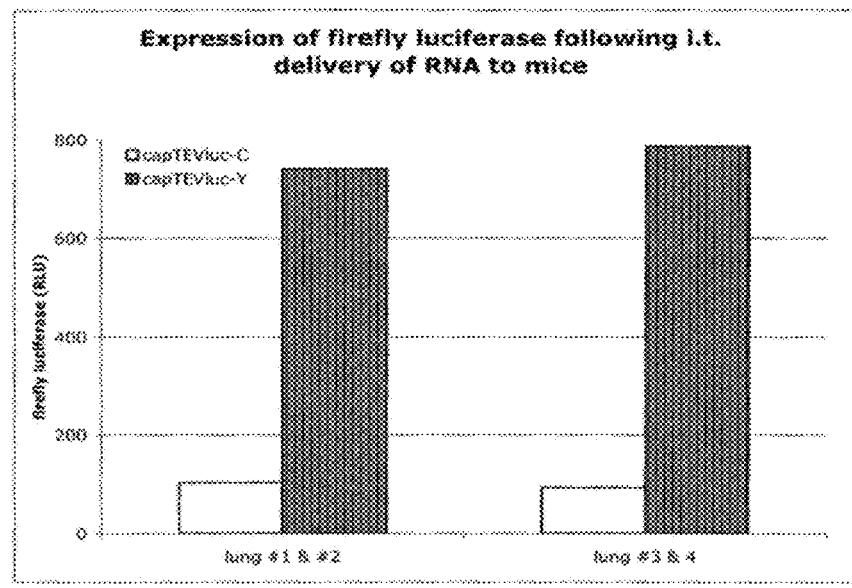

In the next experiment, 0.25 μg mRNA-Lipofectin® was delivered to mouse lungs by intratracheal injection. Capped, pseudouridine-modified RNA was translated more efficiently than capped RNA without pseudouridine modification (FIG. 17D).

Thus, pseudouridine modification increases RNA translation efficiency in vitro, in cultured cells, and in vivo—in multiple animal models and by multiple routes of administration, showing its widespread application as a means of increasing the efficiency of RNA translation.

Example 17

Pseudouridine Modification Enhances RNA Stability In Vivo

Northern analyses of splenic RNA at 1 and 4 h post injection in the animals from the previous Example revealed that the administered mRNAs, in their intact and partially degraded forms, were readily detectable (FIG. 17C, right panel). By contrast, at 24 h, unmodified capTEVlucAn mRNA was below the level of detection, while capTEVlucAn ψmRNA, though partially degraded, was still clearly detectable. Thus, ψmRNA is more stably preserved in vivo than control mRNA.

Figure 18:
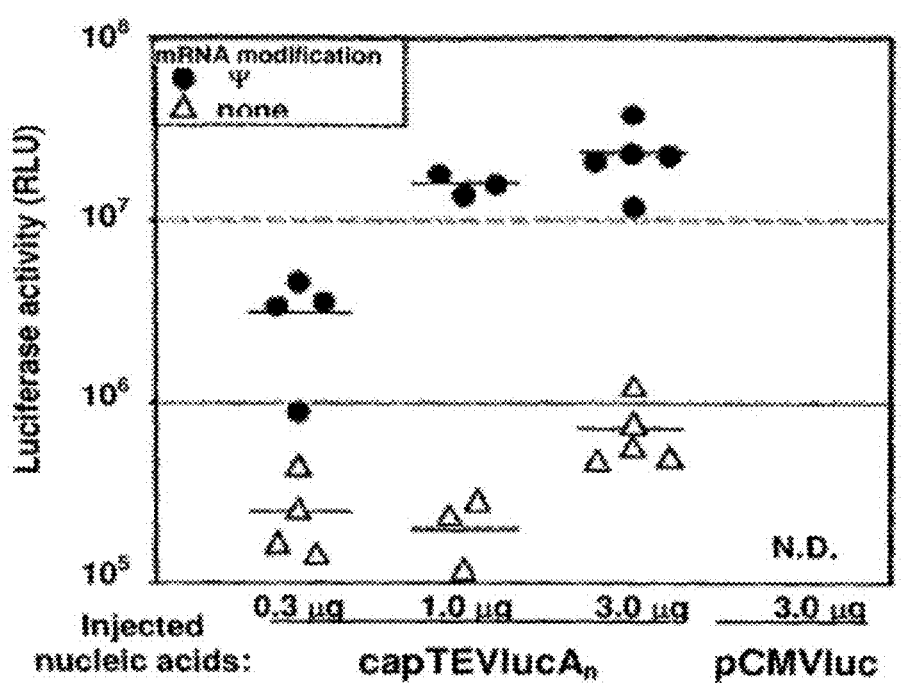
FIG. 18. Protein production is dependent on the amount of mRNA delivered intravenously in mice. The indicated amounts of lipofectin-complexed nucleic acids, capTEVlucAn mRNA with or without ψ constituents and pCMVluc plasmid DNA in a volume of 60 μl/animal were delivered by i.v. injection into mice. Animals injected with mRNA or plasmid DNA were sacrificed at 6 h or 24 h post-injection, respectively, and luciferase activities were measured in aliquots (1/10th) of their spleens homogenized in lysis buffer. The value from each animal is shown, and short horizontal lines indicate the mean; N.D., not detectable.

To test whether in vivo protein production is quantitatively dependent on the concentration of intravenously-delivered mRNA, mRNAs were administered to mice at 0.015-0.150 mg/kg (0.3-3.0 μg capTEVlucAn per animal) and spleens were analyzed 6 hours later as described above. Luciferase expression correlated quantitatively with the amount of injected RNA (FIG. 18) and at each concentration.

These findings confirm the results of Example 15, demonstrating that ψmRNA is more stable than unmodified RNA. Further immunogenicity of ψ-mRNA was less than unmodified RNA, as described herein above (FIG. 12 and FIG. 17C, right panel).

To summarize Examples 16-17, the 3 advantages of ψ-mRNA compared with conventional mRNA (enhanced translation, increased stability and reduced immunogenicity) observed in vitro are also observed in vivo.

Figure 19:
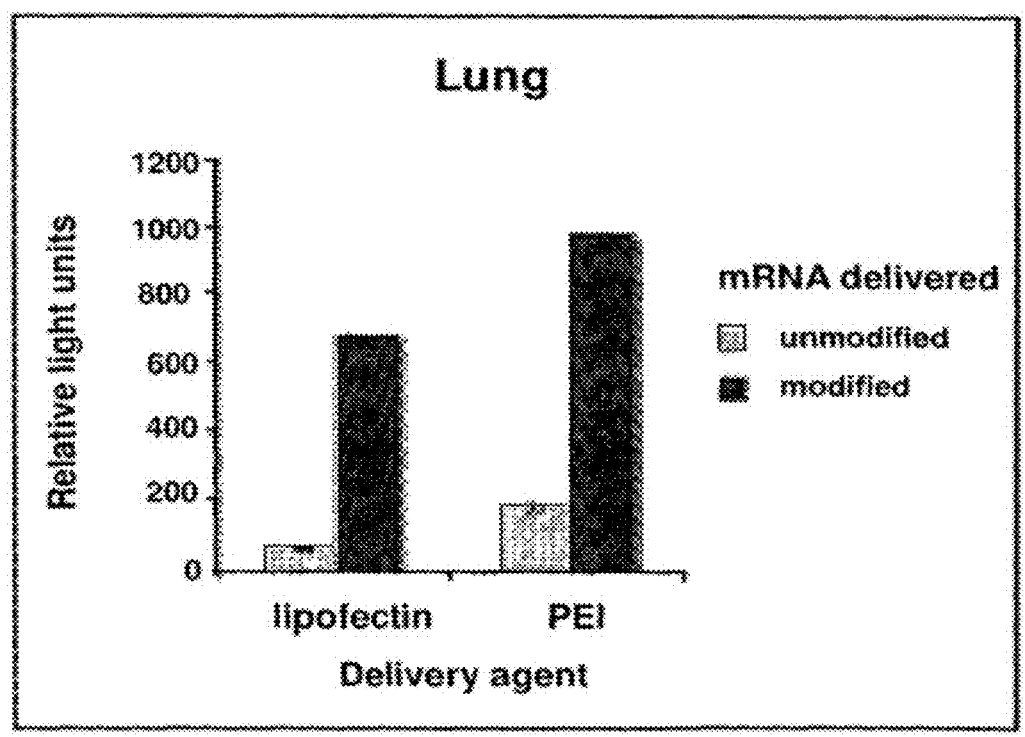
FIG. 19. Expression of firefly luciferase following intratracheal delivery of encoding mRNA. mRNA were complexed to lipofectin (or PEI, as noted) and animals were injected with 0.3 μg firefly luciferase-encoding mRNA with or without ψ modification, then sacrificed 3 hours later. Lungs were harvested and homogenized, and luciferase activity was measured in aliquots of the lysed organs.
Figure 20:
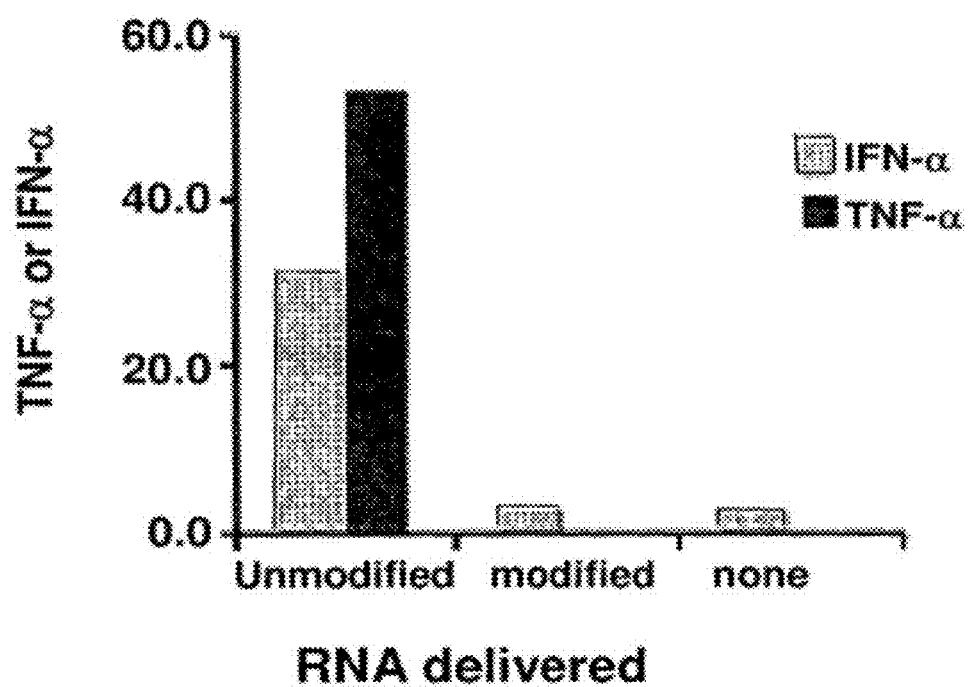
FIG. 20. ψ-modified mRNA does not induce inflammatory mediators after pulmonary delivery. Induction of TNF-α and IFN-α in serum following intratracheal delivery of luciferase-encoding unmodified mRNA or ψ-modified mRNA. Serum levels of TNF-α and IFN-α were determined by ELISA 24 hours after mRNA delivery.
Figure 21A:
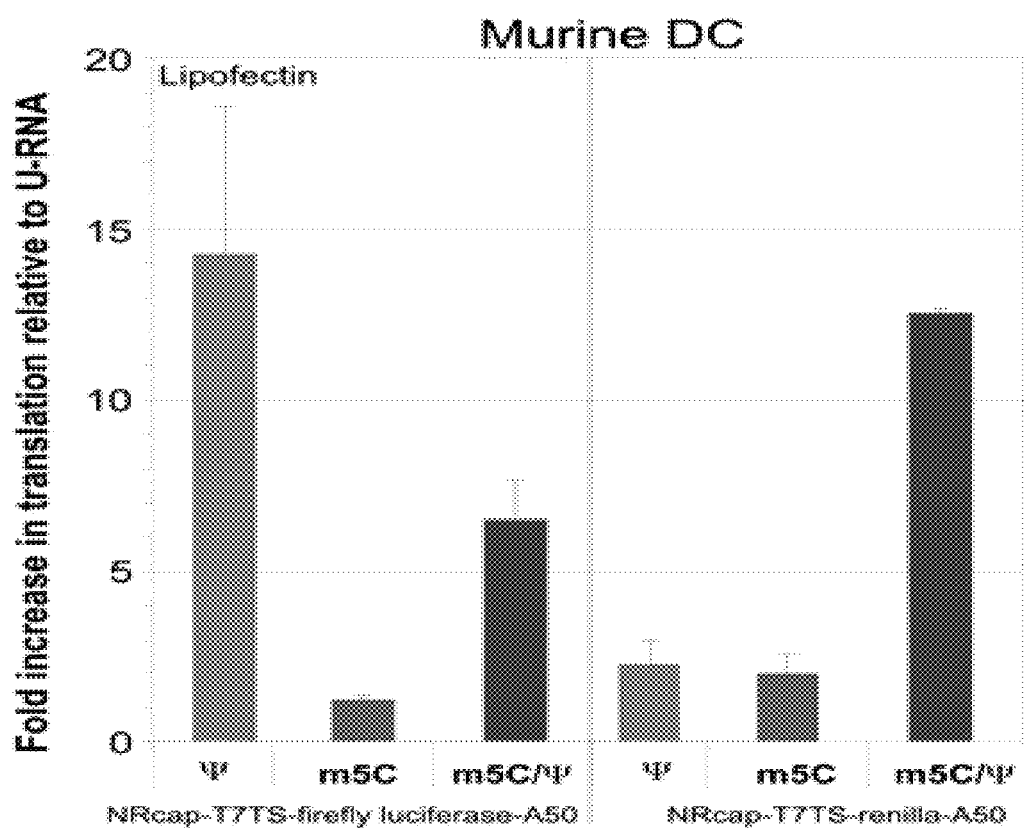
FIGS. 21A-C show the results from Example 35: Firefly or *Renilla* luciferase encoding mRNA with the indicated modifications were complexed to lipofectin and delivered to murine dendritic (A) and HEK293T (B) cells. Human DC were transfected with firefly or *renilla* luciferase-encoding mRNA complexed with TransIT with the indicated modifications (C). Data is expressed as the fold-change compared to unmodified mRNA.
Figure 21B:
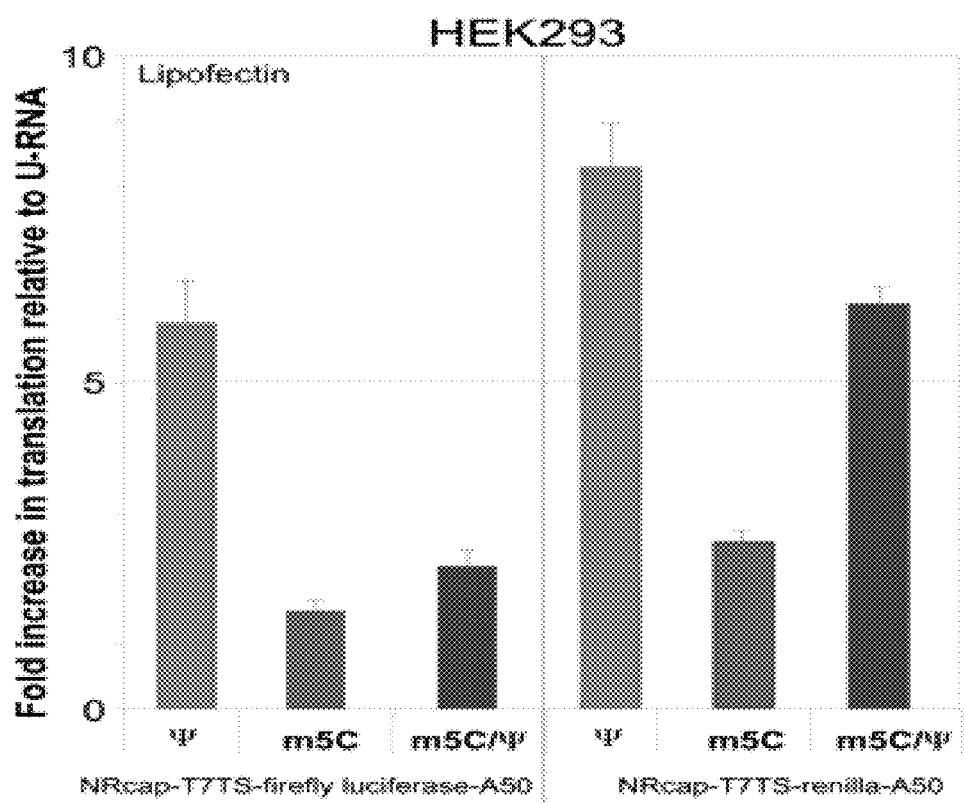
Figure 21C:
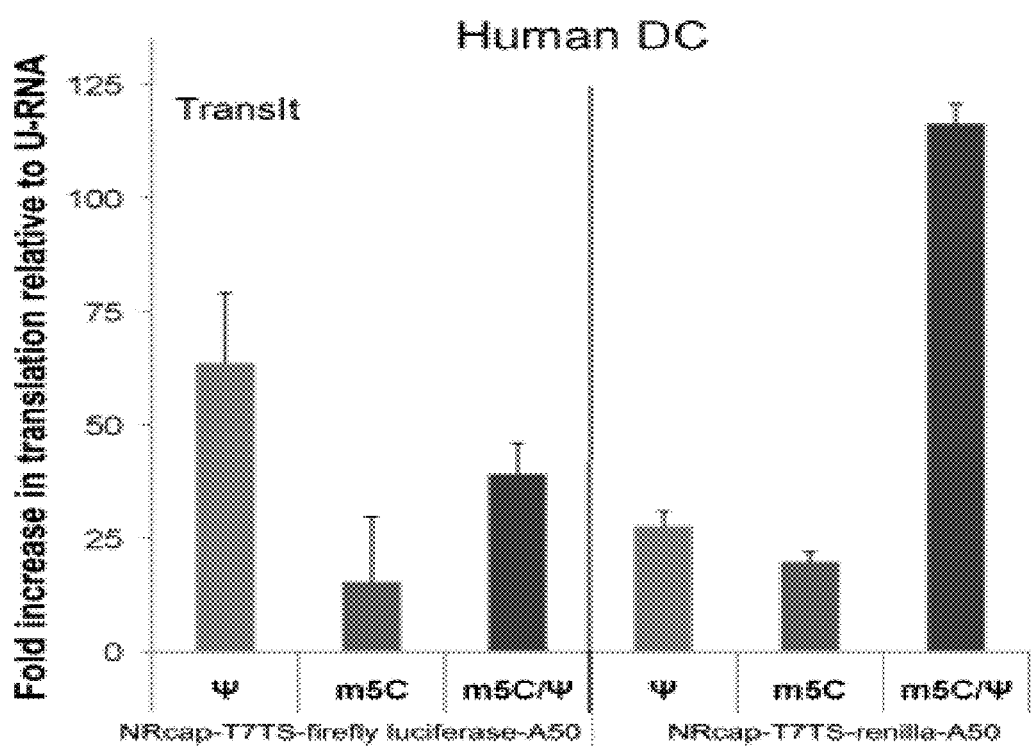

Example 18

ψmRNA Delivered Via the Respiratory Tract Behaves Similarly to Intravenously Administered mRNA To test the ability of ψmRNA to be delivered by inhalation, Lipofectin®- or PEI-complexed mRNAs encoding firefly luciferase were delivered to mice by the intratracheal route, wherein a needle was placed into the trachea and mRNA solution sprayed into the lungs. Similar to intravenous delivery, significantly greater luciferase expression was observed with ψmRNA compared to unmodified mRNA (FIG. 19), although significantly less protein was produced with the intratracheal as compared to the intravenous routes. Unmodified mRNA administered by the intratracheal route was associated with significantly higher concentrations of inflammatory cytokines (IFN-α and TNF-α) compared with vehicle controls, while ψmRNA was not (FIG. 19).

Thus, ψmRNA can be delivered by inhalation without activating the innate immune response.

Example 19

Delivery of EPO-ψmRNA to 293 Cells

ψmRNA was generated from a plasmid containing the human EPO cDNA. When 0.25 µg of EPO-ψmRNA was transfected into $10^6$ cultured 293 cells, greater than 600 mU/ml of EPO protein was produced. Thus, modified RNA molecules of the present invention are efficacious at delivering recombinant proteins to cells.

Example 20

Preparation of Improved EPO-Encoding ψmRNA Constructs

Materials and Experimental Methods

The EPO coding sequence is cloned using restriction enzyme techniques to generate 2 new plasmids, pTEV-EPO and pT7TS-EPO, that are used as templates for EPO-ψmRNA production. EPO-ψmRNAs are produced from these templates by in vitro transcription (MessageMachine® and MegaScript® kits; Ambion,) using T7 RNA polymerase (RNAP), incorporating nucleosides at equimolar (7.5 mM) concentrations. To incorporate the nucleoside-modifications, ψ triphosphate (TriLink, San Diego, Calif.) replaces UTP in the transcription reaction. To ensure capping of the ψmRNA, a non-reversible cap-analog, 6 mM 3'-O-Me-m7GpppG (New England BioLabs, Beverly, Mass.) is also included. The ψmRNAs are poly(A)-tailed in a reaction of ~1.5 µg/µl RNA, 5 mM ATP, and 60 U/µl yeast poly(A) polymerase (USB, Cleveland, Ohio) mixed at 30° C. for 3 to 24 h. Quality of ψmRNAs is assessed by denaturing agarose gel electrophoresis. Assays for LPS in mRNA preparations using the Limulus Amebocyte Lysate gel clot assay with a sensitivity of 3 pg/ml are also performed.

Results

The proximal 3'-untranslated region (3'UTR) of EPO-ψmRNA preserves a ~90 nt-long pyrimidine-rich stabilizing element from the nascent EPO mRNA, which stabilizes EPO mRNA by specific association with a ubiquitous protein, erythropoietin mRNA-binding protein (ERBP). To maximize the stability of EPO-ψmRNA, 2 alterations are incorporated into the EPO plasmid to improve the stability and translational efficiency of the transcribed mRNA: 1) A 5'UTR sequence of the tobacco etch virus (TEV) is incorporated upstream of the EPO coding sequence to generate pTEV-EPO. 2) A plasmid, pT7TS-EPO, is generated, wherein the EPO cDNA is flanked by sequences corresponding to 5' and 3' UTRs of *Xenopus* beta-globin mRNA.

In addition, the length of the poly(A) tail during the production of ψmRNA from these plasmid templates is extended, by increasing the incubation period of the poly(A) polymerase reaction. The longer poly(A) tail diminishes the rate at which ψmRNA degrades during translation.

These improvements result in enhanced translation efficiency in vivo, thus minimizing the therapeutic dose of the final product.

Example 21

In Vitro Analysis of Protein Production from EPO mRNA Constructs

Materials and Experimental Methods
Preparation of Mammalian Cells.

Human embryonic kidney 293 cells (ATCC) are propagated in DMEM supplemented with glutamine (Invitrogen) and 10% FCS (Hyclone, Ogden, Utah) (complete medium). Leukopheresis samples are obtained from HIV-uninfected volunteers through an IRB-approved protocol. DCs are produced as described above and cultured with GM-CSF (50 ng/ml)+IL-4 (100 ng/ml) (R & D Systems) in AIM V Medium® (Invitrogen).

Murine spleen cells and DC are obtained by published procedures. Briefly, spleens from BALB/c mice are aseptically removed and minced with forceps in complete medium. Tissue fragments are sedimented by gravity and the single cell suspension washed and lysed with AKC lysis buffer (Sigma). Murine DCs are derived from bone marrow cells collected from femurs and tibia of 6-9-weekold BALB/c mice. Cells are cultured in DMEM containing 10% FCS (Invitrogen) and 50 ng/ml muGM-CSF (R&D) and used on day 7.

Transfection of Cells and Detection of EPO and Pro-Inflammatory Cytokines

Transfections are performed with Lipofectin in the presence of phosphate buffer, an effective delivery method for splenic and in vitro cell expression. EPO-ψmRNA (0.25 µg/well; 100,000 cells) is added to each cell type in triplicate for 1 hour, and supernatant replaced with fresh medium. 24 hours later, supernatant is collected for ELISA measurement of EPO, IFN-α or β and TNF-α.

Results

To evaluate the impact of unique UTRs on enhancement of ψmRNA translational efficiency, EPO-ψmRNA containing, or not containing, each improvement (5' TEV element, (β-globin 5' and 3' UTRs) with long poly(A) tails are tested for in vitro protein production and in vitro immune activation using EPO mRNA containing conventional nucleosides as controls. Efficiency of protein production from each mRNA is assessed in mammalian cell lines, (HEK293, CHO), human and murine primary DCs, and spleen cells for each mRNA. Measurement of total EPO produced in all cell types and immunogenicity (supernatant-associated proinflammatory cytokines) in primary cells is evaluated. The mRNA construct that demonstrates the optimum combination of high EPO production (in 1 or more cell types) and low cytokine elicitation is used in subsequent studies. Improvements in 5' and 3'UTRs of EPO-ψmRNA and longer poly(A) tails result in an estimated 2-10-fold enhancement in translation efficiency, with no increase in immunogenicity.

Example 22

Characterization of EPO Production and Biological Response to EPO-ψmRNA In Vivo Materials and Experimental Methods
Administration of EPO-ψmRNA to Mice.

All animal studies described herein are performed in accordance with the NIH Guide for Care and Use of Laboratory Animals and approved by the Institutional Animal Care and Use Committee of the University of Pennsylvania. Female BALB/c mice (n=5 per experimental condition; 6 weeks, 18-23 g; Charles River Laboratories) are anesthetized using 3.5% halothane in a mixture of $N_2O$ and $O_2$ (70:30), then halothane reduced to 1% and anesthesia maintained using a nose mask. Animal body temperatures are maintained throughout the procedure using a 37° C. warmed heating pad. EPO-ψmRNA-lipofectin complexes (constructed by mixing varying amounts of nucleic acid with 1

µl lipofectin in 60 µl final volume are injected into the lateral tail vein. Blood samples are collected 3 times a day for 3 days post mRNA injection during the time-course study, at 1 optimal time point in dose-response studies, and daily from days 2-6 in studies for reticulocytosis.
Determination of Reticulocytes by Flow Cytometry.

Whole blood samples are stained using Retic-COUNT reagent (BD Diagnostics) and data events acquired on a FACScan flow cytometer. Red blood cells (RBCs) are selected by forward and side scatter properties and analyzed for uptake of Thiazole Orange. Cells stained with Retic-COUNT reagent are detected by fluorescence and reticulocytes expressed as the percentage of total RBC. At least 50,000 events are counted per sample.
Results To optimize production of biologically functional human EPO protein (hEPO) in response to EPO-encoding mRNA, the following studies are performed:

Time course of EPO production after a single injection of EPO-ψmRNA. Following intravenous administration of 1 µg EPO-ψmRNA, hEPO is measured serially from 1-96 h after EPO-ψmRNA administration by ELISA, to determine the half-life of EPO protein in the serum. This half-life is a result of both the half-life of EPO protein and the functional half-life of the EPO-ψmRNA. The resulting optimal time point for measuring EPO protein after EPO-ψmRNA administration is utilized in subsequent studies.

Dose-response of EPO production after a single injection of EPO-ψmRNA. To determine the correlation between the amount of EPO protein produced and the amount of EPO-ψmRNA administered, increasing concentrations of EPO-ψmRNA (0.01 to 1 µg/animal) are administered and EPO is measured at the optimal time point.

Relationship between hEPO production and reticulocytosis. To measure the effect of EPO-ψmRNA on a biological correlate of EPO activity, flow cytometry is used to determine reticulocyte frequency in blood). Flow cytometry has a coefficient of variation of <3%. Mice receive a single dose of EPO-ψmRNA, and blood is collected from mice daily from days 2-6. The relationship between EPO-ψmRNA dose and reticulocyte frequency is then evaluated at the time point of maximal reticulocytosis. The dose of EPO-ψmRNA that leads to at least a 5% increase in reticulocyte count is used in subsequent studies. Serum hEPO concentrations in mice of an estimated 50 mU/ml and/or an increase in reticulocyte frequency of an estimated 5% are obtained.

Example 23

Measuring Immune Responses to EPO-ψmRNA In Vivo

Materials and Experimental Methods
Detection of Cytokines in Plasma.

Serum samples obtained from blood collected at different times during and after 7 daily lipofectin-complexed mRNA administrations are analyzed for mouse IFN-α, TNF-α, and IL-12 using ELISA kits.
Northern Blot Analysis.

Aliquots (2.0 µg) of RNA samples isolated from spleen are separated by denaturing 1.4% agarose gel electrophoresis, transferred to charged membranes (Schleicher and Schuell) and hybridized in MiracleHyb® (Stratagene). Membranes are probed for TNF-α, down-stream IFN signaling molecules (e.g. IRF7, IL-12 p35 and p40, and GAPDH) and other markers of immune activation. Specificity of all probes is confirmed by sequencing. To probe the membranes, 50 ng of DNA is labeled using Redivue [alpha-$^{32}$P] dCTP® (Amersham) with a random prime labeling kit (Roche). Hybridized membranes are exposed to Kodak BioMax MS film using an MS intensifier screen at −70° C.
Histopathology.

Spleens from EPO-ψmRNA-treated and positive and negative control-treated mice are harvested, fixed, sectioned, stained with hematoxylin and eosin and examined by a veterinary pathologist for signs of immune activation.
Results To confirm the reduced immunogenicity of RNA molecules of the present invention, mice (n=5) receive daily doses of EPO-ψmRNA for 7 days, then are evaluated for immune-mediated adverse events, as indicated by serum cytokine concentrations, splenic expression of mRNAs encoding inflammatory proteins, and pathologic examination. Maximum administered doses are 3 µg or 5× the effective single dose as determined above. Unmodified mRNA and Lipofectin® alone are used as positive and negative controls, respectively.

These studies confirm the reduced immunogenicity of RNA molecules of the present invention.

Example 24

Further Improvement of EPO-ψmRNA Delivery Methods

Nanoparticle Complexing.

Polymer and ψmRNA solutions are mixed to form complexes. Various formulation conditions are tested and optimized: (1) sub-22 nm polyethylenimine (PEI)/mRNA complexes are made by addition of 25 volumes of mRNA to 1 volume of PEI in water with no mixing for 15 minutes. (2) The rod-like poly-L-lysine-polyethylene glycol (PLL-PEG) with average dimensions of 12×150 nm is synthesized by slow addition of 9 volumes of mRNA to 1 volume of $CK_{30}$-$PEG_{10k}$ in acetate counterion buffer while vortexing. (3) For synthesis of biodegradable gene carrier polymer, polyaspartic anhydride co-ethylene glycol (PAE) is synthesized by ring opening polycondensation of N-(Benzyloxycarbonyl)L-aspartic anhydride and ethylene glycol. Then, the pendent amine of aspartic acid is deprotected and protonated by acidification with hydrogen chloride and condensed with mRNA. (4) For latest generation of nanoparticles, aliquot stock $CK_{30}PEG_{10k}$ as ammonium acetate (1.25 mL; 6.4 mg/mL) is added to siliconized Eppendorf tubes. Then mRNA is added slowly to $CK_{30}PEG_{10k}$ (2.5 mg in 11.25 mL RNase free $H_2O$) over 1-2 mins. After 15 mins, it is diluted 1:2 in RNase-free $H_2O$.
Intratracheal Delivery.

Mice are anesthetized with 3% halothane (70% $N_2O$+30% $O_2$) in an anesthetic chamber and maintained with 1% halothane (70% $N_2O$+30% $O_2$) during operation using a nose cone. Trachea os exposed, and 50 µl of mRNA complex is infused with 150 µl air into the lung through the trachea using 250 µl Hamilton syringe (Hamilton, Reno, Nev.) with a 27 G ½" needle.
Results To improve efficiency of delivery and expression of ψmRNA administered via the intratracheal (i.t.) route, ψmRNA is encapsulated in nanoparticles. Nanoparticle packaging involves condensing and encapsulating DNA (for example) into particles that are smaller than the pore of the nuclear membrane, using chemicals including poly-L-lysine and polyethylene glycol. RNA is packaged into 4 different nanoparticle formulations (PEI, PLL, PAE, and $CK_{30}PEG_{10k}$), and efficiency of ψmRNA delivery is compared for luciferase-encoding ψmRNA compare the (Luc-ψmRNA). Delivery kinetics and dose response are then characterized using EPO-ψmRNA.

Example 25

Prevention of Restenosis by Delivery to the Carotid Artery of Recombinant Heat Shock Protein-Encoding, Modified mRNA Materials and Experimental Methods
Experimental Design RNA is administered to the carotid artery of rats by intra-arterial injection near the time of balloon angioplasty, after which blood flow is reinstated. Rats are sacrificed 3 h following injection, carotid artery sections are excised, vascular endothelial cells are harvested and homogenized, and luciferase activity is determined as described in above Examples.

Results

Luciferase-encoding pseudouridine-modified RNA is administered to rat carotid arteries. 3 hours later, luciferase RNA can be detected at the delivery site but not the adjacent sites.

Next, this protocol is used to prevent restenosis of a blood vessel following balloon angioplasty in an animal restenosis model, by delivery of modified RNA encoding a heat shock protein, e.g. HSP70; a growth factor (e.g. platelet-derived growth factor (PDGF), vascular endothelial growth factor (V-EGF), or insulin-like growth factor (IGF); or a protein that down-regulates or antagonizes growth factor signaling. Administration of modified RNA reduces incidence of restenosis.

Example 26

Treatment of Cystic Fibrosis by Delivery of CFTR-Encoding Modified mRNA Molecules to Respiratory Epithelium CFTR-encoding pseudouridine- or nucleoside-modified RNA is delivered, as described in Example 16, to the lungs of a cystic fibrosis animal model, and its effect on the disease is assessed as described in Scholte B J, et al (Animal models of cystic fibrosis. J Cyst Fibros 2004; 3 Suppl2: 183-90) or Copreni E, et al, Lentivirus-mediated gene transfer to the respiratory epithelium: a promising approach to gene therapy of cystic fibrosis. GeneTher 2004; 11 Suppl 1: S67-75). Administration of the RNA ameliorates cystic fibrosis.

In additional experiments, modified mRNA molecules of the present invention are used to deliver to the lungs, other recombinant proteins of therapeutic value, e.g. via an inhaler that delivers RNA.

Example 27

Treatment of XLA by Delivery of ASA-Encoding Modified mRNA Molecules to Hematopoietic Cells ADA-encoding pseudouridine- or nucleoside-modified RNA is delivered to the hematopoietic cells of an X-linked agammaglobulinemia animal model, and its effect on the disease is assessed as described in Tanaka M, Gunawan F, et al, Inhibition of heart transplant injury and graft coronary artery disease after prolonged organ ischemia by selective protein kinase C regulators. J Thorac Cardiovasc Surg 2005; 129(5): 1160-7) or Zonta S, Lovisetto F, et al, Ureteroneocystostomy in a swine model of kidney transplantation: a new technique. J Surg Res. 2005 April; 124(2):250-5). Administration of the RNA is found to improve XLA.

Example 28

Prevention of Organ Rejection by Delivery of Immuno-Modulatory Protein-Encoding Modified mRNA Molecules to a Transplant Site Pseudouridine- or nucleoside-modified RNA encoding a cytokine, a chemokine, or an interferon IS (e.g. IL-4, IL-13, IL-10, or TGF-β) is delivered to the transplant site of an organ transplant rejection animal model, and its effect on the incidence of rejection is assessed as described in Yu P W, Tabuchi R S et al, Sustained correction of B-cell development and function in a murine model of X-linked agammaglobulinemia (XLA) using retroviral-mediated gene transfer. Blood. 2004 104(5): 1281-90) or Satoh M, Mizutani A et al, X-linked immunodeficient mice spontaneously produce lupus-related anti20 RNA helicase A autoantibodies, but are resistant to pristane-induced lupus. Int Immunol 2003, 15(9):1117-24). Administration of the RNA reduces incidence of transplant rejection.

Example 29

Treatment of Niemann-Pick Disease, Mucopolysaccharidosis, and Other Inborn Metabolic Errors by Delivery of Modified mRNA to Body Tissues Sphingomyelinase-encoding pseudouridine- or nucleoside-modified RNA is delivered to the lung, brain, or other tissue of Niemann-Pick disease Type A and B animal models, and its effect on the disease is assessed as described in Passini M A, Macauley S L, et al, AAV vector-mediated correction of brain pathology in a mouse model of Niemann-Pick A disease. Mol Ther 2005; 11(5): 754-62) or Buccoliero R, Ginzburg L, et al, Elevation of lung surfactant phosphatidylcholine in mouse models of Sandhoff and of Niemann-Pick A disease. J Inherit Metab Dis 2004; 27(5): 641-8). Administration of the RNA is found to improve the disease.

Pseudouridine- or nucleoside-modified RNA encoding alpha-L-iduronidase, iduronate-2-sulfatase, or a related enzyme is delivered to the body tissues of a mucopolysaccharidosis animal model of, and its effect on the disease is assessed as described in Simonaro C M, D'Angelo M, et al, Joint and bone disease in mucopolysaccharidoses VI and VII: identification of new therapeutic targets and biomarkers using animal models. Pediatr Res 2005; 57(5 Pt 1): 701-7) or McGlynn R, Dobrenis K, et al, Differential subcellular localization of cholesterol, gangliosides, and glycosaminoglycans in murine models of mucopolysaccharide storage disorders. J Comp Neurol 2004 20; 480(4): 415-26). Administration of the RNA ameliorates the disease.

In additional experiments, modified mRNA molecules of the present invention are used to provide clotting factors (e.g. for hemophiliacs). In additional experiments, modified mRNA molecules of the present invention are used to provide acid-b-glucosidase for treating Gaucher's. In additional experiments, modified mRNA molecules of the present invention are used to provide alpha-galactosidase A for treating Fabry's diseases. In additional experiments, modified mRNA molecules of the present invention are used to provide cytokines for treatment of infectious diseases.

In additional experiments, modified mRNA molecules of the present invention are used to correct other inborn errors of metabolism, by administration of mRNA molecules encoding, e.g. ABCA4; ABCD3; ACADM; AGL; AGT; ALDH4A1; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2; CMM; COL11AI; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPDX; PPT1; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REGIA; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRY; CTNNB1; DEM; ETM1; FANCD2; F1H; FOXL2; GBE1; GLB1; GLC1C; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXPI; PCCB; POU1FI; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3BI; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMD1A; LOX; LTC4S; MAN2A1; MCC; MCCC2; MSH3; MSX2; NR3C1; PCSK1; PDE6A; PFBI; RASA1; SCZD1; SDHA; SGCD; SLC22A5; SLC26A2; SLC6A3; SM1; SMA@; SMN1; SMN2; SPINK5; TCOF1; TELAB1; TGFBI; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; OODD; OFC1; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GNRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANKI; CA1; CA2; CCAL1; CLN8; CMT4A; CNGB3; COH1; CPP; CRH; CYP11B1; CYP11B2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF; BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5K1B; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPSI; IL2RA; LGI1; LIPA; MAT1A; MBL2; MKI67; MXI1; NODAL; OAT; OATL3; PAX2; PCBD; PEO1; PHYH; PNL1P; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOA1; APOA4; APOC3; ATM; BSCL2; BWS; CALCA; CAT; CCND1; CD3E; CD3G; CD59; CDKN1C; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRN1; WT1; WT2; ZNF145; A2M; AAAS; ACADS; ACLS; ACVRL1; ALDH2; AMHR2; AOM; AQP2; ATD; ATP2A2; BDC; C1R; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1;

CLN5; CPB2; ED2; EDNRB; ENUR1; ERCC5; F10; F7; GJB2; GJB6; IPF1; MBS1; MCOR; NYS4; PCCA; RBI; RHOK; SCZD7; SGCG; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MCOP; MJD; MNG1 MPD1; MPS3C; MYH6; MYH7; NP; NPC2; PABN1; PSEN1 PYGL; RPGRIP1; SERPINA1; SERPINA3; SERPINA6; SLC7A7; SPG3A; SPTB; TCL1A; TGMI; TITF1; TMIP; TRA@; TSHR; USH1A; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYO5A; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC2R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VDI; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK1; GCGR; GFAP; GH1; GH2; GP1BA; GPSC; GUCY2D; ITGA2B; ITGB3; ITGB4; KRT10; KRT12; KRT13; KRT14; KRT14L1; KRT14L2; KRT14L3; KRT16; KRT16L1; KRT16L2; KRT17; KRT9; MAPT; MDB; MDCR; MGI; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYB5; DCC; F5F8D; FECH; PEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; E11S; ELA2; EPOR; ERCC2; ETFB; EXT3; EYCL1; FTL; FUT1; FUT2; FUT6; GAMT; GCDH; GPI; GUSM; HB1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NF2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; ARDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN; BTK; BZX; C1HR; CACNA1F; CALB3; CBBM; CCT; CDR1; CFNS; CGF1; CHM; CHR39C; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2C; HYR; IDS; IHG1; IL2RG; INDX; IP1; IP2; JMS; KAL1; KFSD; L1CAM; LAMP2; MAA; MAFD2; MAOA; MAOB; MCF2; MCS; MEAX; MECP2; MF4; MGC1; MIC5; MIDI; MLLT7; MLS; MRSD; MRX14; MRX1; MRX20; MRX2; MRX3; MRX40; MRXA; MSD; MTM1; MYCL2; MYP1; NDP; NHS; NPHL1; NR0B1; NSX; NYS1; NYX; OA1; OASD; OCRL; ODT1; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA; PLP1; POF1; POLA; POU3F4; PPMX; PRD; PRPS1; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIMP1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; SRY; ZFY; ABAT; AEZ; AFA; AFD1; ASAH1; ASD1; ASMT; COAT; CECR9; CEPA; CLA3; CLN4; CSF2RA; CTS1; DF; DIH1; DWS; DYT2; DYT4; EBR3; ECT; EEF1A1L14; EYCL2; FANCB; GCSH; GCSL; GIP; GTS; HHG; HMI; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2; MPFD; MS; MSS; MTATP6; MTCO1; MTCO3; MTCYB; MTND1; MTND2; MTND4; MTND5; MTND6; MTRNR1; MTRNR2; MTTE; MTTG; MTTI; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO; SUOX; THM; or TTD.

Example 30

Treatment of Vasospasm by Delivery of iNOS-Encoding Modified mRNA Molecules to Body Tissues Inducible nitric oxide synthase (iNOS)-encoding pseudouridine- or nucleoside-modified RNA is delivered to the vascular endothelium of vasospasm animals models (e.g. subarachnoid hemorrhage), and its effect on the disease is assessed as described in Pradilla G, Wang P P, et al, Prevention of vasospasm by anti-CD11/CD18 monoclonal antibody therapy following subarachnoid hemorrhage in rabbits. J Neurosurg 2004; 101(1): 88-92) or Park S, Yamaguchi M, et al, Neurovascular protection reduces early brain injury after subarachnoid hemorrhage. Stroke 2004; 35(10): 2412-7). Administration of the RNA ameliorates the disease.

Example 31

Restoration of Hair Growth by Delivery of Modified mRNA Encoding an Immunosuppressive Protein Pseudouridine- or nucleoside-modified RNA encoding a telomerase or an immunosuppressive protein (e.g. α-MSH, TGF-β 1, or IGF-I is delivered to hair follicles of animals used as models of hair loss or balding, and its effect on hair growth is assessed as described in Jiang J, Tsuboi R, et al, Topical application of ketoconazole stimulates hair growth in C3H/HeN mice. J Dermatol 2005; 32(4): 243-7) or McElwee K J, Freyschmidt-Paul P, et al, Transfer of CD8(+) cells induces localized hair loss whereas CD4(+)/CD25(−) cells promote systemic alopecia areata and CD4(+)/CD25 (+) cells blockade disease onset in the C3H/HeJ mouse model. J Invest Dermatol 2005; 124(5): 947-57). Administration of the RNA restores hair growth.

Example 32

Synthesis of an In Vitro-Transcribed RNA Molecule with Altered Nucleosides Containing an siRNA A double-stranded RNA (dsRNA) molecule comprising pseudouridine or a modified nucleoside and further comprising a small interfering RNA (siRNA) or short hairpin RNA (shRNA) is synthesized by the following procedure: Complementary RNA strands with the desired sequence containing uridine or 1 or more modified nucleosides are synthesized by in vitro transcription (e.g. by T7, SP6, or T3 phage RNA polymerase) as described in Example 5. dsRNA molecules exhibit reduced immunogenicity. In other experiments, the dsRNA molecules are designed to be processed by a cellular enzyme to yield the desired siRNA or shRNA. Because dsRNA molecules of several hundred nucleotides are easily synthesized, each dsRNA may also be designed to contain several siRNA or shRNA molecules, to facilitate delivery of multiple siRNA or shRNA to a single target cell.

Example 33

Use of an In Vitro-Transcribed RNA Molecule with Altered Nucleosides to Deliver siRNA The dsRNA molecule of the previous Example is complexed with a transfection reagent (e.g a cationic transfection reagent, a lipid-based transfection reagent, a protein-based transfection reagent, a polyethyleneimine based transfection reagent, or calcium phosphate) and delivered to a target cell of interest. Enzymes in or on the surface of the target cell degrade the dsRNA to the desired siRNA or shRNA molecule(s). This method effectively silences transcription of 1 or more cellular genes corresponding to the siRNA or shRNA sequence(s).

Example 34

Testing the Effect of Additional Nucleoside Modifications on RNA Immunogenicity and Efficiency of Translation Additional nucleoside modifications are introduced into in vitro-transcribed RNA, using the methods described above in Examples 5 and 10, and their effects on immunogenicity translation efficiency are tested as described in Examples 4-11 and 12-18, respectively. Certain additional modifications are found to decrease immunogenicity and enhance translation. These modifications are additional embodiments of methods and compositions of the present invention.

Modifications tested include, e.g.:
$m^1A$; $m^2A$; Am; $ms^2m^6A$; $i^6A$; $ms^2i6A$; $io^6A$; $ms^2io^6A$; $g^6A$; $t^6A$; $ms^2t^6A$; $m^6t^6A$; $hn^6A$; $ms^2hn^6A$; Ar(p); I; $m^1I$; $m^1Im$; $m^3C$; Cm; $S^2C$; $ac^4C$; $f^5c$; $m^5Cm$; $ac^4Cm$; $k^2c$; $m^1G$; $m^2G$; $m^7G$; Gm; $m^2{}_2G$; $m^2Gm$; $m^2{}_2Gm$; Gr(p); yW; $o_2yW$; OHyW; OHyW*; imG; mimG; Q; oQ; galQ; manQ; $preQ_0$; $preQ_1$; $G^+$; D; $m^5Um'$; $m^1\psi$; $\psi m$; $S^4U$; $\bullet m^5s^2U'$; $S^2Um$; $'acp^3U\bullet$, $ho^5u.$, $mo^5U\bullet$; $cmo^5U\bullet$; $mcmo^5U$; $chm^5U$; $mchm^5U\bullet$; $mcm^5U$; $mcm^5Um$; $mcm^5s^2U$; $nm^5s^2U$; $mnm^5U$; $mnm^5s^2U$; $mnm^5se^2U$; $ncm^5U$; $ncm^5Um$; $cmnm^5U$; $cmnm^5Um$; $cmnm^5$ $s^2U$; $m^6{}_2A$; Im; $m^4C$; $m^4Cm$; $hm^5C$; $m^3U$; $m^1acp3\psi$; $cm^5U$; $m^6Am$; $m^6{}_2Am$; $m^{2,7}G$; $m^{2,2,7}G$; $m^3Um$; $m^5D$; $m^3\psi$; $f^5Cm$; $m^1Gm$; $m^1Am$; $\tau m^5U$; $\tau m^5s^2U$; imG-14; imG2; and $ac^6A$.

Materials and Methods for Examples 35-38

HPLC purification of RNA: mRNA produced by T7 polymerase transcription was purified by HPLC using a column matrix of alkylated nonporous polystyrene-divinylbenzene (PS-DVB) copolymer microspheres (2.1 µm) (21 mm×100 mm column) and a buffer system of Triethylammonium acetate (TEAA) with an acetonitrile gradient. Buffer A contained 0.1 M TEAA and Buffer B contained 0.1 M TEAA and 25% acetonitrile. Columns were equilibrated with 38% Buffer B in Buffer A, loaded with RNA, and then run with a linear gradient to 55% Buffer B over 30 minutes at 5 ml/minute. Fractions corresponding to the desired peak were collected. RNA analyses were performed with the same column matrix and buffer system, but using a 7.8 mm×50 mm column at 1.0 ml/min and a gradient duration of 25 minutes.

RNA Isolation from Column Fractions:

Collected fractions were combined, and first their RNA content was concentrated using Amicon Ultra-15 centrifugal filter units with 30K membrane (Millipore). The filter device was filled with 15 ml sample and spin at 4,000×g for 10 min (4° C.) in a Thermo Scientific Sorvall ST16R centrifuge using swinging bucket rotor. Under these conditions, ~98% of the solvent volume can be removed. When the collected fractions had a volume over 15 ml, the filter unit was reused by filling up with additional column fractions and centrifuging again until all of the RNA was in one tube. To remove the salt and solvent from the concentrated RNA, nuclease free water was added (up to 15 ml) and the filter device was spun again. The process of "washing out" was repeated until the concentration of the acetonitrile was <0.001%. The desalted and solvent-free sample was removed from the filtering device and the RNA was recovered by overnight precipitation at −20° C. in NaOAc (0.3 M, pH 5.5), isopropanol (1 volume) and glycogen (3 µl). The precipitated RNA was collected, washed twice with ice-cold 75% ethanol and reconstituted in water.

dsRNA Dot Blot:

RNA (25-100 ng) was blotted onto a nitrocellulose membrane, allowed to dry, blocked with 5% non-fat dried milk in TBS buffer supplemented with 0.05% Tween-20 (TBS-T), and incubated with dsRNA-specific mAb J2 or K1 (English & Scientific Consulting) for 60 minutes. Membranes were washed 6 times with TBS-T and then reacted with HRP-conjugated donkey anti-mouse antibody (Jackson Immunology). After washing 6 times, dsRNA was detected with the addition of SuperSignal West Pico Chemiluminescent substrate (Pierce) and image capture for 30 seconds to 2 minutes on a Fujifilm LAS1000 digital imaging system.

Dendritic Cell Generation:

Monocytopheresis samples were obtained from normal volunteers through an IRB-approved protocol. Human DCs were produced by treating monocytes with GM-CSF (50 ng/ml)+IL-4 (100 ng/ml) (R&D Systems) in AIM V medium (Invitrogen) for 7 days. On days 3 and 6, a 50% volume of new medium with cytokines was added.

Murine DC were generated by isolating bone marrow mononuclear cells from Balb/c mice and culturing in RPMI+ 10% FBS medium supplemented with murine GM-CSF (20 ng/ml, Peprotech). On days 3 and 6, a 50% volume of new medium with GM-CSF was added. Non-adherent cells were used after 7 days of culture.

Lipofectin Complexing of RNA:

Stock phosphate buffer was added to serum-free DMEM to give final concentrations of 20 mM potassium phosphate and 100 ng/ml BSA, pH 6.4. For 3 wells of a 96-well plate, lipofectin complexed RNA was prepared in the following ratios: 2.4 µl of lipofectin was added to 21.3 µl serum-free DMEM medium with phosphate buffer and incubated at room temperature for 10 minutes. Then, 0.75 µg of RNA in 9.9 µl serum-free DMEM was added and the mixture was incubated for 10 additional minutes at room temperature. Lastly, 116.4 ml serum-free DMEM was added to bring up the final volume to 150 ml. The mixture was vortexed.

TransIT Complexing of RNA:

For each well of a 96-well plate, 0.25 µg of RNA was added to 17.3 µl of serum-free DMEM on ice. TransIT mRNA reagent (0.3 ul) was added with vortexing followed by 0.2 µl of mRNA boost reagent and vortexing. Complexed RNA was added within 5 minutes of formation.

Cell Transfections:

For lipofectin complexed RNA, 50 µl (0.25 µg RNA/well) was added directly to cells, $5 \times 10^5$ per well. Transfected cells were incubated for 1 h at 37° C. in a 5% CO2 incubator. The lipofectin-RNA mixture was removed and replaced with 200 µl pre-warmed serum containing medium. For TransIT complexed RNA, 17 µl of complex was added to cells, $5 \times 10^5$ per well, in 200 µl of serum containing medium. Cells were lysed in specific lysis media, 3 to 24 hr after transfection and firefly or *renilla* luciferase activity was measured with specific substrates in a luminometer.

RNA Immunogenicity Analysis:

DCs (murine or human) in 96-well plates ($5 \times 10^5$ cells/well) were treated with medium, or lipofectin or TransIT complexed RNA. Supernatant was harvested after 24 hr and subjected to analysis. The levels of IFN-α (TransIT delivered RNA) or TNF-α (Lipofectin delivered RNA) (Biosource International, Camarillo, Calif.) were measured in supernatants by ELISA. Cultures were performed in triplicate to quadruplicate and measured in duplicate.

Example 35

This example examines the sequence and cell type dependency of translation of ψ-, m5C, and ψ/m5C-modified mRNA relative to the unmodified (U) RNA. Firefly or *Renilla* luciferase encoding mRNA with the indicated modifications were complexed to lipofectin and delivered to murine dendritic (A) and HEK293T (B) cells. Human DC were transfected with firefly or *renilla* luciferase-encoding mRNA with the indicated modifications complexed with TransIT (C). The data demonstrates that depending on the sequence of the RNA and the type of cell translating it, the optimal modification varies. It also shows that the enhancement caused by incorporation of modified nucleosides is substantially greater for primary cells compared to transformed cell lines. Enzyme activity in lysed cells was measured using specific substrates and measurement of light produced in a luminometer and expressed as fold increase compared to unmodified (U) RNA.

Example 36

Figure 22:
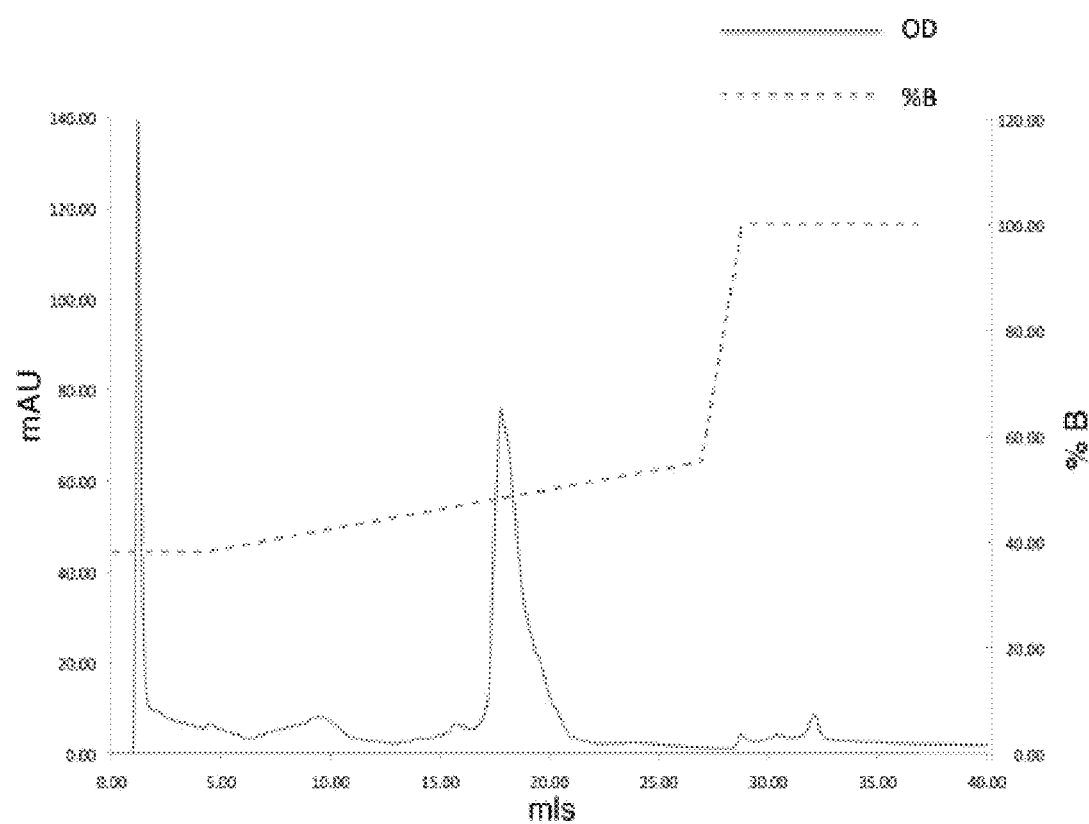
FIG. 22 shows the results from Example 36: T7 polymerase transcription reactions used for the generation of mRNA results in large quantities of RNA of the correct size, but also contains contaminants. This is visualized by application of RNA to a reverse phase HPLC column that separates RNA based on size under denaturing conditions. ψ-modified TEV-luciferase-A51 RNA was applied to the HPLC column in 38% Buffer B and subjected to a linear gradient of increasing Buffer B to 55%. The profile demonstrated both smaller than expected and larger than expected contaminants.

Phage polymerase transcription reactions used for the generation of mRNA results in large quantities of RNA of the correct size, but also contains contaminants. This is visualized by application of RNA to a reverse phase HPLC column that separates RNA based on size under denaturing conditions. Y-modified TEV-luciferase-A51 RNA was applied to the HPLC column in 38% Buffer B and subjected to a linear gradient of increasing Buffer B to 55%. The profile demonstrated both smaller than expected and larger than expected contaminants. These results are shown in FIG. 22.

Example 37

HPLC purification increases translation of all types of modified or unmodified RNA, but ψ-modified mRNA is translated best. The results are shown in FIG. 23: (A) EPO encoding mRNA with the indicated modifications and with or without HPLC purification were delivered to murine DCs and EPO levels in the supernatant were measured 24 hr later. While m5C/Y☐ modified mRNA had the highest level of translation prior to HPLC purification, ψ-modified mRNA had the highest translation after HPLC purification. (B) Human DCs were transfected with *renilla* encoding mRNA with the indicated modifications with or without HPLC purification. Similar to murine DCs and EPO mRNA, after HPLC purification, Y-modified mRNA had the highest level of translation.

Figure 24C:
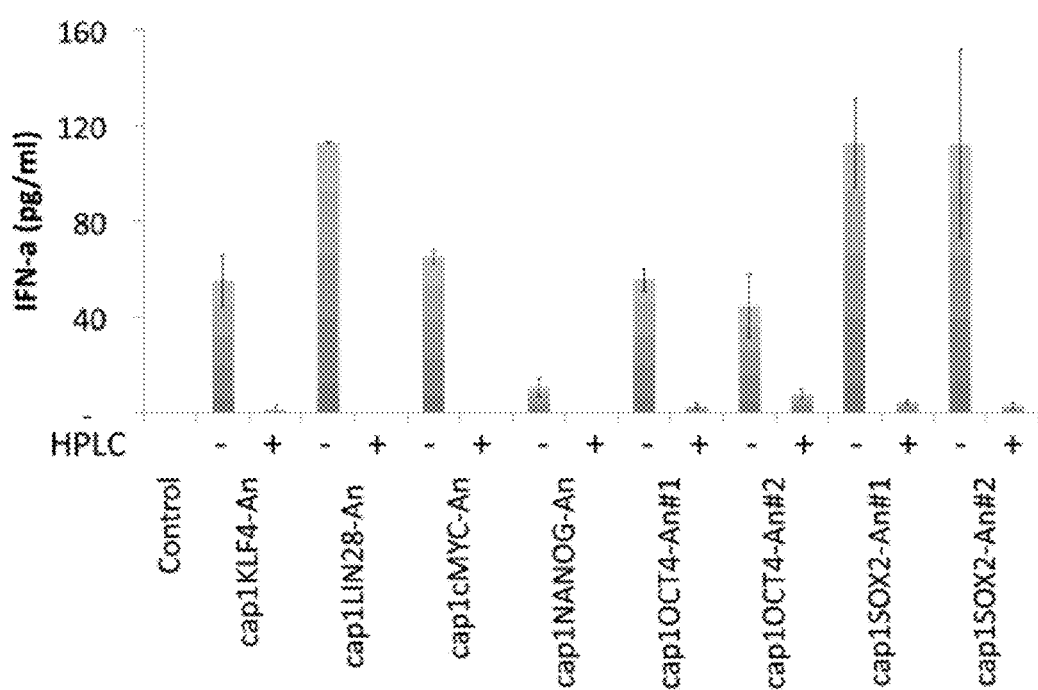

Example 38

ψ, m5C, and ψ/m5C-modified mRNA have low levels of immunogenicity that is reduced to control levels with HPLC purification. The results are shown in FIG. 24: (A) Human DCs were transfected with RNA complexed to TransIT with the indicated modifications with or without HPLC purification. IFN-α levels were measured after 24 hr. HPLC purification increased the immunogenicity of unmodified RNA, which is dependent of the sequence, as other unmodified RNAs had similar levels of IFN-α or reduced levels. ψ-modified RNA had unmeasurable levels of IFN-α similar to control treated DCs. (B) ψ-modified RNA before (−) and after HPLC purification (P1 and P2) was analyzed for dsRNA using dot blotting with a monoclonal antibody specific for dsRNA (J2). Purification of RNA removed dsRNA contamination. (C) ψ-modified RNA encoding iPS factors are immunogenic, which is removed by HPLC purification of the RNA.

Materials and Methods for Examples 39-41

Cell Culture.

Neonatal human epidermal keratinocytes (HEKn) cells (Invitrogen) were cultured in EpiLife Medium supplemented with keratinocyte growth supplement and Penicillin/Streptomycin (Invitrogen). All cells were grown at 37° C. and 5% $CO_2$. The human iPS cells that were induced using methods described herein were transferred to hESC-qualified matrigel matrix (BD Biosciences) coated 6-well plates after transfection.

Constructions of Vectors.
Generally the same as Examples 1-3.
mRNA Production.
Generally the same as for Examples 1-3.
mRNA Purification and Analysis.

In some experimental embodiments, the mRNA was purified by HPLC, column fractions were collected, and the mRNA fractions were analyzed for purity an immunogenicity as described in "Materials and Methods for Examples 35-38" and/or as described and shown for FIGS. 22-24. In some preferred experimental embodiments, purified RNA preparations comprising or consisting of mRNAs encoding one or more reprogramming factors which exhibited little or no immunogenicity were used for the experiments for reprogramming human somatic cells to iPS cells.

Reprogramming of Primary Keratinocytes.

HEKn cells were plated at $1\times10^5$ cells/well of a 6-well dish in EpiLife medium and grown overnight. The cells were transfected with equal amounts of each reprogramming factor mRNA (KLF4, LIN28, c-MYC, NANOG, OCT4, and SOX2) or a subset of the factors using TransIT™ mRNA transfection reagent (MirusBio, Madison, Wis.). Three transfections were performed, every other day, with media changes every day. The day after the third transfection, the cells were trypsinized and plated in mTeSR1 medium (StemCell Technologies) onto matrigel-coated 6-well plates. The mTeSR cell medium was changed daily. Cells were maintained at 37° C. with 5% $CO_2$. Plates were screened for morphology changes using an inverted microscope.

HEKn cells were also reprogrammed by a single transfection by electroporation with equal amounts of each reprogramming factor mRNA. The cells were plated directly onto matrigel-coated plates at a density of $1\times10^5$ cells per 6-well dish or $7.5\times10^5$ cells per 10 cm dish in mTeSR1 medium which was changed daily.

Immunofluorescence.
Generally the same as Examples 1-3
Quantitative RT-PCR (qPCR)

Cellular RNA was reverse-transcribed using standard methods and an oligo $d(T)_{21}$ primer from equivalent amounts of cellular RNA. Three messages were amplified using gene-specific primers and real-time PCR using SYBR green detection and GAPDH normalization. Expression levels were determined in relation to the level of expression in the original HEKn cell line, and depicted as changes in cycle threshold ($C_T$) level.

Example 39

Figure 28:
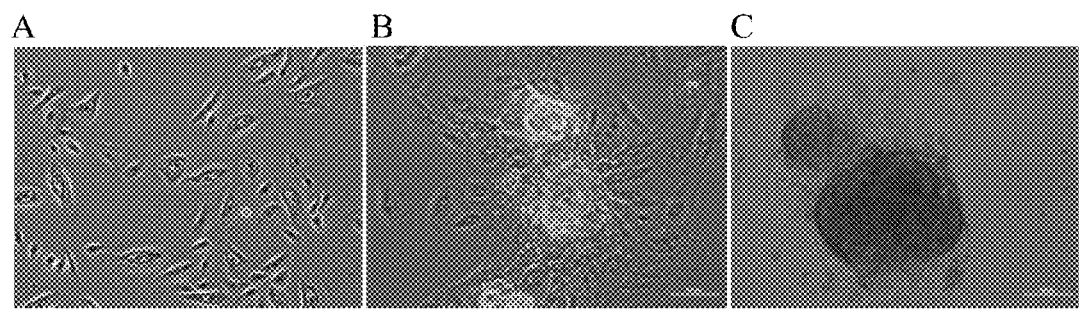
FIG. 28 shows that mRNA encoding human reprogramming factors (KLF4, c-MYC, OCT4, and SOX2) produce iPS cells in primary human keratinocyte cells.

This example describes development of a protocol for iPS cell generation from somatic keratinocytes. Equal amounts (by weight) of KLF4, c-MYC, OCT4, and SOX2 mRNAs were transfected into HEKn cells three times (once every other day) with TransIT™ mRNA Reagent. Medium was changed daily. The day after the third transfection, the cells were plated onto matrigel-coated dishes and grown in mTeSR1 cell medium. By 11 days after the first transfection the reprogrammed cell morphology began to appear (FIG. 28).

Example 40

Figure 29:
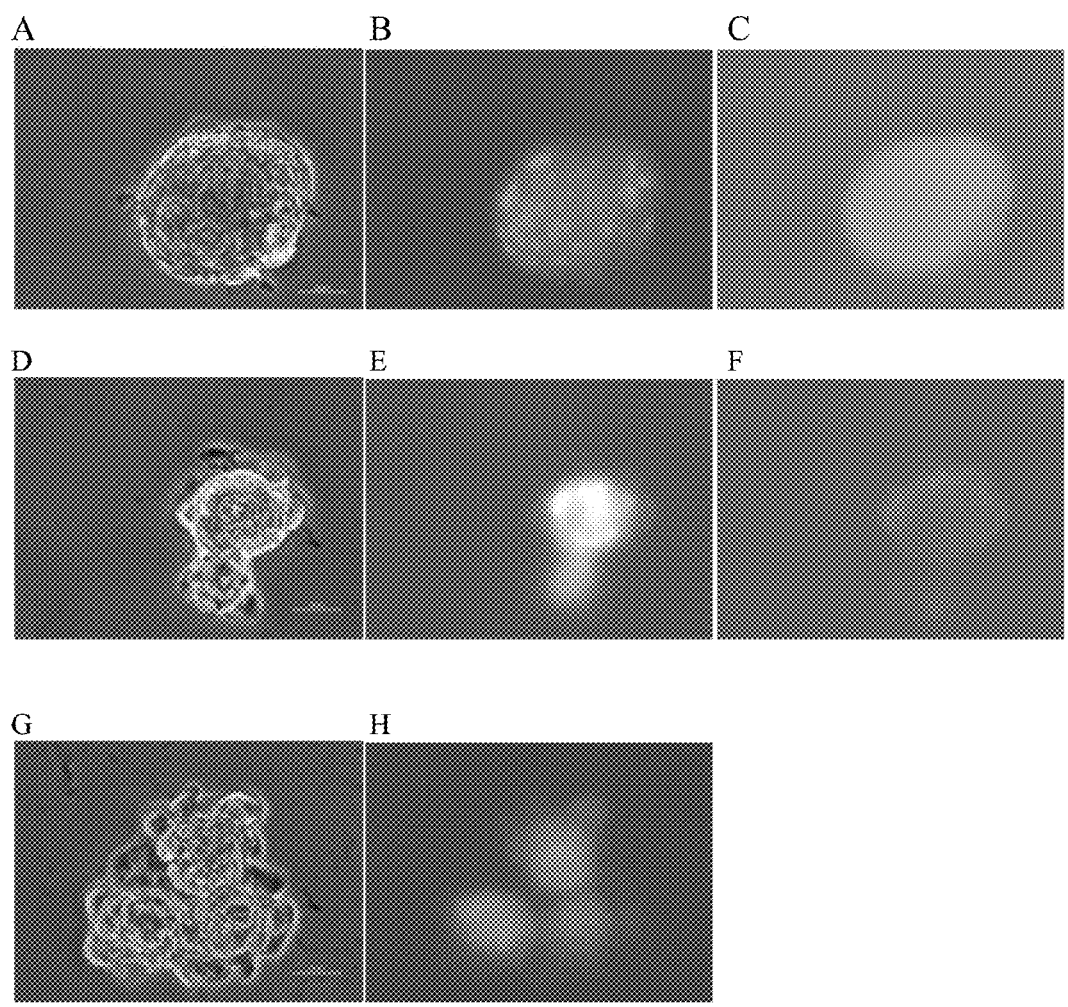
FIG. 29 shows that mRNA encoding human reprogramming factors (KLF4, LIN28, c-MYC, NANOG, OCT4, and SOX2) produce iPS cells in human keratinocytes that are positive for known iPS cell markers.

This example describes the characterization of cells resulting from transfection of primary keratinocytes with equal amounts of KLF4, LIN28, c-MYC, NANOG, OCT4, and SOX2 mRNAs. One million HEKn cells were electoporated once with 5 micrograms of each mRNA and plated on matrigel-coated 10 cm dishes in mTeSR1 cell medium. 15 Days after transfection the cells were fixed for immunofluorescence analysis. The resulting colonies were positive for the iPS markers KLF4, LIN28, SSEA4, TRA-1-60, and NANOG (FIG. 29).

Example 41

Figure 30:
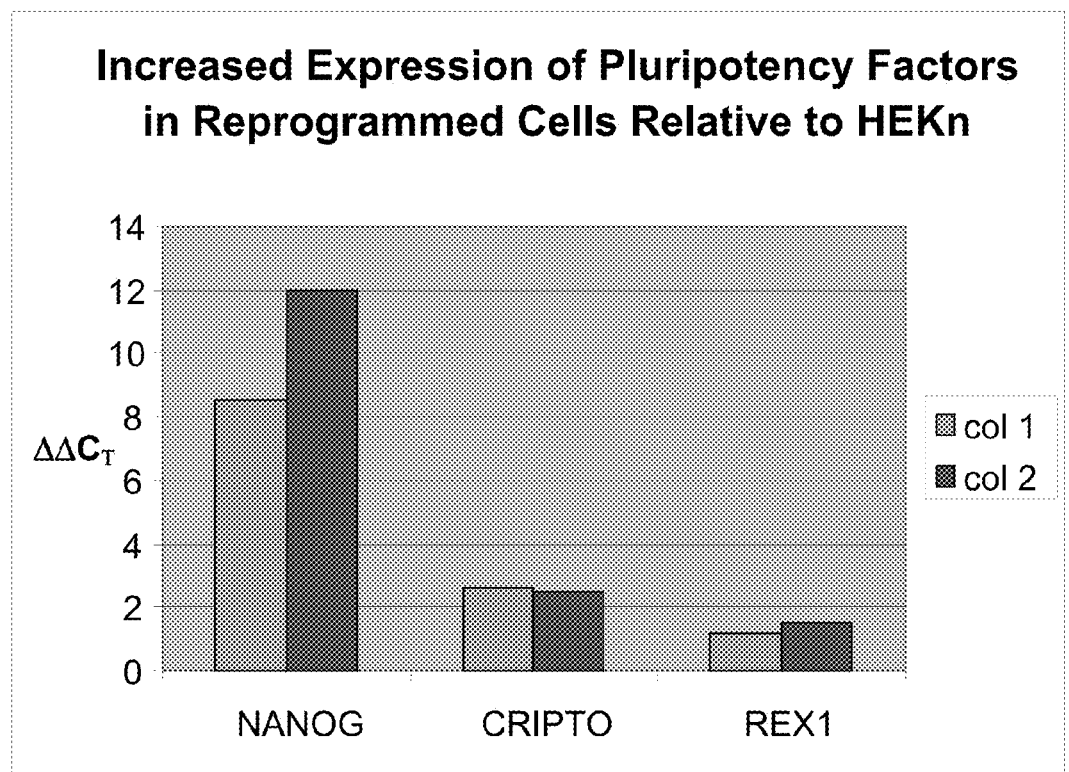
FIG. 30 shows increases in the expression of 3 iPS-associated messages in HEKn cells transfected with 4 reprogramming mRNAs (KLF4, c-MYC, OCT4, and SOX2) which did not include the reprogramming factor NANOG. Increased expression of the messages was detected by qPCR and is normalized to GAPDH expression. The expression level of each message is depicted in relation to the level found in the original cell line.

This example describes expression differences between primary keratinocytes and keratinocytes reprogrammed with equal amounts of KLF4, c-MYC, OCT4, and SOX2 mRNAs. $7.5\times10^5$ HEKn cells were electoporated once with 3 or 5 micrograms of each mRNA and plated on matrigel-coated 10 cm dishes in mTeSR1 medium. Medium was changed daily. 13 days after transfection the cells were transferred to freshly-coated matrigel plates. 21 days after transfection, total cellular RNA was purified from untransfected HEKn cells and two wells of reprogrammed cells. An equal amounts of each cellular RNA was converted to cDNA and analyzed by qPCR. Increased levels of NANOG, CRIPTO and REX1 were detected by qPCR using message-specific primers (FIG. 30). These three messages have been shown to be elevated in iPS cells (Aasen T et al. 2008. Nature Biotech 26: 1276). None of these factors was introduced into the cells by transfection; therefore the changes in expression are due to the influence of the reprogramming factors that were introduced.

Example 42

Transdifferentiating Cells with mRNAs

Cells can be transdifferentiated using the purified mRNA preparations described herein, or the modified mRNAs described herein, or the purified mRNA preparations containing modified mRNAs described herein. In this Example, a purified RNA preparation containing OCT4 mRNA that has at least one pseudouridine or one 5-methycytidine is employed. Such purified and modified OCT4 mRNAs are substituted for the OCT4 encoding vectors in the protocol described by Szabo et al. (Nature 468: 521-528, 2010, which is herein incorporated by reference in its entirety as if fully set forth herein) and in the protocol described in Racila et al. (Gene Therapy, 1-10, 2010, herein incorporated by reference in its entirety as if fully set forth herein). In one embodiment of each of these methods, the purified RNA preparation comprises or consists of OCT 4 mRNA, wherein all of the uridine nucleosides are replaced by pseudouridine nucleosides. In one embodiment of each of these methods, the purified RNA preparation comprises or consists of OCT 4 mRNA, wherein all of the cytidine nucleosides are replaced by 5-methylcytidine nucleosides. In one embodiment of each of these methods, the purified RNA preparation comprises or consists of OCT 4 mRNA, wherein all of the uridine nucleosides are replaced by pseudouridine nucleosides and all of the cytidine nucleosides are replaced by 5-methylcytidine nucleosides. In preferred embodiments, the OCT4 mRNA is purified to be free of contaminating RNAs. The Racilla et al. reference describes a system in which human keratinocytes were transdifferentiated by being redirected to an alternative differentiation pathway. In particular, transient transfection of human skin keratinocytes with the transcription factor OCT4 was employed. After 2 days, these transfected cells displayed expression of endogenous embryonic genes and showed reduced genomic methylation. It was shown that such cells could be converted into neuronal and contractile mesenchymal cell types.

The Szabo et al. reference demonstrated the ability to generate progenitors and mature cells of the haematopoietic fate directly from human dermal fibroblasts without establishing pluripotency. In particular, ectopic expression of OCT4 activated haematopoietic transcription factors, together with specific cytokine treatment, allowed generation of cells expressing the pan-leukocyte marker CD45. These unique fibroblast-derived cells gave rise to granulocytic, monocytic, megakaryocytic and erythroid lineages, and demonstrated in vivo engraftment capacity.

Besides the use of OCT4, both of these protocols also employed cytokines or growth factors, such as tranforming growth factor (TGF), PDGF-BB, stem cell factor (SCF), and FMS-like tyrosine kinase 3 ligand (Flt3L). Other growth factors and cytokines could be used, such as granulocyte-colony stimulating factor (G-CSF), IL-3, IL-6, erythropoietin, basic fibroblast growth factor (bFGF), insulin-like growth factor 2 (IGFII), and bone morphogenetic protein 4 (BMP-4). As such, in certain embodiments, the Racilla et al. or Szabo et al. protocols are repeated with the substitution of modified OCT4 mRNA (e.g., psuedouridine-modified and/or 5-methycytidine-modified), along with the use of the growth factors or cytokines recited above. In some embodiments, the cells are contacted with the cytokine and/or growth factor proteins that are used. In some other embodiments, the cells are contacted with modified mRNAs (e.g., modified mRNAs as described in the present application, e.g., e.g., psuedouridine-modified and/or 5-methycytidine-modified) that encode one or more of the cytokines and/or growth factors that are used in the transdifferentiation protocol. It will be clear from this description, that the present invention includes contacting a human or animal cell with a purified RNA preparation comprising or consisting of mRNA that encodes a reprogramming factor in order to transdifferentiate a cell having a first state of differentiation or phenotype to a cell having a second state of differentiation or phenotype.

REFERENCES

Aoi T, Yae K, Nakagawa M, Ichisaka T, Okita K, Takahashi K, Chiba T, Yamanaka S. 2008. Generation of pluripotent stem cells from adult mouse liver and stomach cells. Science 321: 699-702.

Banerjee A K. 1980. 5'-terminal cap structure in eucaryotic messenger ribonucleic acids. Microbiol Rev 44: 175-205.

Chan E M, et al. 2009. Live cell imaging distinguishes bona fide human iPS cells from partially reprogrammed cells. Nat Biotechnol 27: 1033-1037.

Ebert A D, Yu J, Rose F F, Jr., Mattis V B, Lorson C L, Thomson J A, Svendsen C N. 2009. Induced pluripotent stem cells from a spinal muscular atrophy patient. Nature 457: 277-280.

Edmonds M. 1990. Polyadenylate polymerases. Methods Enzymol 181: 161-170.

Feng, R et al. 2008. PU.1 and C/EBPa/b convert fibroblasts into macrophage-like cells. Proc. Natl. Acad. Sci. USA 105: 6057-6062.

Gershon P D. 2000. (A)-tail of two polymerase structures. Nat Struct Biol 7: 819-821.

Gonzalez F, Barragan Monasterio M, Tiscornia G, Montserrat Pulido N, Vassena R, Batlle Morera L, Rodriguez Piza I, Izpisua Belmonte J C. 2009. Generation of mouse-induced pluripotent stem cells by transient expression of a single nonviral polycistronic vector. Proc Natl Acad Sci USA 106: 8918-8922.

Graf T, Enver T. 2009. Forcing cells to change lineages. Nature 462: 587-594.

Grudzien E, Stepinski J, Jankowska-Anyszka M, Stolarski R, Darzynkiewicz E, Rhoads R E. 2004. Novel cap analogs for in vitro synthesis of mRNAs with high translational efficiency. RNA 10: 1479-1487.

Grudzien-Nogalska E, Jemielty J, Kowalska J, Darzynkiewicz E, Rhoads R. 2007. Phosphorothioate cap analogs stabilize mRNA and increase translational efficiency in mammalian cells. RNA 13: 1745-1755.

Higman M A, Bourgeois N, Niles E G. 1992. The vaccinia virus mRNA (guanine-N7-)-methyltransferase requires both subunits of the mRNA capping enzyme for activity. J Biol Chem 267: 16430-16437.

Higman M A, Christen L A, Niles E G. 1994. The mRNA (guanine-7-)methyltransferase domain of the vaccinia virus mRNA capping enzyme. Expression in *Escherichia coli* and structural and kinetic comparison to the intact capping enzyme. J Biol Chem 269: 14974-14981.

Huangfu D, Osafune K, Maehr R, Guo W, Eijkelenboom A, Chen S, Muhlestein W, Melton D A. 2008. Induction of pluripotent stem cells from primary human fibroblasts with only Oct4 and Sox2. Nat Biotechnol 26: 1269-1275.

Ieda, M et al. 2010. Direct reprogramming broblasts into functional cardiomyocytes by defined factors. Cell 142: 375-386.

Jemielity J, Fowler T, Zuberek J, Stepinski J, Lewdorowicz M, Niedzwiecka A, Stolarski R, Darzynkiewicz E, Rhoads R E. 2003. Novel "anti-reverse" cap analogs with superior translational properties. RNA 9: 1108-1122.

Kariko K, Muramatsu H, Welsh F A, Ludwig J, Kato H, Akira S, Weissman D. 2008. Incorporation of pseudouridine into mRNA yields superior nonimmunogenic vector with increased translational capacity and biological stability. Mol Ther 16: 1833-1840.

Krieg P A, Melton D A. 1984. Functional messenger RNAs are produced by SP6 in vitro transcription of cloned cDNAs. Nucleic Acids Res 12: 7057-7070.

Lee G, et al. 2009. Modelling pathogenesis and treatment of familial dysautonomia using patient-specific iPSCs. Nature 461: 402-406.

Mackie G A. 1988. Vectors for the synthesis of specific RNAs in vitro. Biotechnology 10: 253-267.

Maehr R, Chen S, Snitow M, Ludwig T, Yagasaki L, Goland R, Leibel R L, Melton D A. 2009. Generation of pluripotent stem cells from patients with type 1 diabetes. Proc Natl Acad Sci USA 106: 15768-15773.

Martin S A, Paoletti E, Moss B. 1975. Purification of mRNA guanylyltransferase and mRNA (guanine-7-) methyltransferase from vaccinia virions. J Biol Chem 250: 9322-9329.

Myette J R, Niles E G. 1996. Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem 271: 11936-11944.

Nakagawa M, Koyanagi M, Tanabe K, Takahashi K, Ichisaka T, Aoi T, Okita K, Mochiduki Y, Takizawa N, Yamanaka S. 2008. Generation of induced pluripotent stem cells without Myc from mouse and human fibroblasts. Nat Biotechnol 26: 101-106.

Okita K, Nakagawa M, Hyenjong H, Ichisaka T, Yamanaka S. 2008. Generation of mouse induced pluripotent stem cells without viral vectors. Science 322: 949-953.

Ozawa T, Kishi H, Muraguchi A. 2006. Amplification and analysis of cDNA generated from a single cell by 5'-RACE: application to isolation of antibody heavy and light chain variable gene sequences from single B cells. Biotechniques 40: 469-470, 472, 474 passim.

Peng Z H, Sharma V, Singleton S F, Gershon P D. 2002. Synthesis and application of a chain-terminating dinucleotide mRNA cap analog. Org Lett 4: 161-164.

Racila D et al. 2010. Transient expression of OCT 4 IS sufficient to allow human keratinocytes to change their differentiation pathway. Gene Therapy advance online publication, (Oct. 28, 2010; doi:10.1038/gt.2010.148).

Shuman S. 1995. Capping enzyme in eukaryotic mRNA synthesis. Prog Nucleic Acid Res Mol Biol 50: 101-129.

Shuman. 2001. Structure, mechanism, and evolution of the mRNA capping apparatus. Prog Nucleic Acid Res Mol Biol 66: 1-40.

Shuman S, Surks M, Furneaux H, Hurwitz J. 1980. Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme). J Biol Chem 255: 11588-11598.

Stadtfeld M, Nagaya M, Utikal J, Weir G, Hochedlinger K. 2008. Induced pluripotent stem cells generated without viral integration. Science 322: 945-949.

Stepinski J, Waddell C, Stolarski R, Darzynkiewicz E, Rhoads R E. 2001. Synthesis and properties of mRNAs containing the novel "anti-reverse" cap analogs 7-methyl (3'-O-methyl)GpppG and 7-methyl (3'-deoxy)GpppG. RNA 7: 1486-1495.

Studier F W, Moffatt B A. 1986. Use of bacteriophage T7 RNA polymerase to direct selective high-level expression of cloned genes. J Mol Biol 189: 113-130.

Szabo E, Rampalli S, Risueno R M, Schnerch A, Mitchell R, Fiebig-Comyn A, Levadoux-Martin M, Bhati a M. 2010. Direct conversion of human fibroblasts to multilineage blood progenitors. Nature. 468: 521-526.

Takahashi K, Yamanaka S. 2006. Induction of pluripotent stem cells from mouse embryonic and adult fibroblast cultures by defined factors. Cell 126: 663-676.

Takahashi K, Tanabe K, Ohnuki M, Narita M, Ichisaka T, Tomoda K, Yamanaka S. 2007. Induction of pluripotent stem cells from adult human fibroblasts by defined factors. Cell 131: 861-872.

Vierbuchen T et al. 2010. Direct conversion of fibroblasts to functional neurons by defined factors. Nature 463: 1035-1041.

Wang S P, Deng L, Ho C K, Shuman S. 1997. Phylogeny of mRNA capping enzymes. Proc Natl Acad Sci USA 94: 9573-9578.

Wilusz J, Shenk T. 1988. A 64 kd nuclear protein binds to RNA segments that include the AAUAAA polyadenylation motif. Cell 52: 221-228.

Woltj en K, et al. 2009. piggyBac transposition reprograms fibroblasts to induced pluripotent stem cells. Nature 458: 766-770.

Xu C, Inokuma M S, Denham J, Golds K, Kundu P, Gold J D, Carpenter M K. 2001. Feeder-free growth of undifferentiated human embryonic stem cells. Nat Biotechnol 19: 971-974.

Yu J, Hu K, Smuga-Otto K, Tian S, Stewart R, Slukvin, I I, Thomson J A. 2009. Human induced pluripotent stem cells free of vector and transgene sequences. Science 324: 797-801.

Yu J, et al. 2007. Induced pluripotent stem cell lines derived from human somatic cells. Science 318: 1917-1920.

Zhou H, et al. 2009. Generation of induced pluripotent stem cells using recombinant proteins. Cell Stem Cell 4: 381-384.

We claim:

1. An in vitro method for reprogramming a human or other mammalian somatic cell that exhibits a first differentiated state or phenotype to an induced pluripotent stem cell (iPSC), comprising:
   a) introducing into said cell that exhibits a first differentiated state or phenotype a purified RNA preparation comprising in vitro-synthesized modified mRNA molecules that:
      (i) encode the iPSC induction factors OCT4, SOX2, KLF4 and MYC;
      (ii) comprise pseudouridine that is not further modified ($\psi$) or 1-methylpseudouridine ($m^1\psi$) in place of at least a portion of the unmodified uridine nucleosides; and
      (iii) comprise a 5'-cap and a 3' poly(A) tail;
   wherein said in vitro-synthesized modified mRNA molecules are purified using a process that removes RNA contaminant molecules that are immunogenic and toxic to the cell by inducing an innate immune response, as can be detected by measuring decreased secretion of INF-α cytokine or TNF-α cytokine from dendritic cells transfected with said purified modified mRNA molecules compared to secretion of said cytokine from dendritic cells transfected with the unpurified modified mRNA molecules,
   such that said purified RNA preparation is free of RNA contaminant molecules that, if present, would activate an immune response in said cell sufficient to prevent survival of said cell and prevent generation of a reprogrammed cell; and
   b) repeating said introducing of said purified RNA preparation on multiple days and culturing the cell, such that the cell is reprogrammed to an iPSC.

2. The method of claim 1, wherein said purified RNA preparation comprises in vitro-synthesized modified mRNA molecules wherein:
   (i) said encoded iPSC induction factors further comprise LIN28 and/or NANOG and/or said MYC is selected from c-MYC, l-MYC and N-MYC;
   (ii) the RNA contaminant molecules that are removed from said in vitro-synthesized modified mRNA molecules using said purification process are selected from the group consisting of dsRNA molecules and uncapped mRNA molecules;
   (iii) greater than 98% of said modified mRNA molecules are capped;
   (iv) said modified mRNA molecules comprise a cap with a cap1 structure, wherein the 2' hydroxyl of the ribose in the penultimate nucleotide with respect to the cap nucleotide is methylated;
   (v) substantially all of said modified mRNA molecules comprise a poly-A tail greater than 150 nucleotides;
   (vi) said modified mRNA molecules comprise at least one particular sequence selected from the group consisting of: a heterologous 5' UTR sequence, a Kozak sequence, an IRES sequence, and 3' UTR sequence, wherein said particular sequence results in greater translation of the modified mRNA molecules compared to the same mRNA molecules that do not comprise said particular sequence, including wherein said 5' UTR sequence or 3' UTR sequence is from a *Xenopus* or human alpha globin or beta globin mRNA, or wherein said 5' UTR sequence is a sequence from a tobacco etch virus (TEV) RNA; and/or
   (vii) said pseudouridine ($\psi$) or 1-methylpseudouridine ($m^1\psi$) modified nucleoside is present in place of substantially all of the corresponding unmodified uridine nucleosides.

3. The method of claim 2, wherein said in vitro-synthesized modified mRNA molecules comprise 5-methylcytidine ($m^5C$) modified nucleoside in place of at least a portion of the counterpart unmodified cytidine nucleoside.

4. The method of claim 2, wherein said in vitro-synthesized modified mRNA molecules comprise 5-methylcytidine ($m^5C$) modified nucleoside in place of substantially all of the counterpart unmodified cytidine nucleoside.

5. The method of claim 2, wherein the removal of said RNA contaminant molecules comprising dsRNA molecules can be detected by dot blot immunoassays using a dsRNA-specific antibody.

6. The method of claim 2, wherein said purification process comprises at least one method selected from the group consisting of:
   a) purification of said modified mRNA molecules using an HPLC or gravity flow column purification; and
   b) treating said modified mRNA molecules with a ribonuclease III (RNase III) enzyme such that short RNase III digestion products are generated, and purifying said short RNase III digestion products away from said modified mRNA molecules.

7. The method of claim 2, wherein said repeating said introducing on multiple days comprises repeating said introducing daily for 10-16 days.

8. The method of claim 2, wherein said reprogrammed iPSC is capable of surviving at least 20 days in culture and of maintaining a morphology and expression of markers characteristic of an iPSC, selected from NANOG, KLF4, LIN28, SSEA4, CRIPTO, REX1 and TRA-1-60, after the last said introducing of said purified RNA preparation.

9. The method of claim 8, wherein said reprogrammed iPSC survives and replicates in culture for at least 40 days.

10. An in vitro method for reprogramming a human or other mammalian somatic cell that exhibits a first differentiated state or phenotype to an induced pluripotent stem cell (iPSC), comprising:
    a) introducing into a human or other mammalian somatic cell that exhibits a first differentiated state or phenotype a purified RNA preparation comprising in vitro-synthesized modified mRNA molecules that:
       (i) comprise at least one modified nucleoside selected from the group consisting of 1-methylpseudouridine ($m^1\psi$) in place of at least a portion of the counterpart unmodified uridine nucleoside, pseudouridine that is not further modified ($\psi$) in place of at least a portion of the counterpart unmodified uridine nucleoside, 5-methyluridine ($m^5U$) in place of at least a portion of the counterpart unmodified uridine nucleoside, 2-thiouridine ($s^2U$) in place of at least a portion of the counterpart unmodified nucleoside uridine, 5-methoxyuridine ($mo^5U$) in place of at least a portion of the counterpart unmodified uridine nucleoside, and 5-methylcytidine ($m^5C$) in place of at least a portion of the counterpart unmodified nucleoside cytidine;
       (ii) comprise a 5' cap;
       (iii) comprise a 3' poly(A) tail comprising 50-200 or greater than 150 nucleotides; and
       (iv) encode the iPSC induction factors OCT4, SOX2, KLF4, and MYC;
    wherein the in vitro-synthesized modified mRNA molecules are purified using a process that removes RNA contaminant molecules that are immunogenic and toxic to the cell by inducing an innate immune response, as can be detected by measuring decreased secretion of INF-α cytokine or TNF-α cytokine from dendritic cells transfected with said purified modified mRNA molecules compared to secretion of said cytokine from dendritic cells transfected with the unpurified modified mRNA molecules, such that said purified RNA preparation is free of RNA contaminant molecules that, if present, would activate an immune response in said cell sufficient to prevent survival of said cell and prevent generation of a reprogrammed cell; and b) repeating said introducing of said purified RNA preparation on multiple days and culturing the cell, such that the cell is reprogrammed to an iPSC, which reprogrammed cell is capable of surviving at least 20 days in culture and of maintaining a morphology and expression of markers characteristic of an iPSC, selected from NANOG, KLF4, LIN28, SSEA4, CRIPTO, REX1 and TRA-1-60, after the last said introducing of said purified RNA preparation.

11. The method of claim 10, wherein said purified RNA preparation comprises in vitro-synthesized modified mRNA molecules wherein:

(i) said encoded iPSC induction factors further comprise LIN28 and/or NANOG and/or said MYC is selected from c-MYC, 1-MYC and N-MYC;

(ii) the RNA contaminant molecules that are removed from said in vitro-synthesized modified mRNA molecules using said purification process are selected from the group consisting of dsRNA molecules and uncapped mRNA molecules;

(iii) greater than 98% of said modified mRNA molecules are capped;

(iv) said modified mRNA molecules comprise a cap with a cap1 structure, wherein the 2' hydroxyl of the ribose in the penultimate nucleotide with respect to the cap nucleotide is methylated;

(v) substantially all of said modified mRNA molecules comprise a poly-A tail greater than 150 nucleotides;

(vi) said modified mRNA molecules comprise at least one particular sequence selected from the group consisting of: a heterologous 5' UTR sequence, a Kozak sequence, an IRES sequence, and 3' UTR sequence, wherein said particular sequence results in greater translation of the modified mRNA molecules compared to the same mRNA molecules that do not comprise said particular sequence, including wherein said 5' UTR sequence or 3' UTR sequence is from a *Xenopus* or human alpha globin or beta globin mRNA, or wherein said 5' UTR sequence is a sequence from a tobacco etch virus (TEV) RNA; and/or (vii) said modified nucleoside in place of unmodified uridine nucleoside is 1-methylpseudouridine ($m^1\psi$), pseudouridine that is not further modified ($\psi$), 5-methoxyuridine ($mo^5U$) or 5-methyluridine ($m^5U$) and is present in place of substantially all of said counterpart unmodified uridine nucleoside; or (viii) said modified nucleoside in place of unmodified uridine nucleoside is 2-thiouridine ($s^2U$) or 5-methoxyuridine ($mo^5U$) and the percentage of the modified nucleoside in place of the counterpart unmodified uridine nucleoside is a fraction less than 70%.

12. The method of claim 11 wherein said in vitro-synthesized modified mRNA molecules that comprise 2-thiouridine ($s^2U$) or 5-methoxyuridine ($mo^5U$) in place of a portion of said unmodified uridine nucleoside further comprise 5-methylcytidine ($m^5C$) and the percentage of the modified nucleoside in place of the counterpart unmodified nucleoside cytidine is a fraction selected from 10%, 12%, 14%, 16%, 18%, 20%, 25%, 30%, 35%, 40%, 45% and 50% or is a fraction less than 50%.

13. The method of claim 11, wherein said in vitro-synthesized modified mRNA molecules comprise 5-methylcytidine ($m^5C$) modified nucleoside in place of substantially all of the counterpart unmodified cytidine nucleoside.

14. The method of claim 11, wherein said purification process comprises at least one method selected from the group consisting of:

a) purification of said modified mRNA molecules using an HPLC or gravity flow column purification; and b) treating said modified mRNA molecules with a ribonuclease III (RNase III) enzyme such that short RNase III digestion products are generated, and purifying said short RNase III digestion products away from said modified mRNA molecules.

15. The method of claim 11, wherein the removal of said RNA contaminant molecules that are immunogenic by said purification process can be detected by measuring a lower quantity of at least one cytokine, selected from the group consisting of IL-12, IFN-α, TNF-α, RANTES, MIP-1α, MIP-1β, IL-6, IFN-β or IL-8, in response to said introducing of said purified RNA preparation into a mammalian cell compared to the quantity of the same said cytokine secreted by a like mammalian cell in response to introducing of a preparation of the same quantity of the same said in vitro-synthesized modified mRNA molecules not subjected to said purifying process.

16. The method of claim 11, wherein said repeating said introducing on multiple days comprises repeating said introducing daily for at least 10-16 days.

17. The method of claim 11, wherein said reprogrammed iPSC survives and replicates in culture for at least 40 days.

18. The method of claim 11, further comprising, after said introducing, contacting said cell with at least one growth factor and/or cytokine selected from the group consisting of: IL-12; IFN-α; TNF-α; RANTES; MIP-1α or β; IL-6; IFN-β; IL-8; α-melanocyte-stimulating hormone (α-MSH); transforming growth factor-β 1 (TGF-β 1); insulin-like growth factor-I (IGF-I); TGF; PDGF-BB; stem cell factor (SCF); FMS-like tyrosine kinase 3 ligand (Flt3L); granulocyte-colony stimulating factor (G-CSF); IL-3; IL-6; erythropoietin; basic fibroblast growth factor (bFGF); insulin-like growth factor 2 (IGFII); and bone morphogenetic protein 4 (BMP-4).

19. The method of claim 11, further comprising introducing into said cell modified mRNA encoding at least one cytokine or growth factor selected from the group consisting of: TGF; PDGF-BB; stem cell factor (SCF); FMS-like tyrosine kinase 3 ligand (Flt3L); granulocyte-colony stimulating factor (G-CSF); IL-3; IL-6; erythropoietin; basic fibroblast growth factor (bFGF); insulin-like growth factor 2 (IGFII); bone morphogenetic protein 4 (BMP-4); heat shock protein; HSP70; platelet-derived growth factor (PDGF); vascular endothelial growth factor (VEGF); insulin-like growth factor (IGF); and a protein that down-regulates or antagonizes growth factor signaling.

* * * * *

UNITED STATES PATENT AND TRADEMARK OFFICE
CERTIFICATE OF CORRECTION

PATENT NO. : 10,006,007 B2
APPLICATION NO. : 15/160062
DATED : June 26, 2018
INVENTOR(S) : Katalin Kariko et al.

It is certified that error appears in the above-identified patent and that said Letters Patent is hereby corrected as shown below:

In the Specification

Column 1, Line 15 insert:
--This invention was made with government support under AI050484 and HL087688 awarded by the National Institutes of Health. The government has certain rights in the invention.--

Signed and Sealed this
Twenty-first Day of November, 2023

Katherine Kelly Vidal
*Director of the United States Patent and Trademark Office*

SEQUENCE LISTING

```
<160> NUMBER OF SEQ ID NOS: 17

<210> SEQ ID NO 1
<211> LENGTH: 1864
<212> TYPE: RNA
<213> ORGANISM: Artificial Sequence
<220> FEATURE:
<223> OTHER INFORMATION: Synthetic

<400> SEQUENCE: 1
ggaauucuca acacaacaua uacaaaacaa acgaaucuca agcaaucaag cauucuacuu      60
cuauugcagc aauuuaaauc auuucuuuua aagcaaaagc aauuuucuga aaauuuucac     120
cauuuacgaa cgauagccau ggaagacgcc aaaaacauaa agaaaggccc ggcgccauuc     180
uauccucuag aggauggaac cgcuggagag caacugcaua aggcuaugaa gagauacgcc     240
cugguuccug aacaauugc uuuuacagau gcacauaucg aggugaacau cacgacgcg      300 gaauacuucg aaauguccgu ucgguuggca gaagcuauga aacgauaugg gcugaauaca     360
aaucacagaa ucgucguaug cagugaaaac ucucuucaau ucuuuaugcc gguguugggc     420
gcguuauuua ucggaguugc aguugcgccc gcgaacgaca uuuauaauga acugaauug      480 cucaacagua ugaacauuuc gcagccuacc guaguguuug uuccaaaaa ggguugcaa      540 aaaauuuuga acgugcaaaa aaaauuacca auaauccaga aaauuauuau cauggauucu     600
aaaacggauu accagggauu ucagucgaug uacgcguucg ucacaucuca ucuaccucc     660
```

```
gguuuuaaug aauacgauuu uguaccagag uccuuugauc gugacaaaac aauugcacug      720
auaaugaauu ccucuggauc uacugggutua ccuaagggug uggcccuucc gcauagaacu      780
gccugcguca gauucucgca ugccagagau ccuauuuug gcaaucaaau cauuccggau       840
acugcgauuu uaagguugu uccauuccau cacgguuuug gaauguuuac uacacucgga       900
uauuugauau guggauuucg agucgucuua auguauagau ugaagaaga gcuguuuuua       960 cgaucccuuc aggauuacaa aauucaaagu gcguugcuag uaccaacccu auuucauuc      1020 uucgccaaaa gcacucugau ugacaaauac gauuuaucua auuuacacga aaugcuucu      1080 gggggcgcac cucuuucgaa agaagucggg gaagcgguug caaaacgcuu ccaucuucca     1140
gggauacgac aaggauaugg gcucacugag acuacaucag cuauucugau uacacccgag     1200
ggggaugaua aaccgggcgc ggucgguaaa guuguuccau uuuugaagc gaagguugug      1260 gaucuggaua ccgggaaaac gcugggcguu aaucagagag gcgaauuaug ugucagagga    1320
ccuaugauua uguccgguua uguaaacaau ccggaagcga ccaacgccuu gauugacaag    1380
gauggauggc uacauucugg agacauagcu uacugggacg aagacgaaca cuucuucaua    1440
guugaccgcu ugaagucuuu aauuaaauac aaaggauauc agguggcccc cgcugaauug   1500
gaaucgauau uguuacaaca ccccaacauc uucgacgcgg gcguggcagg ucuucccgac   1560
gaugacgccg gugaacuucc cgccgccguu guuguuuugg agcacggaaa gacgaugacg  1620
gaaaagagaa ucguggauua cguggccagu caaguaacaa ccgcgaaaaa guugcgcgga  1680
ggaguugugu uuguggacga aguaccgaaa ggucuuaccg gaaaacucga cgcaagaaaa  1740
aucagagaga uccucauaaa ggccaagaag ggcggaaagu ccaaauugua aaauguaacu  1800
cuagaggauc cccaaaaaaa aaaaaaaaaa aaaaaaaaa aaaaaaaaa aaaaaaaaaa    1860 aaca                                                                  1864
```

<210> SEQ ID NO 2
<211> LENGTH: 1571
<212> TYPE: RNA
<213> ORGANISM: Artificial Sequence
<220> FEATURE:
<223> OTHER INFORMATION: Synthetic

<400> SEQUENCE: 2

```
ggcuagccac caugacuucg aaaguuuaug auccagaaca aaggaaacgg augauaacug       60
guccgcagug gugggccaga uguaaacaaa ugaauguucu ugauucauuu auuaauuauu      120
augauucaga aaaacaugca gaaaaugcug uuauuuuuuu acauggguaac gcggccucuu     180 cuuauuuaug gcgacauguu gugccacaua uugagccagu agcgcggugu auuauaccag     240
accuuauugg uaugggcaaa ucaggcaaau cugguaaugg uucuuauagg uuacuugauc    300
auuacaaaua ucuacugca ugguuugaac uucuaauuu accaaagaag aucauuuuug       360
ucggccauga uggggugcu uguuuggcau ucauuauag cuaugagcau caagauaaga       420
ucaaagcaau aguucacgcu gaaaguguag uagaugugau ugaaucaugg gaugaauggc    480
cugauauuga agaaugauauu gcguugauca aaucugaaga aggagaaaaa augguuuugg   540 agaauaaccuu cuucgguggaa accauguugc caucaaaaau caugaaaag uuagaaccag   600 aagaauuugc agcauaucuu gaaccauuca agagaaagg ugaaguucgu cguccaacau    660
uaucauggcc ucgugaaauc ccguuaguaa aaggugguaa accgacguu guacaaauug     720 uuaggaauua uaaugcuuau cuacgugcaa gugaugauu accaaaaaug uuuauugaau    780
cggacccagg auucuuuucc aaugcuauug uugaaggugc caagaaguuu ccuaauacug    840
```

```
aauuugucaa aguaaaaggu cuucauuuuu cgcaagaaga ugcaccugau gaaaugggaa      900
aauauaucaa aucguucguu gagcgaguuc ucaaaaauga acaaaugucg acggggggccc      960 cuaggaauuu uuuagggaag aucuggccuu ccuacaaggg aaggccaggg aauuuucuuc     1020
agagcagacc agagccaaca gccccaccag aagagagcuu caggucuggg guagagacaa     1080 caacucccc  ucagaagcag gagccgauag acaaggaacu guauccuuua acuucccuca     1140
gaucacucuu uggcaacgac cccucgucac aauaaagaua gggggggcaac uaaagggauc     1200 ggccgcuucg agcagacaug auaagauaca uugaugaguu uggacaaacc acaacuagaa     1260
ugcagugaaa aaaugcuuu auuugugaaa uuugugaugc uauugcuuua uuuguaacca     1320
uuauaagcug caauaaacaa guuaacaaca acaauugcau ucauuuuaug uuucagguuc     1380 aggggggaggu guggggagguu uuuuaaagca aguaaaaccu cuacaaaugu gguaaaaucg     1440
auaaguuuaa acagauccag guggcacuuu ucggggaaau gugcgcggaa ccccuauuug     1500
uuuauuuuuc uaaauacauu caaauaugua uccgcucaug agacaauaac ccugauaaau     1560
gcuucaauaa u                                                         1571

<210> SEQ ID NO 3
<211> LENGTH: 726
<212> TYPE: RNA
<213> ORGANISM: Artificial Sequence
<220> FEATURE:
<223> OTHER INFORMATION: Synthetic

<400> SEQUENCE: 3
gggaauuugg cccucgaggc caagaauucg gcacgaggca cgcggccagc cagcagacag       60
aggacucuca uuaaggaagg uguccugugc ccugacccua caagaugcca agagaagaug      120
cucacuucau cuaugguuac cccaagaagg ggcacggcca cucuuacacc acggcugaag      180
aggccgcugg gaucggcauc cugacaguga uccuggagu cuuacugcuc aucggcuguu      240
gguauuguag aagacgaaau ggauacagag ccuugaugga uaaaagucuu caugu uggca      300 cucaaugugc cuuaacaaga agaugcccac aagaagggu ugaucaucgg acagcaaag       360 ugucucuuca agagaaaaac ugugaaccug ugguucccaa ugcuccaccu gcuuaugaga      420
aacucucugc agaacaguca ccaccaccuu auucaccuua agagccagcg agacaccuga      480
gacaugcuga aauuauuucu cucacacuuu ugcuugaauu uaauacagac aucuaauguu      540
cuccuuugga augguguagg aaaaaugcaa gccaucucua uaauaaguc aguguuaaaa      600 uuuuaguagg uccgcuagca guacuaauca ugugaggaaa ugaugagaaa uauuaaauug      660
ggaaaacucc aucaauaaau guugcaaugc augauaaaaa aaaaaaaaa aaaaacugcg      720 gccgca                                                                726

<210> SEQ ID NO 4
<211> LENGTH: 712
<212> TYPE: RNA
<213> ORGANISM: Artificial Sequence
<220> FEATURE:
<223> OTHER INFORMATION: Synthetic

<400> SEQUENCE: 4
gggaauaagc uugcggccgc aguuuuuuuu uuuuuuuuu uuaucaugca uugcaacauu        60
uauugaugga guuucccaa uuuaauauuu cuaucauuu ccucacauga uuaguacugc       120
uagcggaccu acuaaaauuu uaacacugac uuauuauuag agauggcuug cauuuuuccu      180
```

| | |
|---|---:|
| acaccauucc aaaggagaac auuagauguc uguauaaauu caagcaaaag gugagagaa | 240 |
| auaauuucag caugucucag gugucucgcu ggcucuuaag gugaauaagg uggugugac | 300 |
| uguucugcag agaguuucuc auaagcaggu ggagcauugg gaaccacagg uucacaguuu | 360 |
| uucucuugaa gagacacuuu gcugucccga ugaucaaacc cuucuugugg gcaucuucuu | 420 |
| guuaaggcac auugagugcc aacaugaaga cuuuuaucca ucaaggcucu guauccauuu | 480 |
| cgucuucuac aauaccaaca gccgaugagc aguaagacuc ccaggaucac ugucaggaug | 540 |
| ccgaucccag cggccucuuc agccguggug uaagaguggc cgugcccuu cuggggguaa | 600 |
| ccauagauga agagagcauc uucucuuggc aucuuuagg gucagggcac aggacaccuu | 660 |
| ccuuaaugag aguccucugu cugcuggcug gccgcgugcc ucgugccgaa uu | 712 |

<210> SEQ ID NO 5
<211> LENGTH: 494
<212> TYPE: RNA
<213> ORGANISM: Artificial Sequence
<220> FEATURE:
<223> OTHER INFORMATION: Synthetic

<400> SEQUENCE: 5

| | |
|---|---:|
| gggagaccca agcuggcuag cagucaucca acagaaucau gagacagacu uugccuugua | 60 |
| ucuacuuuug gggggggccuu uugcccuuug ggaugcugug ugcauccucc accaccaagu | 120 |
| gcacguuag ccaugaaguu gcugacugca gccaccugaa guugacucag guacccgaug | 180 |
| aucuacccac aaacauaaca guguugaacc uucccauaa ucaacucaga agauuaccag | 240 |
| ccgccaacuu cacaagguau agccagcuaa cuagcuugga uguaggauuu aacaccaucu | 300 |
| caaaacugga gccagaauug ugccagaaac uucccauguu aaaaguuuug aaccuccagc | 360 |
| acaaugagcu aucucaacuu ucugauaaaa ccuuugccuu cugcacgaau uugacugaac | 420 |
| uccaucucau guccaacuca auccagaaaa uuaaaaauaa ucccuuuguc aagcagaaga | 480 |
| auuuaaucac auua | 494 |

<210> SEQ ID NO 6
<211> LENGTH: 21
<212> TYPE: RNA
<213> ORGANISM: Artificial Sequence
<220> FEATURE:
<223> OTHER INFORMATION: Synthetic

<400> SEQUENCE: 6

| | |
|---|---:|
| uggauccggc uuugagaucu u | 21 |

<210> SEQ ID NO 7
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (11)..(11)
<223> OTHER INFORMATION: um

<400> SEQUENCE: 7

| | |
|---|---:|
| uggauccggc uuugagaucu u | 21 |

<210> SEQ ID NO 8
<211> LENGTH: 21
<212> TYPE: RNA
<213> ORGANISM: Artificial Sequence

```
<220> FEATURE:
<223> OTHER INFORMATION: Synthetic
<220> FEATURE:
<221> NAME/KEY: modified_base
<222> LOCATION: (6)..(6)
<223> OTHER INFORMATION: m5c

<400> SEQUENCE: 8
uggauccggc uuugagaucu u                                          21

<210> SEQ ID NO 9
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (12)..(12)
<223> OTHER INFORMATION: p

<400> SEQUENCE: 9
uggauccggc uuugagaucu u                                          21

<210> SEQ ID NO 10
<211> LENGTH: 31
<212> TYPE: RNA
<213> ORGANISM: Artificial Sequence
<220> FEATURE:
<223> OTHER INFORMATION: Synthetic

<400> SEQUENCE: 10
gggagacagg gguguccgcc auuccaggu u                                31

<210> SEQ ID NO 11
<211> LENGTH: 31
<212> TYPE: RNA
<213> ORGANISM: Artificial Sequence
<220> FEATURE:
<223> OTHER INFORMATION: Synthetic

<400> SEQUENCE: 11
gggagacagg cuauaacuca cauaauguau u                               31

<210> SEQ ID NO 12
<211> LENGTH: 1440
<212> TYPE: RNA
<213> ORGANISM: Homo sapiens

<400> SEQUENCE: 12
augaggcagc caccuggcga gucugacaug gcugucagcg acgcgcugcu cccaucuuuc    60
uccacguucg cgucuggccc ggcgggaagg gagaagacac ugcgucaagc aggugccccg   120
aauaaccgcu ggcgggagga gcucucccac augaagcgac uuccccagu gcuuccggc    180 cgccccuaug accuggcggc ggcgaccgug gccacagacc uggagagcgg cggagccggu   240
gcggcuugcg gcgguagcaa ccuggcgccc cuaccucgga gagagaccga ggaguucaac   300
gaucuccugg accuggacuu uauucucucc aauucgcuga cccauccucc ggagucagug   360
gccgccaccg uguccucguc agcgucagcc uccucuucgu cgucgccguc gagcagcggc   420
ccugccagcg cgcccuccac cugcagcuuc accauccga uccgggccgg gaacgacccg   480
ggcguggcgc cgggcggcac gggcggaggc cuccucuaug caggagguc cgcucccccu   540 ccgacggcuc ccuucaaccu ggcggacauc aacgacguga gccccucggg cggcuucgug   600
```

```
gccgagcucc ugcggccaga auuggacccg guguacauuc cgccgcagca gccgcagccg    660 ccaggugggcg ggcugauggg caaguucgug cugaaggcgu cgcugagcgc cccuggcagc   720
gaguacggca gcccgucggu caucagcguc agcaaaggca gcccugacgg cagccacccg   780 guggugguggu cgcccuacaa cggcgggccg ccgcgcacgu gccccaagau caagcaggag   840
gcggucucuu cgugcaccca cuugggcgcu ggacccccuc ucagcaaugg ccaccggccg    900
gcugcacacg acuucccccu ggggcggcag cuccccagca ggacuacccc gacccugggu    960
cuugaggaag ugcugagcag cagggacugu caccccugccc ugccgcuucc ucccggcuuc  1020 caucccccacc cggggcccaa uuacccaucc uuccugcccg aucagaugca gccgcaaguc  1080
ccgccgcucc auuaccaaga gcucaugcca cccgguuccu gcaugccaga ggagcccaag   1140
ccaaagaggg gaagacgauc guggcccgg aaaaggaccg ccaccacac uugugauuac     1200 gcgggcugcg gcaaaaccua cacaaagagu ucccaucuca aggcacaccu gcgaacccac   1260
acaggugaga aaccuuacca cuguacugg gacggcugug gauggaaauu cgcccgcuca    1320
gaugaacuga ccaggcacua ccguaaacac acggggcacc gcccguucca gugccaaaaa   1380
ugcgaccgag cauuuuccag gucggaccac cucgccuuac acaugaagag gcauuuuaa    1440

<210> SEQ ID NO 13
<211> LENGTH: 529
<212> TYPE: RNA
<213> ORGANISM: Homo sapiens

<400> SEQUENCE: 13
augggcuccg uguccaacca gcaguuugca ggugggcugcg ccaaggcggc agaagaggcg    60
cccgaggagg cgccggagga cgcggcccgg gcggcggacg agccucagcu gcugcacggu   120
gcgggcaucu guaagugguu caacgugcgc auggggguucg gcuuccuguc caugaccgcc  180
cgcgccgggg ucgcgcucga ccccccagug gaugucuuug cgcaccagag uaagcugcac   240 augaagggu uccggagcuu gaaggagggu gaggcagugg aguucaccuu uaagaaguca   300 gccaagggguc uggaauccau ccgugucacc ggaccuggug gaguauucug uauugggagu   360
gagaggcggc caaaaggaaa gagcaugcag aagcgcagau caaaaggaga caggugcuac   420
aacuguggag gucuagauca ucaugccaag gaaugcaagc ugccaccccca gcccaagaag   480 ugccacuucu gccagagcau cagccauaug guagccucau guccgcuga                529

<210> SEQ ID NO 14
<211> LENGTH: 1365
<212> TYPE: RNA
<213> ORGANISM: Homo sapiens

<400> SEQUENCE: 14
auggauuuuu uucgggguagu ggaaaaccag cagccuccccg cgacgaugcc ccucaacguu     60
agcuucacca acaggaacua ugaccucgac uacgacucgg ugcagccgua uuucuacugc   120
gacgaggagg agaacuucua ccagcagcag cagcagagcc agcugcagcc cccggcgccc   180
agcgaggaua ucuggaagaa auucgagcug cugcccaccc cgccccuguc cccuagccgc   240
cgcuccgggc ucugcucgcc cucuuacguu gcggucacac ccuucccccu ucggggagac   300
aacgacggcg guggcgggag cuucuccacg gccgaccagc uggagauggu gaccgagcug   360 cuggaggag acauggugaa ccagagcuuc aucugcgacc cggacgacga gaccuucauc   420
aaaaacauca ucauccagga cuguaugugg agcggcuucu cggccgccgc caagcucguc   480
ucagagaagc uggccuccuac ccaggcugcg cgcaaagaca gcggcagccc gaaccccgcc    540
```

```
cgcggccaca gcgucugcuc caccuccagc uuguaccugc aggaucugag cgccgccgcc      600
ucagagugca ucgaccccuc ggugucuuc cccuacccuc ucaacgacag cagcucgccc       660
aaguccugcg ccucgcaaga cuccagcgcc uucucuccgu ccucggauuc ucugcucucc      720
ucgacggagu ccuccccgca gggcagcccc gagccccugg ugcuccauga ggagacaccg     780
cccaccacca gcagcgacuc ugaggaggaa caagaagaug aggaagaaau cgauguuguu     840
ucuguggaaa agaggcaggc uccuggcaaa aggucagagu cuggaucacc uucugcugga     900
ggccacagca aacuccucuca cagcccacug guccucaaga ggugccacgu cuccacacau    960
cagcacaacu acgcagcgcc ucccuccacu cggaaggacu auccugcugc caagagggguc   1020 aaguuggaca gugucagagu ccugagacag aucagcaaca accgaaaaug caccagcccc    1080
agguccucgg acaccgagga gaaugucaag aggcgaacac acaacgucuu ggagcgccag    1140
aggaggaacg agcuaaaacg gagcuuuuuu gcccugcgug accagauccc ggaguuggaa    1200
aacaaugaaa aggcccccaa gguaguuauc cuuaaaaaag ccacagcaua caucugucc     1260 guccaagcag aggagcaaaa gcucauuucu gaagaggacu uguugcggaa acgacgagaa    1320
caguugaaac acaaacuuga acagcuacgg aacucuugug cguaa                   1365

<210> SEQ ID NO 15
<211> LENGTH: 918
<212> TYPE: RNA
<213> ORGANISM: Homo sapiens

<400> SEQUENCE: 15
augagugugg auccagcuug uccccaaagc uugccuugcu uugaagcauc cgacuguaaa     60
gaaucuucac cuaugccugu gauuuguggg ccugaaagaa acuauccauc cuugcaaaug    120
ucuucugcug agaugcccuca cacagagacu gucucuccuc uuccuuccuc cauggaucug    180
cuuauucagg acagcccuga uucuccacc agcccaaag gcaaacaacc cacuucugca      240
gagaauagug ucgcaaaaaa ggaagacaag gucccgguca gaaacagaa gaccagaacu     300 guguucucuu ccacccagcu guguguacuc aaugauagau ucagagaca gaaauaccuc     360 agccuccagc agaugcaaga acuuccaac auccugaacc ucagcuacaa acaggugaag    420
accugguucc agaaccagag aaugaaaucu aagagguggc agaaaaacaa cuggccgaag    480
aauagcaaug gugugacgca gaaggccuca gcaccaccu accccagccu cuacucuucc    540
uaccaccagg gaugccuggu gaacccgacu gggaaccuuc caaugguggag caaccagacc    600 uggaacaauu caaccuggag caaccagacc cagaacaucc aguccuggag caaccacucc    660
uggaacacuc agaccugguug cacccaaucc uggaacaauc aggccuggaa caguccuuc    720 uauaacugug gagaggaauc ucugcagucc ugcaugcacu ccagccaaa uucuccugcc    780 agugacuugg aggcugccuu ggaagcugcu ggggaaggcc uuaauguaau acagcagacc    840
acuagguauu uuaguacucc acaaaccaug gauuuauucc uaaacuacuc caugaacaug    900
caaccugaag acguguga                                                  918

<210> SEQ ID NO 16
<211> LENGTH: 1083
<212> TYPE: RNA
<213> ORGANISM: Homo sapiens

<400> SEQUENCE: 16
auggcgggac accuggcuuc agauuuugcc uucucgcccc cuccaggugg uggaggugau    60
```

-continued

| | |
|---|---|
| gggccagggg ggccggagcc gggcuggguu gauccucgga ccuggcuaag cuuccaaggc | 120 |
| ccuccuggag ggccaggaau cgggccgggg guugggccag gcucugaggu guggggauu | 180 |
| cccccaugcc ccccgccgua ugaguucugu gggggaugg cguacugugg gcccaggu | 240 |
| ggaguggggc uagugcccca aggcggcuug gagaccucuc agccugaggg cgaagcagga | 300 |
| gucggggugg agagcaacuc cgauggggcc uccccggagc ccugcaccgu caccccuggu | 360 |
| gccgugaagc uggagaagga gaagcuggag caaaacccgg aggagcccca ggacaucaaa | 420 |
| gcucugcaga agaacucga gcaauuugcc aagcuccuga agcagaagag gaucacccug | 480 |
| ggauauacac aggccgaugu ggggcucacc cugggggguuc uauuugggaa gguauucagc | 540 |
| caaacgacca ucugccgcuu ugaggcucug cagcuuagcu ucaagaacau guguaagcug | 600 |
| cggcccuugc ugcagaagug ggugggaagaa gcugacaaca augaaaaucu ucaggagaua | 660 |
| ugcaaagcag aaacccucgu gcaggcccga agagaaagc gaaccaguau cgagaaccga | 720 |
| gugagaggca accuggagaa uuuguuccug cagugcccga aacccacacu gcagcagauc | 780 |
| agccacaucg cccagcagcu uggguuccgag aaggaugugg uccgaguguq guucuguaac | 840 |
| cggcgccaga agggcaagcg aucaagcagc gacuaugcac aacgagagga uuugaggcu | 900 |
| gcugggucuc cuucucagg gggaccagug uccuucccuc uggccccagg gccccauuuu | 960 |
| gguacccag gcuauggagc cccucacuuc acugcacugu acccucggu cccuuuccu | 1020 |
| gaggggaag ccuuccccc ugucucuguc accacucugg gcucucccau gcauucaaac | 1080 |
| uga | 1083 |

<210> SEQ ID NO 17
<211> LENGTH: 954
<212> TYPE: RNA
<213> ORGANISM: Homo sapiens

<400> SEQUENCE: 17

| | |
|---|---|
| auguacaaca ugauggagac ggagcugaag ccgccgggcc cgcagcaaac uucggggggc | 60 |
| ggcggcggca acuccaccgc ggcggcggcc ggcggcaacc agaaaaacag cccggaccgc | 120 |
| gucaagcggc ccaugaaugc cuucaugguq ugucccgcg ggcagcggcg caagaugggcc | 180 |
| caggagaacc ccaagaugca caacucggag aucagcaagc gccugggcgc cgaguggaaa | 240 |
| cuuuugucgg agacggagaa gcggccguuc aucgacgagg cuaagcggcu gcgagcgcug | 300 |
| cacaugaagg agcacccgga uuauaaauac cggcccggc ggaaaccaa gacgcucaug | 360 |
| aagaaggaua aguacacgcu gcccggcggg cugcuggccc ccgcggcaa uagcauggcg | 420 |
| agcggggucg ggguggggcg cggccuggc gcggcguga accagcgcau ggacaguuac | 480 |
| gcgcacauga acggcuggag caacggcagc uacagcauga ugcaggacca gcugggcuac | 540 |
| ccgcagcacc cgggccucaa ugcgcacggc gcagcgcaga ugcagcccau gcaccgcuac | 600 |
| gacgugagcg cccugcagua caacccaug accagcucgc agaccuacau gaacggcucg | 660 |
| cccaccuaca gcauguccua cucgcagcag ggcaccccug gcauggcucu ggcuccaug | 720 |
| gguucggugg ucaaguccga ggccagcucc agcccccug ugguuaccuc uuccucccac | 780 |
| uccagggcgc ccugcaggc cggggaccuc cgggacauga ucagcaugua ucucccggc | 840 |
| gccgaggugc cggaacccgc cgcccccagc agacuucaca ugucccagca cuaccagagc | 900 |
| ggcccggugc ccggcacggc cauuaacggc acacugcccc ucucacacau guga | 954 |